(12) United States Patent
De Jong et al.

(10) Patent No.: US 11,162,148 B2
(45) Date of Patent: Nov. 2, 2021

(54) VIRUS CAUSING RESPIRATORY TRACT ILLNESS IN SUSCEPTIBLE MAMMALS

(71) Applicant: Erasmus University Medical Center Rotterdam, Rotterdam (NL)

(72) Inventors: Jan Cornelius De Jong, Gouda (NL); Ronaldus Adrianus Maria Fouchier, Rotterdam (NL); Bernadetta Gerarda Van Den Hoogen, Rotterdam (NL); Albertus D. M. E. Osterhaus, Antwerp (BE); Jan Groen, Hilversum (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 6 days.

(21) Appl. No.: 16/730,429

(22) Filed: Dec. 30, 2019

(65) Prior Publication Data

US 2020/0140964 A1 May 7, 2020

Related U.S. Application Data

(63) Continuation of application No. 16/235,030, filed on Dec. 28, 2018, now Pat. No. 10,519,517, which is a continuation of application No. 15/796,500, filed on Oct. 27, 2017, now Pat. No. 10,167,524, which is a continuation of application No. 15/453,764, filed on Mar. 8, 2017, now Pat. No. 9,803,252, which is a continuation of application No. 15/147,653, filed on May 5, 2016, now Pat. No. 9,593,386, which is a continuation of application No. 14/553,957, filed on Nov. 25, 2014, now Pat. No. 9,334,543, which is a continuation of application No. 10/466,811, filed as application No. PCT/NL02/00040 on Jan. 18, 2002, now Pat. No. 8,927,206.

(30) Foreign Application Priority Data

Jan. 19, 2001 (EP) ..................................... 01200213
Oct. 18, 2001 (EP) ..................................... 01203985

(51) Int. Cl.
| | | |
|---|---|---|
| *C12Q 1/70* | (2006.01) | |
| *C07K 14/005* | (2006.01) | |
| *C12N 7/00* | (2006.01) | |
| *A61K 39/12* | (2006.01) | |
| *A61K 39/155* | (2006.01) | |
| *C07K 16/10* | (2006.01) | |
| *G01N 33/50* | (2006.01) | |
| *G01N 33/569* | (2006.01) | |
| *C12N 15/86* | (2006.01) | |
| *A61K 39/00* | (2006.01) | |

(52) U.S. Cl.
CPC .............. *C12Q 1/701* (2013.01); *A61K 39/12* (2013.01); *A61K 39/155* (2013.01); *C07K 14/005* (2013.01); *C07K 16/1027* (2013.01); *C12N 7/00* (2013.01); *C12N 15/86* (2013.01); *G01N 33/502* (2013.01); *G01N 33/5008* (2013.01); *G01N 33/5091* (2013.01); *G01N 33/56983* (2013.01); *A61K 2039/5254* (2013.01); *A61K 2039/5256* (2013.01); *C12N 2760/18321* (2013.01); *C12N 2760/18322* (2013.01); *C12N 2760/18334* (2013.01); *C12N 2760/18343* (2013.01); *C12N 2760/18622* (2013.01); *C12N 2840/203* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,946,778 | A | 8/1990 | Ladner et al. |
| 5,137,819 | A | 8/1992 | Kilburn et al. |
| 5,166,057 | A | 11/1992 | Palese et al. |
| 5,202,247 | A | 4/1993 | Kilburn et al. |
| 5,722,341 | A | 3/1998 | Tornqvist |
| 5,824,307 | A | 10/1998 | Johnson |
| 5,854,037 | A | 12/1998 | Palese et al. |
| 5,869,036 | A | 2/1999 | Belshe et al. |
| 6,033,886 | A | 3/2000 | Conzelmann |
| 6,146,642 | A | 11/2000 | Garcia-Sastre et al. |
| 6,180,398 | B1 | 1/2001 | Klein et al. |
| 6,379,881 | B1 | 4/2002 | Fouchier et al. |
| 6,605,283 | B1 | 8/2003 | Seal et al. |
| 7,192,593 | B2 | 3/2007 | Murphy et al. |
| 7,238,481 | B2 | 7/2007 | Haller et al. |
| 7,341,729 | B2 | 3/2008 | Haller et al. |

(Continued)

FOREIGN PATENT DOCUMENTS

| | | | |
|---|---|---|---|
| CA | 2378661 | A1 | 1/2001 |
| CA | 2403701 | A1 | 9/2001 |

(Continued)

OTHER PUBLICATIONS

Van den Hoogen et al., Nature Medicine vol. 7, No. 6, pp. 719-724 (Year: 2001).*

(Continued)

*Primary Examiner* — Shanon A. Foley
*Assistant Examiner* — Myron G Hill
(74) *Attorney, Agent, or Firm* — Patent Law Works, LLP

(57) ABSTRACT

The invention relates to the field of virology. The invention provides an isolated essentially mammalian negative-sense single-stranded RNA virus (MPV) within the subfamily Pneumovirinae of the family Paramyxoviridae and identifiable as phylogenetically corresponding to the genus *Metapneumovirus* and components thereof.

16 Claims, 39 Drawing Sheets

Specification includes a Sequence Listing.

(56) References Cited

U.S. PATENT DOCUMENTS

| | | | |
|---|---|---|---|
| 7,449,324 | B2 | 11/2008 | Fouchier et al. |
| 7,531,342 | B2 | 5/2009 | Fouchier et al. |
| 7,678,376 | B2 | 3/2010 | Haller et al. |
| 7,704,491 | B2 | 4/2010 | Collins et al. |
| 7,704,509 | B2 | 4/2010 | Murphy et al. |
| 7,704,720 | B2 | 4/2010 | Tang et al. |
| 8,084,037 | B2 | 12/2011 | Haller et al. |
| 8,715,922 | B2 | 5/2014 | De Jong et al. |
| 8,841,433 | B2 | 9/2014 | Fouchier et al. |
| 8,927,206 | B2 | 1/2015 | De Jong et al. |
| 9,152,845 | B2 | 10/2015 | Yamada et al. |
| 9,334,543 | B2 | 5/2016 | De Jong et al. |
| 9,376,726 | B2 | 6/2016 | Fouchier et al. |
| 9,593,386 | B2 | 3/2017 | De Jong et al. |
| 2002/0110606 | A1 | 8/2002 | Graus et al. |
| 2002/0155581 | A1 | 10/2002 | Murphy et al. |
| 2003/0232061 | A1 | 12/2003 | Fouchier et al. |
| 2003/0232326 | A1 | 12/2003 | Fouchier et al. |
| 2004/0005544 | A1 | 1/2004 | Fouchier et al. |
| 2004/0005545 | A1 | 1/2004 | Fouchier et al. |
| 2004/0096451 | A1 | 5/2004 | Young et al. |
| 2004/0097584 | A1 | 5/2004 | Graus et al. |
| 2004/0142448 | A1 | 7/2004 | Murphy et al. |
| 2004/0229219 | A1 | 11/2004 | Gallaher et al. |
| 2004/0241188 | A1 | 12/2004 | Collins et al. |
| 2005/0019891 | A1 | 1/2005 | Fouchier et al. |
| 2005/0053919 | A1 | 3/2005 | De Jong et al. |
| 2005/0118195 | A1 | 6/2005 | De Jong et al. |
| 2005/0142148 | A1 | 6/2005 | Fouchier et al. |
| 2005/0146046 | A1 | 7/2005 | Fouchier |
| 2006/0008810 | A1 | 1/2006 | Lee et al. |
| 2006/0203645 | A1 | 9/2006 | Van Den Hoogen et al. |
| 2006/0216700 | A1 | 9/2006 | Schickli |
| 2006/0228367 | A1 | 10/2006 | Ulbrandt et al. |
| 2007/0033993 | A1 | 2/2007 | Fouchier |
| 2007/0053878 | A1 | 3/2007 | Haagmans et al. |
| 2007/0087333 | A1 | 4/2007 | Gruters et al. |
| 2008/0044426 | A1 | 2/2008 | De Jong et al. |
| 2008/0050401 | A1 | 2/2008 | De Wit et al. |
| 2008/0102444 | A1 | 5/2008 | Lee et al. |
| 2008/0230856 | A1 | 9/2008 | Fouchier |
| 2008/0292658 | A1 | 11/2008 | De Wit et al. |
| 2009/0151030 | A1 | 6/2009 | Fouchier |
| 2009/0186050 | A1 | 7/2009 | Fouchier et al. |
| 2009/0246855 | A1 | 10/2009 | Fouchier et al. |
| 2010/0143407 | A1 | 6/2010 | Fouchier et al. |
| 2010/0278813 | A1 | 11/2010 | Young et al. |
| 2010/0297730 | A1 | 11/2010 | Fouchier et al. |
| 2011/0020391 | A1 | 1/2011 | Suzer et al. |
| 2012/0045471 | A1 | 2/2012 | Haller et al. |
| 2012/0156241 | A1 | 6/2012 | De Wit et al. |
| 2013/0129770 | A1 | 5/2013 | Osterhaus et al. |
| 2014/0295409 | A1 | 10/2014 | Fouchier et al. |
| 2014/0370497 | A1 | 12/2014 | Fouchier et al. |
| 2015/0093746 | A1 | 4/2015 | De Jong et al. |
| 2015/0275183 | A1 | 10/2015 | Haagmans et al. |
| 2016/0244850 | A1 | 8/2016 | De Jong et al. |

FOREIGN PATENT DOCUMENTS

| | | | |
|---|---|---|---|
| CA | 2435180 | A1 | 7/2002 |
| CA | 2477234 | A1 | 9/2003 |
| CA | 2477235 | A1 | 9/2003 |
| CA | 2743750 | A1 | 9/2003 |
| CA | 2523319 | A1 | 11/2004 |
| CA | 2523657 | A1 | 3/2005 |
| CN | 109402065 | A * | 3/2019 |
| EP | 0702085 | A1 | 3/1996 |
| EP | 0780475 | A1 | 6/1997 |
| EP | 1351981 | A2 | 10/2003 |
| FR | 2801607 | A1 | 6/2001 |
| JP | 2002557978 | | 6/2001 |
| JP | 5503096 | B2 | 10/2004 |
| JP | 2004531220 | A | 10/2004 |
| WO | 8910405 | A1 | 11/1989 |
| WO | 9314207 | A1 | 7/1993 |
| WO | 9634625 | A1 | 11/1996 |
| WO | 9706270 | A1 | 2/1997 |
| WO | 9712032 | A1 | 4/1997 |
| WO | 9734008 | A1 | 9/1997 |
| WO | 9802530 | A1 | 1/1998 |
| WO | 9813501 | A2 | 4/1998 |
| WO | 9853078 | A1 | 11/1998 |
| WO | 9902657 | A1 | 1/1999 |
| WO | 9915672 | A1 | 4/1999 |
| WO | 2000020600 | A1 | 4/2000 |
| WO | 2000070070 | A1 | 11/2000 |
| WO | 2001004320 | A1 | 1/2001 |
| WO | 0138497 | A1 | 5/2001 |
| WO | 2001038362 | A2 | 5/2001 |
| WO | 2001042445 | A2 | 6/2001 |
| WO | 0244334 | A2 | 6/2002 |
| WO | 2002057302 | A2 | 7/2002 |
| WO | 2003043587 | A2 | 5/2003 |
| WO | 2003072720 | A2 | 9/2003 |
| WO | 2003097089 | A2 | 11/2003 |
| WO | 2004057021 | A2 | 7/2004 |
| WO | 2005014626 | A2 | 2/2005 |

OTHER PUBLICATIONS

Geneseq database comparison (Year: 2020).*
Geneseq item sequence (Year: 2020).*
Kido et al., 1992, "Isolation and characterization of a novel trypsin-like protease found in rat bronchiolar epithelial Clara cells: a possible activator of the viral fusion glycoprolein," J. Biol. Chem. 267: 13573-13579.
Kido et al., 1996, "Cellular proteases involved in the pathogenicity of enveloped animal viruses, human Immunodeficiency virus, influenza virus A and Sendai virus," Adv. Enzyme Regul. 36: 325-47.
Kim et al., 1969, "Respiratory syncytial virus disease in infants despite prior administration of antigenic inactivated vaccine", Am J Epidemiol. 89(4):422-434.
Klenk et al., 1988, "The molecular biology of influenza virus pathogenicity," Adv. Virus Res. 34: 247-281.
Klenk et al., 1994, "Host cell proteases controlling virus pathogenicity," Trends Microbial.2 (2): 39-43.
Klippmark et al. 1990, "Antigenic variation of human and bovine parainfluenza virus type 3 strains," J Gen Virol. 71 (Pt. 7):1577-80.
Korean Office Action of application No. 10-2010-7005359, dated Jun. 3, 2010.
Korean Office Action of Korean application No. 10-2005-7020308, dated Feb. 8, 2012 (with English translation).
Korean Office Action of Korean Application No. 10-2011-7016892, dated Jul. 11, 2012 (with English translation).
Korean Office Action of Korean Application No. 2011-7020851, dated Dec. 13, 2012 (English translation only).
Krempl et al., 2002, "Recombinant respiratory syncytial virus with the G and F genes shilled to the promoter-proximal positions", J Virol. 76(23):11931-11942.
Krystal et al., 1986, "Expression of the three influenza virus polymerase proteins in a single cell allows growth complementation of viral mutants", Proc Natl Acad Sci USA. 83(8):2709-13.
Kunkel et al. 1985, "Rapid and efficient site-specific mutagenesis without phenotypic selection," Proc Nall Acad Sci U S A. 82(2):488-492.
Lamb, 1993, "Paramyxovirus fusion: A hypothesis for changes," Virology 197: 1-11.
Lamprecht et al., 1976, "Role of maternal antibody in pneumonia and bronchiolitis due to respiratory syncytial virus", J Infect Dis. 134(3):211-217.
Letter from Japanese foreign associate regarding status of copending Japanese Patent Application No. 2013-142224 dated Dec. 9, 2014.
Ling et al., 1992, "Sequence analysis of the 22K, SH and G genes of turkey rhinotracheitis virus and their inlergenic regions reveals a gene order different from that of other pneumoviruses", J Gen Virol. 73 ( PI 7):1709-1715.

(56) References Cited

OTHER PUBLICATIONS

Lopez et al., 1998, "Antigenic structure of human respiratory syncytial virus fusion glycoprolein", J Virol. 72(8):6922-6928.
MacDonald et al., 1982, "Respiratory syncytial viral infection in infants with congenital heart disease", N Engl J Med. 307(7):397-400.
Maggi et al., 2003, "Human melapneumovirus associated with respiratory tract infections in a 3-year study of nasal swabs from infants in Italy," J. Clinical Microbiology 41: 2987-2991.
Marriott and Easton, 1999, "Reverse Genetics of the Paramyxoviridae", Adv Virus Res. 53:321-340.
Marriott et al., 2001, "Fidelity of leader and trailer sequence usage by the respiratory syncytial virus and avian pneumovirus replication complexes", J Virol. 75(14):6265-6272.
Mexican Office Action of application No. PA/a/2003/006430, dated Apr. 16, 2010.
Mexican Office Action of application No. PA/a/2003/006430, dated Feb. 25, 2011.
Mexican Office Action of application No. PA/a/2005/011268, dated Dec. 7, 2010.
Morell et al. eds., 1986, Clinical Use of Intravenous Immunoglobulins. Academic Press, London, pp. 285.
Morrison, 2003, "Structure and function of a paramyxovirus fusion protein," Biochimica El Biophysica Acta 1614: 73-84.
Murphy et al., 1988, "Passive transfer of respiratory syncylial virus (RSV) antiserum suppresses the immune response to the RSV fusion (F) and large (G) glycoproleins expressed by recombinant vaccinia viruses", J Virol. 62(10):3907-3910.
Murphy et al., 1991, "Effect of passive antibody on the immune response of cotton rats to purified F and G glycoproleins of respiratory syncytial virus (RSV)", Vaccine. 9(3):185-189.
Murphy et al., 1994, "An update on approaches to the development of respiratory syncytial virus (RSV) and parainfluenza virus type 3 (PIV3) vaccines", Virus Res. 32(1):13-36.
Nagai et al., 1989, "Molecular biology of Newcastle disease virus," Prog. Vet. Microbial. 5: 16-64.
Navas et al., 1992, "Improved outcome of respiratory syncytial virus infection in a high-risk hospitalized population of Canadian children. Pediatric Investigators Collaborative Network on Infections in Canada", J Pediatr. 121(3):348-354.
Naylor et al., 1998, "The ectodomains but not the transmembrane domains of the fusion proteins of subtypes A and B avian pneumovirus are conserved to a similar extent as those of human respiratory syncytial virus", J Gen Virol. 79 (Pt. 5):1393-1398.
Neumann et al., 2002, "Reverse genetics demonstrates that proteolytic processing of the Ebola virus glycoprotein is not essential for replication in cell culture", J Virol. 76(1):406-410.
New Vaccine Development, Establishing Priorities, vol. 1, 1985, National Academy Press, Washington DC pp. 397-409.
Nissen et al., 2002, "Evidence of human metapneumovirus in Australian children", Med J Australia. 176(4): 188.
Notice of Reasons for Rejection on copending Japanese Patent application No. 2013-142224 dated Oct. 28, 2014.
O'Brien, 1985, "Swollen head syndrome in broiler breeders", Vet Rec. 117(23):619-620.
Ogra et al., 1988, "Respiratory syncytial virus infection and the immunocompromised host", Pediatr Infect Dis J. 7(4):246-249.
Oomens et al., 2003, "Recovery of infectious human respiratory syncytial virus lacking all transmembrane glycoprotein Jenes via trans-complementati on," 12th Intl. Cont. on Negative Strand Viruses, Pisa, Italy, Abstr #205.
Osterhaus et al., 2000, "Infruenza B virus in seals," Science 288(5468):1051-3.
Palese et al., 1996, "Negative-strand RNA viruses: genetic engineering and applications", Proc Natl Acad Sci U S A. 3(21):11354-11358.
Peeters et al., 1999, "Rescue of Newcastle disease virus from cloned cDNA: evidence that cleavability of the fusion protein is a major determinant for virulence", J Virol. 73(6):5001-5009.

Peiris et al., 2003, "Children with respiratory disease associated with metapneumovirus in Hong Kong," Emerg. Infect. Dis. 9: 628-633.
Peret et al., 2002, "Characterization of human metapneumoviruses isolated from patients in North America", J Infect Dis. 185(11):1660-1663.
Peret et al., 2004, "Sequence polymorphism of the predicted human metapneumovirus G glycoprotein," J. Infect. Dis. 35: 679-686.
Poch et al., 1989, "Identification of four conserved motifs among the RNA-dependent polymerase encoding elements", EMBO J. 8(12): 3867-3874.
Poch et al., 1990, "Sequence comparison of five polymerases (L proteins) of unsegmented negative-strand RNA viruses: theoretical assignment offunctional domains", J Gen Virol. 71 (Pt 5):1153-1162.
Pohl et al., 1992, "Respiratory syncytial virus infections in pediatric liver transplant recipients", J Infect Dis. 165(1):166-169.
Polish Office Action of application No. P-367826, dated Jul. 13, 2011.
GenBank accession No. AY145257, Bastien et al., Oct. 8, 2003.
GenBank accession No. AY145287, Bastien et al., Oct. 8, 2003.
Giraud et al., 1986, "Turkey rhinotracheitis in France: preliminary investigations on a ciliostatic virus", Vet Rec. 119(24):606-607.
Glezen et al., 1981, "Risk of respiratory syncytial virus infection for infants from low-income families in relationship to age, sex, ethnic group, and maternal antibody level", J Pediatr. 98(5):708-715.
Glickman et al., 1988, "Quantitative basic residue requirements in the cleavage-activation site of the fusion glycoprotein as a determinant of virulence for Newcastle disease virus," J. Virol. 62: 354-356.
Gonzalez-Reyes et al., 2001, "Cleavage of the human respiratory syncytial virus fusion protein at two distinct sites is required for activation of membrane fusion," PNAS 98, pp. 9859-9864.
Greensill et al., 2003, "Human metapneumovirus in severe respiratory syncytial virus bronchiolitis", Emerg. Infect. Dis. (3):372-5.
Groothuis et al., 1988, "Respiratory syncytial virus infection in children with bronchopulmonary dysplasia", Pediatrics 82(2):199-203.
Groothuis et al., 1993, "Prophylactic administration of respiratory syncytial virus immune globulin to high-risk infants and young children. The Respiratory Syncytial Virus Immune Globulin Study Group", N Engl J Med. 329(21):1524-1530.
Hall et al, 1992, "Cold-passaged human parainfluenza type 3 viruses contain is and non-ts mutations leading to attenuation in rhesus monkeys", Virus Research: 2(3):173-184 (geen doc).
Hall et al., 1979, "Neonatal respiratory syncytial virus infection", N Engl J Med. 300(8):393-396.
Hall, 1993, "Respiratory Syncytial Virus: What We Know Now," Contemp. Pediatr. 10:92-110.
Haller et al. 2000, "Expression of the surface glycoproteins of human parainfluenza virus type 3 by bovine parainfluenza virus type 3, a novel attenuated virus vaccine vector," J Virol. 74(24):11626-11635.
Hamelin et al., 2004, "Human metapneumovirus: a new player among respiratory viruses," Clinical Infectious Diseases 38: 983-990.
Heckert et al., 1993, "Absence of antibodies to avian pneumovirus in Canadian poultry", Vet Rec. 132(7):172.
Hemming et al., 1985, "Studies of passive immunolherapy for infections of respiratory syncytial virus in the respiratory tract of a primate model", J Infect Dis. 152(5):1083-1087.
Henderson et al., 1979, "Respiratory-syncytial-virus infections, reinfections and immunity. A prospective, longitudinal study in young children", N Engl J Med. 300(10):530-534.
Herfst, 2004, "Recovery of human melapneumovirus genetic lineages A and B from cloned cDNA," J. Virol. 78:8264-8270.
Hertz et al., 1989, "Respiratory syncytial virus-induced acute lung injury in adult patients with bone marrow transplants: clinical approach and review of the literature", Medicine (Baltimore). 68(5.sub.-:269-281 . Review.
Hoffmann et al., 200, Unidirectional RNA polymerase 1-polymerase II transcription system for the generation of Influenza A virus from eight plasmids, J. Gen Virol.(Pi 12):2843-2847.

(56) References Cited

OTHER PUBLICATIONS

Hoffmann et al., 2000, "A DNA transfection system for generation of influenza A virus from eight plasmids", Proc Nall Acad Sci USA. 97(11):6108-6113.
Howe, 2002, "Australian find suggests worldwide reach for melapneumovirus," Lancet Infect. Dis. 2:202.
Human RSV genome P sequence NC 001781.1 version dated May 2000.
Huygelen et al., 1977, "Laboratory and clinical evaluation of new live influenza virus vaccines. Need for minimum requiremenls", Dev Biol Stand. 39:155-160.
Ijpma et al., 2004, "Human melapneumovirus infection in hospital referred South African children," J. Med. Virol. 73: 486-493.
Indian Office Action of application No. 3970/CHENP/2007, dated Aug. 4, 2010.
Inoue et al., 2003, "An improved method for recovering rabies virus from cloned cDNA", J Virol Methods. 107(2):229-236.
International Search Report of International application No. PCT/NL02/00040, dated Oct. 7, 2002.
Ishida et al., 1978, "Sendai virus," Adv. Virus Res. 23: 349-383.
Ishiguro et al., 2004, "High genetic diversity of the attachment (G) protein of human metapneumovirus", J Clin Microbial.42(8):3406-3414.
Israeli Office Action of Israeli application No. 157003, dated Aug. 16, 2011 (un-formal translation).
Israeli Office Action of Israeli Application No. 171568, dated May 29, 2012 (English translation only).
Israeli Office Action of Israeli application No. 212138, dated Mar. 11, 2012 (un-formal translation).
Japanese Office Action of Application No. 2002-557978, dated Aug. 14, 2012 (with English translation).
Japanese Office Action of application No. 2002-557978, dated Jul. 14, 2009.
Japanese Office Action of application No. 2006-513300, dated Apr. 30, 2010.
Japanese Office Action of Application No. 2006-513300, dated Aug. 14, 2012 (with English translation).
Japanese Office Action of application No. 2006-513301, dated Apr. 6, 2010.
Japanese Office Action of application No. 2006-513301, dated Dec. 7, 2010.
Japanese Office Action of application No. 2009-035820, dated Aug. 2, 2011 (with translation).
Japanese Office Action of Japanese application No. 2011-084567, dated Apr. 24, 2012.
Japanese Office Action of Japanese application No. 2011-084567, dated Dec. 11, 2012 (English translation only).
Japanese Office Action of Japanese application No. 2011-084567, dated Jul. 12, 2011 (with translation).
Johnson et al. 1997, "Development of a humanized monoclonal antibody (MEDI-493) with potent in vitro and in vivo Activity against respiratory syncytial virus," J Infect Dis. 176(5):1215-1224.
Johnson et al., 1987, "The G glycoprotein of human respiratory syncytial viruses of subgroups A and B: extensive sequence divergence between antigenically related proteins", Proc Natl Acad Sci USA. 84(16):5625-5629.
Juhasz et al., 1994, "Extensive sequence variation in the attachment (G) protein gene of avian pneumovirus: evidence or two distinct subgroups", J Gen Virol. 75 ( PI 11):2873-2880.
Kapikian et al., 1969, "An epidemiologic study of altered clinical reactivity to respiratory syncytial (RS) virus infection in children previously vaccinated with an inactivated RS virus vaccine", Am J Epidemiol. 89(4):405-421.
Karron et al. 1995, "A live attenuated bovine parainfluenza virus type 3 vaccine is safe, infectious, immunogenic, and phenotypically stable in infants and children," J Infect Dis. 171(5):1107-1114.
Karron et al. 1996, "Evaluation of a live attenuated bovine parainfluenza type 3 vaccine in two- to six-month-old Infants," Pediatr Infect Dis J. 15(8):650-654.

Kawaoka et al., 1984, "Is virulence of H5N2 influenza viruses in chickens associated with loss of carbohydrate from the hemagglulinin" Virology 139: 303-316.
Abman et al., 1988, "Role of respiratory syncytial virus in early hospitalizations for respiratory distress of young infants with cystic fibrosis", J. Pediatr. 113(5):826-830.
Ahmadian et al., 1999, "Detection and characterization of proteins encoded by the second ORF of the M2 gene of pneumoviruses," J. Gen. Virol. 80(8):2011-2016. XP 002176552 Ahmadian.
Alvarez et al, 2003. "Nucleotide and predicted amino acid sequence-based analysis of the avian C251 metapneumovirus type C cell attachment glycoprotein gene: phylogenetic analysis and molecular epidemiology of U.S. Pneumoviruses", J Clin Micreobiol; 41(4):1730-1735.
Australian Examination Report of patent application No. 2008202111, dated Oct. 12, 2010.
Bailly et al., 2000, "Recombinant human parainfluenza virus type 3 (PIV3) in which the nucleocapsid N protein has been replaced by that of bovine PIV3 is attenuated in primates," J. Virol. 74(7):3188-95.
Barr, 1991, "Mammalian subtilisins: the long-sought dibasic processing endoproteases," Cell 66: 1-3.
Bastien et al., 2003, "Human metapneumovirus infection in the Canadian population," J. Clin. Microbiol. 41: 4642-4646.
Bastien et al., 2003, "Sequence analysis of the N, P, M and F genes of Canadian human metapneumovirus strains", Virus Res. 93(1):51-62.
Bayon-Auboyer et al., 1999, "Comparison of F-, G- and N-based RT-PCR protocols with conventional virological procedures for the detection and typing of turkey rhinotracheitis virus", Arch Virol. 144(6):1091-1109. http://dx.doi.org/10.1007/s007050050572 (XP 002213815).
Bayon-Auboyer et al., 2000, "Nucleotide sequences of the F, L and G protein genes of two non-A/non-B avian pneumoviruses (APV) reveal a novel APV subgroup", J Gen Virol. 81(Pt 11):2723-2733.
Beare et al., 1975, "Trials in man with live recombinants made from A/PR/8/34 (HO N1) and wild H3 N2 influenza iruses", Lancet. 2(7938):729-732.
Beeler et al., 1989, "Neutralization epitopes of the F glycoprotein of respiratory syncytial virus: effect of mutation upon usion function", J Virol. 63(7):2941-2950.
Belshe et al., 1982, "Cold adaptation of parainfluenza virus type 3: Induction of three phenotypic markers", J Medical Virol; 10(4):235-242.
Bentley et al., 1980, "Human immunoglobulin variable region genes—DNA sequences of two V kappa genes and a seudogene", Nature. 288(5792):730-733.
Biacchesi et al., 2003, "Genetic diversity between human metapneumovirus subgroups," Virology 315: 1-9.
Biacchesi et al., 2006, "Modification of the Trypsin-Dependent Cleavage Activation Site of the Human Metapneumovirus Fusion Protein to Be Trypsin Independent Does Not Increase Replication or Spread in Rodents or Nonhuman Primates" in J. Virology; 80(12):5798-5806.
Boivin et al., 2002, Virological features and clinical manifestations associated with human metapneumovirus: a new aramyxovirus responsible for acute respiratory-tract infections in all age groups, J. Infect. Dis. 186: 1330-1334.
Boivin et al., 2003, "Human metapneumovirus infections in hospitalized children," Emerg. Infect. Dis. 9: 634-640.
Bosch et al., 1981, "Proteolytic cleavage of influenza virus hemagglutinin. Primary structure of the connecting peptide Between HA1 and HA2 determines proteolytic cleavability and pathogenicity of avian influenza viruses," Virology 113: 725-735.
Botts and Takashi et al., 1984, "On the mechanism of energy transduction in myosin subfragment 1", Proc Natl Acad Sci USA. 81(7):2060-4.
Brazilian Office Action of application No. PI0206591-6, dated Mar. 10, 2011.
Breker-Klassen et al. 1996, "Comparisons of the F and HN gene sequences of different strains of bovine parainfluenza virus type 3: relationship to phenotype and pathogenicity," Can J Vet Res. 60(3):228-236.

(56) References Cited

OTHER PUBLICATIONS

Bridgen et al., 1996, "Rescue of a segmented negative-strand RNA virus entirely from cloned complementary DNAs", Droc Natl Acad Sci USA. 93(26):15400-15404.
Buchholz et al., 1999, "Generation of bovine respiratory syncytial virus (BRSV) from cDNA: BRSV NS2 is not essential or virus replication in tissue culture, and the human RSV leader region acts as a functional BRSV genome promoter", J Virol. 73(1):251-259.
Buys et al. 1980, "A Preliminary Report on the Isolation of a Virus Causing Sinusitis in Turkeys in south Africa and Attempts to Attenuate the Virus," Turkey 28:36-46.
Cavanagh et al., 1988, "Pneumovirus-like characteristics of the mRNA and proteins of turkey rhinotracheitis virus", Virus Res. 11(3):241-256.
Chanock et al. 1989, "Respiratory Syncytial Virus" Chapter 20 IN Evans, ed., 1989, Viral Infections of Humans: Epidemiology and Control, 3rd ed., Plenum Medical Book, New York, pp. 525-544.
Chinese Office Action of Chinese Application No. 200480017803.2, dated Jul. 23, 2012 (with English translation).
Chinese Office Action of Chinese application No. 200480017850.7, dated Oct. 26, 2011.
Chinese Office Action of Chinese application No. 200910206209.2, dated Jan. 5, 2012.
Chinese Office Action, dated Sep. 11, 2009.
Clements et al. 1991, "Evaluation of bovine, cold-adapted human, and wild-type human parainfluenza type 3 viruses in adult volunteers and in chimpanzees," J Clin Microbial.29(6): 1175-1182.
Collins et al., 1988, "Characterization of a virus associated with turkey rhinotracheitis", J Gen Virol. 69 ( PI 4):909-916.
Collins et al., 1991, "Post translational processing and oligomerization of the fusion glycoprolein of human respiratory syncytial virus," J. Gen. Virol. 72: 3095-3101.
Collins et al., 1993, "Deduced amino acid sequences at the fusion protein cleavage site of Newcastle disease viruses showing variation in antigenicity and pathogenicity," Arch. Virol. 128: 363-370.
Collins et al., 1993, Characterization of a virus associated with turkey rhinotracheitis, J Avian Pathology, 22:469-479.
Collins et al., 1995, "Production of infectious human respiratory syncytial virus from cloned cDNA confirms an essential ale for the transcription elongation factor from the 5 proximal open reading frame of the M2 mRNA in gene expression nd provides a capability for vaccine development", Proc Nall Acad Sci USA. 92(25): 11563-11567.
Collins et al., 1996, Fields Virology, ed. V.N. Knipe, Howley, P.M., Philadelphia: Lippencott-Raven. pp. 1313-1351.
Collins et al., 2001 (Eds.), Fields Virology, fourth ed. Lippincott Williams and Wilkins, Philadelphia, PA, pp. 1443-1485.
Collins, 1991, "The Molecular Biology of Human Respiratory Syncytial Virus (RSV) of the Genus Pneumovirus", the Paramyxoviruses, D.W. Kingsbury, ed. Plenum Press, New York, pp. 103-162.
Communication issued by European Patent Office regarding Application No. 11192988.1, dated Sep. 10, 2012.
Communication of a Notice of Opposition in copending EP 02710551.9 dated May 14, 2013.
Communication pursuant to Rule 114(2) EPC, for European Patent Application 02710551.9 dated Oct. 28, 2014.
Toyoda et al., 1987, "Structural comparison of the cleavage-activation site of the fusion glycoprotein between virulent and avirulent strains of Newcastle disease virus," Virology 158: 242-247.
Ukrainian Office Action of application No. 2003087814/(MI-2341), dated Mar. 15, 2010.
Van Den Hoogen et al., 2001, "A newly discovered human pneumovirus isolated from young children with respiratory tract disease", Nat Med. 7(6):719-724. DOI: http://dx.doi.org/10.1038/89098—XP 002176554 Hoogen van den et al.
Van Den Hoogen et al., 2002, "Analysis of the genomic sequence of a human metapneumovirus", Virology. 295(1):119-132.
Van Den Hoogen et al., 2003, "Prevalence and clinical symptoms of human metapneumovirus infection in hospitalized patients," J. Infect. Dis. 188: 1571-1577.
Van Den Hoogen et al., 2004, "Antigenic and genetic variability of human metapneumoviruses," Emerging Infectious Diseases 10: 658-666.
Van Den Hoogen et al., 2004, "Clinical impact and diagnosis of hMPV infections," Pediatric Infectious Disease Journal, 23: s25-32.
Van Wyke Coelingh et al. 1990, "Antibody responses of humans and nonhuman primates to individual antigenic sites of the hemagglutinin-neuraminidase and fusion glycoproteins after primary infection or reinfection with parainfluenza type 3 virus," J Virol. 64(8):3833-3843.
Volchkov et al., 2001, "Recovery of infectious Ebola virus from complementary DNA: RNA editing of the GP gene and viral cytotoxicity", Science. 291(5510): 1965-1969.
Wang et al., 2003, "Both heptad repeats of human respiratory syncytial virus fusion protein are potent inhibitors of viral fusion," Biochem. Biophys. Res. Commun. 302(3):469-75.
White, 1990, "Viral and cellular membrane fusion proteins," Annual Review Physiology 52: 675-697.
Williams et al., 2004, "Human metapneumovirus and lower respiratory tract disease in otherwise healthy infants and children," N. Engl.J. Med. 350: 443-450.
Williams et al., 2006, "The role of human metapneumovirus in upper respiratory tract infections in children: a 20-year experience", J Infect Dis. 193(3):387-395.
Wolf et al., D., 2003, "High seroprevalence of human metapneumovirus among young children in Israel," J. Inf. Dis. 188: 1865-1867.
Yu et al., 1991, "Deduced amino acid sequence of the fusion glycoprotein of turkey rhinotracheitis virus has greater Identity with that of human respiratory syncytial virus, a pneumovirus, than that of paramyxoviruses and rnorbilliviruses", J Gen. Virol. 72(1):75-81. XP 002095554 Yu Q et al.
Yu et al., 1992, "Cloning and sequencing of the matrix protein (M) gene of turkey rhinotracheitis virus reveal a gene order different from that of respiratory syncytial virus", Virology. 186(2):426-434.
Yu et al., 1992, "Sequence and in vitro expression of the M2 gene of turkey rhinotracheitis pneumovirus", J Gen Virol. 3 ( Pt 6):1355-1363.
Polish Office Action of Polish application No. P-367826, dated Dec. 4, 2011.
Press et al., 1970, "The amino acid sequences of the Fd fragments of two human gamma-1 heavy chains", Biochem J. 117(4):641-660.
Prince et al., 1983, "Mechanisms of immunity to respiratory syncylial virus in cotton rats", Infect Immun. 42(1):81-87.
Prince et al., 1985, "Immunoprophylaxis and immunotherapy of respiratory syncylial virus infection in the cotton rat", Virus Res. 3(3):193-206.
Prince et al., 1985, "Quantitative aspects of passive immunity to respiratory syncytial virus infection in infant cotton rats", J Virol. 55(3):517-520.
Prince et al. 1990, "Mechanism of antibody-mediated viral clearance in immunotherapy of respiratory syncytial virus infection of cotton rats", J Virol. 64(6):3091-3092.
Prince, Ph.D. diss., University of California, LA 1975.
Pringle, 1998, "Virus taxonomy—San Diego 1998", Arch Virol. 143(7):1449-1459.
Pringle, 1999, "Virus taxonomy at the XIth international congress of virology, Sydney, Australia, Aug. 9-13, 1999," Arch. Virol. 144(10):2065-2070. http://dx.doi.org/10.1007/s007050050728 XP 002213816 Pringle.
Randhawa et al., 1996 "Nucleotide sequence of the gene encoding the viral polymerase of avian pneumovirus." J. 3en. Virol. 77: 3047-3051.
Randhawa J.S. et al, Journal of Virology, vol. 71, No. 12, 1997, s 9849-9854, XP 002083386.
Russell et al., 2001, "Membrane fusion machines of paramyxoviruses: capture of intermediates of fusion," EMBO J. 20 f024-4034.
Ruuskanen et al., 1993, "Respiratory syncytial virus", Cliff Probl Pediatr. 23(2):50-79.
Sambrook, "Molecular Cloning" A Laboratory Manual Cold Spring harbor Laboratory Press 1989, Ed. 2nd ed., vol. 2, Hybridization of

(56) References Cited

OTHER PUBLICATIONS

Radiolabeled Probes to Immobilized Nucleic Acids, Analysis and Cloning of Eukaryotic Genomic DNA, pp. 9.47-9.55.
Scheid et al., 1974, "Identification of the biological activities of paramyxovirus glycoproteins. Activation of cell fusion, hemolysis and infectivity by proteolytic cleavage of an inactive precursor protein of Sendaivirus," Virology 57:475-490.
Scheid et al., 1977, "Two disulfide linked polypeptide chains constitute the active F protein of paramyxoviruses," Virology 80: 54-66.
Schickli et al., 2005, "An S101P substitution in the putative cleavage motif of the human metapneumovirus fusion protein is a major determinant for trypsin-independent growth in Vero cells and does not alter tissue tropism in hamsters," J. Virol. 79(16):10678-89.
Schmidt et al. 2000, "Bovine parainfluenza virus type 3 (BPIV3) fusion and hemagglutinin-neuraminidase glycoproteins make an important contribution to the restricted replication of BPIV3 in primates," J Virol. 74(19):8922-8929.
Schmidt et al., 2001, "Recombinant bovine/human parainfluenza virus type 3 (B/HPIV3) expressing the respiratory syncytial virus (RSV) G and F proteins can be used to achieve simultaneous mucosal immunization against RSV and HPIV3", J Virol. 75(10):4594-603.
Schmidt et al., 2002, "Mucosal immunization of Rhesus monkeys against respiratory syncytial virus subgroups A and B and human parainfluenza virus type 3 by using a live cDNA-derived vaccine based on a host range-attenuated bovine parainfluenza virus type 3 vector backbone," J. Virol. 76 :1089-1099.
Schnell et al., 1994, "Infectious rabies viruses from cloned cDNA", EMBO J. 13(18):4195-4203.
Seal BS. 2000, "Avian pneumoviruses and emergence of a new type in the United States of America," Anim Health Res Rev. 1(1):67-72.
Seal et al., 2000, "Fusion protein predicted amino acid sequence of the first US avian pneumovirus isolate and lack of heterogeneity among other US isolates," Virus. Res. 66: 139-147.
Seal, 1998, "Matrix protein gene nucleotide and predicted amino acid sequence demonstrate that the first US avian pneumovirus isolate is distinct from European strains", Virus Res. 58(1-2):45-52.
Senne et al., 1998, In: Proc. 47th WPDC, CA, pp. 67-68.
Shibuta, 1977, "Characterization of bovine parainfluenza virus type 3," Microbial. Immunol. 23(7)617-628.
Shin et al., Avian Pneumovirus (APV) RNA from Wild and Sentinel Birds in the United States Has Genetic Homology with RNA and APV Isolated from Domestic Turkeys, Journal of Clinical Microbiology, 2000, pp. 4282-4284, vol. 38, No. 11.
Skiadopoulos et al., 1998, "Three amino acid substitutions in the L protein of the human parainfluenza virus type 3 p45 live attenuated vaccine candidate contribute to its temperature-sensitive and attenuation phenotypes", J Virol. 72(3):1762-1768.
Skiadopoulos et al.2001, "A chimeric human-bovine parainfluenza virus type 3 expressing measles virus hemagglutinin is attenuated for replication but is still immunogenic in rhesus monkeys," J Virol. 75(21):10498-504.
Skiadopoulos, 2004, "The two major human metapneumovirus genetic lineages are highly related antigenically, and the fusion (F) protein is a major contributor to this antigenic relatedness," J. Virol. 78: 6927-6937.
Stockton et al., 2002, "Human metapneumovirus as a cause of community-acquired respiratory illness," Emerg. Infect. Dis. 8, 897-901.
Sullender et al., 2000, "Respiratory syncytial virus genetic and antigenic diversity", Clin Microbiol Rev. 13(1):1-15, table of contents.
Supplemental European Search Report of EP application No. 04750614, dated Sep. 14, 2009.
Taiwanese Office Action of application No. 092103641, dated Aug. 27, 2010.
Taiwanese Office Action of application No. 092103642, dated Mar. 24, 2011.
Taiwanese Office Action of application No. 098112076, dated May 7, 2012 (with English translation).
Taiwanese Office Action of application No. 098137418, dated Mar. 24, 2011.
Takashi et al. 1984, "Angiomyolipoma of the kidney: report of three cases and a statistical study of 194 cases in Japan Hinyokika Kiyo", 30(1):65-75.
Takashi et al., 1984, "On the mechanism of energy transduction in myosin subfragment 1," PNAS USA vol. 81:2060-2064.
Tang et al., 2003, "Effects of human metapneumovirus and respiratory syncytial virus antigen insertion in two 3 proximal genome positions of bovine/human parainfluenza virus type 3 on virus replication and immunogenicity", J Virol. 77(20):10819-28.
Tao et al., 1998, "Recovery of a fully viable chimeric human parainfluenza virus (PIV) type 3 in which the hiemagglutinin-neuraminidase and fusion glycoproteins have been replaced by those of PIV type 1", J Virol. 72(4):2955-2961.
Tao et al., 1999, "A live attenuated chimeric recombinant parainfluenza virus (PIV) encoding the internal proteins of PIV type 3 and the surface glycoproteins of PIV type 1 induces complete resistance to PIV1 challenge and partial resistance to PIV3 challenge", Vaccine. 17(9-10):1100-1108.
Tao et al., 2000, "Replacement of the ectodomains of the hemagglutinin-neuraminidase and fusion glycoproteins of recombinant parainfluenza virus type 3 (PIV3) with their counterparts from PIV2 yields attenuated PIV2 vaccine candidates," J. Virol. 74(14):6448-58.
Tashiro et al., 1983, "Pneumotropism of Sendai virus in relation to protease-mediated activation in mouse lungs," Infect. Immun. 39: 879-888.
Tashiro et al., 1988, "Characterization of a pantropic variant of Sendai virus derived from a host-range mutant," Virology 165: 577-583.
Tashiro et al., 1992, "Budding site of sendai virus in polarized epithelial cells is one of the determinants for tropism and pathogenicity in mice", Virology; 187(2):413-422.
Teng et al., 2000, "Recombinant respiratory syncytial virus that does not express the NS1 or M2-2 protein is highly attenuated and immunogenic in chimpanzees", J Virol. 74(19):9317-9321.
Toquin et al., 2003, "Subgroup C avian metapneumovirus (MPV) and the recently isolated human MPV exhibit a common organization but have extensive sequence divergence in their putative SH and G genes," J. of General Virology. 84: 2169-2178.
Towatari et al., 2002, "Identification of ectopic anionic trypsin I in rat lungs potentiating pneumotropic virus infectivity and increased enzyme level after virus infection," Eur. J. Biochem. 269: 2613-2621.
Cook et al., 1988, "Demonstration of antibodies to Turkey rhinotracheitis virus in serum from commercially reared flocks of chickens," Avian Pathology, 17:403-410.
Cook et al., 1993, "Antigenic differentiation of strains of turkey rhinotracheitis virus using monoclonal antibodies", Avian Pathology, 22:257-273.
Cook et al., 1999, "Preliminary antigenic characterization of an avian pneumovirus isolated from Turkeys in Colorado, USA," Avian Palhol.28:607-617.
Cook, 2000, "Avian rhinotracheitis," Rev. Sci.Tech. 19(2):602-613.
Crookshanks et al., 1984, "Evaluation of cold-adapted and temperature-sensitive mutants of parainfluenza virus type 3 in weanling hamsters," J Med Virol. 13(3):243-249.
Das et al., 2000, "Improved technique for transient expression and negative strand virus rescue using fowlpoxT7 ecombinant virus in mammalian cells", J Virol Methods; 89(1-2): 119-127.
Database EBI Online Swall; Dec. 1, 2001 (Van Den hoogen et al.) "Fusion protein" Database Accession No. Q91F55; XP 002213823 Swall.
Database EBI Online Swall; Dec. 1, 2001 (Van Den hoogen et al.) "Matrix protein" Database Accession No. Q91F56; XP 002213821 Swall.
Database EBI Online Swall; Dec. 1, 2001 (Van Den hoogen et al.) "Nucleoprotein" Database Accession No. Q91F57; XP 002213817 Swall.

(56) References Cited

OTHER PUBLICATIONS

Database EBI Online Swall; Dec. 1, 2001 (Van Den hoogen et al.) "Phosphoprotein" Database Accession No. Q91KZ5; XP 002213819 Swall.
Database EBI Online Swall; Dec. 1, 2001 (Van Den hoogen et al.) "RNA-dependent RNA polymerase" Database Accession No. Q91L20; XP 002213825 Swall.
Database EBI Online Swall; May 1, 1997 (Randhawa, J.S. et al.) "RNA-dependent RNA polymerase" Database Accession No. P87509; XP 002213826 Swall.
Database EBI Online Swall; May 1, 2000 (Dar et al.) "Phosphoprotein" Database Accession No. Q9QF47; XP 002213820 Swall.
Database EBI Online Swall; May 1, 2000 (Dar, Kupur) "Nucleocapsid protein" Database Accession No. Q9QF48; XP 302213818 Swall.
Database EBI Online Swall; May 1, 2000 (Seal, Sellers, Meinersmann) "Fusion protein" Database Accession No. Q9QDI1; XP 002213824 Swall.
Database EBI Online Swall; Nov. 1, 1998 (Seal et al.) "Matrix protein" Database Accession No. O90244; XP 002213822 Swall.
Database EMBL Online, 2001, Database Accession No. AF371337.
Database EMBL Online, 2002, Database Accession No. AY145294.
Database NCBI Accession No. AF371337, dated Apr. 15, 2002.
Database NCBI Accession Nos. AF371361, AF371352, AF371344, AF371335, Human metapneumovirus isolate 99-1, dated Jun. 17, 2001.
Database NCBI NIH (USA) Apr. 15, 2002, "Human Metapneumovirus isolate 00-1 complete genome" Database accession No. AF371337, AF37146, AF371355, AF131364, AF371365, AF371366, AF371367.
Database NCBI NIH (USA) Jun. 17, 2001, "Human Metapneumovirus isolate 99-1 matrix (M) gene, partial eds" Database accession No. AF371352.
Database NCBI NIH (USA) Jun. 17, 2001, "Human Metapneumovirus isolate 99-1 nucleoprotein (N) gene, partial eds" Database accession No. AF371361.
Database NCBI NIH (USA) Jun. 17, 2001, "Human Metapneumovirus isolate 99-1 RNA-dependent RNA polymerase (L) gene, partial eds" Database accession No. AF 371335.
Database NCBI, Jun. 17, 2001, "Human Metapneumovirus isolate 99-1 fusion (F) gene, partial eds" Database accession No. AF371344.
Dimcock et al., 1993, "Rescue of synthetic analogs of genomic RNA and replicative-intermediate RNA of human parainfluenza virus type 3," J Virol 67(5):2772-8.
Domachowske et al., 1999, "Respiratory syncytial virus infection: immune response, immunopathogenesis, and treatment", Clin Microbial Rev. 12(2):298-309.
Durbin et al., 1997, "Recovery of infectious human parainfluenza virus type 3 from cDNA", Virology. 235(2):323-332.
Durbin et al., 2000, "Human parainfluenza virus type 3 (PIV3) expressing the hemagglutinin protein of measles virus provides a potential method for immunization against measles virus and PIV3 in early infancy", J Virol. 74(15):6821-6831.
EMBL Sequence No. AY145285, dated Nov. 29, 2002.
Ennis et al., 1976, "Recombination of influenza A virus strains: effect on pathogenicity", Dev Biol Stand. 33:220-225.
European Office Action of application No. 02710551.9-2403, dated Dec. 28, 2009.
European Office Action of application No. 03716116.3-1223, dated Jan. 26, 2010.
European Office Action of application No. 04750614.2-2406, dated Dec. 4, 2009.
European Office Action of application No. 04750614.2-2406, dated Jul. 7, 2010.
European Office Action of application No. 04809338.9-2401, dated Feb. 26, 2010.
European Office Action of EP application No. 04750614.2-2406, dated Feb. 28, 2012.
European Office Action of EP application No. 04750614.2-2406, dated Jul. 7, 2011.
European Office Action of EP application No. 10011015.4-2401, dated Feb. 7, 2012.
Evans eds., 1989, Viral infections of Humans, Epidemiology and Control. 3rd edition, pp. 22-28, Plenum Publishing Corp. New York.
Falsey et al., 1991, "Noninfluenza respiratory virus infection in long-term care facilities", Infect Control Hosp Epidemiol. 12(10):602-608.
Feigen et al. eds., 1987, Textbook of Pediatric Infectious Diseases, WB Saunders, Philadelphia, pp. 1653-1675.
Fields et al., eds. Fields Virology, 2nd ed. vol. I, Revan Press, New York, 1990, pp. 1045-1072.
Fisher et al, 1984, "Molecular hybridization under conditions of high stringency permits cloned DNA segments containing reiterated DNA sequences to be assigned to specific chromosomal locations", Proc Natl Acad Sci USA 81:520-524.
Flint et al., 2000, Principles of Virology, Molecular Biology, Pathogenesis and Control.ASM Press, pp. 25-56.
Florent et al., 1977, "RNAs of influenza virus recombinanls derived from parents of known virulence for man", Arch Virol. 54(1-2):19-28.
Garvie et al., 1980, "Outbreak of respiratory syncytial virus infection in the elderly", Br Med J. 281(6250):1253-1254.
GenBank Accession No. AAC5707, dated Mar. 28, 1997.
GenBank Accession No. AAK62968, Apr. 15, 2002.
GenBank accession No. AY145242, Bastien et al., Oct. 8, 2003.

\* cited by examiner

TABLE 1

M

| | 00-1 | hRSV | bRSV | PMV | APV-A | APV-C | APV-B |
|---|---|---|---|---|---|---|---|
| 00-1 | 1.00 | 0.37 | 0.37 | 0.37 | 0.77 | 0.87 | 0.75 |
| hRSV | --- | 1.00 | 0.91 | 0.41 | 0.37 | 0.37 | 0.37 |
| bRSV | --- | --- | 1.00 | 0.42 | 0.35 | 0.36 | 0.35 |
| PMV | --- | --- | --- | 1.00 | 0.37 | 0.38 | 0.38 |
| APV-A | --- | --- | --- | --- | 1.00 | 0.78 | 0.89 |
| APV-C | --- | --- | --- | --- | --- | 1.00 | 0.77 |
| APV-B | --- | --- | --- | --- | --- | --- | 1.00 |

N

| | 00-1 | hRSV | bRSV | PMV | APV-A | APV-C | APV-B |
|---|---|---|---|---|---|---|---|
| 00-1 | 1.00 | 0.20 | 0.22 | 0.21 | 0.40 | 0.52 | 0.40 |
| hRSV | --- | 1.00 | 0.59 | 0.30 | 0.18 | 0.21 | 0.18 |
| bRSV | --- | --- | 1.00 | 0.31 | 0.21 | 0.23 | 0.21 |
| PMV | --- | --- | --- | 1.00 | 0.21 | 0.23 | 0.21 |
| APV-A | --- | --- | --- | --- | 1.00 | 0.42 | 1.00 |
| APV-C | --- | --- | --- | --- | --- | 1.00 | 0.42 |
| APV-B | --- | --- | --- | --- | --- | --- | 1.00 |

F

| | 00-1 | hRSV | bRSV | PMV | APV-A | APV-C | APV-B |
|---|---|---|---|---|---|---|---|
| 00-1 | 1.00 | 0.32 | 0.33 | 0.37 | 0.67 | 0.80 | 0.66 |
| hRSV | --- | 1.00 | 0.82 | 0.40 | 0.35 | 0.35 | 0.35 |
| bRSV | --- | --- | 1.00 | 0.41 | 0.34 | 0.36 | 0.34 |
| PMV | --- | --- | --- | 1.00 | 0.38 | 0.38 | 0.39 |
| APV-A | --- | --- | --- | --- | 1.00 | 0.72 | 0.84 |
| APV-C | --- | --- | --- | --- | --- | 1.00 | 0.72 |
| APV-B | --- | --- | --- | --- | --- | --- | 1.00 |

P

| | 00-1 | hRSV | bRSV | PMV | APV-A | APV-C |
|---|---|---|---|---|---|---|
| 00-1 | 1.00 | 0.25 | 0.26 | 0.27 | 0.55 | 0.67 |
| hRSV | --- | 1.00 | 0.81 | 0.30 | 0.28 | 0.26 |
| bRSV | --- | --- | 1.00 | 0.29 | 0.28 | 0.26 |
| PMV | --- | --- | --- | 1.00 | 0.23 | 0.27 |
| APV-A | --- | --- | --- | --- | 1.00 | 0.52 |
| APV-C | --- | --- | --- | --- | --- | 1.00 |

L8

| | 00-1 | hRSV | bRSV | APV-A |
|---|---|---|---|---|
| 00-1 | 1.00 | 0.36 | 0.35 | 0.56 |
| hRSV | --- | 1.00 | 0.79 | 0.36 |
| bRSV | --- | --- | 1.00 | 0.35 |
| APV-A | --- | --- | --- | 1.00 |

L9/10

| | 00-1 | hRSV | bRSV | APV-A |
|---|---|---|---|---|
| 00-1 | 1.00 | 0.30 | 0.30 | 0.53 |
| hRSV | --- | 1.00 | 9.83 | 0.34 |
| bRSV | --- | --- | 1.00 | 0.32 |
| APV-A | --- | --- | --- | 1.00 |

FIG. 1A

TABLE 2

Seroprevalence of hMPV in humans categorized by age group using immunofluorescence and virus neutralization assays

| Age (Years) | Immunofluorescence assays | | Virus neutralization assays | | Titer range |
| --- | --- | --- | --- | --- | --- |
| | N tested | N positive | N tested | N positive | |
| < 1 | 20 | 5 | 12 | 3 | 16-32 |
| 1-2 | 20 | 11 | 13 | 4 | 16-32 |
| 2-5 | 20 | 14 | 8 | 3 | 16-512 |
| 5-10 | 20 | 20 | 4 | 4 | 32-256 |
| 10-20 | 20 | 20 | 4 | 3 | 32-128 |
| > 20 | 20 | 20 | 4 | 3 | 32-128 |
| 8-99[1] | 72 | 72 | 11 | 11 | 16-128 |

[1] Sero-archeological analysis using sera collected in 1958

FIG. 3A

Nucleo protein

```
00-1 NP  MSLQGIHLSDLSYKHAILKESQYTIKRDVGTTAVTPSSLQQEITLLCGEILYAKHADYKYAAEIGIQYISTALGSERVQQILRNSGGSEVQVLTRTYSL  10
APV A    ...ES.R....E....ED....R....A....I....E.PQVST...M

FIG. 3B

```
00-1 matrix  IMIMTMNNPKGIFKKLGAGTQVIVELGAYVQAESISKICKTWSHQGTRYVLKSR.              25
APV-B        .LL.A

FIG. 3D

```
L polymerase RAP-PCR fragment 9/10

00-1 fragment 9/10  --KLVDKITSDQHIFSPDKIDMLTLGKMLMP--TIKGQKTDQ-----FLNKRENYFHGNNLIESLSAALAXHWCGILTEQC    72
APV-A               -F.S.R..VT.....N..H..LVM...L.L.---.VRSNINNN-----KPAT..F.N...IV.A.TSC..C...TV.ILLT    72
bRSV                -ICKLNQVIQK..M.L....SLSQYVELFLSNK.L.NSPHISSNLVLVH..MSD..LHKYV----..TN..G..IM.IQLMK   76
hRSV                DIHKLKQVIQK..M.L....SLTQYVELFLSNK.L.SGSHVNSNLLIAH..ISD...NTYI----..TN..G..IL.IQLML   77
00-1 fragment 9/10  IENNIFKKDWGDGFISDHAFMDFKIFLCVFKTKLLC                                                 10
APV-A               T..S...Q.E.....T....IN.TW..MS...Y...EW                                               11
bRSV                DSKG..E....E.Y.T..M.L.LNV.FDAY..Y.                                                   11
hRSV                DSKG..E....E.Y.T..M.INL.V.FNAY..Y                                                    11
```

```
                                                                                   50
HMPV      MSLQGIHLSDLSYKHAILKESQYTIKRDVGTTTAVTPSSLQQEITLLCGE
APVC      ......Q..................................R.VS....
APVB      ...ES.R....E......D......R....A...I...E..PKVST...M
APVA      ...ES.R....E......ED.....R....A...I...E..PQVST...M
HRSVA     .A.SKVK.N.TLN.DQL.SS.K...Q.ST.DSIDTPNYDV.KH.NK...M
HRSVB     .A.SKVK.N.TLN.DQL.SS.K...Q.ST.DNIDTPNYDV.KHLNK...M
BRSV      .A.SKVK.N.TFN.DQL.ST.K...Q.ST.DNIDIPNYDV.KHLNK...M
PVM       ...DRLK.N.V.N.DSL.SNCK.SVT.ST.DV.S.SGHAM.KALARTL.M
                                                                                   100
HMPV      ILYAKHADYKYAAEIGIQYISTALGSERVQQILRNSGSEVQVVLTRTYSL
APVC      ......T..SH...V.M..V..T...A...T....K......A...K....
APVB      ..F......EP..QV.M........ADKT....KS......G.M.KIVT.
APVA      V.F...T..EP...V.M........AD.T....K.......G.M.KIVT.
HRSVA     L.ITED.NH.FTGL..ML.AMSR..R.DTIK...DA.YH.KANGVDVTTH
HRSVB     L.ITED.NH.FTGL..ML.AMSR..R.DTIK..KDA.YH.KANGVDITTY
BRSV      L.ITED.NH.FTGL..ML.AMSR..R.DTLK..KDA.YQ.RANGVDVITH
PVM       F.LTAFNRCEEV....L...AMSL..RDDSIK...EA.YN..KC.D.QLKDF
                                                                                   150
HMPV      GKIKNNKGEDLQMLDIHGVEKSWVEEIDKEARKTMATLLKESSGNIPQNQ
APVC      ..G...S...E.........R...I..V.......SAT.DN..P.....
APVB      PAEGPIR--KREV.N..DIGPA.ADNVERT..E...SLMV..K-AQ...K..
APVA      SAEGSVR--KREV.N..D.GVG.ADDVERTT.EA.SAMVR.K-VQLTK...
HRSVA     RQDI..G.EMKFEV.TLASLTTEIQIN..EI.S..SYKKM...M-.EVAPEY
HRSVB     RQDI..G.EMKFEV.TLSSLTSEIQVN..EI.S..SYKKM...M-.EVAPEY
BRSV      RQDV..G.EMKFEV.TLVSLTSEVQGN..EI.S..SYKKM...M-.EVAPEY
PVM       TIKLQG..EYKI.V...V..IDAANLADLEIQ...GVV.KE..TG-ARL.D.R
                                       A                                           200
HMPV      RPSAPDTPII|LLCVGALIFTKLA|STIEVGLETTVRRANRVLSDALKRYPR
APVC      ...S..A...|...I.........|..........A......N.....F..
APVB      K...L.A.V.|...I.........|.V......AI...S......IS....
APVA      K...L.A.V.|...I.........|.V......AI...S......IS....
HRSVA     .HDS..CGM.|I..IA..VI....|AGDRS..TAVI....N..KNEM...KG
HRSVB     .HDS..CGM.|I..IA..VI....|AGDRS..TAVI....N..KNEI...KG
BRSV      .HDS..CGM.|V...A..VI....|AGDRS..TAVL....N..RNEM...KG
PVM       .HD...CGV.|V..IA..VVS...|AGDRG..DAVE...LN..KAEKA...N
                                                                                   250
HMPV      MDIPKIARSFYDLFEQKVYHRSLFIEYGKALGSSSTGSKAESLFVNIFMQ
APVC      I..............Y..................................
APVB      ....R..K..FE...K...Y.N.............T.S..RM........
APVA      ....R..K..FE...K...Y.N.............T....RM........
HRSVA     LLPKD..N...EV..KHPHFIDV..VHF.I..QS.TRG...RV.GI.AGL..N
HRSVB     LIPKD..N...EV..KHPHLIDV..VHF.I..QS.TRG...RV.GI.AGL..N
BRSV      LIPKD..N...EV..KYPHYIDV..VHF.I..QS.TRG...RV.GI.AGL..N
PVM       .EVKQ..E.......R.P.YIDV..TF.L..QS.VRG....V.G..SGL..N
                    B                                          C    300
HMPV      |AYGAGQTMLRWGV|IARSSNNIMLGHVS|VQAELKQVTEVYDLVREMGPESG
APVC      |.............|..............|......................
APVB      |..........R..|V.............|.....R..S.......K......
APVA      |..........R..|..............|.....R..S.......K......
HRSVA     |......V......|L.K.VK......A.|ME..V..EYAQKL.G.A.
HRSVB     |...S..V......|L.K.VK......A.|ME..V..EYAQKL.G.A.
BRSV      |......V......|L.K.VK......A.|ME..V..EYAQKL.G.A.
PVM       |......V......|L.K.VK......A.|ME..V..EYAQKO.G.A.
                                                                                   350
HMPV      |LLHLRQSPKAGLLSLANCPNFASVVLQ|NASGLGIIGMYRGRVPNTELFSA
APVC      |......N....................|..L.................A.
APVB      |...............TS..........|.A.........K..A..L.....
APVA      |...............T...........|.A.........K..A..L...A.
HRSVA     |FY.ILNN...S....TQF.H.S.....|.A.....M.E...TPR.QD.YD.
HRSVB     |FY.ILNN...S....TQF...S.....|.A.....M.E...TPR.QD.YD.
BRSV      |FY.ILNN...S....TQF...S.....|.A.....M.E...TPR.QD.YD.
PVM       |FY.I.NN...S....T......T....|.A.....S.K.APR.R...D.
                                                                                   395
HMPV      AESYAKSLKESNKINFSSLGLTDEEKEAAEHFLNVSDDS-QNDYE
APVC      .....R.................E.......N...INEEG-.....
APVB      .....R.......LAA....ED.R...TSY.GGDE.K-SQKF.
APVA      .....RT.R.N..LAA.....D.R...TSY.GGD.ER-SSKF.
HRSVA     .KA..EQ...NGV..Y.V.D..A..L..IK.Q...PK.N--DVEL-
HRSVB     .KA..EQ...NGV..Y.V.D..A..L..IKNQ...PKE.--DVEL-
BRSV      .KA..EQ...NGV..Y.V.D..T..L..IKNQ...PK.N--DVEL-
PVM       .KD..ER..DN.V..Y.A.N..A..R.LISQQ...IV..TPDD.I-
```

FIG. 8

```
                                                              50
HMPV     MSFPEGKDILFMGNEAAKLAEAFQKSLRKPGHKRS--------QSIIGEK
APVC     ..........L.......A.....R..K.I..R.T--------...V.D.
APVB     ..L.......M..S........Y.Q.IKNSTSV.--------R...S.DP
APVA     ..........M..S....M.D.Y.R...NTSAGG--------R...S..P
HRSVA    ---M.KFAPE.H.ED.NNR.TK.LE.-------------------------
HRSVB    ----M.KFAPE.H.ED.NNK.TK.LE.------------------------
BRSV     ---M.KFAPE.H.ED.NTK.TK.LE.-------------------------
PVM      ---M.KFAPE.V.ED.N.K...E.L.HRSF.SE.PLAGIPNTATHVTKYNM
                                                             100
HMPV     VNTVSETLELPTISRPAKPTIPSEPKLAWTDKGGATKTEIKQAIKVMDPI
APVC     II.....V.K....KST.V.T.P.R.N...GE.PDT.RSQTEE.RNEAT.E
APVB     .S....KVP..PLCSSETS--------------R.ACIRPT-.STLPPIK--
APVA     I..IA.KVP..PLCN.TT.--------------..SCI.PN-.APVPKVK--
HRSVA    ----IKGKFTS.----------------------KDPKK.DS.ISVNS.
HRSVB    ----IKGKFASS----------------------KDPKK.DS.ISVNS.
BRSV     ----LKGKFTSS----------------------KDSRK.DS.ISVNSV
PVM      PPILRSSFK...SPRVA.NL.E...A.P----TTPPP.PPQN.EEQPKESDV
                                                             150
HMPV     EEEESTEKKVLPSSDGKTPAEKKLKPSTNTKKK-----VSFTPNEPGKYT
APVC     DASRLY.EVFA.T.........GKETPEKP....------.T.KND.S.R..
APVB     .V.SIYP.LPTAPP.AMIETAHPIGAPKKAQ.R------.K.ESSKA....
APVA     .I.SIYP.LPTAPVATD.YTSTSTESAKKS..------.K.DNPKV....
HRSVA    DI.VTK.SPITSN.TIIN.TNETDDTAG.KPNYQRKPL...KEDPTPSDN
HRSVB    DI.VTK.SPITSGTNIIN.TSEADSTPETKANYPRKPL...KEDLTPSDN
BRSV     DI.LPK.SPITSTNQNINQPSEINDTIATNQVHIRKPL...KEEL.SSEN
PVM      DI.TMHVC..PDNPERSKKPCCSDDTD.KKT---RKPM.T.VEP.EKFVG
                                                             200
HMPV     KLEKDALDLLSD-NEEEDAESSILTFEERD--TSSLSIEARLESIEEKLS
APVC     ...ME..E...-..DD......V.....K.--.A..L........D....
APVB     ...EE..E....PD.DN.EK..V.....K.--NAPS.........A....
APVA     ...EEG.E....PE.DN.EK........K.--A.T..........A....
HRSVA    PFS.LYKETIETFDNN--E.E.SYSY..INDQ.NDN-.T...DR.D....
HRSVB    PFS.LYKETIETFDNN--E.E.SYSY..INDQ.NDN-.T...DR.D....
BRSV     PFTRLYKETIETFDNN--E.E.SYSYD.INDQ.NDN-.T...DR.D....
PVM      LGASLYRETMQTFAADGYD.E.N.S...TNQEPG.S.V.Q..DR......
                                                             250
HMPV     MILGLLRTLNIATAGPTAARDGIRDAMIGVREELIADIIKEAKGK-----
APVC     ..........V...................V.L...........---...
APVB     ....M.K..S....................V.......NS.MA..---...
APVA     ....M.K...............M.......M.......NS.MT...D---
HRSVA    E...M.H..VV.S....S............L...M.EK.RT..LMTNDRLE
HRSVB    E...M.H..VV.S....S............V.L..M.EK.RA..LMTNDRLE
BRSV     E.I.M.H..VV.S................V.L...M.EK.RS..LMTNDRLE
PVM      Y.I...N.IMV......T...E....L...T......EM.KSDILTVNDRIV
                                                             300
HMPV     --AAEMMEEEMSQRSKIGNGSVKLTEKAKELNKIVEDESTSGESEEEEEPK
APVC     -.....K..AK.K........G..................EE
APVB     -I..IIK..DA..A...D........R...RML..Q.S.....T.S.ET
APVA     -I....K..DT..A...D............L..Q.S.....S...SG
HRSVA    AM.RLRN...SEKMA.DTSDE..S.NPTSEK..NLL.G----------N
HRSVB    AM.RLRN...SEKMA.DTSDE.P.NPTS.K.SDLL..-----------N
BRSV     AM.RLRD...SEKMT.DTSDE....PTSEK..MVL..-----------E
PVM      AMEKLRD..C.RADTDDGSACY..DR.RI.D...SSNA----------E
                316
HMPV     DTQDNSQEDDIYQLIM
APVC     .EEESNPD..L.S.T.
APVB     EPDTDGEN....SFD.
APVA     ESESDEE.S...N.DL
HRSVA    .SDNDLSLE.F-----
HRSVB    .SDNDLSL..F-----
BRSV     SSDNDLSLE.F-----
PVM      EAKEDLDV...MGINF
```

FIG. 9

```
                                                                      50
HMPV        MESYLVDTYQGIPYTAAVQVDLIEKDLLPASLTIWFPLFQANTPPAVLLD
APVC        ...........V.......T..V...Q...R..V.V....T....T...E
APVB        ....II.....V..........V...NN..K..V......SS..AP....
APVA        ....II.....V............SN..T..V......SS..AP....
HRSVA       ..T.VNKLHE.ST......YNVL...DD.......V.M..SSM.ADL.IK
HRSVB       ..T.VNKLHE.ST......YNVL...DD.......V.M..SSV.ADL.IK
BRSV        ..T.VNKLHE.ST......YNV....DD.......V.M..SSISADL.IK
PVM         ..A...EM.H.V.......LN.V..HSANI...V.I.M..TSL.KNSVM.
                                                                     100
HMPV        QLKTLTITTLYAASQNGPILKVNASAQGAAMSVLPKKFEVNATVALDEYS
APVC        ...........T.................A...S.D.S.S....D..
APVB        .....S...Q.TV.PE..V.Q...T.......A......S.S.AA......
APVA        .....S...Q.T..PE..V.Q...A.......A......A.S.A.......
HRSVA       E.ANVN.LVKQISTPK..S.R.MINSRS.VLAQM.S..TIC.N.S...R.
HRSVB       E.ASIN.LVKQISTPK..S.R.TINSRS.VLAQM.SN.IIS.N.S...R.
BRSV        E.INVN.LVRQISTLK..S..IMINSRS.VLAQM.S..TIS.N.S...R.
PVM         L.HDV.VICTQISTVH..MI..DL.SSN.GLATM.RQ.LI..II...DWG
                                                                     150
HMPV        KLEFDKLTVCEVKTVYLTTMKPYGMVSKFVSSAKSVGKKTHDLIALCDFM
APVC        ............L.A..........N...A.................L
APVB        ..D.GV....D.RA.....L.........I.TNMNT..R...........I
APVA        R...GT....D.RSI....L........IMTDVR...R...........I
HRSVA       ..AY.VT.P..I.ACS..CL.SKN.LTTVKDLTMKTLNP...I....E.E
HRSVB       ..AY.VT.P..I.ACS..CL.VKS.LTTVKDLTMKTFNP..EI....E.E
BRSV        ..AY.IT.P..I.ACS..CL.VKN.LTTVKDLTMKTFNP..EI....E.E
PVM         NMDYEVPVAFDK.SFCV.IL..KN.LYTVP.ITP-TNRP..E...V.S.H
                                                                     200
HMPV        DLEKNTPVTIPAFIKSVSIKESESATVEAAISSEADQALTQAKIAPYAGL
APVC        ....GV......Y.................G.....I...R........
APVB        .M.RGI......Y..A....D.........G.....I...R........
APVA        .I..GV.I....Y..A....D.........G.....I...R........
HRSVA       NIVTSKK.I..TYLR.I.VRNKDLN.L.NITTT.FKN.I.N...I..S..
HRSVB       NIMTSKR.I..TYLRPI.V.NKDLNSL.NIATT.FKN.I.N...I.....
BRSV        NIMTSKR.V..T.LR.INV.AKDLDSL.NIATT.FKN.I.N...I.....
PVM         NRVTLKSFN..V..RALY.RQQGLDS..Q....DV.H.I.T.RV......
                                                                     250
HMPV        IMIMTMNNPKGIFKKLGAGTQVIVELGAYVQAESISKICKTWSHQGTRYV
APVC        ...................V.................R..RN......
APVB        .LL.A........R.............P......LG......N..R...I
APVA        .L...........M.............P......LG......N..R....
HRSVA       LLVI.VTDN..A..YIKPQS.F..D....LEK...YYVTTN.K.TA..FA
HRSVB       VLVI.VTDN..A..YIKPQS.F..D....LEK...YYVTTN.K.TA..FS
BRSV        VLVI.VTDN..A..YIKPQS.F..D....LEK...YYVTTN.K.TA.KFS
PVM         TLVINITST..A..L.K..S.ILA...P.LTQV.LHDVIMN.K.T..S.I
                  258
HMPV        LKSR----
APVC        ....----
APVB        ....----
APVA        .R..----
HRSVA       I.PMED--
HRSVB       I.PLED--
BRSV        I.PIED--
PVM         ...SSTSG
```

```
            #      #  #                                      50
A  HMPV   MSRKAPCKYEVRGKCNRGSECKFNHNYWSWPDRYLLIRSNYLLNQLLRNT
   APVC   ..................................L...............
   APVB   ..GRN..R..T..R.....S.T..........HV..V.A..M....V...
   APVA   ...RN..R..I........S.T..........HV..V.A..M........
   HRSVA  ...RN...F.I..H.LN.KR.H.S...FE..PHA..V.Q.FM..RI.KSM
   HRSVB  ...RN...F.I..H.LN.RR.HYS...FE..PHA..V.Q.FM..KI.KSM
   BRSV   ...RN.....I..H.LN.KK.H.S...FE..PHA..V.Q.FM..KI.KSM
   PVM    ..VR-...F..Q.F.S..RN..YS.K..E..LKT.ML.Q..M..RIY.FL

#  100
   HMVP   DPA-DGLSIISGAGREDRTQDFVLGSTNVVQGYIDDNQSITKAAACYSLH
   APVC   ..S-....L......D...............N...N.EN....ST....Y
   APVB   ..T-....L................A....N..EG.AT...S......Y
   APVA   ..T-....L................A....N..EG.TT...S......Y
   HRSVA  .KSI.T..E....AEL...EEYA..VVG.LES..GSINN...QS..VAMS
   HRSVB  .KSI.T..E....AEL...EEYA..IVG.LES..GSINN...QS..VAMS
   BRSV   ..NN.T..E....AEL...EEYA..VIG.LES.LGSINN...QS..VAMS
   PVM    .TNT.AI.DV..FDAPQ..AEYA..TIG.LKS.LEKTNN...SI..G..I

150
   HMPV   NIIKQLQEVEVRQARDNKLSDSKHVALHNLVLSYMEMS-KTPASLINNLK
   APVC   ........TD........VD..................-...........
   APVB   ........ND.KS...LMVD.P.............ID..-.N..N...S..
   APVA   ........ND.KTS..SM.E.P..........I...VD..-.N.......S..
   HRSVA  KLLTE.NSDDIKKL...EELN.PKIRVY.T.I..I.SNR.NNKQT.HL..
   HRSVB  KLLIEINSDDIKKL...EEPN.PKIRVY.T.I..I.SNR.NNKQT.HL..
   BRSV   KLLAEINNDDIKRL.NKEVPT.PKIRIY.T.I..IDSNKRNTKQT.HL..
   PVM    TVLQN.DVGL.I....SNTE.TNYLRSC.TI...IDKIL.K-RQI.HI..

195
   HMPV   RLPREKLKKLAKLIIDLSAGAE--NDSSYALQDSESTNQVQ----
   APVC   K..K...........E....V.--...TA.M...ANSD-------
   APVB   ...K.........I..Q....S.GE.AN.NT..KGD.S.-------
   APVA   .............I.LQ....P.SD.A.GNT..KGD.N.-------
   HRSVA  ...ADV...TI.NTL.IHKSITIN.PKESTVS.TNDHAKNNDTT-
   HRSVB  ...ADV...TI.NTL.IHKSIIIS.PKESTVN.QNDQTKNNDITG
   BRSV   ...ADV...TI.NT..IHNEINGN.QGDIIVNEQNE---------
   PVM    ...VGV.CN.IQSV.SIEEKINSSMKTE-----------------

50
B  HMPV   ---------MTLHMP-CKTVKALIKCS--------EHGPVFITIEVDDMIW
   APVC   ---------...QL.-..I.QT....G--------...LI.LKMKL...V.
   APVB   ---------.PIVI.-..R.T.V.R.N--------TL.VCLFKRTYEHN.I
   APVA   ---------.PVVI.-.RR.T.I...N--------AL.LCMVRKIY.YS.A
   HRSVA  MTMPKIMILPDKY.-.SITSI..TSRCRVTMYNQKNTLY.NQNNPNNHMY
   HRSVB  MTKPKIMILPDKY.-.SISSI..SSESMIATFNHKNILQ.NHNHL.NHQR
   BRSV   MNNSNIIIFPEKY.-.SISSL...NENDVIVLSHQNVLDYLQFQYPCNMY
   PVM    MQSDPICHLHRGEDKFFYENRM.RLPKYYPAILHKMYIIRVNRNLTYDGS

97
   HMPV   THKDLKEA---L---SDGIVKSHTNIYNCYLENIEIIYVKAYLS----
   APVC   .KNE.VDI---I---.TE...V.A..FK.R..D.......TF..----
   APVB   NLG..I.E---V---ARM.IID.I.RKQ.NECRKDFEF.AV.T.YT--
   APVA   SWS..I.E---V---ANMVLID.I.RKQ.VECRKDFEFIAI.T.YN--
   HRSVA  SPNQTFNE---IHWT.QELIDTIQ.FLQHLGIIED.YTIYILV.----
   HRSVB  LLNNIFDE---IHWTPKNLLDATQQFLQHLNIPED.YTIYILV.----
   BRSV   SQNHMLDD---IYWT.QELIEDVLK.LHLSGIS.SKYVIYLVL----
   PVM    GPSTIID.GKSVVWNRVDVIACVKEALC.IEFSWNNQVIIDFDYSQAR
```

FIG. 12

A
```
                                                  50
MITLDVIKSIDGSSKTCTHLKKIIKDHSGKVLIVLKLILALLTFLTVTITI
                                                 100
NYIKVENNLQICQSKTESDKKDSSNTTSVTTKTTLNHDITQYFKSLIQR
                                                 150
YTNSAINSDTCWKINRNQCTNITTYKFLCFKSEDTKTNNCDKLTDLCRNK
              183
PKPAVGVYHIVECHCIYTVKWKCYHYPTDETQS
```

A

```
                                                    50
MEVKVENIRTIDMLKARVKNRVARSKCFKNASLVLIGITTLSIALNIYLI

100
INYKMQKNTSESEHHTSSSPMESSRETPTVPTDNSDTNSSPQHPTQQSTE

150
GSTLYFAASASSPETEPTSTPDTTNRPPFVDTHTTPPSASRTKTSPAVHT

200
KNNPRTSSRTHSPPRATTRTARRTTTLRTSSTRKRPSTASVQPDISATTH

236
KNEEASPASPQTSASTTRIQRKSVEANTSTTYNQTS
```

```
                           A                                                  674
HMPV    NYIARA SIVTDLSKFNQAF RYETTAICADVADELHGTQSLFCWLHLIVPM
APVA    ...... ......SV.... ....SV................T.SS
HRSVA   ...SKC ..I......... ....SC...S...L......V....F....AI.H
HRSVB   ...SKC ..I......... ....SC...S...L......V....S....TI.L
BRSV    ...SKC ..I......... ....SC...S...L......V....S....TI.F
HPIV2   FELSAC F.T...A.YCLQW ..Q.IIHF.RTLNRMY.VPH...E.I..RLIR
NDV     RRRVAT F.T....Q.YCLNW ..Q.IKLF.HAINQ.M.LPHF.E.I..RLMD
SV      YETLSC FLT...K.YCLNW F.S...LFGQRCN.IF.FKTF.N.M.PVLEK
HPIV3   YETVSC FLT...K.YCLNW ...S...LFGETCNQIF.LNK..N...PRLEG
MV      YETVS. F.T...K.YCLNW ....ISLF.QRLN.IY.LP.F.Q...KRLET
NIPAH   FDTVS. FLT...K..CLNW ..SM...F.ERL..IY.LPGF.N.M.KRLER

B              723
HMPV    TTMICAYRHAPPETKG-EYDIDKIEEQS GLYRYHMGGIEGWCQKLWTMEA
APVA    .....T......D.G.-I.....Q.P... ....F............M...
HRSVA   V.I..T......YIRDHIV.LNNVD... .....................I..
HRSVB   V.I..T......FI.DHVVNLNEVD... .....................I..
BRSV    A.V..T......YIRNHIT.LN.VD... .....................I..
HPIV2   S.LYVGDPFN..AATD-AF.L..VLNGD IFIVSK-......L...M...IS
NDV     ...FVGDPFN..SDPT-DC.LSRVPNDD IYIVSAR......L........IS
SV      C.IYVGDPYC.VADRM-HRQLQDHADSG IFIHNPR......Y......LIS
HPIV3   S.IYVGDPYC..SD.E-HISLEDHPDSG FYVHNPR......F......LIS
MV      SVLYVSDP.C...DLDA-HIPLY.VPNDQ IFIK.P......Y......IST
NIPAH   SVIYV.DPNC..NIDK-HMELE.TP.DD IFIH.PK.....YS..T..IAT

C                                     772
HMPV    ISLI DVVSVKTRCQMT SLLNGDNQSI DVSKPVKLSEG-LDEVKADYSLAV
APVA    .... ......RN.V.L. ..........R.TGA-QT.IQ......I
HRSVA   .... LI.L.GKFSI A.I........I....R.M..-QTHAQ...L..L
HRSVB   .... LI.L.GKFSI A.I........I....R.I..-QTHAQ...L..L
BRSV    .... LI.I.GKFSI A.I........I...I..N..-QTHAQ...L..L
HPIV2   ..VI ILS.AESKTRVM .MVQ....A.A.TTR.PR.LPSIQKKELA.AASK
NDV     .AAI QLAAARSH.RVA CMVQ....V.A.TRE.RSDDSPEMVLTQLHQASD
SV      ..AI HLAA.RVGVRVS AMVQ....A.A.TSR.PVAQTYKQKKNHV.EEIT
HPIV3   ..AI HLAA.RIGVRV. AMVQ....A.A.TTR.PNNYDYRIKKEIV.KDV.
MV      .PY. YLAAYESGVRIA ..VQ....T.A.T.R.PSTWPYNLKKREAARVTR
NIPAH   .PF. FLSAYE.NTRIA AIVQ....E..AITQK.HPNLPYKVKKEICAKQ.Q

D                 822
HMPV    KMLKEIRDAYRNIGHKLKEGETYISRDLQFISKVI QSEGVMHPTPIKKI L
APVA    ...TAV....Y............V......M..T. .......Y.AA...V.
HRSVA   NS..LLYKE.AG......GT........M..M..T. .HN..YY.AS...V.
HRSVB   NS..LLYKE.AG......GT........M..M..T. .HN..YY.AS...V.
BRSV    .S..LLYKE.AS......GT........M..M..T. .HN..YY.AS...V.
HPIV2   LFFERL.ANNYGL..Q..AQ..I..STFFIY..RV FYQ.RILTQAL.NAS
NDV     NFF..LIHVNHL...N..DR..IR.DTFFIY..R. FKD.AILSQVL.NSS
SV      RYFGAL.HVMFD...E..LN..I..SMKFVY..R. YYD.KIL.QCL.ALT
HPIV3   RFFDSL.EVMDDL..E..LN..I..SMKFIY..R. YYD.RIL.QAL.ALS
MV      DYFVIL.QRLHD...H..AN..IV.SHFFVY..G. YYD.LLVSQSL.S.A
NIPAH   LYFERL.MNL.AL..N..AT..I..TH.FIY..K. HYD.AVLSQAL.SMS

847
HMPV    RVGPWINTILDDIKTSAESIGSLCQ
APVA    ............M.A......
HRSVA   ............F.V.L......T.
HRSVB   ............F.V.L......T.
BRSV    ............F.V.M......T.
HPIV2   KLCLTADVLGECTQA.CSNSATTIM
NDV     KLVLVSGDLSENTVM.CAN.A.TVA
SV      .CVF.SE.LV.ENRSACSN.STSIA
HPIV3   .CVF.SE.VI.ETRSASSNLATSFA
MV      .CVF.SE..V.ETRAACSN.ATTMA
NIPAH   .CCF.SE.LV.ETRSACSN.STTIA
```

FIG. 15

Comparison of two prototypic hMPV isolates with APV-A and APV-C

DNA similarity matrices

| N | 00-1 | 99-1 | APVC | APVA |
|---|---|---|---|---|
| 00-1 | 1.000 | 0.862 | 0.757 | 0.660 |
| 99-1 | - - - | 1.000 | 0.757 | 0.663 |
| APVC | - - - | - - - | 1.000 | 0.656 |
| APVA | - - - | - - - | - - - | 1.000 |

| P | 00-1 | 99-1 | APVC | APVA |
|---|---|---|---|---|
| 00-1 | 1.000 | 0.811 | 0.677 | 0.588 |
| 99-1 | - - - | 1.000 | 0.674 | 0.593 |
| APVC | - - - | - - - | 1.000 | 0.584 |
| APVA | - - - | - - - | - - - | 1.000 |

| M | 00-1 | 99-1 | APVC | APVA |
|---|---|---|---|---|
| 00-1 | 1.000 | 0.865 | 0.766 | 0.695 |
| 99-1 | - - - | 1.000 | 0.773 | 0.707 |
| APVC | - - - | - - - | 1.000 | 0.705 |
| APVA | - - - | - - - | - - - | 1.000 |

| F | 00-1 | 99-1 | APVC | APVA |
|---|---|---|---|---|
| 00-1 | 1.000 | 0.838 | 0.706 | 0.662 |
| 99-1 | - - - | 1.000 | 0.716 | 0.655 |
| APVC | - - - | - - - | 1.000 | 0.685 |
| APVA | - - - | - - - | - - - | 1.000 |

| M2-1 | 00-1 | 99-1 | APVC | APVA |
|---|---|---|---|---|
| 00-1 | 1.000 | 0.863 | 0.764 | 0.668 |
| 99-1 | - - - | 1.000 | 0.744 | 0.657 |
| APVC | - - - | - - - | 1.000 | 0.670 |
| APVA | - - - | - - - | - - - | 1.000 |

| M2-2 | 00-1 | 99-1 | APVC | APVA |
|---|---|---|---|---|
| 00-1 | 1.000 | 0.861 | 0.648 | 0.486 |
| 99-1 | - - - | 1.000 | 0.675 | 0.486 |
| APVC | - - - | - - - | 1.000 | 0.463 |
| APVA | - - - | - - - | - - - | 1.000 |

| SH | 00-1 | 99-1 | APVC | APVA |
|---|---|---|---|---|
| 00-1 | 1.000 | 0.688 | N.A. | 0.421 |
| 99-1 | - - - | 1.000 | N.A. | 0.380 |
| APVC | - - - | - - - | N.A. | N.A. |
| APVA | - - - | - - - | - - - | 1.000 |

| G | 00-1 | 99-1 | APVC | APVA |
|---|---|---|---|---|
| 00-1 | 1.000 | 0.543 | N.A. | 0.262 |
| 99-1 | - - - | 1.000 | N.A. | 0.263 |
| APVC | - - - | - - - | N.A. | N.A. |
| APVA | - - - | - - - | - - - | 1.000 |

| 5'L | 00-1 | 99-1 | APVC | APVA |
|---|---|---|---|---|
| 00-1 | 1.000 | 0.835 | N.A. | 0.596 |
| 99-1 | - - - | 1.000 | N.A. | 0.605 |
| APVC | - - - | - - - | N.A. | 0.463 |
| APVA | - - - | - - - | - - - | 1.000 |

5'L: only the first 1500 nucleotides of 99-1 were available.
N.A.: sequence not available

FIG. 18

Protein similarity matrices

| N    | 00-1  | 99-1  | APVC  | APVA  |
|------|-------|-------|-------|-------|
| 00-1 | 1.000 | 0.949 | 0.880 | 0.685 |
| 99-1 | - - - | 1.000 | 0.883 | 0.682 |
| APVC | - - - | - - - | 1.000 | 0.700 |
| APVA | - - - | - - - | - - - | 1.000 |

| P    | 00-1  | 99-1  | APVC  | APVA  |
|------|-------|-------|-------|-------|
| 00-1 | 1.000 | 0.860 | 0.683 | 0.552 |
| 99-1 | - - - | 1.000 | 0.676 | 0.549 |
| APVC | - - - | - - - | 1.000 | 0.528 |
| APVA | - - - | - - - | - - - | 1.000 |

| M    | 00-1  | 99-1  | APVC  | APVA  |
|------|-------|-------|-------|-------|
| 00-1 | 1.000 | 0.976 | 0.874 | 0.775 |
| 99-1 | - - - | 1.000 | 0.874 | 0.763 |
| APVC | - - - | - - - | 1.000 | 0.775 |
| APVA | - - - | - - - | - - - | 1.000 |

| F    | 00-1  | 99-1  | APVC  | APVA  |
|------|-------|-------|-------|-------|
| 00-1 | 1.000 | 0.938 | 0.810 | 0.677 |
| 99-1 | - - - | 1.000 | 0.803 | 0.674 |
| APVC | - - - | - - - | 1.000 | 0.719 |
| APVA | - - - | - - - | - - - | 1.000 |

| M2-1 | 00-1  | 99-1  | APVC  | APVA  |
|------|-------|-------|-------|-------|
| 00-1 | 1.000 | 0.946 | 0.844 | 0.719 |
| 99-1 | - - - | 1.000 | 0.834 | 0.703 |
| APVC | - - - | - - - | 1.000 | 0.704 |
| APVA | - - - | - - - | - - - | 1.000 |

| M2-2 | 00-1  | 99-1  | APVC  | APVA  |
|------|-------|-------|-------|-------|
| 00-1 | 1.000 | 0.901 | 0.563 | 0.246 |
| 99-1 | - - - | 1.000 | 0.577 | 0.232 |
| APVC | - - - | - - - | 1.000 | 0.191 |
| APVA | - - - | - - - | - - - | 1.000 |

| SH   | 00-1  | 99-1  | APVC  | APVA  |
|------|-------|-------|-------|-------|
| 00-1 | 1.000 | 0.570 | N.A.  | 0.178 |
| 99-1 | - - - | 1.000 | N.A.  | 0.162 |
| APVC | - - - | - - - | N.A.  | N.A.  |
| APVA | - - - | - - - | - - - | 1.000 |

| G    | 00-1  | 99-1  | APVC  | APVA  |
|------|-------|-------|-------|-------|
| 00-1 | 1.000 | 0.326 | N.A.  | 0.094 |
| 99-1 | - - - | 1.000 | N.A.  | 0.107 |
| APVC | - - - | - - - | N.A.  | N.A.  |
| APVA | - - - | - - - | - - - | 1.000 |

| 5'L  | 00-1  | 99-1  | APVC  | APVA  |
|------|-------|-------|-------|-------|
| 00-1 | 1.000 | 0.921 | N.A.  | 0.600 |
| 99-1 | - - - | 1.000 | N.A.  | 0.594 |
| APVC | - - - | - - - | N.A.  | N.A.  |
| APVA | - - - | - - - | - - - | 1.000 |

5'L: only the first 500 amino acid residues of 99-1 were available.
N.A.: sequence not available

FIG. 19

Amino acid sequence alignment of two prototype hMPV isolates

```
Nucleoprotein (N)

10        20        30        40        50        60
     ....|....|....|....|....|....|....|....|....|....|....|....|
00-1 MSLQGIHLSDLSYKHAILKESQYTIKRDVGTTTAVTPSSLQQEITLLCGEILYAKHADYK  60
99-1 MSLQGIHLSDLSYKHAILKESQYTIKRDVGTTTAVTPSSLQQEITLLCGEILYTKHTDYK  60

70        80        90       100       110       120
     ....|....|....|....|....|....|....|....|....|....|....|....|
00-1 YAAEIGIQYISTALGSERVQQILRNSGSEVQVVLTRTYSLGKIKNNKGEDLQMLDIHGVE  120
99-1 YAAEIGIQYICTALGSERVQQILRNSGSEVQVVLTKTYSLGKGKNSKGEELQMLDIHGVE  120

130       140       150       160       170       180
     ....|....|....|....|....|....|....|....|....|....|....|....|
00-1 KSWVEEIDKEARKTMATLLKESSGNIPQNQRPSAPDTPIILLCVGALIFTKLASTIEVGL  180
99-1 KSWIEEIDKEARKTMVTLLKESSGNIPQNQRPSAPDTPIILLCVGALIFTKLASTIEVGL  180

190       200       210       220       230       240
     ....|....|....|....|....|....|....|....|....|....|....|....|
00-1 ETTVRRANRVLSDALKRYPRMDIPKIARSFYDLFEQKVYHRSLFIEYGKALGSSSTGSKA  240
99-1 ETTVRRANRVLSDALKRYPRIDIPKIARSFYELFEQKVYYRSLFIEYGKALGSSSTGSKA  240

250       260       270       280       290       300
     ....|....|....|....|....|....|....|....|....|....|....|....|
00-1 ESLFVNIFMQAYGAGQTMLRWGVIARSSNNIMLGHVSVQAELKQVTEVYDLVREMGPESG  300
99-1 ESLFVNIFMQAYGAGQTLLRWGVIARSSNNIMLGHVSVQSELKQVTEVYDLVREMGPESG  300

310       320       330       340       350       360
     ....|....|....|....|....|....|....|....|....|....|....|....|
00-1 LLHLRQSPKAGLLSLANCPNFASVVLGNASGLGIIGMYRGRVPNTELFSAAESYAKSLKE  360
99-1 LLHLRQSPKAGLLSLANCPNFASVVLGNASGLGIIGMYRGRVPNTELFSAAESYARSLKE  360

370       380       390
     ....|....|....|....|....|....|....
00-1 SNKINFSSLGLTDEEKEAAEHFLNVSDDSQNDYE  394
99-1 SNKINFSSLGLTDEEKEAAEHFLNMSGDNQDDYE  394
```

FIG. 20

Phosphoprotein (P)

```
             10        20        30        40        50        60
         ....|....|....|....|....|....|....|....|....|....|....|....|
00-1     MSFPEGKDILFMGNEAAKLAEAFQKSLRKPGHKRSQSIIGEKVNTVSETLELPTISRPAK   60
99-1     MSFPEGKDILFMGNEAAKIAEAFQKSLKKSGHKRTQSIVGEKVNTISETLELPTISKPAR   60

70        80        90       100       110       120
         ....|....|....|....|....|....|....|....|....|....|....|....|
00-1     PTIPSEPKLAWTDKGGATKTEIKQAIKVMDPIEEEESTEKKVLPSSDGKTPAEKKLKPST  120
99-1     SSTLLEPKLAWADNSGITKITEKPATKTTDPVEEEEFNEKKVLPSSDGKTPAEKKSKPST  120

130       140       150       160       170       180
         ....|....|....|....|....|....|....|....|....|....|....|....|
00-1     NTKKKVSFTPNEPGKYTKLEKDALDLLSDNEEEDAESSILTFEERDTSSLSIEARLESIE  180
99-1     SVKKKVSFTSNEPGKYTKLEKDALDLLSDNEEEDAESSILTFEEKDTSSLSIEARLESIE  180

190       200       210       220       230       240
         ....|....|....|....|....|....|....|....|....|....|....|....|
00-1     EKLSMILGLLRTLNIATAGPTAARDGIRDAMIGVREELIADIIKEAKGKAAEMMEEEMSQ  240
99-1     EKLSMILGLLRTLNIATAGPTAARDGIRDAMIGIREELIAEIIKEAKGKAAEMMEEEMNQ  240

250       260       270       280       290
         ....|....|....|....|....|....|....|....|....|....|....|...
00-1     RSKIGNGSVKLTEKAKELNKIVEDESTSGESEEEEEPKDTQDNSQEDDIYQLIM        294
99-1     RSKIGNGSVKLTEKAKELNKIVEDESTSGESEEEEEPKETQDNNQGEDIYQLIM        294
```

FIG. 21

Matrix protein (M)

```
             10        20        30        40        50        60
         ....|....|....|....|....|....|....|....|....|....|....|....|
00-1     MESYLVDTYQGIPYTAAVQVDLIEKDLLPASLTIWFPLFQANTPPAVLLDQLKTLTITTL   60
99-1     MESYLVDTYQGIPYTAAVQVDLVEKDLLPASLTIWFPLFQANTPPAVLLDQLKTLTITTL   60

70        80        90       100       110       120
         ....|....|....|....|....|....|....|....|....|....|....|....|
00-1     YAASQNGPILKVNASAQGAAMSVLPKKFEVNATVALDEYSKLEFDKLTVCEVKTVYLTTM  120
99-1     YAASQNGPILKVNASAQGAAMSVLPKKFEVNATVALDEYSKLDFDKLTVCDVKTVYLTTM  120

130       140       150       160       170       180
         ....|....|....|....|....|....|....|....|....|....|....|....|
00-1     KPYGMVSKFVSSAKSVGKKTHDLIALCDFMDLEKNTPVTIPAFIKSVSIKESESATVEAA  180
99-1     KPYGMVSKFVSSAKSVGKKTHDLIALCDFMDLEKNIPVTIPAFIKSVSIKESESATVEAA  180

190       200       210       220       230       240
         ....|....|....|....|....|....|....|....|....|....|....|....|
00-1     ISSEADQALTQAKIAPYAGLIMIMTNNPKGIFKKLGAGTQVIVELGAYVQAESISKICK   240
99-1     ISSEADQALTQAKIAPYAGLIMIMTNNPKGIFKKLGAGTQVIVELGAYVQAESISRICK   240

250
         ....|....|...
00-1     TWSHQGTRYVLKSR  254
99-1     SWSHQGTRYVLKSR  254
```

FIG. 22

Fusion protein (F)

```
              10         20         30         40         50         60
        ....|....|....|....|....|....|....|....|....|....|....|....|
00-1    MSWKVVIIFSLLITPQHGLKESYLEESCSTITEGYLSVLRTGWYTNVFTLEVGDVENLTC    60
99-1    MSWKVMIIISLLITPQHGLKESYLEESCSTITEGYLSVLRTGWYTNVFTLEVGDVENLTC    60

70         80         90        100        110        120
        ....|....|....|....|....|....|....|....|....|....|....|....|
00-1    ADGPSLIKTELDLTKSALRELRTVSADQLAREEQIENPRQSRFVLGAIALGVATAAAVTA   120
99-1    TDGPSLIKTELDLTKSALRELKTVSADQLAREEQIENPRQSRFVLGAIALGVATAAAVTA   120

130        140        150        160        170        180
        ....|....|....|....|....|....|....|....|....|....|....|....|
00-1    GVAIAKTIRLESEVTAIKNALKKTNEAVSTLGNGVRVLATAVRELKDFVSKNLTRAINKN   180
99-1    GIAIAKTIRLESEVNAIKGALKQTNEAVSTLGNGVRVLATAVRELKEFVSKNLTSAINRN   180

190        200        210        220        230        240
        ....|....|....|....|....|....|....|....|....|....|....|....|
00-1    KCDIADLKMAVSFSQFNRRFLNVVRQFSDNAGITPAISLDLMTDAELARAVSNMPTSAGQ   240
99-1    KCDIADLKMAVSFSQFNRRFLNVVRQFSDNAGITPAISLDLMTDAELARAVSYMPTSAGQ   240

250        260        270        280        290        300
        ....|....|....|....|....|....|....|....|....|....|....|....|
00-1    IKLMLENRAMVRRKGFGFLIGVYGSSVIYMVQLPIFGVIDTPCWIVKAAPSCSGKKGNYA   300
99-1    IKLMLENRAMVRRKGFGILIGVYGSSVIYMVQLPIFGVIDTPCWIIKAAPSCSEKNGNYA   300

310        320        330        340        350        360
        ....|....|....|....|....|....|....|....|....|....|....|....|
00-1    CLLREDQGWYCQNAGSTVYYPNEKDCETRGDHVFCDTAAGINVAEQSKECNINISTTNYP   360
99-1    CLLREDQGWYCKNAGSTVYYPNEKDCETRGDHVFCDTAAGINVAEQSRECNINISTTNYP   360

370        380        390        400        410        420
        ....|....|....|....|....|....|....|....|....|....|....|....|
00-1    CKVSTGRHPISMVALSPLGALVACYKGVSCSIGSNRVGIIKQLNKGCSYITNQDADTVTI   420
99-1    CKVSTGRHPISMVALSPLGALVACYKGVSCSIGSNWVGIIKQLPKGCSYITNQDADTVTI   420

430        440        450        460        470        480
        ....|....|....|....|....|....|....|....|....|....|....|....|
00-1    DNTVYQLSKVEGEQHVIKGRPVSSSFDPVKFPEDQFNVALDQVFESIENSQALVDQSNRI   480
99-1    DNTVYQLSKVEGEQHVIKGRPVSSSFDPIKFPEDQFNVALDQVFESIENSQALVDQSNKI   480

490        500        510        520        530
        ....|....|....|....|....|....|....|....|....|....|...
00-1    LSSAEKGNTGFIIVIILIAVLGSTMILVSVFIIIKKTKKPTGAPPELSGVTNNGFIPHN   539
99-1    LNSAEKGNTGFIIVVILVAVLGLTMISVSIIIIKKTRKPTGAPPELNGVTNGGFIPHS   539
```

FIG. 23

22K protein (M2-1)

```
              10         20         30         40         50         60
     ....|....|....|....|....|....|....|....|....|....|....|....|
00-1 MSRKAPCKYEVRGKCNRGSECKFNHNYWSWPDRYLLIRSNYLLNQLLRNTDRADGLSIIS  60
99-1 MSRKAPCKYEVRGKCNRGSDCKFNHNYWSWPDRYLLLRSNYLLNQLLRNTDKADGLSIIS  60

70         80         90        100        110        120
     ....|....|....|....|....|....|....|....|....|....|....|....|
00-1 GAGREDRTQDFVLGSTNVVQGYIDDNQSITKAAACYSLHNIIKQLQEVEVRQARDNKLSD  120
99-1 GAGREDRTQDFVLGSTNVVQGYIDDNQGITKAAACYSLHNIIKQLQETEVRQARDNKLSD  120

130        140        150        160        170        180
     ....|....|....|....|....|....|....|....|....|....|....|....|
00-1 SKHVALHNLVLSYMEMSKTPASLINNLKRLPREKLKKLAKLIIDLSAGAENDSSYALQDS  180
99-1 SKHVALHNLILSYMEMSKTPASLINNLKKLPREKLKKLARLIIDLSAGTDNDSSYALQDS  180

....|..
00-1 ESTNQVQ  187
99-1 ESTNQVQ  187
```

FIG. 24

M2-2 protein (M2-2)

```
              10         20         30         40         50         60
     ....|....|....|....|....|....|....|....|....|....|....|....|
00-1 MTLHMPCKTVKALIKCSEHGPVFITIEVDDMIWTHKDLKEALSDGIVKSHTNIYNCYLEN  60
99-1 MTLHMPCKTVKALIKCSKHGPKFITIEADDMIWTHKELKETLSDGIVKSHTNIYSCYLEN  60

70
     ....|....|.
00-1 IEIIYVKAYLS  71
99-1 IEIIYVKTYLS  71
```

FIG. 25

Short hydrophobic protein (SH)

```
              10        20        30        40        50        60
      ....|....|....|....|....|....|....|....|....|....|....|....|
00-1  MITLDVIKSDGSSKTCTHLKKIIKDHSGKVLIVLKLILALLTFLTVTITINYIKVENNLQ  60
99-1  MKTLDVIKSDGSSETCNQLKKIIKKHSGKVLIALKLILALLTFFTATITVNYIKVENNLQ  60

70        80        90       100       110       120
      ....|....|....|....|....|....|....|....|....|....|....|....|
00-1  ICQSKTESDKKDSSSNTTSVTTKTTLNHDITQYFKSLIQRYTNSAIN SDTCWKINRNQC  119
99-1  ACQPKNESDKKVTKPNTTSTTIRPTPDPTVVHHLKRLIQRHTNSVTKDSDTCWRIHKNQR  120

130       140       150       160       170       180
      ....|....|....|....|....|....|....|....|....|....|....|....|
00-1  TNITTYKFLCFKSEDTKTNNCDKLTDLCRNKPKPAVGVYHIVECHCIYTVKWKCYHYPTD  179
99-1  TNIKIYKFLCSGFTNSKGTDCEEPTALCDKKLKTIVEKHRKAECHCLHTTEWGCLHP     177

....
00-1  ETQS  183
99-1        177
```

FIG. 26

Attachment glycoprotein (G)

```
              10        20        30        40        50        60
      ....|....|....|....|....|....|....|....|....|....|....|....|
00-1  MEVKVENIRTIDMLKARVKNRVARSKCFKNASLVLIGITTLSIALNIYLIINYKMQKNTS  60
99-1  MEVRVENIRAIDMFKAKIKNRIRSSRCYRNATLILIGLTALSMALNIFLIIDHATLRNMI  60

70        80        90       100       110       120
      ....|....|....|....|....|....|....|....|....|....|....|....|
00-1  ESEHHTSSSPMESSRETPTVPTDNSDTNSSPQHPTQQSTEGSTLYFAASASSPETEPTST  120
99-1  KTENCANMPSAEPSKKTPMTSTAGPNTKPNPQQATQWTTENSTSPVATPEGHPYTGTTQT  120

130       140       150       160       170       180
      ....|....|....|....|....|....|....|....|....|....|....|....|
00-1  PDTTNRPPFVDTHTTPPSASRTKTSPAVHTKNNPRTSSRTHSPPRATTRTARRTTTLRTS  180
99-1  SDTTAPQQTTDKHTAPLKSTNEQITQTTTEKKTIRATTQKREKGKENTNQTTSTAATQTT  180

190       200       210       220       230
      ....|....|....|....|....|....|....|....|....|....|....|.
00-1  STRKRPSTASVQPDISATTHKNEEASPASPQTSASTTRIQRKSVEANTSTTYNQTS  236
99-1  NTTNQIRNASET       ITTSDRPRTDTTTQSSEQTTRATDPSSPPHHA          224
```

FIG. 27

N-terminus of polymerase protein (L)

```
              10        20        30        40        50        60
         ....|....|....|....|....|....|....|....|....|....|....|....|
00-1   MDPLNESTVNVYLPDSYLKGVISFSETNAIGSCLLKRPYLKNDNTAKVAIENPVIEHVRL    60
99-1   MDPFCESTVNVYLPDSYLKGVISFSETNAIGSCLLKRPYLKNDNTAKVAVENPVVEHVRL    60

70        80        90       100       110       120
         ....|....|....|....|....|....|....|....|....|....|....|....|
00-1   KNAVNSKMKISDYKIVEPVNMQHEIMKNVHSCELTLLKQFLTRSKNISTLKLNMICDWLQ   120
99-1   RNAVMTKMKISDYKVVEPVNMQHEIMKNIHSCELTLLKQFLTRSKNISSLKLNMICDWLQ   120

130       140       150       160       170       180
         ....|....|....|....|....|....|....|....|....|....|....|....|
00-1   LKSTSDDTSILSFIDVEFIPSWVSNWFSNWYNLNKLILEFRKEEVIRTGSILCRSLGKLV   180
99-1   LKSTSDNTSILNFIDVEFIPVWVSNWFSNWYNLNKLILEFRREEVIRTGSILCRSLGKLV   180

190       200       210       220       230       240
         ....|....|....|....|....|....|....|....|....|....|....|....|
00-1   FVVSSYGCIVKSNKSKRVSFFTYNQLLTWKDVMLSRFNANFCIWVSNSLNENQEGLGLRS   240
99-1   FIVSSYGCVVKSNKSKRVSFFTYNQLLTWKDVMLSRFNANFCIWVSNNLNKNQEGLGLRS   240

250       260       270       280       290       300
         ....|....|....|....|....|....|....|....|....|....|....|....|
00-1   NLQGILTNKLYETVDYMLSLCCNEGFSLVKEFEGFIMSEILRITEHAQFSTRFRNTLLNG   300
99-1   NLQGMLTNKLYETVDYMLSLCCNEGFSLVKEFEGFIMSEILKITEHAQFSTRFRNTLLNG   300

310       320       330       340       350       360
         ....|....|....|....|....|....|....|....|....|....|....|....|
00-1   LTDQLTKLKNKNRLRVHGTVLENNDYPMYEVVLKLLGDTLRCIKLLINKNLENAAELYYI   360
99-1   LTEQLSVLKAKNRSRVLGTILENNNYPMYEVVLKLLGDTLKSIKLLINKNLENAAELYYI   360

370       380       390       400       410       420
         ....|....|....|....|....|....|....|....|....|....|....|....|
00-1   FRIFGHPMVDERDAMDAVKLNNEITKILRWESLTELRGAFILRIIKGFVDNNKRWPKIKN   420
99-1   FRIFGHPMVDEREAMDAVKLNNEITKILKLESLTELRGAFILRIIKGFVDNNKRWPKIKN   420

430       440       450       460       470       480
         ....|....|....|....|....|....|....|....|....|....|....|....|
00-1   LKVLSKRWTMYFKAKSYPSQLELSEQDFLELAAIQFEQEFSVPEKTNLEMVLNDKAISPP   480
99-1   LKVLSKRWAMYFKAKSYPSQLELSVQDFLELAAVQFEQEFSVPEKTNLEMVLNDKAISPP   480

490
         ....|....|....|....|
00-1   KRLIWSVYPKNYLPEKIKN   499
99-1   KKLIWSVYPKNYLPETIKN   499
```

FIG. 28

+ = positive; - = negative; T = throat swabs; NO = nose swab; N = not done; ? = not sure; D = dead; 0 to 12: days post-infection; 2e infection is only tested on nose swabs.

| nr | 1e infection | swab | 0 | 1 | 2 | 3 | 4 | 5 | 8 | 10 | 11 | 12 | 2e infection | 0 | 1 | 2 | 3 | 4 | 5 |
|---|---|---|---|---|---|---|---|---|---|---|---|---|---|---|---|---|---|---|---|
| 1 | 00-1 | T | - | + | + | + | - | + | + | + | - | - | 99-1 | N | N | N | N | N | N |
|  |  | NO | - | + | + | + | + | + | N | + | - | - |  | - | - | - | - | - | - |
| 2 | 00-1 | T | - | + | + | + | + | + | - | - | - | D |  | N | N | N | N | N | N |
|  |  | NO |  | + | + | + | + | + | N | + | - | D |  | - | - | - | - | - | - |
| 3 | 00-1 | T | - | - | ? | - | - | - | - | - | - | N | 99-1 | N | N | ? | N | N | N |
|  |  | NO |  | + | ? | ? |  | - | N | - | - | - |  | - | - | ? | + | + | - |
| 4 | 00-1 | T | - | + | + | + | + | + | - | ? | - | N | 00-1 | N | N | N | N | N | N |
|  |  | NO | - | + | + | + | + | + | N | ? | - | - |  | - | - | - | + | - | - |
| 5 | 00-1 | T | - | ? | + | + | + | + | + | + | - | N | 00-1 | N | N | N | N | N | N |
|  |  | NO |  | + | + | + | + | + | N | + | - | - |  | - | - | - | - | - | - |
| 6 | 00-1 | T | - | - | + | + | + | + | - | + | - | N | 00-1 | N | N | N | N | N | N |
|  |  | NO | - | + | + | + | + | + | N | + | + | ? |  | - | - | - | - | - | - |
| 7 | 99-1 | T | - | - | - | + | + | - | + | D | - | - |  | N | N | N | N | N | N |
|  |  | NO | - | - | -- | + | + | + | N | D | - | - |  | - | - | - | - | - | - |
| 8 | 99-1 | T | - | - | + | + | - | - | - | - | - | N | 00-1 | N | N | N | N | N | N |
|  |  | NO | - | ? | - | + | + | ? | N | - | - | -- |  | - | - | + | + | + | + |
| 9 | 99-1 | T | - | - | - | - | - | - | - | - | - | N | 00-1 | N | N | N | N | N | N |
|  |  | NO | - | - | - | - | + | + | N | - | - | -- |  | - | ? | + | + | - | - |
| 10 | 99-1 | T | - | - | - | + | + | - | - | - | - | N | 99-1 | N | N | N | N | N | N |
|  |  | NO | - | + | + | + | + | + | N | - | - | -- |  | - | - | - | - | - | - |
| 11 | 99-1 | T | - | - | + | + | + | - | - | - | - | N | 99-1 | N | N | N | N | N | N |
|  |  | NO | - | + | ? | + | + | + | N | - | - | - |  | - | - | - | + | - | - |
| 12 | 99-1 | T | - | - | + | + | ? | - | - | - | - | N | 99-1 | N | N | N | N | N | N |
|  |  | NO | - | + | + | + | + | + | N | - | - | - |  | - | - | - | - | - | - |

FIG. 29

| | Against 00-1 | Against 99-1 | Against APV-C |
|---|---|---|---|
| 1 infection with 00-1 | 20 - 60 | < 10 | < 10 |
| 2 infections with 00-1 | > 320 - 1280 | 40 - 80 | < 10 - 60 |
| 1 infection with 99-1 | < 10 - 60 | 10 - 80 | < 10 |
| 2 infections with 99-1 | 20 - 40 | 80 - 400 | < 10 - 40 |

| nr | 1st infection | 0 | 2 | 3 | 4 | 5 | 6 | 7 | 8 | 9 | 11 | 2nd infection | 0 | 1 | 2 | 3 | 4 | 5 | 7 | 10 |
|---|---|---|---|---|---|---|---|---|---|---|---|---|---|---|---|---|---|---|---|---|
| 3 | 00-1 | - | - | - | + | + | + | + | + | N | - | | - | + | + | + | + | - | ? | - |
| 6 | 00-1 | - | + | + | + | + | + | + | - | - | - | | - | + | + | + | + | - | - | - |

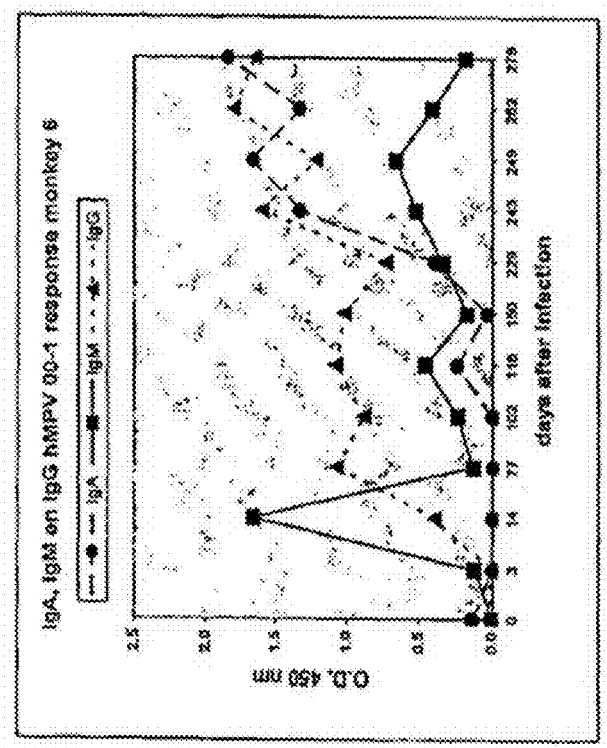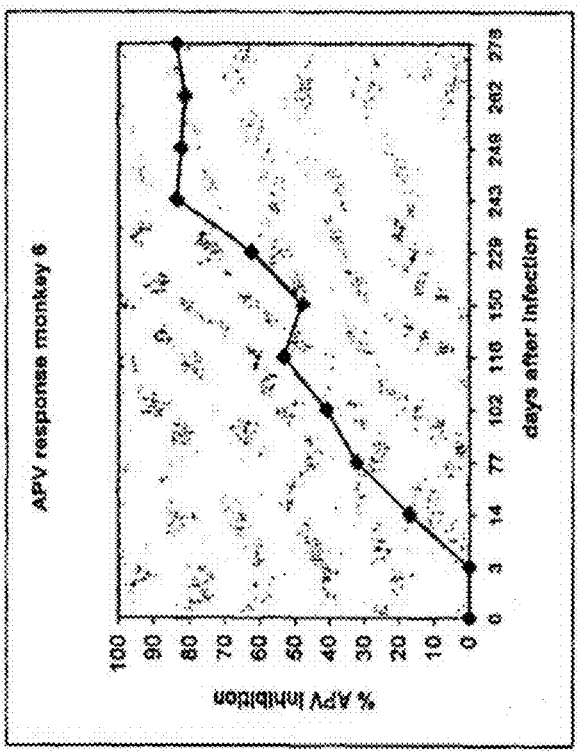
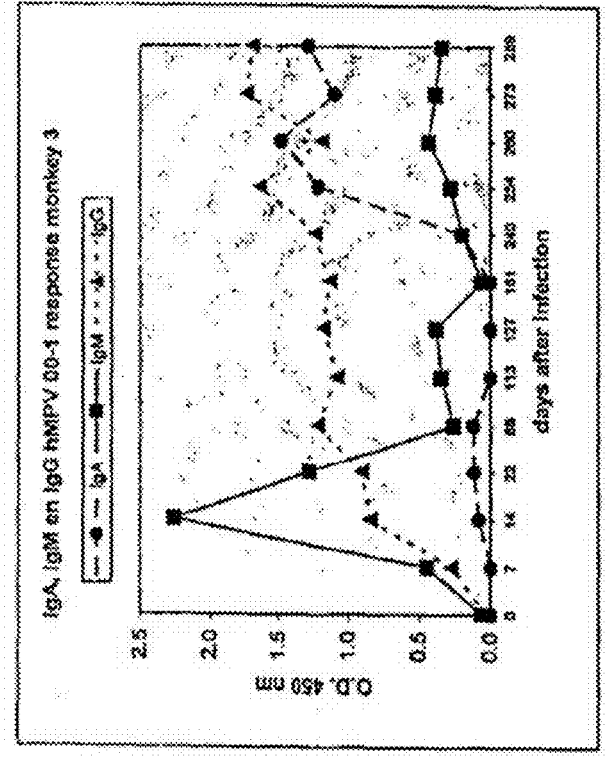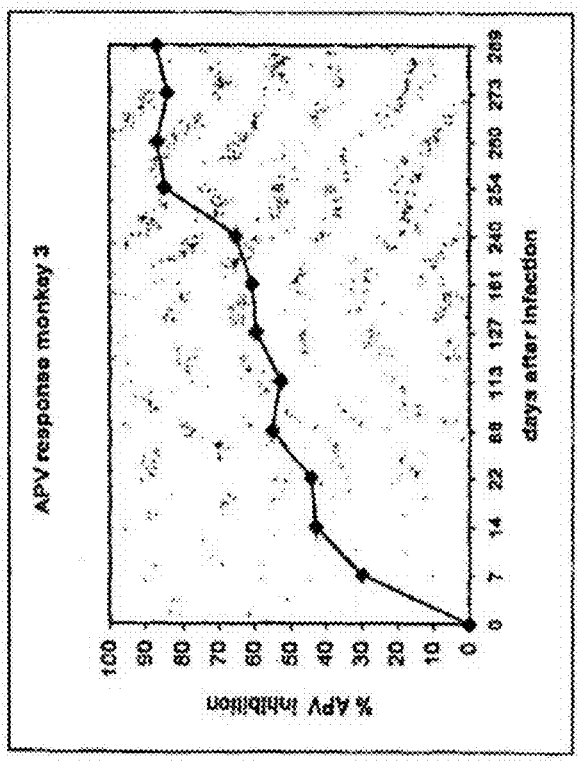
FIG. 36A
FIG. 36B

SEQUENCE LISTING

```
<160> NUMBER OF SEQ ID NOS: 173

<210> SEQ ID NO 1
<211> LENGTH: 394
<212> TYPE: PRT
<213> ORGANISM: Human metapneumovirus 00-1

<400> SEQUENCE: 1

Met Ser Leu Gln Gly Ile His Leu Ser Asp Leu Ser Tyr Lys His Ala
1               5                   10                  15

Ile Leu Lys Glu Ser Gln Tyr Thr Ile Lys Arg Asp Val Gly Thr Thr
            20                  25                  30

Thr Ala Val Thr Pro Ser Ser Leu Gln Gln Glu Ile Thr Leu Leu Cys
        35                  40                  45

Gly Glu Ile Leu Tyr Ala Lys His Ala Asp Tyr Lys Tyr Ala Ala Glu
    50                  55                  60

Ile Gly Ile Gln Tyr Ile Ser Thr Ala Leu Gly Ser Glu Arg Val Gln
65                  70                  75                  80

Gln Ile Leu Arg Asn Ser Gly Ser Glu Val Gln Val Val Leu Thr Arg
                85                  90                  95

Thr Tyr Ser Leu Gly Lys Ile Lys Asn Asn Lys Gly Glu Asp Leu Gln
            100                 105                 110

Met Leu Asp Ile His Gly Val Glu Lys Ser Trp Val Glu Glu Ile Asp
        115                 120                 125

Lys Glu Ala Arg Lys Thr Met Ala Thr Leu Leu Lys Glu Ser Ser Gly
    130                 135                 140

Asn Ile Pro Gln Asn Gln Arg Pro Ser Ala Pro Asp Thr Pro Ile Ile
145                 150                 155                 160

Leu Leu Cys Val Gly Ala Leu Ile Phe Thr Lys Leu Ala Ser Thr Ile
                165                 170                 175

Glu Val Gly Leu Glu Thr Thr Val Arg Arg Ala Asn Arg Val Leu Ser
            180                 185                 190

Asp Ala Leu Lys Arg Tyr Pro Arg Met Asp Ile Pro Lys Ile Ala Arg
        195                 200                 205

Ser Phe Tyr Asp Leu Phe Glu Gln Lys Val Tyr His Arg Ser Leu Phe
210                 215                 220
```

```
Ile Glu Tyr Gly Lys Ala Leu Gly Ser Ser Thr Gly Ser Lys Ala
225                 230                 235                 240

Glu Ser Leu Phe Val Asn Ile Phe Met Gln Ala Tyr Gly Ala Gly Gln
            245                 250                 255

Thr Met Leu Arg Trp Gly Val Ile Ala Arg Ser Ser Asn Asn Ile Met
            260                 265                 270

Leu Gly His Val Ser Val Gln Ala Glu Leu Lys Gln Val Thr Glu Val
        275                 280                 285

Tyr Asp Leu Val Arg Glu Met Gly Pro Glu Ser Gly Leu Leu His Leu
290                 295                 300

Arg Gln Ser Pro Lys Ala Gly Leu Leu Ser Leu Ala Asn Cys Pro Asn
305                 310                 315                 320

Phe Ala Ser Val Val Leu Gly Asn Ala Ser Gly Leu Gly Ile Ile Gly
                325                 330                 335

Met Tyr Arg Gly Arg Val Pro Asn Thr Glu Leu Phe Ser Ala Ala Glu
            340                 345                 350

Ser Tyr Ala Lys Ser Leu Lys Glu Ser Asn Lys Ile Asn Phe Ser Ser
        355                 360                 365

Leu Gly Leu Thr Asp Glu Glu Lys Glu Ala Ala Glu His Phe Leu Asn
370                 375                 380

Val Ser Asp Asp Ser Gln Asn Asp Tyr Glu
385                 390

<210> SEQ ID NO 2
<211> LENGTH: 391
<212> TYPE: PRT
<213> ORGANISM: Avian pneumovirus A

<400> SEQUENCE: 2

Met Ser Leu Glu Ser Ile Arg Leu Ser Asp Leu Glu Tyr Lys His Ala
1               5                   10                  15

Ile Leu Glu Asp Ser Gln Tyr Thr Ile Arg Arg Asp Val Gly Ala Thr
            20                  25                  30

Thr Ala Ile Thr Pro Ser Glu Leu Gln Pro Gln Val Ser Thr Leu Cys
        35                  40                  45

Gly Met Val Leu Phe Ala Lys His Thr Asp Tyr Glu Pro Ala Ala Glu
    50                  55                  60

Val Gly Met Gln Tyr Ile Ser Thr Ala Leu Gly Ala Asp Arg Thr Gln
65                  70                  75                  80

Gln Ile Leu Lys Asn Ser Gly Ser Glu Val Gln Gly Val Met Thr Lys
                85                  90                  95

Ile Val Thr Leu Ser Ala Glu Gly Ser Val Arg Lys Arg Glu Val Leu
            100                 105                 110

Asn Ile His Asp Val Gly Val Gly Trp Ala Asp Asp Val Glu Arg Thr
        115                 120                 125

Thr Arg Glu Ala Met Gly Ala Met Val Arg Glu Lys Val Gln Leu Thr
    130                 135                 140

Lys Asn Gln Lys Pro Ser Ala Leu Asp Ala Pro Val Ile Leu Leu Cys
145                 150                 155                 160

Ile Gly Ala Leu Ile Phe Thr Lys Leu Ala Ser Thr Val Glu Val Gly
                165                 170                 175

Leu Glu Thr Ala Ile Arg Arg Ala Ser Arg Val Leu Ser Asp Ala Ile
            180                 185                 190

Ser Arg Tyr Pro Arg Met Asp Ile Pro Arg Ile Ala Lys Ser Phe Phe
```

```
                195                 200                 205
Glu Leu Phe Glu Lys Lys Val Tyr Tyr Arg Asn Leu Phe Ile Glu Tyr
210                 215                 220

Gly Lys Ala Leu Gly Ser Thr Ser Thr Gly Ser Arg Met Glu Ser Leu
225                 230                 235                 240

Phe Val Asn Ile Phe Met Gln Ala Tyr Gly Ala Gly Gln Thr Met Leu
                245                 250                 255

Arg Trp Gly Val Ile Ala Arg Ser Ser Asn Asn Ile Met Leu Gly His
                260                 265                 270

Val Ser Val Gln Ala Glu Leu Arg Gln Val Ser Glu Val Tyr Asp Leu
            275                 280                 285

Val Arg Lys Met Gly Pro Glu Ser Gly Leu Leu His Leu Arg Gln Ser
290                 295                 300

Pro Lys Ala Gly Leu Leu Ser Leu Thr Asn Cys Pro Asn Phe Ala Ser
305                 310                 315                 320

Val Val Leu Gly Asn Ala Ala Gly Leu Gly Ile Ile Gly Met Tyr Lys
                325                 330                 335

Gly Arg Ala Pro Asn Leu Glu Leu Phe Ala Ala Ala Glu Ser Tyr Ala
                340                 345                 350

Arg Thr Leu Arg Glu Asn Asn Lys Ile Asn Leu Ala Ala Leu Gly Leu
            355                 360                 365

Thr Asp Asp Glu Arg Glu Ala Ala Thr Ser Tyr Leu Gly Gly Asp Asp
370                 375                 380

Glu Arg Ser Ser Lys Phe Glu
385                 390

<210> SEQ ID NO 3
<211> LENGTH: 391
<212> TYPE: PRT
<213> ORGANISM: Avian pneumovirus B

<400> SEQUENCE: 3

Met Ser Leu Glu Ser Ile Arg Leu Ser Asp Leu Glu Tyr Lys His Ala
1               5                   10                  15

Ile Leu Asp Glu Ser Gln Tyr Thr Ile Arg Arg Asp Val Gly Ala Thr
                20                  25                  30

Thr Ala Ile Thr Pro Ser Glu Leu Gln Pro Lys Val Ser Thr Leu Cys
            35                  40                  45

Gly Met Ile Leu Phe Ala Lys His Ala Asp Tyr Glu Pro Ala Ala Gln
        50                  55                  60

Val Gly Met Gln Tyr Ile Ser Thr Ala Leu Gly Ala Asp Lys Thr Gln
65                  70                  75                  80

Gln Ile Leu Lys Ser Ser Gly Ser Glu Val Gln Gly Val Met Thr Lys
                85                  90                  95

Ile Val Thr Leu Pro Ala Glu Gly Pro Ile Arg Lys Arg Glu Val Leu
            100                 105                 110

Asn Ile His Asp Ile Gly Pro Ala Trp Ala Asp Asn Val Glu Arg Thr
        115                 120                 125

Ala Arg Glu Thr Met Ser Leu Met Val Lys Lys Ala Gln Ile Pro
    130                 135                 140

Lys Asn Gln Lys Pro Ser Ala Leu Asp Ala Pro Val Ile Leu Leu Cys
145                 150                 155                 160

Ile Gly Ala Leu Ile Phe Thr Lys Leu Ala Ser Thr Val Glu Val Gly
                165                 170                 175
```

Leu Glu Thr Ala Ile Arg Arg Ala Ser Arg Val Leu Ser Asp Ala Ile
            180                 185                 190

Ser Arg Tyr Pro Arg Met Asp Ile Pro Arg Ile Ala Lys Ser Phe Phe
        195                 200                 205

Glu Leu Phe Glu Lys Lys Val Tyr Tyr Arg Asn Leu Phe Ile Glu Tyr
    210                 215                 220

Gly Lys Ala Leu Gly Ser Thr Ser Ser Gly Ser Arg Met Glu Ser Leu
225                 230                 235                 240

Phe Val Asn Ile Phe Met Gln Ala Tyr Gly Ala Gly Gln Thr Met Leu
                245                 250                 255

Arg Arg Gly Val Val Ala Arg Ser Ser Asn Asn Ile Met Leu Gly His
            260                 265                 270

Val Ser Val Gln Ala Glu Leu Arg Gln Val Ser Glu Val Tyr Asp Leu
        275                 280                 285

Val Arg Lys Met Gly Pro Glu Ser Gly Leu Leu His Leu Arg Gln Ser
    290                 295                 300

Pro Lys Ala Gly Leu Leu Ser Leu Thr Ser Cys Pro Asn Phe Ala Ser
305                 310                 315                 320

Val Val Leu Gly Asn Ala Ala Gly Leu Gly Ile Ile Gly Met Tyr Lys
                325                 330                 335

Gly Arg Ala Pro Asn Leu Glu Leu Phe Ser Ala Ala Glu Ser Tyr Ala
            340                 345                 350

Arg Ser Leu Lys Glu Ser Asn Lys Ile Asn Leu Ala Ala Leu Gly Leu
        355                 360                 365

Thr Glu Asp Glu Arg Glu Ala Ala Thr Ser Tyr Leu Gly Gly Asp Glu
    370                 375                 380

Asp Lys Ser Gln Lys Phe Glu
385                 390

<210> SEQ ID NO 4
<211> LENGTH: 394
<212> TYPE: PRT
<213> ORGANISM: Avian pneumovirus C

<400> SEQUENCE: 4

Met Ser Leu Gln Gly Ile Gln Leu Ser Asp Leu Ser Tyr Lys His Ala
1               5                   10                  15

Ile Leu Lys Glu Ser Gln Tyr Thr Ile Lys Arg Asp Val Gly Thr Thr
            20                  25                  30

Thr Ala Val Thr Pro Ser Ser Leu Gln Arg Glu Val Ser Leu Leu Cys
        35                  40                  45

Gly Glu Ile Leu Tyr Ala Lys His Thr Asp Tyr Ser His Ala Ala Glu
    50                  55                  60

Val Gly Met Gln Tyr Val Ser Thr Thr Leu Gly Ala Glu Arg Thr Gln
65                  70                  75                  80

Gln Ile Leu Lys Asn Ser Gly Ser Glu Val Gln Ala Val Leu Thr Lys
                85                  90                  95

Thr Tyr Ser Leu Gly Lys Gly Lys Asn Ser Lys Gly Glu Glu Leu Gln
            100                 105                 110

Met Leu Asp Ile His Gly Val Glu Arg Ser Trp Ile Glu Glu Val Asp
        115                 120                 125

Lys Glu Ala Arg Lys Thr Met Ala Ser Ala Thr Lys Asp Asn Ser Gly
    130                 135                 140

Pro Ile Pro Gln Asn Gln Arg Pro Ser Ser Pro Asp Ala Pro Ile Ile
145                 150                 155                 160

Leu Leu Cys Ile Gly Ala Leu Ile Phe Thr Lys Leu Ala Ser Thr Ile
                165                 170                 175

Glu Val Gly Leu Glu Thr Ala Val Arg Arg Ala Asn Arg Val Leu Asn
            180                 185                 190

Asp Ala Leu Lys Arg Phe Pro Arg Ile Asp Ile Pro Lys Ile Ala Arg
        195                 200                 205

Ser Phe Tyr Asp Leu Phe Glu Gln Lys Val Tyr Tyr Arg Ser Leu Phe
    210                 215                 220

Ile Glu Tyr Gly Lys Ala Leu Gly Ser Ser Thr Gly Ser Lys Ala
225                 230                 235                 240

Glu Ser Leu Phe Val Asn Ile Phe Met Gln Ala Tyr Gly Ala Gly Gln
                245                 250                 255

Thr Met Leu Arg Trp Gly Val Ile Ala Arg Ser Ser Asn Asn Ile Met
            260                 265                 270

Leu Gly His Val Ser Val Gln Ala Glu Leu Lys Gln Val Thr Glu Val
        275                 280                 285

Tyr Asp Leu Val Arg Glu Met Gly Pro Glu Ser Gly Leu Leu His Leu
    290                 295                 300

Arg Gln Asn Pro Lys Ala Gly Leu Leu Ser Leu Ala Asn Cys Pro Asn
305                 310                 315                 320

Phe Ala Ser Val Val Leu Gly Asn Ala Ser Gly Leu Gly Ile Leu Gly
                325                 330                 335

Met Tyr Arg Gly Arg Val Pro Asn Thr Glu Leu Phe Ala Ala Ala Glu
            340                 345                 350

Ser Tyr Ala Arg Ser Leu Lys Glu Ser Asn Lys Ile Asn Phe Ser Ser
        355                 360                 365

Leu Gly Leu Thr Glu Glu Glu Lys Glu Ala Ala Glu Asn Phe Leu Asn
    370                 375                 380

Ile Asn Glu Glu Gly Gln Asn Asp Tyr Glu
385                 390

<210> SEQ ID NO 5
<211> LENGTH: 391
<212> TYPE: PRT
<213> ORGANISM: Bovine respiratory syncytial virus

<400> SEQUENCE: 5

Met Ala Leu Ser Lys Val Lys Leu Asn Asp Thr Phe Asn Lys Asp Gln
1               5                   10                  15

Leu Leu Ser Thr Ser Lys Tyr Thr Ile Gln Arg Ser Thr Gly Asp Asn
            20                  25                  30

Ile Asp Ile Pro Asn Tyr Asp Val Gln Lys His Leu Asn Lys Leu Cys
        35                  40                  45

Gly Met Leu Leu Ile Thr Glu Asp Ala Asn His Lys Phe Thr Gly Leu
    50                  55                  60

Ile Gly Met Leu Tyr Ala Met Ser Arg Leu Gly Arg Glu Asp Thr Leu
65                  70                  75                  80

Lys Ile Leu Lys Asp Ala Gly Tyr Gln Val Arg Ala Asn Gly Val Asp
                85                  90                  95

Val Ile Thr His Arg Gln Asp Val Asn Gly Lys Glu Met Lys Phe Glu
            100                 105                 110

Val Leu Thr Leu Val Ser Leu Thr Ser Glu Val Gln Gly Asn Ile Glu
        115                 120                 125

Ile Glu Ser Arg Lys Ser Tyr Lys Lys Met Leu Lys Glu Met Gly Glu

```
               130                 135                 140
Val Ala Pro Glu Tyr Arg His Asp Ser Pro Asp Cys Gly Met Ile Val
145                 150                 155                 160

Leu Cys Val Ala Ala Leu Val Ile Thr Lys Leu Ala Ala Gly Asp Arg
                165                 170                 175

Ser Gly Leu Thr Ala Val Ile Arg Arg Ala Asn Asn Val Leu Arg Asn
                180                 185                 190

Glu Met Lys Arg Tyr Lys Gly Leu Ile Pro Lys Asp Ile Ala Asn Ser
                195                 200                 205

Phe Tyr Glu Val Phe Glu Lys Tyr Pro His Tyr Ile Asp Val Phe Val
        210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ala Gly Gln Val
                245                 250                 255

Met Leu Arg Trp Gly Val Leu Ala Lys Ser Val Lys Asn Ile Met Leu
                260                 265                 270

Gly His Ala Ser Val Gln Ala Glu Met Glu Gln Val Val Glu Val Tyr
                275                 280                 285

Glu Tyr Ala Gln Lys Leu Gly Gly Glu Ala Gly Phe Tyr His Ile Leu
        290                 295                 300

Asn Asn Pro Lys Ala Ser Leu Leu Ser Leu Thr Gln Phe Pro Asn Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
                340                 345                 350

Tyr Ala Glu Gln Leu Lys Glu Asn Gly Val Ile Asn Tyr Ser Val Leu
        355                 360                 365

Asp Leu Thr Thr Glu Glu Leu Glu Ala Ile Lys Asn Gln Leu Asn Pro
370                 375                 380

Lys Asp Asn Asp Val Glu Leu
385                 390

<210> SEQ ID NO 6
<211> LENGTH: 391
<212> TYPE: PRT
<213> ORGANISM: Human respiratory syncytial virus

<400> SEQUENCE: 6

Met Ala Leu Ser Lys Val Lys Leu Asn Asp Thr Le

Val Leu Thr Leu Ser Ser Leu Thr Ser Glu Ile Gln Val Asn Ile Glu
115                 120                 125

Ile Glu Ser Arg Lys Ser Tyr Lys Lys Met Leu Lys Glu Met Gly Glu
130                 135                 140

Val Ala Pro Glu Tyr Arg His Asp Ser Pro Asp Cys Gly Met Ile Ile
145                 150                 155                 160

Leu Cys Ile Ala Ala Leu Val Ile Thr Lys Leu Ala Ala Gly Asp Arg
                165                 170                 175

Ser Gly Leu Thr Ala Val Ile Arg Arg Ala Asn Asn Val Leu Lys Asn
                180                 185                 190

Glu Ile Lys Arg Tyr Lys Gly Leu Ile Pro Lys Asp Ile Ala Asn Ser
            195                 200                 205

Phe Tyr Glu Val Phe Glu Lys His Pro His Leu Ile Asp Val Phe Val
        210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ser Gly Gln Val
                245                 250                 255

Met Leu Arg Trp Gly Val Leu Ala Lys Ser Val Lys Asn Ile Met Leu
            260                 265                 270

Gly His Ala Ser Val Gln Ala Glu Met Glu Gln Val Val Glu Val Tyr
        275                 280                 285

Glu Tyr Ala Gln Lys Leu Gly Gly Glu Ala Gly Phe Tyr His Ile Leu
    290                 295                 300

Asn Asn Pro Lys Ala Ser Leu Leu Ser Leu Thr Gln Phe Pro Asn Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
            340                 345                 350

Tyr Ala Glu Gln Leu Lys Glu Asn Gly Val Ile Asn Tyr Ser Val Leu
        355                 360                 365

Asp Leu Thr Ala Glu Glu Leu Glu Ala Ile Lys Asn Gln Leu Asn Pro
    370                 375                 380

Lys Glu Asp Asp Val Glu Leu
385                 390

<210> SEQ ID NO 7
<211> LENGTH: 393
<212> TYPE: PRT
<213> ORGANISM: Pneumonia virus of mice

<400> SEQUENCE: 7

Met Ser Leu Asp Arg Leu Lys Leu Asn Asp Val Ser Asn Lys Asp Ser
1               5                   10                  15

Leu Leu Ser Asn Cys Lys Tyr Ser Val Thr Arg Ser Thr Gly Asp Val
                20                  25                  30

Thr Ser Val Ser Gly His Ala Met Gln Lys Ala Leu Ala Arg Thr Leu
            35                  40                  45

Gly Met Phe Leu Leu Thr Ala Phe Asn Arg Cys Glu Glu Val Ala Glu
        50                  55                  60

Ile Gly Leu Gln Tyr Ala Met Ser Leu Leu Gly Arg Asp Asp Ser Ile
65                  70                  75                  80

Lys Ile Leu Arg Glu Ala Gly Tyr Asn Val Lys Cys Val Asp Thr Gln
                85                  90                  95

```
Leu Lys Asp Phe Thr Ile Lys Leu Gln Gly Lys Glu Tyr Lys Ile Gln
                100                 105                 110

Val Leu Asp Ile Val Gly Ile Asp Ala Ala Asn Leu Ala Asp Leu Glu
                115                 120                 125

Ile Gln Ala Arg Gly Val Val Ala Lys Glu Leu Lys Thr Gly Ala Arg
            130                 135                 140

Leu Pro Asp Asn Arg Arg His Asp Ala Pro Asp Cys Gly Val Ile Val
145                 150                 155                 160

Leu Cys Ile Ala Ala Leu Val Val Ser Lys Leu Ala Ala Gly Asp Arg
                165                 170                 175

Gly Gly Leu Asp Ala Val Glu Arg Ala Leu Asn Val Leu Lys Ala
                180                 185                 190

Glu Lys Ala Arg Tyr Pro Asn Met Glu Val Lys Gln Ile Ala Glu Ser
                195                 200                 205

Phe Tyr Asp Leu Phe Glu Arg Lys Pro Tyr Tyr Ile Asp Val Phe Ile
                210                 215                 220

Thr Phe Gly Leu Ala Gln Ser Ser Val Arg Gly Gly Ser Lys Val Glu
225                 230                 235                 240

Gly Leu Phe Ser Gly Leu Phe Met Asn Ala Tyr Gly Ala Gly Gln Val
                245                 250                 255

Met Leu Arg Trp Gly Leu Leu Ala Lys Ser Val Lys Asn Ile Met Leu
                260                 265                 270

Gly His Ala Ser Val Gln Ala Glu Met Glu Gln Val Val Glu Val Tyr
                275                 280                 285

Glu Tyr Ala Gln Lys Gln Gly Gly Glu Ala Gly Phe Tyr His Ile Arg
                290                 295                 300

Asn Asn Pro Lys Ala Ser Leu Leu Ser Leu Thr Asn Cys Pro Asn Phe
305                 310                 315                 320

Thr Ser Val Val Leu Gly Asn Ala Ala Gly Leu Gly Ile Ile Gly Ser
                325                 330                 335

Tyr Lys Gly Ala Pro Arg Asn Arg Glu Leu Phe Asp Ala Ala Lys Asp
                340                 345                 350

Tyr Ala Glu Arg Leu Lys Asp Asn Asn Val Ile Asn Tyr Ser Ala Leu
                355                 360                 365

Asn Leu Thr Ala Glu Glu Arg Glu Leu Ile Ser Gln Gln Leu Asn Ile
                370                 375                 380

Val Asp Asp Thr Pro Asp Asp Ile
385                 390

<210> SEQ ID NO 8
<211> LENGTH: 294
<212> TYPE: PRT
<213> ORGANISM: Human metapneumovirus 00-1

<400> SEQUENCE: 8

Met Ser Phe Pro Glu Gly Lys Asp Ile Leu Phe Met Gly Asn Glu Ala
1                 5                   10                  15

Ala Lys Leu Ala Glu Ala Phe Gln Lys Ser Leu Arg Lys Pro Gly His
                20                  25                  30

Lys Arg Ser Gln Ser Ile Ile Gly Glu Lys Val Asn Thr Val Ser Glu
            35                  40                  45

Thr Leu Glu Leu Pro Thr Ile Ser Arg Pro Ala Lys Pro Thr Ile Pro
        50                  55                  60

Ser Glu Pro Lys Leu Ala Trp Thr Asp Lys Gly Gly Ala Thr Lys Thr
```

```
                65                  70                  75                  80
Glu Ile Lys Gln Ala Ile Lys Val Met Asp Pro Ile Glu Glu Glu
                    85                  90                  95
Ser Thr Glu Lys Lys Val Leu Pro Ser Ser Asp Gly Lys Thr Pro Ala
                100                 105                 110
Glu Lys Lys Leu Lys Pro Ser Thr Asn Thr Lys Lys Val Ser Phe
                115                 120                 125
Thr Pro Asn Glu Pro Gly Lys Tyr Thr Lys Leu Glu Lys Asp Ala Leu
                130                 135                 140
Asp Leu Leu Ser Asp Asn Glu Glu Asp Ala Glu Ser Ser Ile Leu
145                 150                 155                 160
Thr Phe Glu Glu Arg Asp Thr Ser Ser Leu Ser Ile Glu Ala Arg Leu
                    165                 170                 175
Glu Ser Ile Glu Glu Lys Leu Ser Met Ile Leu Gly Leu Leu Arg Thr
                180                 185                 190
Leu Asn Ile Ala Thr Ala Gly Pro Thr Ala Ala Arg Asp Gly Ile Arg
                195                 200                 205
Asp Ala Met Ile Gly Val Arg Glu Glu Leu Ile Ala Asp Ile Ile Lys
                210                 215                 220
Glu Ala Lys Gly Lys Ala Ala Glu Met Met Glu Glu Met Ser Gln
225                 230                 235                 240
Arg Ser Lys Ile Gly Asn Gly Ser Val Lys Leu Thr Glu Lys Ala Lys
                    245                 250                 255
Glu Leu Asn Lys Ile Val Glu Asp Ser Thr Ser Gly Glu Ser Glu
                260                 265                 270
Glu Glu Glu Glu Pro Lys Asp Thr Gln Asp Asn Ser Gln Glu Asp Asp
                275                 280                 285
Ile Tyr Gln Leu Ile Met
                290

<210> SEQ ID NO 9
<211> LENGTH: 278
<212> TYPE: PRT
<213> ORGANISM: Avian pneumovirus A

<400> SEQUENCE: 9

Met Ser Phe Pro Glu Gly Lys Asp Ile Leu Met Met Gly Ser Glu Ala
1               5                   10                  15
Ala Lys Met Ala Asp Ala Tyr Gln Arg Ser Leu Arg Asn Thr Ser Ala
                20                  25                  30
Gly Gly Arg Ser Ile Ser Gly Glu Pro Ile Asn Thr Ile Ala Glu Lys
            35                  40                  45
Val Pro Leu Pro Pro Leu Cys Asn Pro Thr Thr Pro Lys Gly Ser Cys
        50                  55                  60
Ile Lys Pro Asn Lys Ala Pro Val Pro Lys Val Lys Glu Ile Glu Ser
65                  70                  75                  80
Ile Tyr Pro Lys Leu Pro Thr Ala Pro Val Ala Thr Asp Thr Tyr Thr
                85                  90                  95
Ser Thr Ser Thr Glu Ser Ala Lys Lys Ser Lys Lys Val Lys Phe Asp
                100                 105                 110
Asn Pro Lys Val Gly Lys Tyr Thr Lys Leu Glu Glu Glu Gly Leu Glu
            115                 120                 125
Leu Leu Ser Asp Pro Glu Glu Asp Asn Asp Glu Lys Ser Ser Ile Leu
        130                 135                 140
```

Thr Phe Glu Glu Lys Asp Thr Ala Ser Thr Ile Glu Ala Arg Leu
145                 150                 155                 160

Glu Ala Ile Glu Glu Lys Leu Ser Met Ile Leu Gly Met Leu Lys Thr
            165                 170                 175

Leu Asn Ile Ala Thr Ala Gly Pro Thr Ala Ala Arg Asp Gly Ile Arg
                180                 185                 190

Asp Ala Met Ile Gly Met Arg Glu Glu Leu Ile Asn Ser Ile Met Thr
            195                 200                 205

Glu Ala Lys Asp Lys Ile Ala Glu Met Met Lys Glu Glu Asp Thr Gln
        210                 215                 220

Arg Ala Lys Ile Gly Asp Gly Ser Val Lys Leu Thr Glu Lys Ala Lys
225                 230                 235                 240

Glu Leu Asn Lys Ile Leu Glu Asp Gln Ser Ser Ser Gly Glu Ser Glu
                245                 250                 255

Ser Glu Glu Glu Ser Gly Glu Ser Glu Asp Glu Glu Ser Asp
            260                 265                 270

Ile Tyr Asn Leu Asp Leu
            275

<210> SEQ ID NO 10
<211> LENGTH: 294
<212> TYPE: PRT
<213> ORGANISM: Avian pneumovirus strain C

<400> SEQUENCE: 10

Met Ser Phe Pro Glu Gly Lys Asp Ile Leu Leu Met Gly Asn Glu Ala
1               5                   10                  15

Ala Lys Ala Ala Glu Ala Phe Gln Arg Ser Leu Lys Lys Ile Gly His
            20                  25                  30

Arg Arg Thr Gln Ser Ile Val Gly Asp Lys Ile Ile Thr Val Ser Glu
        35                  40                  45

Thr Val Glu Lys Pro Thr Ile Ser Lys Ser Thr Lys Val Thr Thr Pro
    50                  55                  60

Pro Glu Arg Lys Asn Ala Trp Gly Glu Lys Pro Asp Thr Thr Arg Ser
65                  70                  75                  80

Gln Thr Glu Glu Ala Arg Asn Glu Ala Thr Pro Glu Asp Ala Ser Arg
                85                  90                  95

Leu Tyr Glu Glu Val Phe Ala Pro Thr Ser Asp Gly Lys Thr Pro Ala
            100                 105                 110

Glu Lys Gly Lys Glu Thr Pro Glu Lys Pro Lys Lys Val Thr Phe
        115                 120                 125

Lys Asn Asp Glu Ser Gly Arg Tyr Thr Lys Leu Glu Met Glu Ala Leu
130                 135                 140

Glu Leu Leu Ser Asp Asn Glu Asp Asp Ala Glu Ser Ser Val Leu
145                 150                 155                 160

Thr Phe Glu Glu Lys Asp Thr Ser Ala Leu Ser Leu Glu Ala Arg Leu
                165                 170                 175

Glu Ser Ile Asp Glu Lys Leu Ser Met Ile Leu Gly Leu Leu Arg Thr
            180                 185                 190

Leu Asn Val Ala Thr Ala Gly Pro Thr Ala Ala Arg Asp Gly Ile Arg
        195                 200                 205

Asp Ala Met Val Gly Leu Arg Glu Glu Leu Ile Ala Asp Ile Ile Lys
    210                 215                 220

Glu Ala Lys Gly Lys Ala Ala Glu Met Met Lys Glu Glu Ala Lys Gln
225                 230                 235                 240

```
Lys Ser Lys Ile Gly Asn Gly Ser Val Gly Leu Thr Glu Ala Lys
                245                 250                 255

Glu Leu Asn Lys Ile Val Glu Asp Glu Ser Thr Ser Gly Glu Ser Glu
            260                 265                 270

Glu Glu Glu Glu Glu Glu Asp Glu Glu Ser Asn Pro Asp Asp Asp
        275                 280                 285

Leu Tyr Ser Leu Thr Met
        290

<210> SEQ ID NO 11
<211> LENGTH: 241
<212> TYPE: PRT
<213> ORGANISM: Bovine respiratory syncytial virus

<400> SEQUENCE: 11

Met Glu Lys Phe Ala Pro Glu Phe His Gly Glu Asp Ala Asn Thr Lys
1               5                   10                  15

Ala Thr Lys Phe Leu Glu Ser Leu Lys Gly Lys Phe Thr Ser Ser Lys
            20                  25                  30

Asp Ser Arg Lys Lys Asp Ser Ile Ile Ser Val Asn Ser Val Asp Ile
        35                  40                  45

Glu Leu Pro Lys Glu Ser Pro Ile Thr Ser Thr Asn Gln Asn Ile Asn
    50                  55                  60

Gln Pro Ser Glu Ile Asn Asp Thr Ile Ala Thr Asn Gln Val His Ile
65                  70                  75                  80

Arg Lys Pro Leu Val Ser Phe Lys Glu Glu Leu Pro Ser Ser Glu Asn
                85                  90                  95

Pro Phe Thr Arg Leu Tyr Lys Glu Thr Ile Glu Thr Phe Asp Asn Asn
            100                 105                 110

Glu Glu Glu Ser Ser Tyr Ser Tyr Asp Glu Ile Asn Asp Gln Thr Asn
        115                 120                 125

Asp Asn Ile Thr Ala Arg Leu Asp Arg Ile Asp Glu Lys Leu Ser Glu
    130                 135                 140

Ile Ile Gly Met Leu His Thr Leu Val Val Ala Ser Ala Gly Pro Thr
145                 150                 155                 160

Ala Ala Arg Asp Gly Ile Arg Asp Ala Met Val Gly Leu Arg Glu Glu
                165                 170                 175

Met Ile Glu Lys Ile Arg Ser Glu Ala Leu Met Thr Asn Asp Arg Leu
            180                 185                 190

Glu Ala Met Ala Arg Leu Arg Asp Glu Glu Ser Glu Lys Met Thr Lys
        195                 200                 205

Asp Thr Ser Asp Glu Val Lys Leu Thr Pro Thr Ser Glu Lys Leu Asn
    210                 215                 220

Met Val Leu Glu Asp Glu Ser Ser Asp Asn Asp Leu Ser Leu Glu Asp
225                 230                 235                 240

Phe

<210> SEQ ID NO 12
<211> LENGTH: 241
<212> TYPE: PRT
<213> ORGANISM: Human respiratory syncytial virus

<400> SEQUENCE: 12

Met Glu Lys Phe Ala Pro Glu Phe His Gly Glu Asp Ala Asn Asn Lys
1               5                   10                  15
```

-continued

```
Ala Thr Lys Phe Leu Glu Ser Ile Lys Gly Lys Phe Ala Ser Ser Lys
            20                  25                  30

Asp Pro Lys Lys Lys Asp Ser Ile Ile Ser Val Asn Ser Ile Asp Ile
        35                  40                  45

Glu Val Thr Lys Glu Ser Pro Ile Thr Ser Gly Thr Asn Ile Ile Asn
50                  55                  60

Pro Thr Ser Glu Ala Asp Ser Thr Pro Glu Thr Lys Ala Asn Tyr Pro
65                  70                  75                  80

Arg Lys Pro Leu Val Ser Phe Lys Glu Asp Leu Thr Pro Ser Asp Asn
                85                  90                  95

Pro Phe Ser Lys Leu Tyr Lys Glu Thr Ile Glu Thr Phe Asp Asn Asn
            100                 105                 110

Glu Glu Glu Ser Ser Tyr Ser Tyr Glu Glu Ile Asn Asp Gln Thr Asn
        115                 120                 125

Asp Asn Ile Thr Ala Arg Leu Asp Arg Ile Asp Glu Lys Leu Ser Glu
130                 135                 140

Ile Leu Gly Met Leu His Thr Leu Val Val Ala Ser Ala Gly Pro Thr
145                 150                 155                 160

Ser Ala Arg Asp Gly Ile Arg Asp Ala Met Val Gly Leu Arg Glu Glu
                165                 170                 175

Met Ile Glu Lys Ile Arg Ala Glu Ala Leu Met Thr Asn Asp Arg Leu
            180                 185                 190

Glu Ala Met Ala Arg Leu Arg Asn Glu Glu Ser Glu Lys Met Ala Lys
        195                 200                 205

Asp Thr Ser Asp Glu Val Pro Leu Asn Pro Thr Ser Lys Lys Leu Ser
210                 215                 220

Asp Leu Leu Glu Asp Asn Asp Ser Asp Asn Asp Leu Ser Leu Asp Asp
225                 230                 235                 240

Phe

<210> SEQ ID NO 13
<211> LENGTH: 295
<212> TYPE: PRT
<213> ORGANISM: Pneumonia virus of mice

<400> SEQUENCE: 13

Met Glu Lys Phe Ala Pro Glu Phe Val Gly Glu Asp Ala Asn Lys Lys
1               5                   10                  15

Ala Glu Glu Phe Leu Lys His Arg Ser Phe Pro Ser Glu Lys Pro Leu
            20                  25                  30

Ala Gly Ile Pro Asn Thr Ala Thr His Val Thr Lys Tyr Asn Met Pro
        35                  40                  45

Pro Ile Leu Arg Ser Ser Phe Lys Leu Pro Ser Pro Arg Val Ala Ala
50                  55                  60

Asn Leu Thr Glu Pro Ser Ala Pro Pro Thr Thr Pro Pro Thr Pro Thr
65                  70                  75                  80

Pro Gln Asn Lys Glu Glu Gln Pro Lys Glu Ser Asp Val Asp Ile Glu
                85                  90                  95

Thr Met His Val Cys Lys Val Pro Asp Asn Pro Glu His Ser Lys Lys
            100                 105                 110

Pro Cys Cys Ser Asp Asp Thr Asp Thr Lys Lys Thr Arg Lys Pro Met
        115                 120                 125

Val Thr Phe Val Glu Pro Glu Glu Lys Phe Val Gly Leu Gly Ala Ser
130                 135                 140
```

```
Leu Tyr Arg Glu Thr Met Gln Thr Phe Ala Ala Asp Gly Tyr Asp Glu
145                 150                 155                 160

Glu Ser Asn Leu Ser Phe Glu Glu Thr Asn Gln Glu Pro Gly Ser Ser
            165                 170                 175

Ser Val Glu Gln Arg Leu Asp Arg Ile Glu Glu Lys Leu Ser Tyr Ile
        180                 185                 190

Ile Gly Leu Leu Asn Thr Ile Met Val Ala Thr Ala Gly Pro Thr Thr
    195                 200                 205

Ala Arg Asp Glu Ile Arg Asp Ala Leu Ile Gly Thr Arg Glu Glu Leu
210                 215                 220

Ile Glu Met Ile Lys Ser Asp Ile Leu Thr Val Asn Asp Arg Ile Val
225                 230                 235                 240

Ala Met Glu Lys Leu Arg Asp Glu Glu Cys Ser Arg Ala Asp Thr Asp
            245                 250                 255

Asp Gly Ser Ala Cys Tyr Leu Thr Asp Arg Ala Arg Ile Leu Asp Lys
        260                 265                 270

Ile Val Ser Ser Asn Ala Glu Gly Ala Lys Glu Asp Leu Asp Val Asp
    275                 280                 285

Asp Ile Met Gly Ile Asn Phe
290                 295

<210> SEQ ID NO 14
<211> LENGTH: 254
<212> TYPE: PRT
<213> ORGANISM: Human metapneumovirus 00-1

<400> SEQUENCE: 14

Met Glu Ser Tyr Leu Val Asp Thr Tyr Gln Gly Ile Pro Tyr Thr Ala
1               5                   10                  15

Ala Val Gln Val Asp Leu Ile Glu Lys Asp Leu Leu Pro Ala Ser Leu
            20                  25                  30

Thr Ile Trp Phe Pro Leu Phe Gln Ala Asn Thr Pro Pro Ala Val Leu
        35                  40                  45

Leu Asp Gln Leu Lys Thr Leu Thr Ile Thr Thr Leu Tyr Ala Ala Ser
    50                  55                  60

Gln Asn Gly Pro Ile Leu Lys Val Asn Ala Ser Ala Gln Gly Ala Ala
65                  70                  75                  80

Met Ser Val Leu Pro Lys Lys Phe Glu Val Asn Ala Thr Val Ala Leu
            85                  90                  95

Asp Glu Tyr Ser Lys Leu Glu Phe Asp Lys Leu Thr Val Cys Glu Val
        100                 105                 110

Lys Thr Val Tyr Leu Thr Thr Met Lys Pro Tyr Gly Met Val Ser Lys
    115                 120                 125

Phe Val Ser Ser Ala Lys Ser Val Gly Lys Lys Thr His Asp Leu Ile
130                 135                 140

Ala Leu Cys Asp Phe Met Asp Leu Glu Lys Asn Thr Pro Val Thr Ile
145                 150                 155                 160

Pro Ala Phe Ile Lys Ser Val Ser Ile Lys Glu Ser Glu Ser Ala Thr
            165                 170                 175

Val Glu Ala Ala Ile Ser Ser Glu Ala Asp Gln Ala Leu Thr Gln Ala
        180                 185                 190

Lys Ile Ala Pro Tyr Ala Gly Leu Ile Met Ile Met Thr Met Asn Asn
    195                 200                 205

Pro Lys Gly Ile Phe Lys Lys Leu Gly Ala Gly Thr Gln Val Ile Val
210                 215                 220
```

```
Glu Leu Gly Ala Tyr Val Gln Ala Glu Ser Ile Ser Lys Ile Cys Lys
225                 230                 235                 240

Thr Trp Ser His Gln Gly Thr Arg Tyr Val Leu Lys Ser Arg
                245                 250

<210> SEQ ID NO 15
<211> LENGTH: 254
<212> TYPE: PRT
<213> ORGANISM: Turkey rhinotracheitis virus B

<400> SEQUENCE: 15

Met Glu Ser Tyr Ile Ile Asp Thr Tyr Gln Gly Val Pro Tyr Thr Ala
1               5                   10                  15

Ala Val Gln Val Asp Leu Val Glu Lys Asp Asn Asn Pro Ala Lys Leu
                20                  25                  30

Thr Val Trp Phe Pro Leu Phe Gln Ser Ser Thr Pro Ala Pro Val Leu
            35                  40                  45

Leu Asp Gln Leu Lys Thr Leu Ser Ile Thr Thr Gln Tyr Thr Val Ser
        50                  55                  60

Pro Glu Gly Pro Val Leu Gln Val Asn Ala Thr Ala Gln Gly Ala Ala
65                  70                  75                  80

Met Ser Ala Leu Pro Lys Lys Phe Ser Val Ser Ala Ala Ala Ala Leu
                85                  90                  95

Asp Glu Tyr Ser Lys Leu Asp Phe Gly Val Leu Thr Val Cys Asp Val
                100                 105                 110

Arg Ala Val Tyr Leu Thr Thr Leu Lys Pro Tyr Gly Met Val Ser Lys
            115                 120                 125

Ile Val Thr Asn Met Asn Thr Val Gly Arg Lys Thr His Asp Leu Ile
        130                 135                 140

Ala Leu Cys Asp Phe Ile Asp Met Glu Arg Gly Ile Pro Val Thr Ile
145                 150                 155                 160

Pro Ala Tyr Ile Lys Ala Val Ser Ile Lys Asp Ser Glu Ser Ala Thr
                165                 170                 175

Val Glu Ala Ala Ile Ser Gly Glu Ala Asp Gln Ala Ile Thr Gln Ala
                180                 185                 190

Arg Ile Ala Pro Tyr Ala Gly Leu Ile Leu Leu Met Ala Met Asn Asn
            195                 200                 205

Pro Lys Gly Ile Phe Arg Lys Leu Gly Ala Gly Thr Gln Val Ile Val
        210                 215                 220

Glu Leu Gly Pro Tyr Val Gln Ala Glu Ser Leu Gly Lys Ile Cys Lys
225                 230                 235                 240

Thr Trp Asn His Gln Arg Thr Arg Tyr Ile Leu Lys Ser Arg
                245                 250

<210> SEQ ID NO 16
<211> LENGTH: 254
<212> TYPE: PRT
<213> ORGANISM: Turkey rhinotracheitis virus A

<400> SEQUENCE: 16

Met Glu Ser Tyr Ile Ile Asp Thr Tyr Gln Gly Val Pro Tyr Thr Ala
1               5                   10                  15

Ala Val Gln Val Asp Leu Ile Glu Lys Asp Ser Asn Pro Ala Thr Leu
                20                  25                  30

Thr Val Trp Phe Pro Leu Phe Gln Ser Ser Thr Pro Ala Pro Val Leu
            35                  40                  45
```

```
Leu Asp Gln Leu Lys Thr Leu Ser Ile Thr Thr Gln Tyr Thr Ala Ser
 50                  55                  60

Pro Glu Gly Pro Val Leu Gln Val Asn Ala Ala Gln Gly Ala Ala
65              70                  75                  80

Met Ser Ala Leu Pro Lys Lys Phe Ala Val Ser Ala Ala Val Ala Leu
                 85                  90                  95

Asp Glu Tyr Ser Arg Leu Glu Phe Gly Thr Leu Thr Val Cys Asp Val
                100                 105                 110

Arg Ser Ile Tyr Leu Thr Thr Leu Lys Pro Tyr Gly Met Val Ser Lys
                115                 120                 125

Ile Met Thr Asp Val Arg Ser Val Gly Arg Lys Thr His Asp Leu Ile
                130                 135                 140

Ala Leu Cys Asp Phe Ile Asp Ile Glu Lys Gly Val Pro Ile Thr Ile
145                 150                 155                 160

Pro Ala Tyr Ile Lys Ala Val Ser Ile Lys Asp Ser Glu Ser Ala Thr
                165                 170                 175

Val Glu Ala Ala Ile Ser Gly Glu Ala Asp Gln Ala Ile Thr Gln Ala
                180                 185                 190

Arg Ile Ala Pro Tyr Ala Gly Leu Ile Leu Ile Met Thr Met Asn Asn
                195                 200                 205

Pro Lys Gly Ile Phe Lys Lys Leu Gly Ala Gly Met Gln Val Ile Val
                210                 215                 220

Glu Leu Gly Pro Tyr Val Gln Ala Glu Ser Leu Gly Lys Ile Cys Lys
225                 230                 235                 240

Thr Trp Asn His Gln Arg Thr Arg Tyr Val Leu Arg Ser Arg
                245                 250

<210> SEQ ID NO 17
<211> LENGTH: 254
<212> TYPE: PRT
<213> ORGANISM: Avian pneumovirus C

<400> SEQUENCE: 17

Met Glu Ser Tyr Leu Val Asp Thr Tyr Gln Gly Val Pro Tyr Thr Ala
1               5                   10                  15

Ala Val Gln Thr Asp Leu Val Glu Lys Asp Gln Leu Pro Ala Arg Leu
                20                  25                  30

Thr Val Trp Val Pro Leu Phe Gln Thr Asn Thr Pro Thr Val Leu
            35                  40                  45

Leu Glu Gln Leu Lys Thr Leu Thr Ile Thr Thr Leu Tyr Thr Ala Ser
 50                  55                  60

Gln Asn Gly Pro Ile Leu Lys Val Asn Ala Ser Ala Gln Gly Ala Ala
65              70                  75                  80

Met Ser Ala Leu Pro Lys Ser Phe Asp Val Ser Ala Ser Val Ala Leu
                 85                  90                  95

Asp Asp Tyr Ser Lys Leu Glu Phe Asp Lys Leu Thr Val Cys Glu Leu
                100                 105                 110

Lys Ala Val Tyr Leu Thr Thr Met Lys Pro Tyr Gly Met Val Ser Lys
                115                 120                 125

Phe Val Asn Ser Ala Lys Ala Val Gly Lys Lys Thr His Asp Leu Ile
                130                 135                 140

Ala Leu Cys Asp Phe Leu Asp Leu Glu Lys Gly Val Pro Val Thr Ile
145                 150                 155                 160

Pro Ala Tyr Ile Lys Ser Val Ser Ile Lys Glu Ser Glu Ser Ala Thr
```

165                 170                 175

Val Glu Ala Ala Ile Ser Gly Glu Ala Asp Gln Ala Ile Thr Gln Ala
                180                 185                 190

Arg Ile Ala Pro Tyr Ala Gly Leu Ile Met Ile Met Thr Met Asn Asn
            195                 200                 205

Pro Lys Gly Ile Phe Lys Lys Leu Gly Ala Gly Val Gln Val Ile Val
        210                 215                 220

Glu Leu Gly Ala Tyr Val Gln Ala Glu Ser Ile Ser Arg Ile Cys Arg
225                 230                 235                 240

Asn Trp Ser His Gln Gly Thr Arg Tyr Val Leu Lys Ser Arg
                245                 250

<210> SEQ ID NO 18
<211> LENGTH: 256
<212> TYPE: PRT
<213> ORGANISM: Bovine respiratory syncytial virus

<400> SEQUENCE: 18

Met Glu Thr Tyr Val Asn Lys Leu His Glu Gly Ser Thr Tyr Thr Ala
1               5                   10                  15

Ala Val Gln Tyr Asn Val Ile Glu Lys Asp Asp Pro Ala Ser Leu
            20                  25                  30

Thr Ile Trp Val Pro Met Phe Gln Ser Ser Ile Ser Ala Asp Leu Leu
        35                  40                  45

Ile Lys Glu Leu Ile Asn Val Asn Ile Leu Val Arg Gln Ile Ser Thr
    50                  55                  60

Leu Lys Gly Pro Ser Leu Lys Ile Met Ile Asn Ser Arg Ser Ala Val
65                  70                  75                  80

Leu Ala Gln Met Pro Ser Lys Phe Thr Ile Ser Ala Asn Val Ser Leu
                85                  90                  95

Asp Glu Arg Ser Lys Leu Ala Tyr Asp Ile Thr Thr Pro Cys Glu Ile
            100                 105                 110

Lys Ala Cys Ser Leu Thr Cys Leu Lys Val Lys Asn Met Leu Thr Thr
        115                 120                 125

Val Lys Asp Leu Thr Met Lys Thr Phe Asn Pro Thr His Glu Ile Ile
    130                 135                 140

Ala Leu Cys Glu Phe Glu Asn Ile Met Thr Ser Lys Arg Val Val Ile
145                 150                 155                 160

Pro Thr Phe Leu Arg Ser Ile Asn Val Lys Ala Lys Asp Leu Asp Ser
                165                 170                 175

Leu Glu Asn Ile Ala Thr Thr Glu Phe Lys Asn Ala Ile Thr Asn Ala
            180                 185                 190

Lys Ile Ile Pro Tyr Ala Gly Leu Val Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Lys Phe Ser Ile Lys Pro Ile Glu Asp
                245                 250                 255

<210> SEQ ID NO 19
<211> LENGTH: 256
<212> TYPE: PRT
<213> ORGANISM: Human respiratory syncytial virus

<400> SEQUENCE: 19

```
Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Pro Ala Ser Leu
            20                  25                  30

Thr Ile Trp Val Pro Met Phe Gln Ser Ser Val Pro Ala Asp Leu Leu
        35                  40                  45

Ile Lys Glu Leu Ala Ser Ile Asn Ile Leu Val Lys Gln Ile Ser Thr
    50                  55                  60

Pro Lys Gly Pro Ser Leu Arg Val Thr Ile Asn Ser Arg Ser Ala Val
65                  70                  75                  80

Leu Ala Gln Met Pro Ser Asn Phe Ile Ile Ser Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Val Lys Ser Met Leu Thr Thr
        115                 120                 125

Val Lys Asp Leu Thr Met Lys Thr Phe Asn Pro Thr His Glu Ile Ile
    130                 135                 140

Ala Leu Cys Glu Phe Glu Asn Ile Met Thr Ser Lys Arg Val Ile Ile
145                 150                 155                 160

Pro Thr Tyr Leu Arg Pro Ile Ser Val Lys Asn Lys Asp Leu Asn Ser
                165                 170                 175

Leu Glu Asn Ile Ala Thr Thr Glu Phe Lys Asn Ala Ile Thr Asn Ala
            180                 185                 190

Lys Ile Ile Pro Tyr Ala Gly Leu Val Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ser Ile Lys Pro Leu Glu Asp
                245                 250                 255
```

<210> SEQ ID NO 20
<211> LENGTH: 257
<212> TYPE: PRT
<213> ORGANISM: Pneumonia virus of mice

<400> SEQUENCE: 20

```
Met Glu Ala Tyr Leu Val Glu Met Tyr His Gly Val Pro Tyr Thr Ala
1               5                   10                  15

Ala Val Gln Leu Asn Leu Val Gly Lys His Ser Ala Asn Ile Ser Leu
            20                  25                  30

Thr Val Trp Ile Pro Met Phe Gln Thr Ser Leu Pro Lys Asn Ser Val
        35                  40                  45

Met Asp Leu Leu His Asp Val Thr Val Ile Cys Thr Gln Ile Ser Thr
    50                  55                  60

Val His Gly Pro Met Ile Lys Val Asp Leu Ser Ser Ser Asn Ala Gly
65                  70                  75                  80

Leu Ala Thr Met Pro Arg Gln Phe Leu Ile Asn Ala Ile Ile Ala Leu
                85                  90                  95

Asp Asp Trp Gly Asn Met Asp Tyr Glu Val Pro Val Ala Phe Asp Lys
            100                 105                 110
```

```
Lys Ser Phe Cys Val Thr Ile Leu Lys Pro Lys Asn Met Leu Tyr Thr
            115                 120                 125
Val Pro Ser Ile Thr Pro Thr Asn Arg Pro Thr His Glu Leu Ile Ala
        130                 135                 140
Val Cys Ser Phe His Asn Arg Val Thr Leu Lys Ser Phe Asn Ile Pro
145                 150                 155                 160
Val Phe Ile Arg Ala Leu Tyr Ile Arg Gln Gln Gly Leu Asp Ser Val
                165                 170                 175
Glu Gln Ala Ile Ser Ser Asp Val Asp His Ala Ile Thr Thr Ala Arg
            180                 185                 190
Val Ala Pro Tyr Ala Gly Leu Thr Leu Val Ile Asn Ile Thr Ser Thr
        195                 200                 205
Lys Gly Ala Phe Lys Leu Leu Lys Ala Gly Ser Gln Ile Leu Ala Glu
210                 215                 220
Leu Gly Pro Tyr Leu Thr Gln Val Ser Leu His Asp Val Ile Met Asn
225                 230                 235                 240
Trp Lys His Thr Gly Thr Ser Tyr Ile Leu Lys Ser Ser Ser Thr Ser
                245                 250                 255
Gly

<210> SEQ ID NO 21
<211> LENGTH: 539
<212> TYPE: PRT
<213> ORGANISM: Human metapneumovirus 00-1

<400> SEQUENCE: 21

Met Ser Trp Lys Val Val Ile Ile Phe Ser Leu Leu Ile Thr Pro Gln
1               5                   10                  15
His Gly Leu Lys Glu Ser Tyr Leu Glu Glu Ser Cys Ser Thr Ile Thr
            20                  25                  30
Glu Gly Tyr Leu Ser Val Leu Arg Thr Gly Trp Tyr Thr Asn Val Phe
        35                  40                  45
Thr Leu Glu Val Gly Asp Val Glu Asn Leu Thr Cys Ala Asp Gly Pro
    50                  55                  60
Ser Leu Ile Lys Thr Glu Leu Asp Leu Thr Lys Ser Ala Leu Arg Glu
65                  70                  75                  80
Leu Arg Thr Val Ser Ala Asp Gln Leu Ala Arg Glu Glu Gln Ile Glu
                85                  90                  95
Asn Pro Arg Gln Ser Arg Phe Val Leu Gly Ala Ile Ala Leu Gly Val
            100                 105                 110
Ala Thr Ala Ala Ala Val Thr Ala Gly Val Ala Ile Ala Lys Thr Ile
        115                 120                 125
Arg Leu Glu Ser Glu Val Thr Ala Ile Lys Asn Ala Leu Lys Lys Thr
    130                 135                 140
Asn Glu Ala Val Ser Thr Leu Gly Asn Gly Val Arg Val Leu Ala Thr
145                 150                 155                 160
Ala Val Arg Glu Leu Lys Asp Phe Val Ser Lys Asn Leu Thr Arg Ala
                165                 170                 175
Ile Asn Lys Asn Lys Cys Asp Ile Ala Asp Leu Lys Met Ala Val Ser
            180                 185                 190
Phe Ser Gln Phe Asn Arg Arg Phe Leu Asn Val Val Arg Gln Phe Ser
        195                 200                 205
Asp Asn Ala Gly Ile Thr Pro Ala Ile Ser Leu Asp Leu Met Thr Asp
    210                 215                 220
```

```
Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
            245                 250                 255

Gly Phe Leu Ile Gly Val Tyr Gly Ser Ser Val Ile Tyr Met Val Gln
        260                 265                 270

Leu Pro Ile Phe Gly Val Ile Asp Thr Pro Cys Trp Ile Val Lys Ala
    275                 280                 285

Ala Pro Ser Cys Ser Gly Lys Gly Asn Tyr Ala Cys Leu Leu Arg
290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Phe Asp Pro
        435                 440                 445

Val Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Thr Met Ile Leu Val Ser Val Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
530                 535

<210> SEQ ID NO 22
<211> LENGTH: 538
<212> TYPE: PRT
<213> ORGANISM: Turkey rhinotracheitis virus A

<400> SEQUENCE: 22

Met Asp Val Arg Ile Cys Leu Leu Leu Phe Leu Ile Ser Asn Pro Ser
1               5                   10                  15

Ser Cys Ile Gln Glu Thr Tyr Asn Glu Glu Ser Cys Ser Val Thr
            20                  25                  30

Arg Gly Tyr Lys Ser Val Leu Arg Thr Gly Trp Tyr Thr Asn Val Phe
        35                  40                  45

Asn Leu Glu Ile Gly Asn Val Glu Asn Ile Thr Cys Asn Asp Gly Pro
    50                  55                  60
```

-continued

```
Ser Leu Ile Asp Thr Glu Leu Val Leu Thr Lys Asn Ala Leu Arg Glu
 65                  70                  75                  80

Leu Lys Thr Val Ser Ala Asp Gln Val Ala Lys Glu Ser Arg Leu Ser
                 85                  90                  95

Ser Pro Arg Arg Arg Phe Val Leu Gly Ala Ile Ala Leu Gly Val
            100                 105                 110

Ala Thr Ala Ala Ala Val Thr Ala Gly Val Ala Leu Ala Lys Thr Ile
            115                 120                 125

Arg Leu Glu Gly Glu Val Lys Ala Ile Lys Asn Ala Leu Arg Asn Thr
            130                 135                 140

Asn Glu Ala Val Ser Thr Leu Gly Asn Gly Val Arg Val Leu Ala Thr
145                 150                 155                 160

Ala Val Asn Asp Leu Lys Glu Phe Ile Ser Lys Lys Leu Thr Pro Ala
                165                 170                 175

Ile Asn Gln Asn Lys Cys Asn Ile Ala Asp Ile Lys Met Ala Ile Ser
            180                 185                 190

Phe Gly Gln Asn Asn Arg Arg Phe Leu Asn Val Val Arg Gln Phe Ser
            195                 200                 205

Asp Ser Ala Gly Ile Thr Ser Ala Val Ser Leu Asp Leu Met Thr Asp
    210                 215                 220

Asp Glu Leu Val Arg Ala Ile Asn Arg Met Pro Thr Ser Ser Gly Gln
225                 230                 235                 240

Ile Ser Leu Met Leu Asn Asn Arg Ala Met Val Arg Arg Lys Gly Phe
                245                 250                 255

Gly Ile Leu Ile Gly Val Tyr Asp Gly Thr Val Val Tyr Met Val Gln
            260                 265                 270

Leu Pro Ile Phe Gly Val Ile Glu Thr Pro Cys Trp Arg Val Val Ala
            275                 280                 285

Ala Pro Leu Cys Arg Lys Glu Lys Gly Asn Tyr Ala Cys Ile Leu Arg
    290                 295                 300

Glu Asp Gln Gly Trp Tyr Cys Thr Asn Ala Gly Ser Thr Ala Tyr Tyr
305                 310                 315                 320

Pro Asn Lys Asp Asp Cys Glu Val Arg Asp Tyr Val Phe Cys Asp
                325                 330                 335

Thr Ala Gly Ile Asn Val Ala Leu Glu Val Glu Gln Cys Asn Tyr
            340                 345                 350

Asn Ile Ser Thr Ser Lys Tyr Pro Cys Lys Val Ser Thr Gly Arg His
            355                 360                 365

Pro Val Ser Met Val Ala Leu Thr Pro Leu Gly Gly Leu Val Ser Cys
    370                 375                 380

Tyr Glu Ser Val Ser Cys Ser Ile Gly Ser Asn Lys Val Gly Ile Ile
385                 390                 395                 400

Lys Gln Leu Gly Lys Gly Cys Thr His Ile Pro Asn Asn Glu Ala Asp
                405                 410                 415

Thr Ile Thr Ile Asp Asn Thr Val Tyr Gln Leu Ser Lys Val Val Gly
            420                 425                 430

Glu Gln Arg Thr Ile Lys Gly Ala Pro Val Val Asn Asn Phe Asn Pro
    435                 440                 445

Ile Leu Phe Pro Glu Asp Gln Phe Asn Val Ala Leu Asp Gln Val Phe
    450                 455                 460

Glu Ser Ile Asp Arg Ser Gln Asp Leu Ile Asp Lys Ser Asn Asp Leu
465                 470                 475                 480
```

-continued

```
Leu Gly Ala Asp Ala Lys Ser Lys Ala Gly Ile Ala Ile Ala Ile Val
                485                 490                 495
Val Leu Val Ile Leu Gly Ile Phe Phe Leu Leu Ala Val Ile Tyr Tyr
            500                 505                 510
Cys Ser Arg Val Arg Lys Thr Lys Pro Lys His Asp Tyr Pro Ala Thr
            515                 520                 525
Thr Gly His Ser Ser Met Ala Tyr Val Ser
            530                 535

<210> SEQ ID NO 23
<211> LENGTH: 542
<212> TYPE: PRT
<213> ORGANISM: Avian pneumovirus B

<400> SEQUENCE: 23

Gly Ala Ser Lys Met Tyr Leu Lys Leu Leu Ile Ile Tyr Leu Val
1               5                   10                  15
Val Gly Ala Ser Gly Lys Ile Gln Glu Thr Tyr Ser Glu Glu Ser Cys
            20                  25                  30
Ser Thr Val Thr Arg Gly Tyr Lys Ser Val Leu Arg Thr Gly Trp Tyr
            35                  40                  45
Thr Asn Val Phe Asn Leu Glu Ile Gly Asn Val Glu Asn Ile Thr Cys
        50                  55                  60
Asn Asp Gly Pro Ser Leu Ile Ser Thr Glu Leu Ser Leu Thr Gln Asn
65                  70                  75                  80
Ala Leu Gln Glu Leu Arg Thr Val Ser Ala Asp Gln Ile Thr Lys Glu
                85                  90                  95
Asn Arg Ile Leu Ser His Arg Lys Lys Arg Phe Val Leu Gly Ala Ile
            100                 105                 110
Ala Leu Gly Val Ala Thr Thr Ala Ala Val Thr Ala Gly Val Ala Leu
            115                 120                 125
Ala Lys Thr Ile Arg Leu Glu Gly Glu Val Lys Ala Ile Lys Leu Ala
        130                 135                 140
Leu Arg Ser Thr Asn Glu Ala Val Ser Thr Leu Gly Asn Gly Val Arg
145                 150                 155                 160
Ile Leu Ala Thr Ala Val Asn Asp Leu Lys Glu Phe Ile Ser Lys Lys
                165                 170                 175
Leu Thr Pro Ala Ile Asn Gln Asn Lys Cys Asn Ile Ala Asp Ile Arg
            180                 185                 190
Met Ala Ile Ser Phe Gly Gln Asn Asn Arg Arg Phe Leu Asn Val Val
            195                 200                 205
Arg Gln Phe Ser Asp Ser Ala Gly Ile Thr Ser Ala Val Ser Leu Asp
        210                 215                 220
Leu Met Thr Asp Ala Glu Leu Val Lys Ala Ile Asn Arg Met Pro Thr
225                 230                 235                 240
Ser Ser Gly Gln Ile Ser Leu Met Leu Asn Asn Arg Ala Met Val Arg
                245                 250                 255
Arg Lys Gly Phe Gly Ile Leu Ile Gly Val Tyr Gly Gly Thr Val Val
            260                 265                 270
Tyr Met Val Gln Leu Pro Ile Phe Gly Val Ile Glu Thr Pro Cys Trp
            275                 280                 285
Arg Val Val Ala Ala Pro Leu Cys Arg His Glu Arg Glu Ser Tyr Ala
        290                 295                 300
Cys Leu Leu Arg Glu Asp Gln Gly Trp Tyr Cys Thr Asn Ala Gly Ser
305                 310                 315                 320
```

```
Thr Ala Tyr Tyr Pro Asn Glu Asp Asp Cys Glu Val Arg Asp Asp Tyr
            325                 330                 335

Val Phe Cys Asp Thr Ala Ala Gly Ile Asn Val Ala Ser Glu Val Glu
            340                 345                 350

Gln Cys Asn His Asn Ile Ser Thr Ser Thr Tyr Pro Cys Lys Val Ser
            355                 360                 365

Thr Gly Arg His Pro Val Ser Met Val Ala Leu Thr Pro Leu Gly Gly
            370                 375                 380

Leu Val Ser Cys Tyr Glu Gly Val Ser Cys Ser Ile Gly Ser Asn Lys
385                 390                 395                 400

Val Gly Ile Ile Lys Gln Leu Asn Lys Gly Cys Thr His Ile Pro Asn
            405                 410                 415

Asn Glu Ala Asp Thr Ile Thr Ile Asp Asn Thr Ile Tyr Gln Leu Ser
            420                 425                 430

Lys Val Val Gly Glu Gln Arg Thr Ile Lys Gly Ala Pro Val Val Asn
            435                 440                 445

Asn Phe Asn Pro Leu Leu Phe Pro Glu Asp Gln Phe Asn Val Ala Leu
            450                 455                 460

Asp Gln Val Phe Glu Ser Val Asp Lys Ser Lys Asp Leu Ile Asp Lys
465                 470                 475                 480

Ser Asn Asp Leu Leu Asp Ile Glu Val Lys Ser Asn Ile Gly Ala Ala
            485                 490                 495

Leu Ala Ile Thr Ile Leu Val Val Leu Ser Met Leu Ile Ile Val Gly
            500                 505                 510

Ile Ala Tyr Tyr Val Val Lys Lys Arg Lys Ala Lys Thr Ser Asn Gly
            515                 520                 525

Tyr Pro Lys Thr Thr Gly Gln Ser Asn Met Gly Tyr Ile Ser
            530                 535                 540

<210> SEQ ID NO 24
<211> LENGTH: 537
<212> TYPE: PRT
<213> ORGANISM: Avian pneumovirus C

<400> SEQUENCE: 24

Met Ser Trp Lys Val Val Leu Leu Val Leu Leu Ala Thr Pro Thr
1               5                   10                  15

Gly Gly Leu Glu Glu Ser Tyr Leu Glu Glu Ser Tyr Ser Thr Val Thr
            20                  25                  30

Arg Gly Tyr Leu Ser Val Leu Arg Thr Gly Trp Tyr Thr Asn Val Phe
            35                  40                  45

Thr Leu Glu Val Gly Asp Val Glu Asn Leu Thr Cys Thr Asp Gly Pro
        50                  55                  60

Ser Leu Ile Arg Thr Glu Leu Glu Leu Thr Lys Asn Ala Leu Glu Glu
65                  70                  75                  80

Leu Lys Thr Val Ser Ala Asp Gln Leu Ala Lys Glu Ala Arg Ile Met
            85                  90                  95

Ser Pro Arg Lys Ala Arg Phe Val Leu Gly Ala Ile Ala Leu Gly Val
            100                 105                 110

Ala Thr Ala Ala Ala Val Thr Ala Gly Val Ala Ile Ala Lys Thr Ile
            115                 120                 125

Arg Leu Glu Gly Glu Val Ala Ala Ile Lys Gly Ala Leu Arg Lys Thr
            130                 135                 140

Asn Glu Ala Val Ser Thr Leu Gly Asn Gly Val Arg Val Leu Ala Thr
```

```
            145                 150                 155                 160
Ala Val Asn Asp Leu Lys Asp Phe Ile Ser Lys Lys Leu Thr Pro Ala
                165                 170                 175

Ile Asn Arg Asn Lys Cys Asp Ile Ser Asp Leu Lys Met Ala Val Ser
                180                 185                 190

Phe Gly Gln Tyr Asn Arg Arg Phe Leu Asn Val Val Arg Gln Phe Ser
                195                 200                 205

Asp Asn Ala Gly Ile Thr Pro Ala Ile Ser Leu Asp Leu Met Thr Asp
            210                 215                 220

Ala Glu Leu Val Arg Ala Val Ser Asn Met Pro Thr Ser Ser Gly Gln
225                 230                 235                 240

Ile Asn Leu Met Leu Glu Asn Arg Ala Met Val Arg Arg Lys Gly Phe
                245                 250                 255

Gly Ile Leu Ile Gly Val Tyr Gly Ser Ser Val Val Tyr Ile Val Gln
                260                 265                 270

Leu Pro Ile Phe Gly Val Ile Asp Thr Pro Cys Trp Lys Val Lys Ala
                275                 280                 285

Ala Pro Leu Cys Ser Gly Lys Asp Gly Asn Tyr Ala Cys Leu Leu Arg
                290                 295                 300

Glu Asp Gln Gly Trp Tyr Cys Gln Asn Ala Gly Ser Thr Val Tyr Tyr
305                 310                 315                 320

Pro Asn Glu Glu Asp Cys Glu Val Arg Ser Asp His Val Phe Cys Asp
                325                 330                 335

Thr Ala Ala Gly Ile Asn Val Ala Lys Glu Ser Glu Glu Cys Asn Arg
                340                 345                 350

Asn Ile Ser Thr Thr Lys Tyr Pro Cys Lys Val Ser Thr Gly Arg His
                355                 360                 365

Pro Ile Ser Met Val Ala Leu Ser Pro Leu Gly Ala Leu Val Ala Cys
                370                 375                 380

Tyr Asp Gly Met Ser Cys Ser Ile Gly Ser Asn Lys Val Gly Ile Ile
385                 390                 395                 400

Arg Pro Leu Gly Lys Gly Cys Ser Tyr Ile Ser Asn Gln Asp Ala Asp
                405                 410                 415

Thr Val Thr Ile Asp Asn Thr Val Tyr Gln Leu Ser Lys Val Glu Gly
                420                 425                 430

Glu Gln His Thr Ile Lys Gly Lys Pro Val Ser Ser Asn Phe Asp Pro
                435                 440                 445

Ile Glu Phe Pro Glu Asp Gln Phe Asn Ile Ala Leu Asp Gln Val Phe
450                 455                 460

Glu Ser Val Glu Lys Ser Gln Asn Leu Ile Asp Gln Ser Asn Lys Ile
465                 470                 475                 480

Leu Asp Ser Ile Glu Lys Gly Asn Ala Gly Phe Val Ile Val Ile Val
                485                 490                 495

Leu Ile Val Leu Leu Met Leu Ala Ala Val Gly Val Gly Val Phe Phe
                500                 505                 510

Val Val Lys Lys Arg Lys Ala Ala Pro Lys Phe Pro Met Glu Met Asn
                515                 520                 525

Gly Val Asn Asn Lys Gly Phe Ile Pro
                530                 535

<210> SEQ ID NO 25
<211> LENGTH: 574
<212> TYPE: PRT
<213> ORGANISM: Bovine respiratory syncytial virus
```

<400> SEQUENCE: 25

Met Ala Thr Thr Ala Met Arg Met Ile Ile Ser Ile Ile Phe Ile Ser
1               5                   10                  15

Thr Tyr Val Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Val Glu Leu Gln Ser Leu
                85                  90                  95

Met Gln Asn Glu Pro Ala Ser Phe Ser Arg Ala Lys Arg Gly Ile Pro
            100                 105                 110

Glu Leu Ile His Tyr Thr Arg Asn Ser Thr Lys Lys Phe Tyr Gly Leu
        115                 120                 125

Met Gly Lys Lys Arg Lys Arg Arg Phe Leu Gly Phe Leu Leu Gly Ile
    130                 135                 140

Gly Ser Ala Val Ala Ser Gly Val Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Glu Leu Leu Pro Gln Val Asn
        195                 200                 205

Asn His Asp Cys Arg Ile Ser Asn Ile Glu Thr Val Ile Glu Phe Gln
    210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Val Val Lys Glu Glu Val Ile Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asp Asn Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Thr Glu Thr Cys Lys Val Gln Ser Asn Arg Val Phe Cys Asp
        355                 360                 365

Thr Met Asn Ser Leu Thr Leu Pro Thr Asp Val Asn Leu Cys Asn Thr
    370                 375                 380

Asp Ile Phe Asn Thr Lys Tyr Asp Cys Lys Ile Met Thr Ser Lys Thr
385                 390                 395                 400

Asp Ile Ser Ser Ser Val Ile Thr Ser Ile Gly Ala Ile Val Ser Cys

-continued

```
                    405                 410                 415
Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
        450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
            500                 505                 510

Leu His Ser Val Asp Val Gly Lys Ser Thr Thr Asn Val Val Ile Thr
        515                 520                 525

Thr Ile Ile Ile Val Ile Val Val Ile Leu Met Leu Ile Ala Val
530                 535                 540

Gly Leu Leu Phe Tyr Cys Lys Thr Lys Ser Thr Pro Ile Met Leu Gly
545                 550                 555                 560

Lys Asp Gln Leu Ser Gly Ile Asn Asn Leu Ser Phe Ser Lys
                565                 570
```

<210> SEQ ID NO 26
<211> LENGTH: 574
<212> TYPE: PRT
<213> ORGANISM: Human respiratory syncytial virus

<400> SEQUENCE: 26

```
Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205
```

Gln Gln Ser Cys Arg Ile Ser Asn Ile Glu Thr Val Ile Glu Phe Gln
210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Ser Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Asp Thr Cys Lys Val Gln Ser Asn Arg Val Phe Cys Asp
    355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Leu Glu Gly
450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Arg Ser Asp Glu Leu
        500                 505                 510

Leu His Asn Val Asn Thr Gly Lys Ser Thr Thr Asn Ile Met Ile Thr
    515                 520                 525

Thr Ile Ile Ile Val Ile Ile Val Val Leu Leu Ser Leu Ile Ala Ile
530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
            565                 570

<210> SEQ ID NO 27
<211> LENGTH: 537
<212> TYPE: PRT
<213> ORGANISM: Pneumonia virus of mice

<400> SEQUENCE: 27

Met Ile Pro Gly Arg Ile Phe Leu Val Leu Val Ile Phe Asn Thr
1               5                   10                  15

```
Lys Pro Ile His Pro Asn Thr Leu Thr Glu Lys Tyr Tyr Glu Ser Thr
             20                  25                  30

Cys Ser Val Glu Thr Ala Gly Tyr Lys Ser Ala Leu Arg Thr Gly Trp
             35                  40                  45

His Met Thr Val Met Ser Ile Lys Leu Ser Gln Ile Asn Ile Glu Ser
 50                  55                  60

Cys Lys Ser Ser Asn Ser Leu Leu Ala His Glu Leu Ala Ile Tyr Ser
 65                  70                  75                  80

Ser Ala Val Asp Glu Leu Arg Thr Leu Ser Ser Asn Ala Leu Lys Ser
                 85                  90                  95

Lys Arg Lys Lys Arg Phe Leu Gly Leu Ile Leu Gly Leu Gly Ala Ala
            100                 105                 110

Val Thr Ala Gly Val Ala Leu Ala Lys Thr Val Gln Leu Glu Ser Glu
            115                 120                 125

Ile Ala Leu Ile Arg Asp Ala Val Arg Asn Thr Asn Glu Ala Val Val
            130                 135                 140

Ser Leu Thr Asn Gly Met Ser Val Leu Ala Lys Val Val Asp Asp Leu
145                 150                 155                 160

Lys Asn Phe Ile Ser Lys Glu Leu Leu Pro Lys Ile Asn Arg Val Ser
                165                 170                 175

Cys Asp Val His Asp Ile Thr Ala Val Ile Arg Phe Gln Gln Leu Asn
            180                 185                 190

Lys Arg Leu Leu Glu Val Ser Arg Glu Phe Ser Ser Asn Ala Gly Leu
            195                 200                 205

Thr His Thr Val Ser Ser Phe Met Leu Thr Asp Arg Glu Leu Thr Ser
            210                 215                 220

Ile Val Gly Gly Met Ala Val Ser Ala Gly Gln Lys Glu Ile Met Leu
225                 230                 235                 240

Ser Ser Lys Ala Ile Met Arg Arg Asn Gly Leu Ala Ile Leu Ser Ser
                245                 250                 255

Val Asn Ala Asp Thr Leu Val Tyr Val Ile Gln Leu Pro Leu Phe Gly
            260                 265                 270

Val Met Asp Thr Asp Cys Trp Val Ile Arg Ser Ser Ile Asp Cys His
            275                 280                 285

Asn Ile Ala Asp Lys Tyr Ala Cys Leu Ala Arg Ala Asp Asn Gly Trp
            290                 295                 300

Tyr Cys His Asn Ala Gly Ser Leu Ser Tyr Phe Pro Ser Pro Thr Asp
305                 310                 315                 320

Cys Glu Ile His Asn Gly Tyr Ala Phe Cys Asp Thr Leu Lys Ser Leu
                325                 330                 335

Thr Val Pro Val Thr Ser Arg Glu Cys Asn Ser Asn Met Tyr Thr Thr
            340                 345                 350

Asn Tyr Asp Cys Lys Ile Ser Thr Ser Lys Thr Tyr Val Ser Thr Ala
            355                 360                 365

Val Leu Thr Thr Met Gly Cys Leu Val Ser Cys Tyr Gly His Asn Ser
            370                 375                 380

Cys Thr Val Ile Asn Asn Asp Lys Gly Ile Ile Arg Thr Leu Pro Asp
385                 390                 395                 400

Gly Cys His Tyr Ile Ser Asn Lys Gly Val Asp Arg Val Gln Val Gly
                405                 410                 415

Asn Thr Val Tyr Tyr Leu Ser Lys Glu Val Gly Lys Ser Ile Val Val
            420                 425                 430
```

```
Arg Gly Glu Pro Leu Val Leu Lys Tyr Asp Pro Leu Ser Phe Pro Asp
            435                 440                 445

Asp Lys Phe Asp Val Ala Ile Arg Asp Val Glu His Ser Ile Asn Gln
450                 455                 460

Thr Arg Thr Phe Phe Lys Ala Ser Asp Gln Leu Leu Asp Leu Ser Glu
465                 470                 475                 480

Asn Arg Glu Asn Lys Asn Leu Asn Lys Ser Tyr Ile Leu Thr Thr Leu
                485                 490                 495

Leu Phe Val Val Met Leu Ile Ile Met Ala Val Ile Gly Phe Ile
                500                 505                 510

Leu Tyr Lys Val Leu Lys Met Ile Arg Asp Asn Lys Leu Lys Ser Lys
                515                 520                 525

Ser Thr Pro Gly Leu Thr Val Leu Ser
            530                 535

<210> SEQ ID NO 28
<211> LENGTH: 269
<212> TYPE: PRT
<213> ORGANISM: Human metapneumovirus 00-1

<400> SEQUENCE: 28

Thr Val Asn Val Tyr Leu Pro Asp Ser Tyr Leu Lys Gly Val Ile Ser
1               5                   10                  15

Phe Ser Glu Thr Asn Ala Ile Gly Ser Cys Leu Leu Lys Arg Pro Tyr
                20                  25                  30

Leu Lys Asn Asp Asn Thr Ala Lys Val Ala Ile Glu Asn Pro Val Ile
            35                  40                  45

Glu His Val Arg Leu Lys Asn Ala Val Asn Ser Lys Met Lys Ile Ser
50                  55                  60

Asp Tyr Lys Ile Val Glu Pro Val Asn Met Gln His Glu Ile Met Lys
65                  70                  75                  80

Asn Val His Ser Cys Glu Leu Thr Leu Leu Lys Gln Phe Leu Thr Arg
                85                  90                  95

Ser Lys Asn Ile Ser Thr Leu Lys Leu Asn Met Ile Cys Asp Trp Leu
                100                 105                 110

Gln Leu Lys Ser Thr Ser Asp Asp Thr Ser Ile Leu Ser Phe Ile Asp
            115                 120                 125

Val Glu Phe Ile Pro Ser Trp Val Ser Asn Trp Phe Ser Asn Trp Tyr
130                 135                 140

Asn Leu Asn Lys Leu Ile Leu Glu Phe Arg Lys Glu Glu Val Ile Arg
145                 150                 155                 160

Thr Gly Ser Ile Leu Cys Arg Ser Leu Gly Lys Leu Val Phe Val Val
                165                 170                 175

Ser Ser Tyr Gly Cys Ile Val Lys Ser Asn Lys Ser Lys Arg Val Ser
                180                 185                 190

Phe Phe Thr Tyr Asn Gln Leu Leu Thr Trp Lys Asp Val Met Leu Ser
            195                 200                 205

Arg Phe Asn Ala Asn Phe Cys Ile Trp Val Ser Asn Ser Leu Asn Glu
210                 215                 220

Asn Gln Glu Gly Leu Gly Leu Arg Ser Asn Leu Gln Gly Ile Leu Thr
225                 230                 235                 240

Asn Lys Leu Tyr Glu Thr Val Asp Tyr Met Leu Ser Leu Cys Cys Asn
                245                 250                 255

Glu Gly Phe Ser Leu Val Lys Glu Phe Glu Gly Phe Ile
                260                 265
```

<210> SEQ ID NO 29
<211> LENGTH: 249
<212> TYPE: PRT
<213> ORGANISM: Avian pneumovirus A

<400> SEQUENCE: 29

Met Glu Ile Ser Asn Glu Ser Val Val Asn Val Tyr Leu Pro Asp Ser
1               5                   10                  15

Tyr Leu Lys Gly Val

-continued

Leu Glu Glu Pro Thr Tyr Phe Gln Ser Leu Leu Met Thr Tyr Lys Ser
                85                  90                  95

Leu Ser Thr Ser Glu Leu Ile Thr Thr Thr Leu Phe Lys Lys Ile
            100                 105                 110

Ile Arg Arg Ala Ile Glu Ile Ser Asp Val Lys Val Tyr Ala Ile Leu
        115                 120                 125

Asn Lys Leu Gly Leu Lys Glu Lys Gly Lys Val Asp Arg Cys Asp Asp
130                 135                 140

Thr Asn Thr Thr Leu Ser Asn Ile Val Arg Asp Asn Ile Leu Ser Val
145                 150                 155                 160

Ile Ser Asp Asn Thr Pro Ser Thr Lys Lys Pro Asn Asn Ser Ser Cys
                165                 170                 175

Lys Pro Asp Gln Pro Ile Lys Thr Thr Ile Leu Cys Lys Leu Leu Ser
            180                 185                 190

Ser Met Ser His Pro Pro Thr Trp Leu Ile His Trp Phe Asn Leu Tyr
        195                 200                 205

Thr Lys Leu Asn Asp Ile Leu Thr Gln Tyr Arg Thr Asn Glu Ala Arg
    210                 215                 220

Asn His Gly Tyr Ile Leu Ile Asp Thr Arg Thr Leu Gly Glu Phe Gln
225                 230                 235                 240

Phe Ile Leu Asn Gln Tyr Gly Cys Ile Val Tyr His Lys Lys Leu Lys
                245                 250                 255

Lys Ile Thr Ile Thr Thr Tyr Asn Gln Phe Leu Thr Trp Lys Asp Ile
            260                 265                 270

Ser Leu Ser Arg Leu Asn Val Cys Met Ile Thr Trp Ile Ser Asn Cys
        275                 280                 285

Leu Asn Thr Leu Asn Lys Ser Leu Gly Leu Arg Cys
    290                 295                 300

<210> SEQ ID NO 31
<211> LENGTH: 300
<212> TYPE: PRT
<213> ORGANISM: Respiratory syncytial virus

<400> SEQUENCE: 31

Met Asp Pro Ile Ile Asn Gly Asn Ser Ala Asn Val Tyr Leu Thr Asp
1               5                   10                  15

Ser Tyr Leu Lys Gly Val Ile Ser Phe Ser Glu Cys Asn Ala Leu Gly
            20                  25                  30

Ser Tyr Ile Phe Asn Gly Pro Tyr Leu Lys Asn Asp Tyr Thr Asn Leu
        35                  40                  45

Ile Ser Arg Gln Asn Pro Leu Ile Glu His Ile Asn Leu Lys Lys Leu
    50                  55                  60

Asn Ile Thr Gln Ser Leu Met Ser Lys Tyr His Lys Gly Glu Ile Lys
65                  70                  75                  80

Ile Glu Glu Pro Thr Tyr Phe Gln Ser Leu Leu Met Thr Tyr Lys Ser
                85                  90                  95

Met Thr Ser Leu Glu Gln Ile Thr Thr Thr Asn Leu Leu Lys Lys Ile
            100                 105                 110

Ile Arg Arg Ala Ile Glu Ile Ser Asp Val Lys Val Tyr Ala Ile Leu
        115                 120                 125

Asn Lys Leu Gly Leu Lys Glu Lys Asp Lys Ile Lys Ser Asn Asn Gly
    130                 135                 140

Gln Asp Glu Asp Asn Ser Val Ile Thr Thr Ile Ile Lys Asp Asp Ile

-continued

```
145                 150                 155                 160

Leu Leu Ala Val Lys Asp Asn Gln Ser His Leu Lys Ala Val Lys Asn
                165                 170                 175

His Ser Thr Lys Gln Lys Asp Thr Ile Lys Thr Thr Leu Leu Lys Lys
            180                 185                 190

Leu Met Cys Ser Met Gln His Pro Pro Ser Trp Leu Ile His Trp Phe
        195                 200                 205

Asn Leu Tyr Thr Lys Leu Asn Asn Ile Leu Thr Gln Tyr Arg Ser Ser
    210                 215                 220

Glu Val Lys Asn His Gly Phe Ile Leu Ile Asp Asn His Thr Leu Asn
225                 230                 235                 240

Gly Phe Gln Phe Ile Leu Asn Gln Tyr Gly Cys Ile Val Tyr His Lys
                245                 250                 255

Glu Leu Lys Arg Ile Thr Val Thr Thr Tyr Asn Gln Phe Leu Thr Trp
            260                 265                 270

Lys Asn Ile Ser Leu Ser Arg Leu Asn Val Cys Leu Ile Thr Trp Ile
        275                 280                 285

Ser Asn Cys Leu Asn Thr Leu Asn Lys Ser Leu Gly
    290                 295                 300

<210> SEQ ID NO 32
<211> LENGTH: 108
<212> TYPE: PRT
<213> ORGANISM: Human metapneumovirus 00-1

<400> SEQUENCE: 32

Lys Leu Val Asp Lys Ile Thr Ser Asp Gln His Ile Phe Ser Pro Asp
1               5                   10                  15

Lys Ile Asp Met Leu Thr Leu Gly Lys Met Leu Met Pro Thr Ile Lys
            20                  25                  30

Gly Gln Lys Thr Asp Gln Phe Leu Asn Lys Arg Glu Asn Tyr Phe His
        35                  40                  45

Gly Asn Asn Leu Ile Glu Ser Leu Ser Ala Ala Leu Ala Cys His Trp
    50                  55                  60

Cys Gly Ile Leu Thr Glu Gln Cys Ile Glu Asn Asn Ile Phe Lys Lys
65                  70                  75                  80

Asp Trp Gly Asp Gly Phe Ile Ser Asp His Ala Phe Met Asp Phe Lys
                85                  90                  95

Ile Phe Leu Cys Val Phe Lys Thr Lys Leu Leu Cys
            100                 105

<210> SEQ ID NO 33
<211> LENGTH: 110
<212> TYPE: PRT
<213> ORGANISM: Avian pneumovirus A

<400> SEQUENCE: 33

Phe Lys Ser Val Arg Lys Ile Val Thr Asp Gln His Ile Phe Asn Pro
1               5                   10                  15

Asp His Ile Asp Leu Val Met Leu Gly Lys Leu Leu Leu Pro Thr Val
            20                  25                  30

Arg Ser Asn Ile Asn Asn Asn Lys Pro Ala Thr Glu Asn Phe Phe Asn
        35                  40                  45

Gly Asn Asn Ile Val Glu Ala Leu Thr Ser Cys Leu Ala Cys His Trp
    50                  55                  60

Cys Thr Val Leu Ile Leu Leu Thr Thr Glu Asn Ser Ile Phe Gln Lys
```

```
                65                  70                  75                  80
Glu Trp Gly Asp Gly Phe Ile Thr Asp His Ala Phe Ile Asn Phe Thr
                    85                  90                  95

Trp Phe Leu Met Ser Phe Lys Thr Tyr Leu Leu Cys His Trp
                100                 105                 110

<210> SEQ ID NO 34
<211> LENGTH: 110
<212> TYPE: PRT
<213> ORGANISM: Bovine respiratory syncytial virus

<400> SEQUENCE: 34

Ile Cys Lys Leu Asn Gln Val Ile Gln Lys Gln His Met Phe Leu Pro
1               5                   10                  15

Asp Lys Ile Ser Leu Ser Gln Tyr Val Glu Leu Phe Leu Ser Asn Lys
            20                  25                  30

Thr Leu Lys Asn Ser Pro His Ile Ser Ser Asn Leu Val Leu Val His
        35                  40                  45

Lys Met Ser Asp Tyr Phe Leu His Lys Tyr Val Leu Ser Thr Asn Leu
    50                  55                  60

Ala Gly His Trp Ile Met Ile Gln Leu Met Lys Asp Ser Lys Gly
65                  70                  75                  80

Ile Phe Glu Lys Asp Trp Gly Glu Gly Tyr Ile Thr Asp His Met Phe
                85                  90                  95

Leu Asp Leu Asn Val Phe Phe Asp Ala Tyr Lys Thr Tyr Leu
                100                 105                 110

<210> SEQ ID NO 35
<211> LENGTH: 110
<212> TYPE: PRT
<213> ORGANISM: Respiratory syncytial virus

<400> SEQUENCE: 35

Asp Ile His Lys Leu Lys Gln Val Ile Gln Lys Gln His Met Phe Leu
1               5                   10                  15

Pro Asp Lys Ile Ser Leu Thr Gln Tyr Val Glu Leu Phe Leu Ser Asn
            20                  25                  30

Lys Thr Leu Lys Ser Gly Ser His Val Asn Ser Asn Leu Ile Leu Ala
        35                  40                  45

His Lys Ile Ser Asp Tyr Phe His Asn Thr Tyr Ile Leu Ser Thr Asn
    50                  55                  60

Leu Ala Gly His Trp Ile Leu Ile Gln Leu Met Lys Asp Ser Lys Gly
65                  70                  75                  80

Ile Phe Glu Lys Asp Trp Gly Glu Gly Tyr Ile Thr Asp His Met
                85                  90                  95

Phe Ile Asn Leu Lys Val Phe Phe Asn Ala Tyr Lys Thr Tyr
                100                 105                 110

<210> SEQ ID NO 36
<211> LENGTH: 4739
<212> TYPE: DNA
<213> ORGANISM: Human metapneumovirus 00-1

<400> SEQUENCE: 36
acgcgtataa attagattca aaaaatatg  ggacaagtga aaatgtctct tcaagggatt        60
cacctgagtg atttatcata caagcatgct atattaaaag agtctcagta cacaataaaa       120
agagatgtgg gtacaacaac tgcagtgaca ccctcatcat tgcaacaaga aataacactg       180
```

```
ttgtgtggag aaattctgta tgctaaacat gctgactaca aatatgctgc agaaatagga      240
atacaatata ttagcacagc tttaggatca gagagagtgc agcagattct gaggaactca      300
ggcagtgaag tccaagtggt cttaaccaga acgtactctc tggggaaaat taaaaacaat      360
aaaggagaag atttacagat gttagacata cacggggtag agaagagctg ggtagaagag      420
atagacaaag aagcaaggaa aacwatggca accttgctta aggaatcatc aggtaatatc      480
ccacaaaatc agaggccctc agcaccagac acacccataa tcttattatg tgtaggtgcc      540
ttaatattca ctaaactagc atcaaccata gaagtgggac tagagaccac agtcagaagg      600
gctaaccgtg tactaagtga tgcactcaag agatacccta gaatggacat accaaagatt      660
gccagatcct tctatgactt atttgaacaa aaagtgtatc acagaagttt gttcattgag      720
tatggcaaag cattaggctc atcatctaca ggcagcaaag cagaaagtct atttgttaat      780
atattcatgc aagcttatgg ggccggtcaa acaatgctaa ggtgggggt cattgccagg      840 tcatccaaca atataatgtt aggacatgta tccgtccaag ctgagttaaa acaggtcaca      900
gaagtctatg acttggtgcg agaaatgggc cctgaatctg gacttctaca tttaaggcaa      960
agcccaaaag ctggactgtt atcactagcc aactgtccca actttgcaag tgttgttctc      1020
ggaaatgcct caggcttagg cataatcggt atgtatcgag ggagagtacc aaacacagaa      1080
ttattttcag cagctgaaag ttatgccaaa agtttgaaag aaagcaataa aataaatttc      1140
tcttcattag gacttacaga tgaagagaaa gaggctgcag aacatttctt aaatgtgagt      1200
gacgacagtc aaaatgatta tgagtaatta aaaaagtggg acaagtcaaa atgtcattcc      1260
ctgaaggaaa agatattctt ttcatgggta atgaagcagc aaaattagca gaagctttcc      1320
agaaatcatt aagaaaacca ggtcataaaa gatctcaatc tattatagga gaaaaagtga      1380
atactgtatc agaaacattg gaattaccta ctatcagtag acctgcaaaa ccaaccatac      1440
cgtcagaacc aaagttagca tggacagata aaggtgggc aaccaaaact gaaataaagc      1500
aagcaatcaa agtcatggat cccattgaag aagaagagtc taccgagaag aaggtgctac      1560
cctccagtga tgggaaaacc cctgcagaaa agaaactgaa accatcaact aacaccaaaa      1620
agaaggtttc atttacacca aatgaaccag ggaaatatac aaagttggaa aaagatgctc      1680
tagatttgct ctcagataat gaagaagaag atgcagaatc ttcaatctta accttgaag      1740 aaagagatac ttcatcatta agcattgagg ccagattgga atcaatagag gagaaattaa      1800
gcatgatatt agggctatta agaacactca acattgctac agcaggaccc acagcagcaa      1860
gagatgggat cagagatgca atgattggcg taagagagga attaatagca gacataataa      1920
aggaagctaa agggaaagca gcagaaatga tggaagagga aatgaktcaa cgatcaaaaa      1980
taggaaatgg tagtgtaaaa ttaacagaaa aagcaaaaga gctcaacaaa attgttgaag      2040
atgaaagcac aagtggagaa tccgaagaag aagaagaacc aaaagacaca caagacaata      2100
gtcaagaaga tgacatttac cagttaatta tgtagtttaa taaaataaa caatgggaca      2160 agtaaaaatg gagtcctacc tagtagacac ctatcaaggc attccttaca cagcagctgt      2220
tcaagttgat ctaatagaaa aggacctgtt acctgcaagc ctaacaatat ggttcccttt      2280
gtttcaggcc aacacaccac cagcagtgct gctcgatcag ctaaaaaccc tgacaataac      2340
cactctgtat gctgcatcac aaaatggtcc aatactcaaa gtgaatgcat cagcccaagg      2400
tgcagcaatg tttgtacttc ccaaaaaatt tgaagtcaat gcgactgtag camtcgatga      2460
atatagcaaa ctggaatttg acaaactcac agtctgtgaa gtaaaaacag tttacttaac      2520
```

-continued

| | |
|---|---|
| aaccatgaaa ccatacggga tggtatcaaa atttgtgagc tcagccaaat cagttggcaa | 2580 |
| aaaaacacat gatctaatcg cactatgtga ttttatggat ctagaaaaga acacacctgt | 2640 |
| tacaatacca gcattcatca aatcagtttc aatcaaagag agtgagtcag ctactgttga | 2700 |
| agctgctata agcagtgaag cagaccaagc tctaacacag gccaaaattg caccttatgc | 2760 |
| gggattaatt atgatcatga ctatgaacaa tcccaaaggc atattcaaaa agcttggagc | 2820 |
| tgggactcaa gtcatagtag aactaggagc atatgtccag gctgaaagca taagcaaaat | 2880 |
| atgcaagact tggagccatc aagggacaag atatgtcttg aagtccagat aacaaccaag | 2940 |
| caccttggcc aagagctact aaccctatct catagatcat aaagtcacca ttctagttat | 3000 |
| ataaaaatca agttagaaca agaattaaat caatcaagaa cgggacaaat aaaaatgtct | 3060 |
| tggaaagtgg tgatcakttt ttcattgtta ataacacctc racacggtct aaagagagc | 3120 |
| tacttagaag agtcatgtag cactataact gaaggatatc tcagtgttct gaggacaggt | 3180 |
| tggtacacca atgtttttac actggaggta ggcgatgtag agaaccttac atgtgccgat | 3240 |
| ggacccagct taataaaaac agaattagac ctgaccaaaa gtgcactaag agagctcaga | 3300 |
| acagtttctg ctgatcaact ggcaagagag gagcaaattg aaaatcccag acaatctaga | 3360 |
| ttcgttctag gagcaatagc actcggtgtt gcaactgcag ctgcagttac agcaggtgtt | 3420 |
| gcaattgcca aaaccatccg gcttgaaagt gaagtaacag caattaagaa tgccctcaaa | 3480 |
| aagaccaatg aagcagtatc tacattgggg aatggagttc gtgtgttggc aactgcagtg | 3540 |
| agagaactga agattttgt gagcaagaat ctaacacgtg caatcaacaa aaacaagtgc | 3600 |
| gacattgctg acctgaaaat ggccgttagc ttcagtcaat tcaacagaag gttcctaaat | 3660 |
| gttgtgcggc aattttcaga caacgctgga ataacaccag caatatcttt ggacttaatg | 3720 |
| acagatgctg aactagccag agctgtttcc aacatgccaa catctgcagg acaaataaaa | 3780 |
| ctgatgttgg agaaccgtgc aatggtaaga agaaaagggt tcggattcct gataggagtt | 3840 |
| tacgaagct ccgtaattya catggtgcaa ctgccaatct ttgggggttat agacacgcct | 3900 |
| tgctggatag taaaagcagc cccttcttgt tcaggaaaaa agggaaacta tgcttgcctc | 3960 |
| ttaagagaag accaaggatg gtattgtcaa aatgcagggt caactgttta ctacccaaat | 4020 |
| gaaaaagact gtgaaacaag aggagaccat gtcttttgcg acacagcagc aggaatcaat | 4080 |
| gttgctgagc agtcaargga gtgcaacata aacatatcta ctactaatta cccatgcaaa | 4140 |
| gttagcacag gaagacatcc tatcagtatg gttgcactat ctcctcttgg ggctytggtt | 4200 |
| gcttgctaca agggagtgag ctgttccatt ggcagcaaca gagtagggat catcaagcaa | 4260 |
| ctgaacaaag gctgctctta tataaccaac caagacgcag acacagtgac aatagacaac | 4320 |
| actgtatacc agctaagcaa agttgaaggc aacagcatg ttataaaagg aaggccagtg | 4380 |
| tcaagcagct ttgacccagt caagtttcct gaagatcaat tcaatgttgc acttgaccaa | 4440 |
| gttttcgaga gcattgagaa cagtcaggcc ttggtggatc aatcaaacag aatcctaagc | 4500 |
| agtgcagaga aaggaaacac tggcttcatc attgtaataa ttctaattgc tgtccttggc | 4560 |
| tctaccatga tcctagtgag tgttttttatc ataataaaga aaacaaagag acccacagga | 4620 |
| gcacctccag agctgagtgg tgtcacaaac aatggcttca tacccacataa ttagttaatt | 4680 |
| aaaaataaat taaataaat taaattaaa aataaaaatt tgggacaaat cataatgtc | 4739 |

<210> SEQ ID NO 37
<211> LENGTH: 399
<212> TYPE: PRT
<213> ORGANISM: Human metapneumovirus 00-1

<400> SEQUENCE: 37

```
Met Gly Gln Val Lys Met Ser Leu Gln Gly Ile His Leu Ser Asp Leu
1               5                   10                  15

Ser Tyr Lys His Ala Ile Leu Lys Glu Ser Gln Tyr Thr Ile Lys Arg
            20                  25                  30

Asp Val Gly Thr Thr Ala Val Thr Pro Ser Ser Leu Gln Gln Glu
        35                  40                  45

Ile Thr Leu Leu Cys Gly Glu Ile Leu Tyr Ala Lys His Ala Asp Tyr
    50                  55                  60

Lys Tyr Ala Ala Glu Ile Gly Ile Gln Tyr Ile Ser Thr Ala Leu Gly
65                  70                  75                  80

Ser Glu Arg Val Gln Gln Ile Leu Arg Asn Ser Gly Ser Glu Val Gln
                85                  90                  95

Val Val Leu Thr Arg Thr Tyr Ser Leu Gly Lys Ile Lys Asn Asn Lys
            100                 105                 110

Gly Glu Asp Leu Gln Met Leu Asp Ile His Gly Val Glu Lys Ser Trp
        115                 120                 125

Val Glu Glu Ile Asp Lys Glu Ala Arg Lys Thr Met Ala Thr Leu Leu
130                 135                 140

Lys Glu Ser Ser Gly Asn Ile Pro Gln Asn Gln Arg Pro Ser Ala Pro
145                 150                 155                 160

Asp Thr Pro Ile Ile Leu Leu Cys Val Gly Ala Leu Ile Phe Thr Lys
                165                 170                 175

Leu Ala Ser Thr Ile Glu Val Gly Leu Glu Thr Thr Val Arg Arg Ala
            180                 185                 190

Asn Arg Val Leu Ser Asp Ala Leu Lys Arg Tyr Pro Arg Met Asp Ile
        195                 200                 205

Pro Lys Ile Ala Arg Ser Phe Tyr Asp Leu Phe Glu Gln Lys Val Tyr
210                 215                 220

His Arg Ser Leu Phe Ile Glu Tyr Gly Lys Ala Leu Gly Ser Ser Ser
225                 230                 235                 240

Thr Gly Ser Lys Ala Glu Ser Leu Phe Val Asn Ile Phe Met Gln Ala
                245                 250                 255

Tyr Gly Ala Gly Gln Thr Met Leu Arg Trp Gly Val Ile Ala Arg Ser
            260                 265                 270

Ser Asn Asn Ile Met Leu Gly His Val Ser Val Gln Ala Glu Leu Lys
        275                 280                 285

Gln Val Thr Glu Val Tyr Asp Leu Val Arg Glu Met Gly Pro Glu Ser
290                 295                 300

Gly Leu Leu His Leu Arg Gln Ser Pro Lys Ala Gly Leu Leu Ser Leu
305                 310                 315                 320

Ala Asn Cys Pro Asn Phe Ala Ser Val Leu Gly Asn Ala Ser Gly
                325                 330                 335

Leu Gly Ile Ile Gly Met Tyr Arg Gly Arg Val Pro Asn Thr Glu Leu
            340                 345                 350

Phe Ser Ala Ala Glu Ser Tyr Ala Lys Ser Leu Lys Glu Ser Asn Lys
        355                 360                 365

Ile Asn Phe Ser Ser Leu Gly Leu Thr Asp Glu Lys Glu Ala Ala
    370                 375                 380

Glu His Phe Leu Asn Val Ser Asp Asp Ser Gln Asn Asp Tyr Glu
385                 390                 395
```

<210> SEQ ID NO 38
<211> LENGTH: 781
<212> TYPE: DNA
<213> ORGANISM: Human metapneumovirus 00-1

<400> SEQUENCE: 38

```
caagaaaaaa actgttccac tgttaatgtc tatcttcctg actcatatct taaaggagtg      60
atttccttta gtgagactaa tgcaattggt tcatgtctct taaaaagacc ttacctaaaa     120
aatgacaaca ctgcaaaagt tgccatagag aatcctgtta tcgagcatgt tagactcaaa     180
aatgcagtca attctaagat gaaaatatca gattacaaga tagtagagcc agtaaacatg     240
caacatgaaa ttatgaagaa tgtacacagt tgtgagctca cattattaaa acagttttta     300
acaaggagta aaaatattag cactctcaaa ttaaatatga tatgtgattg gctgcagtta     360
aagtctacat cagatgatac ctcaatccta agtttatag atgtagaatt tatacctagc      420
tgggtaagca attggtttag taattggtac aatctcaaca agttgattct ggaattcagg     480
aaagaagaag taataagaac tggttcaatc ttgtgtaggt cattgggtaa attagttttt     540
gttgtatcat catatggatg tatagtcaag agcaacaaaa gcaaagagt gagcttcttc      600
acatacaatc aactgttaac atggaaagat gtgatgttaa gtagattcaa tgcaaatttt     660
tgtatatggg taagcaacag tctgaatgaa atcaagaag gggtagggtt gagaagtaat       720
ttgcaaggca tattaactaa taagctatat gaaactgtag attatatgct tagtttatgt     780
t                                                                     781
```

<210> SEQ ID NO 39
<211> LENGTH: 260
<212> TYPE: PRT
<213> ORGANISM: Human metapneumovirus 00-1

<400> SEQUENCE: 39

```
Gln Glu Lys Asn Cys Ser Thr Val Asn Val Tyr Leu Pro Asp Ser Tyr
1               5                   10                  15
Leu Lys Gly Val Ile Ser Phe Ser Glu Thr Asn Ala Ile Gly Ser Cys
            20                  25                  30
Leu Leu Lys Arg Pro Tyr Leu Lys Asn Asp Asn Thr Ala Lys Val Ala
        35                  40                  45
Ile Glu Asn Pro Val Ile Glu His Val Arg Leu Lys Asn Ala Val Asn
    50                  55                  60
Ser Lys Met Lys Ile Ser Asp Tyr Lys Ile Val Glu Pro Val Asn Met
65                  70                  75                  80
Gln His Glu Ile Met Lys Asn Val His Ser Cys Glu Leu Thr Leu Leu
                85                  90                  95
Lys Gln Phe Leu Thr Arg Ser Lys Asn Ile Ser Thr Leu Lys Leu Asn
            100                 105                 110
Met Ile Cys Asp Trp Leu Gln Leu Lys Ser Thr Ser Asp Asp Thr Ser
        115                 120                 125
Ile Leu Ser Phe Ile Asp Val Glu Phe Ile Pro Ser Trp Val Ser Asn
    130                 135                 140
Trp Phe Ser Asn Trp Tyr Asn Leu Asn Lys Leu Ile Leu Glu Phe Arg
145                 150                 155                 160
Lys Glu Glu Val Ile Arg Thr Gly Ser Ile Leu Cys Arg Ser Leu Gly
                165                 170                 175
Lys Leu Val Phe Val Val Ser Ser Tyr Gly Cys Ile Val Lys Ser Asn
            180                 185                 190
```

```
Lys Ser Lys Arg Val Ser Phe Phe Thr Tyr Asn Gln Leu Leu Thr Trp
        195                 200                 205
Lys Asp Val Met Leu Ser Arg Phe Asn Ala Asn Phe Cys Ile Trp Val
    210                 215                 220
Ser Asn Ser Leu Asn Glu Asn Gln Glu Gly Val Gly Leu Arg Ser Asn
225                 230                 235                 240
Leu Gln Gly Ile Leu Thr Asn Lys Leu Tyr Glu Thr Val Asp Tyr Met
                245                 250                 255
Leu Ser Leu Cys
            260

<210> SEQ ID NO 40
<211> LENGTH: 327
<212> TYPE: DNA
<213> ORGANISM: Human metapneumovirus 00-1

<400> SEQUENCE: 40
ataagctagt agataagata acttctgatc aacatatctt cagtccagac aaaatagata      60
tgttaacact ggggaaaatg ctcatgccca ctataaaagg tcagaaaaca gatcagttcc     120
tgaacaagag agagaattat ttccatggga ataatcttat tgagtctttg tcagcagcgt     180
tagcatgtca ttggtgtggg atattaacag agcaatgtat agaaaataat attttcaaga     240
aagactgggg tgacgggttc atatcggatc atgcttttat ggacttcaaa atattcctat     300
gtgtctttaa aactaaactt ttatgta                                         327

<210> SEQ ID NO 41
<211> LENGTH: 108
<212> TYPE: PRT
<213> ORGANISM: Human metapneumovirus 00-1

<400> SEQUENCE: 41

Lys Leu Val Asp Lys Ile Thr Ser Asp Gln His Ile Phe Ser Pro Asp
1               5                   10                  15
Lys Ile Asp Met Leu Thr Leu Gly Lys Met Leu Met Pro Thr Ile Lys
            20                  25                  30
Gly Gln Lys Thr Asp Gln Phe Leu Asn Lys Arg Glu Asn Tyr Phe His
        35                  40                  45
Gly Asn Asn Leu Ile Glu Ser Leu Ser Ala Ala Leu Ala Cys His Trp
    50                  55                  60
Cys Gly Ile Leu Thr Glu Gln Cys Ile Glu Asn Asn Ile Phe Lys Lys
65                  70                  75                  80
Asp Trp Gly Asp Gly Phe Ile Ser Asp His Ala Phe Met Asp Phe Lys
                85                  90                  95
Ile Phe Leu Cys Val Phe Lys Thr Lys Leu Leu Cys
            100                 105

<210> SEQ ID NO 42
<211> LENGTH: 391
<212> TYPE: PRT
<213> ORGANISM: Human respiratory syncytial virus A

<400> SEQUENCE: 42

Met Ala Leu Ser Lys Val Lys Leu Asn Asp Thr Leu Asn Lys Asp Gln
1               5                   10                  15

Leu Leu Ser Ser Ser Lys Tyr Thr Ile Gln Arg Ser Thr Gly Asp Ser
            20                  25                  30

Ile Asp Thr Pro Asn Tyr Asp Val Gln Lys His Ile Asn Lys Leu Cys
```

```
            35                  40                  45
Gly Met Leu Leu Ile Thr Glu Asp Ala Asn His Lys Phe Thr Gly Leu
         50                  55                  60

Ile Gly Met Leu Tyr Ala Met Ser Arg Leu Gly Arg Glu Asp Thr Ile
 65                  70                  75                  80

Lys Ile Leu Arg Asp Ala Gly Tyr His Val Lys Ala Asn Gly Val Asp
                 85                  90                  95

Val Thr Thr His Arg Gln Asp Ile Asn Gly Lys Glu Met Lys Phe Glu
                100                 105                 110

Val Leu Thr Leu Ala Ser Leu Thr Thr Glu Ile Gln Ile Asn Ile Glu
            115                 120                 125

Ile Glu Ser Arg Lys Ser Tyr Lys Lys Met Leu Lys Glu Met Gly Glu
        130                 135                 140

Val Ala Pro Glu Tyr Arg His Asp Ser Pro Asp Cys Gly Met Ile Ile
145                 150                 155                 160

Leu Cys Ile Ala Ala Leu Val Ile Thr Lys Leu Ala Ala Gly Asp Arg
                165                 170                 175

Ser Gly Leu Thr Ala Val Ile Arg Arg Ala Asn Asn Val Leu Lys Asn
            180                 185                 190

Glu Met Lys Arg Tyr Lys Gly Leu Leu Pro Lys Asp Ile Ala Asn Ser
        195                 200                 205

Phe Tyr Glu Val Phe Glu Lys His Pro His Phe Ile Asp Val Phe Val
210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ala Gly Gln Val
                245                 250                 255

Met Leu Arg Trp Gly Val Leu Ala Lys Ser Val Lys Asn Ile Met Leu
            260                 265                 270

Gly His Ala Ser Val Gln Ala Glu Met Glu Gln Val Val Glu Val Tyr
        275                 280                 285

Glu Tyr Ala Gln Lys Leu Gly Gly Glu Ala Gly Phe Tyr His Ile Leu
    290                 295                 300

Asn Asn Pro Lys Ala Ser Leu Leu Ser Leu Thr Gln Phe Pro His Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
            340                 345                 350

Tyr Ala Glu Gln Leu Lys Glu Asn Gly Val Ile Asn Tyr Ser Val Leu
        355                 360                 365

Asp Leu Thr Ala Glu Glu Leu Glu Ala Ile Lys His Gln Leu Asn Pro
    370                 375                 380

Lys Asp Asn Asp Val Glu Leu
385                 390

<210> SEQ ID NO 43
<211> LENGTH: 279
<212> TYPE: PRT
<213> ORGANISM: Avian pneumovirus B

<400> SEQUENCE: 43

Met Ser Leu Pro Glu Gly Lys Asp Ile Leu Met Met Gly Ser Glu Ala
 1               5                  10                  15
```

```
Ala Lys Leu Ala Glu Ala Tyr Gln Gln Ser Ile Lys Asn Ser Thr Ser
            20                  25                  30

Val Arg Arg Ser Ile Ser Gly Asp Pro Val Ser Thr Val Ser Glu Lys
        35                  40                  45

Val Pro Leu Pro Pro Leu Cys Ser Ser Glu Thr Ser Arg Gly Ala Cys
50                  55                  60

Ile Arg Pro Thr Lys Ser Thr Leu Pro Pro Ile Lys Glu Val Glu Ser
65                  70                  75                  80

Ile Tyr Pro Lys Leu Pro Thr Ala Pro Pro Asp Ala Met Ile Glu Thr
                85                  90                  95

Ala His Pro Ile Gly Ala Pro Lys Lys Ala Gln Lys Arg Val Lys Phe
            100                 105                 110

Glu Ser Ser Lys Ala Gly Lys Tyr Thr Lys Leu Glu Glu Glu Ala Leu
        115                 120                 125

Glu Leu Leu Ser Asp Pro Asp Glu Asp Asn Asp Glu Lys Ser Ser Val
130                 135                 140

Leu Thr Phe Glu Glu Lys Asp Asn Ala Pro Ser Ser Ile Glu Ala Arg
145                 150                 155                 160

Leu Glu Ala Ile Glu Glu Lys Leu Ser Met Ile Leu Gly Met Leu Lys
                165                 170                 175

Thr Leu Ser Ile Ala Thr Ala Gly Pro Thr Ala Ala Arg Asp Gly Ile
            180                 185                 190

Arg Asp Ala Met Val Gly Val Arg Glu Glu Leu Ile Asn Ser Ile Met
        195                 200                 205

Ala Glu Ala Lys Gly Lys Ile Ala Glu Ile Ile Lys Glu Glu Asp Ala
210                 215                 220

Gln Arg Ala Lys Ile Gly Asp Gly Ser Val Lys Leu Thr Glu Lys Ala
225                 230                 235                 240

Arg Glu Leu Asn Arg Met Leu Glu Asp Gln Ser Ser Ser Gly Glu Ser
                245                 250                 255

Glu Thr Glu Ser Glu Glu Thr Ser Pro Asp Thr Asp Gly Glu Asn Asp
            260                 265                 270

Asp Ile Tyr Ser Phe Asp Met
            275

<210> SEQ ID NO 44
<211> LENGTH: 241
<212> TYPE: PRT
<213> ORGANISM: Human respiratory syncytial virus A

<400> SEQUENCE: 44

Met Glu Lys Phe Ala Pro Glu Phe His Gly Glu Asp Ala Asn Asn Arg
1               5                   10                  15

Ala Thr Lys Phe Leu Glu Ser Ile Lys Gly Lys Phe Thr Ser Pro Lys
            20                  25                  30

Asp Pro Lys Lys Lys Asp Ser Ile Ile Ser Val Asn Ser Ile Asp Ile
        35                  40                  45

Glu Val Thr Lys Glu Ser Pro Ile Thr Ser Asn Ser Thr Ile Ile Asn
    50                  55                  60

Pro Thr Asn Glu Thr Asp Asp Thr Ala Gly Asn Lys Pro Asn Tyr Gln
65                  70                  75                  80

Arg Lys Pro Leu Val Ser Phe Lys Glu Asp Pro Thr Pro Ser Asp Asn
                85                  90                  95

Pro Phe Ser Lys Leu Tyr Lys Glu Thr Ile Glu Thr Phe Asp Asn Asn
            100                 105                 110
```

```
Glu Glu Glu Ser Ser Tyr Ser Tyr Glu Glu Ile Asn Asp Gln Thr Asn
            115                 120                 125

Asp Asn Ile Thr Ala Arg Leu Asp Arg Ile Asp Glu Lys Leu Ser Glu
        130                 135                 140

Ile Leu Gly Met Leu His Thr Leu Val Val Ala Ser Ala Gly Pro Thr
145                 150                 155                 160

Ser Ala Arg Asp Gly Ile Arg Asp Ala Met Ile Gly Leu Arg Glu Glu
                165                 170                 175

Met Ile Glu Lys Ile Arg Thr Glu Ala Leu Met Thr Asn Asp Arg Leu
                180                 185                 190

Glu Ala Met Ala Arg Leu Arg Asn Glu Glu Ser Glu Lys Met Ala Lys
            195                 200                 205

Asp Thr Ser Asp Glu Val Ser Leu Asn Pro Thr Ser Glu Lys Leu Asn
        210                 215                 220

Asn Leu Leu Glu Gly Asn Asp Ser Asp Asn Asp Leu Ser Leu Glu Asp
225                 230                 235                 240

Phe

<210> SEQ ID NO 45
<211> LENGTH: 256
<212> TYPE: PRT
<213> ORGANISM: Human respiratory syncytial virus A

<400> SEQUENCE: 45

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Lys Asp Leu Thr Met Lys Thr Leu Asn Pro Thr His Asp Ile Ile
130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
210                 215                 220

Asp Leu Gly Ala Tyr Leu Glu Lys Glu Ser Ile Tyr Tyr Val Thr Thr
225                 230                 235                 240
```

```
Asn Trp Lys His Thr Ala Thr Arg Phe Ala Ile Lys Pro Met Glu Asp
            245                 250                 255

<210> SEQ ID NO 46
<211> LENGTH: 574
<212> TYPE: PRT
<213> ORGANISM: Human respiratory syncytial virus A

<400> SEQUENCE: 46

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
```

```
                355                 360                 365
Thr Met Asn Ser Leu Thr Leu Pro Ser Glu Ile Asn Leu Cys Asn Val
        370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Met Asp
                435                 440                 445
Thr Val Ser Val Gly Asn Thr Leu Tyr Tyr Val Asn Lys Gln Glu Gly
        450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
            500                 505                 510
Leu His Asn Val Asn Ala Gly Lys Ser Thr Thr Asn Ile Met Ile Thr
                515                 520                 525
Thr Ile Ile Ile Val Ile Ile Val Ile Leu Leu Ser Leu Ile Ala Val
        530                 535                 540
Gly Leu Leu Leu Tyr Cys Lys Ala Arg Ser Thr Pro Val Thr Leu Ser
545                 550                 555                 560
Lys Asp Gln Leu Ser Gly Ile Asn Asn Ile Ala Phe Ser Asn
                565                 570

<210> SEQ ID NO 47
<211> LENGTH: 187
<212> TYPE: PRT
<213> ORGANISM: Human metapneumovirus

<400> SEQUENCE: 47

Met Ser Arg Lys Ala Pro Cys Lys Tyr Glu Val Arg Gly Lys Cys Asn
1               5                   10                  15
Arg Gly Ser Glu Cys Lys Phe Asn His Asn Tyr Trp Ser Trp Pro Asp
            20                  25                  30
Arg Tyr Leu Leu Ile Arg Ser Asn Tyr Leu Leu Asn Gln Leu Leu Arg
        35                  40                  45
Asn Thr Asp Arg Ala Asp Gly Leu Ser Ile Ile Ser Gly Ala Gly Arg
    50                  55                  60
Glu Asp Arg Thr Gln Asp Phe Val Leu Gly Ser Thr Asn Val Val Gln
65                  70                  75                  80
Gly Tyr Ile Asp Asp Asn Gln Ser Ile Thr Lys Ala Ala Ala Cys Tyr
                85                  90                  95
Ser Leu His Asn Ile Ile Lys Gln Leu Gln Glu Val Glu Val Arg Gln
            100                 105                 110
Ala Arg Asp Asn Lys Leu Ser Asp Ser Lys His Val Ala Leu His Asn
        115                 120                 125
Leu Val Leu Ser Tyr Met Glu Met Ser Lys Thr Pro Ala Ser Leu Ile
    130                 135                 140
Asn Asn Leu Lys Arg Leu Pro Arg Glu Lys Leu Lys Lys Leu Ala Lys
145                 150                 155                 160
```

Leu Ile Ile Asp Leu Ser Ala Gly Ala Glu Asn Asp Ser Ser Tyr Ala
                165                 170                 175

Leu Gln Asp Ser Glu Ser Thr Asn Gln Val Gln
        180                 185

<210> SEQ ID NO 48
<211> LENGTH: 184
<212> TYPE: PRT
<213> ORGANISM: Avian pneumovirus C

<400> SEQUENCE: 48

Met Ser Arg Lys Ala Pro Cys Lys Tyr Glu Val Arg Gly Lys Cys Asn
1               5                   10                  15

Arg Gly Ser Glu Cys Lys Phe Asn His Asn Tyr Trp Ser Trp Pro Asp
            20                  25                  30

Arg Tyr Leu Leu Leu Arg Ser Asn Tyr Leu Leu Asn Gln Leu Leu Arg
        35                  40                  45

Asn Thr Asp Arg Ser Asp Gly Leu Ser Leu Ile Ser Gly Ala Gly Arg
    50                  55                  60

Asp Asp Arg Thr Gln Asp Phe Val Leu Gly Ser Thr Asn Val Val Gln
65                  70                  75                  80

Asn Tyr Ile Asp Asn Asn Glu Asn Ile Thr Lys Ala Ser Thr Cys Tyr
                85                  90                  95

Ser Leu Tyr Asn Ile Ile Lys Gln Leu Gln Glu Thr Asp Val Arg Gln
            100                 105                 110

Ala Arg Asp Asn Lys Val Asp Asp Ser Lys His Val Ala Leu His Asn
        115                 120                 125

Leu Val Leu Ser Tyr Met Glu Met Ser Lys Thr Pro Ala Ser Leu Ile
    130                 135                 140

Asn Asn Leu Lys Lys Leu Pro Lys Glu Lys Leu Lys Lys Leu Ala Lys
145                 150                 155                 160

Leu Ile Ile Glu Leu Ser Ala Gly Val Glu Asn Asp Ser Thr Ala Ala
                165                 170                 175

Met Gln Asp Ser Ala Asn Ser Asp
            180

<210> SEQ ID NO 49
<211> LENGTH: 186
<212> TYPE: PRT
<213> ORGANISM: Avian pneumovirus B

<400> SEQUENCE: 49

Met Ser Gly Arg Asn Pro Cys Arg Tyr Glu Thr Arg Gly Arg Cys Asn
1               5                   10                  15

Arg Gly Ser Ser Cys Thr Phe Asn His Asn Tyr Trp Ser Trp Pro Asp
            20                  25                  30

His Val Leu Leu Val Arg Ala Asn Tyr Met Leu Asn Gln Leu Val Arg
        35                  40                  45

Asn Thr Asp Arg Thr Asp Gly Leu Ser Leu Ile Ser Gly Ala Gly Arg
    50                  55                  60

Glu Asp Arg Thr Gln Asp Phe Val Leu Gly Ser Ala Asn Val Val Gln
65                  70                  75                  80

Asn Tyr Ile Glu Gly Asn Ala Thr Ile Thr Lys Ser Ala Ala Cys Tyr
                85                  90                  95

Ser Leu Tyr Asn Ile Ile Lys Gln Leu Gln Glu Asn Asp Val Lys Ser
            100                 105                 110

-continued

```
Ala Arg Asp Leu Met Val Asp Pro Lys His Val Ala Leu His Asn
        115                 120                 125

Leu Val Leu Ser Tyr Ile Asp Met Ser Lys Asn Pro Ala Asn Leu Ile
130                 135                 140

Asn Ser Leu Lys Arg Leu Pro Lys Glu Lys Leu Lys Lys Leu Ala Lys
145                 150                 155                 160

Ile Ile Ile Gln Leu Ser Ala Gly Ser Glu Gly Glu Asn Ala Asn Ser
                165                 170                 175

Asn Thr Leu Gln Lys Gly Asp Ser Ser Asn
            180                 185

<210> SEQ ID NO 50
<211> LENGTH: 186
<212> TYPE: PRT
<213> ORGANISM: Turkey rhinotracheitis virus A

<400> SEQUENCE: 50

Met Ser Arg Arg Asn Pro Cys Arg Tyr Glu Ile Arg Gly Lys Cys Asn
1               5                   10                  15

Arg Gly Ser Ser Cys Thr Phe Asn His Asn Tyr Trp Ser Trp Pro Asp
                20                  25                  30

His Val Leu Leu Val Arg Ala Asn Tyr Met Leu Asn Gln Leu Leu Arg
            35                  40                  45

Asn Thr Asp Arg Thr Asp Gly Leu Ser Leu Ile Ser Gly Ala Gly Arg
50                  55                  60

Glu Asp Arg Thr Gln Asp Phe Val Leu Gly Ser Ala Asn Val Val Gln
65                  70                  75                  80

Asn Tyr Ile Glu Gly Asn Thr Thr Ile Thr Lys Ser Ala Ala Cys Tyr
                85                  90                  95

Ser Leu Tyr Asn Ile Ile Lys Gln Leu Gln Glu Asn Asp Val Lys Thr
            100                 105                 110

Ser Arg Asp Ser Met Leu Glu Asp Pro Lys His Val Ala Leu His Asn
        115                 120                 125

Leu Ile Leu Ser Tyr Val Asp Met Ser Lys Asn Pro Ala Ser Leu Ile
130                 135                 140

Asn Ser Leu Lys Arg Leu Pro Arg Glu Lys Leu Lys Lys Leu Ala Lys
145                 150                 155                 160

Ile Ile Leu Gln Leu Ser Ala Gly Pro Glu Ser Asp Asn Ala Ser Gly
                165                 170                 175

Asn Thr Leu Gln Lys Gly Asp Ser Asn Asn
            180                 185

<210> SEQ ID NO 51
<211> LENGTH: 194
<212> TYPE: PRT
<213> ORGANISM: Human respiratory syncytial virus A

<400> SEQUENCE: 51

Met Ser Arg Arg Asn Pro Cys Lys Phe Glu Ile Arg Gly His Cys Leu
1               5                   10                  15

Asn Gly Lys Arg Cys His Phe Ser His Asn Tyr Phe Glu Trp Pro Pro
                20                  25                  30

His Ala Leu Leu Val Arg Gln Asn Phe Met Leu Asn Arg Ile Leu Lys
            35                  40                  45

Ser Met Asp Lys Ser Ile Asp Thr Leu Ser Glu Ile Ser Gly Ala Ala
50                  55                  60
```

```
Glu Leu Asp Arg Thr Glu Glu Tyr Ala Leu Gly Val Val Gly Val Leu
 65                  70                  75                  80

Glu Ser Tyr Ile Gly Ser Ile Asn Asn Ile Thr Lys Gln Ser Ala Cys
             85                  90                  95

Val Ala Met Ser Lys Leu Leu Thr Glu Leu Asn Ser Asp Asp Ile Lys
            100                 105                 110

Lys Leu Arg Asp Asn Glu Glu Leu Asn Ser Pro Lys Ile Arg Val Tyr
            115                 120                 125

Asn Thr Val Ile Ser Tyr Ile Glu Ser Asn Arg Lys Asn Asn Lys Gln
            130                 135                 140

Thr Ile His Leu Leu Lys Arg Leu Pro Ala Asp Val Leu Lys Lys Thr
145                 150                 155                 160

Ile Lys Asn Thr Leu Asp Ile His Lys Ser Ile Thr Ile Asn Asn Pro
                165                 170                 175

Lys Glu Ser Thr Val Ser Asp Thr Asn Asp His Ala Lys Asn Asn Asp
            180                 185                 190

Thr Thr
```

<210> SEQ ID NO 52
<211> LENGTH: 195
<212> TYPE: PRT
<213> ORGANISM: Human respiratory syncytial virus B

<400> SEQUENCE: 52

```
Met Ser Arg Arg Asn Pro Cys Lys Phe Glu Ile Arg Gly His Cys Leu
  1               5                  10                  15

Asn Gly Arg Arg Cys His Tyr Ser His Asn Tyr Phe Glu Trp Pro Pro
             20                  25                  30

His Ala Leu Leu Val Arg Gln Asn Phe Met Leu Asn Lys Ile Leu Lys
             35                  40                  45

Ser Met Asp Lys Ser Ile Asp Thr Leu Ser Glu Ile Ser Gly Ala Ala
         50                  55                  60

Glu Leu Asp Arg Thr Glu Glu Tyr Ala Leu Gly Ile Val Gly Val Leu
 65                  70                  75                  80

Glu Ser Tyr Ile Gly Ser Ile Asn Asn Ile Thr Lys Gln Ser Ala Cys
             85                  90                  95

Val Ala Met Ser Lys Leu Leu Ile Glu Ile Asn Ser Asp Asp Ile Lys
            100                 105                 110

Lys Leu Arg Asp Asn Glu Glu Pro Asn Ser Pro Lys Ile Arg Val Tyr
            115                 120                 125

Asn Thr Val Ile Ser Tyr Ile Glu Ser Asn Arg Lys Asn Asn Lys Gln
            130                 135                 140

Thr Ile His Leu Leu Lys Arg Leu Pro Ala Asp Val Leu Lys Lys Thr
145                 150                 155                 160

Ile Lys Asn Thr Leu Asp Ile His Lys Ser Ile Ile Ile Ser Asn Pro
                165                 170                 175

Lys Glu Ser Thr Val Asn Asp Gln Asn Asp Gln Thr Lys Asn Asn Asp
            180                 185                 190

Ile Thr Gly
        195
```

<210> SEQ ID NO 53
<211> LENGTH: 186
<212> TYPE: PRT
<213> ORGANISM: bovine respiratory syncytial virus

```
<400> SEQUENCE: 53

Met Ser Arg Arg Asn Pro Cys Lys Tyr Glu Ile Arg Gly His Cys Leu
1               5                   10                  15

Asn Gly Lys Lys Cys His Phe Ser His Asn Tyr Phe Glu Trp Pro Pro
            20                  25                  30

His Ala Leu Leu Val Arg Gln Asn Phe Met Leu Asn Lys Ile Leu Lys
        35                  40                  45

Ser Met Asp Arg Asn Asn Asp Thr Leu Ser Glu Ile Ser Gly Ala Ala
50                  55                  60

Glu Leu Asp Arg Thr Glu Glu Tyr Ala Leu Gly Val Ile Gly Val Leu
65                  70                  75                  80

Glu Ser Tyr Leu Gly Ser Ile Asn Asn Ile Thr Lys Gln Ser Ala Cys
                85                  90                  95

Val Ala Met Ser Lys Leu Leu Ala Glu Ile Asn Asn Asp Asp Ile Lys
            100                 105                 110

Arg Leu Arg Asn Lys Glu Val Pro Thr Ser Pro Lys Ile Arg Ile Tyr
        115                 120                 125

Asn Thr Val Ile Ser Tyr Ile Asp Ser Asn Lys Arg Asn Thr Lys Gln
130                 135                 140

Thr Ile His Leu Leu Lys Arg Leu Pro Ala Asp Val Leu Lys Lys Thr
145                 150                 155                 160

Ile Lys Asn Thr Ile Asp Ile His Asn Glu Ile Asn Gly Asn Asn Gln
                165                 170                 175

Gly Asp Ile Ile Val Asn Glu Gln Asn Glu
            180                 185

<210> SEQ ID NO 54
<211> LENGTH: 176
<212> TYPE: PRT
<213> ORGANISM: Pneumonia virus of mice

<400> SEQUENCE: 54

Met Ser Val Arg Pro Cys Lys Phe Glu Val Gln Gly Phe Cys Ser Arg
1               5                   10                  15

Gly Arg Asn Cys Lys Tyr Ser His Lys Tyr Trp Glu Trp Pro Leu Lys
            20                  25                  30

Thr Leu Met Leu Arg Gln Asn Tyr Met Leu Asn Arg Ile Tyr Arg Phe
        35                  40                  45

Leu Asp Thr Asn Thr Asp Ala Ile Ser Asp Val Ser Gly Phe Asp Ala
50                  55                  60

Pro Gln Arg Thr Ala Glu Tyr Ala Leu Gly Thr Ile Gly Val Leu Lys
65                  70                  75                  80

Ser Tyr Leu Glu Lys Thr Asn Asn Ile Thr Lys Ser Ile Ala Cys Gly
                85                  90                  95

Ser Leu Ile Thr Val Leu Gln Asn Leu Asp Val Gly Leu Val Ile Gln
            100                 105                 110

Ala Arg Asp Ser Asn Thr Glu Asp Thr Asn Tyr Leu Arg Ser Cys Asn
        115                 120                 125

Thr Ile Leu Ser Tyr Ile Asp Lys Ile Leu Lys Arg Gln Ile Ile
130                 135                 140

His Ile Leu Lys Arg Leu Pro Val Gly Val Leu Cys Asn Leu Ile Gln
145                 150                 155                 160

Ser Val Ile Ser Ile Glu Glu Lys Ile Asn Ser Ser Met Lys Thr Glu
                165                 170                 175
```

<210> SEQ ID NO 55
<211> LENGTH: 71
<212> TYPE: PRT
<213> ORGANISM: Human metapneumovirus

<400> SEQUENCE: 55

```
Met Thr Leu His Met Pro Cys Lys Thr Val Lys Ala Leu Ile Lys Cys
1               5                   10                  15

Ser Glu His Gly Pro Val Phe Ile Thr Ile Glu Val Asp Asp Met Ile
            20                  25                  30

Trp Thr His Lys Asp Leu Lys Glu Ala Leu Ser Asp Gly Ile Val Lys
        35                  40                  45

Ser His Thr Asn Ile Tyr Asn Cys Tyr Leu Glu Asn Ile Glu Ile Ile
    50                  55                  60

Tyr Val Lys Ala Tyr Leu Ser
65                  70
```

<210> SEQ ID NO 56
<211> LENGTH: 71
<212> TYPE: PRT
<213> ORGANISM: Avian pneumovirus C

<400> SEQUENCE: 56

```
Met Thr Leu Gln Leu Pro Cys Lys Ile Val Gln Thr Leu Ile Lys Cys
1               5                   10                  15

Gly Glu His Gly Leu Ile Phe Leu Lys Met Lys Leu Asp Asp Met Val
            20                  25                  30

Trp Thr Lys Asn Glu Leu Val Asp Ile Ile Ser Thr Glu Ile Val Lys
        35                  40                  45

Val His Ala Asn Ile Phe Lys Cys Arg Leu Glu Asp Ile Glu Ile Ile
    50                  55                  60

Tyr Val Lys Thr Phe Leu Ser
65                  70
```

<210> SEQ ID NO 57
<211> LENGTH: 73
<212> TYPE: PRT
<213> ORGANISM: Avian pneumovirus B

<400> SEQUENCE: 57

```
Met Pro Ile Val Ile Pro Cys Lys Arg Val Thr Ala Val Ile Arg Cys
1               5                   10                  15

Asn Thr Leu Gly Val Cys Leu Phe Lys Arg Thr Tyr Glu His Asn Ile
            20                  25                  30

Ile Asn Leu Gly Asp Leu Ile Glu Glu Val Ala Arg Met Ile Ile Ile
        35                  40                  45

Asp His Ile Asn Arg Lys Gln Cys Asn Glu Cys Arg Lys Asp Phe Glu
    50                  55                  60

Phe Val Ala Val Tyr Thr Ser Tyr Thr
65                  70
```

<210> SEQ ID NO 58
<211> LENGTH: 73
<212> TYPE: PRT
<213> ORGANISM: Turkey rhinotracheitis virus A

<400> SEQUENCE: 58

```
Met Pro Val Val Ile Pro Cys Arg Arg Val Thr Ala Ile Ile Lys Cys
1               5                   10                  15
```

```
Asn Ala Leu Gly Leu Cys Met Val Arg Lys Ile Tyr Asp Tyr Ser Ile
                20                  25                  30

Ala Ser Trp Ser Asp Leu Ile Glu Glu Val Ala Asn Met Val Leu Ile
        35                  40                  45

Asp His Ile Asn Arg Lys Gln Cys Val Glu Cys Arg Lys Asp Phe Glu
 50                  55                  60

Phe Ile Ala Ile Tyr Thr Ser Tyr Asn
 65                  70

<210> SEQ ID NO 59
<211> LENGTH: 90
<212> TYPE: PRT
<213> ORGANISM: Human respiratory syncytial virus A

<400> SEQUENCE: 59

Met Thr Met Pro Lys Ile Met Ile Leu Pro Asp Lys Tyr Pro Cys Ser
 1               5                   10                  15

Ile Thr Ser Ile Leu Ile Thr Ser Arg Cys Arg Val Thr Met Tyr Asn
                20                  25                  30

Gln Lys Asn Thr Leu Tyr Phe Asn Gln Asn Pro Asn Asn His Met Met
        35                  40                  45

Tyr Ser Pro Asn Gln Thr Phe Asn Glu Ile His Trp Thr Ser Gln Glu
 50                  55                  60

Leu Ile Asp Thr Ile Gln Asn Phe Leu Gln His Leu Gly Ile Ile Glu
 65                  70                  75                  80

Asp Ile Tyr Thr Ile Tyr Ile Leu Val Ser
                85                  90

<210> SEQ ID NO 60
<211> LENGTH: 90
<212> TYPE: PRT
<213> ORGANISM: Human respiratory syncytial virus B

<400> SEQUENCE: 60

Met Thr Lys Pro Lys Ile Met Ile Leu Pro Asp Lys Tyr Pro Cys Ser
 1               5                   10                  15

Ile Ser Ser Ile Leu Ile Ser Ser Glu Ser Met Ile Ala Thr Phe Asn
                20                  25                  30

His Lys Asn Ile Leu Gln Phe Asn His Asn Leu Asp Asn His Gln
        35                  40                  45

Arg Leu Leu Asn Asn Ile Phe Asp Glu Ile His Trp Thr Pro Lys Asn
 50                  55                  60

Leu Leu Asp Ala Thr Gln Gln Phe Leu Gln His Leu Asn Ile Pro Glu
 65                  70                  75                  80

Asp Ile Tyr Thr Ile Tyr Ile Leu Val Ser
                85                  90

<210> SEQ ID NO 61
<211> LENGTH: 90
<212> TYPE: PRT
<213> ORGANISM: Bovine respiratory syncytial virus

<400> SEQUENCE: 61

Met Asn Asn Ser Asn Ile Ile Ile Phe Pro Glu Lys Tyr Pro Cys Ser
 1               5                   10                  15

Ile Ser Ser Leu Leu Ile Lys Asn Glu Asn Asp Val Ile Val Leu Ser
                20                  25                  30
```

```
His Gln Asn Val Leu Asp Tyr Leu Gln Phe Gln Tyr Pro Cys Asn Met
        35                  40                  45

Tyr Ser Gln Asn His Met Leu Asp Asp Ile Tyr Trp Thr Ser Gln Glu
    50                  55                  60

Leu Ile Glu Asp Val Leu Lys Ile Leu His Leu Ser Gly Ile Ser Ile
65                  70                  75                  80

Ser Lys Tyr Val Ile Tyr Val Leu Val Leu
                85                  90

<210> SEQ ID NO 62
<211> LENGTH: 97
<212> TYPE: PRT
<213> ORGANISM: Pneumonia virus of mice
<400> SEQUENCE: 62

Met Gln Ser Asp Pro Ile Cys His Leu His Arg Gly Glu Asp Lys Phe
1               5                   10                  15

Phe Tyr Glu Asn Arg Met Ile Arg Leu Pro Lys Tyr Tyr Pro Ala Ile
            20                  25                  30

Leu His Lys Met Tyr Ile Ile Arg Val Asn Arg Asn Thr Tyr Asp Gly
        35                  40                  45

Ser Gly Pro Ser Thr Ile Ile Asp Ala Gly Lys Ser Val Val Trp Asn
    50                  55                  60

Arg Val Asp Val Ile Ala Cys Val Lys Glu Ala Leu Cys Cys Ile Glu
65                  70                  75                  80

Phe Ser Trp Asn Asn Gln Val Ile Ile Asp Phe Asp Tyr Ser Gln Ala
                85                  90                  95

Arg

<210> SEQ ID NO 63
<211> LENGTH: 183
<212> TYPE: PRT
<213> ORGANISM: Human metapneumovirus
<400> SEQUENCE: 63

Met Ile Thr Leu Asp Val Ile Lys Ser Asp Gly Ser Ser Lys Thr Cys
1               5                   10                  15

Thr His Leu Lys Lys Ile Ile Lys Asp His Ser Gly Lys Val Leu Ile
            20                  25                  30

Val Leu Lys Leu Ile Leu Ala Leu Leu Thr Phe Leu Thr Val Thr Ile
        35                  40                  45

Thr Ile Asn Tyr Ile Lys Val Glu Asn Asn Leu Gln Ile Cys Gln Ser
    50                  55                  60

Lys Thr Glu Ser Asp Lys Lys Asp Ser Ser Ser Asn Thr Thr Ser Val
65                  70                  75                  80

Thr Thr Lys Thr Thr Leu Asn His Asp Ile Thr Gln Tyr Phe Lys Ser
                85                  90                  95

Leu Ile Gln Arg Tyr Thr Asn Ser Ala Ile Asn Ser Asp Thr Cys Trp
            100                 105                 110

Lys Ile Asn Arg Asn Gln Cys Thr Asn Ile Thr Thr Tyr Lys Phe Leu
        115                 120                 125

Cys Phe Lys Ser Glu Asp Thr Lys Thr Asn Asn Cys Asp Lys Leu Thr
    130                 135                 140

Asp Leu Cys Arg Asn Lys Pro Lys Pro Ala Val Gly Val Tyr His Ile
145                 150                 155                 160

Val Glu Cys His Cys Ile Tyr Thr Val Lys Trp Lys Cys Tyr His Tyr
```

```
                        165           170           175

Pro Thr Asp Glu Thr Gln Ser
                180

<210> SEQ ID NO 64
<211> LENGTH: 236
<212> TYPE: PRT
<213> ORGANISM: Human metapneumovirus

<400> SEQUENCE: 64

Met Glu Val Lys Val Glu Asn Ile Arg Thr Ile Asp Met Leu Lys Ala
1               5                   10                  15

Arg Val Lys Asn Arg Val Ala Arg Ser Lys Cys Phe Lys Asn Ala Ser
            20                  25                  30

Leu Val Leu Ile Gly Ile Thr Thr Leu Ser Ile Ala Leu Asn Ile Tyr
        35                  40                  45

Leu Ile Ile Asn Tyr Lys Met Gln Lys Asn Thr Ser Glu Ser Glu His
    50                  55                  60

His Thr Ser Ser Ser Pro Met Glu Ser Ser Arg Glu Thr Pro Thr Val
65                  70                  75                  80

Pro Thr Asp Asn Ser Asp Thr Asn Ser Ser Pro Gln His Pro Thr Gln
                85                  90                  95

Gln Ser Thr Glu Gly Ser Thr Leu Tyr Phe Ala Ala Ser Ala Ser Ser
            100                 105                 110

Pro Glu Thr Glu Pro Thr Ser Thr Pro Asp Thr Thr Asn Arg Pro Pro
        115                 120                 125

Phe Val Asp Thr His Thr Thr Pro Pro Ser Ala Ser Arg Thr Lys Thr
    130                 135                 140

Ser Pro Ala Val His Thr Lys Asn Asn Pro Arg Thr Ser Ser Arg Thr
145                 150                 155                 160

His Ser Pro Pro Arg Ala Thr Arg Thr Ala Arg Arg Thr Thr Thr
                165                 170                 175

Leu Arg Thr Ser Ser Thr Arg Lys Arg Pro Ser Thr Ala Ser Val Gln
            180                 185                 190

Pro Asp Ile Ser Ala Thr Thr His Lys Asn Glu Glu Ala Ser Pro Ala
        195                 200                 205

Ser Pro Gln Thr Ser Ala Ser Thr Thr Arg Ile Gln Arg Lys Ser Val
    210                 215                 220

Glu Ala Asn Thr Ser Thr Thr Tyr Asn Gln Thr Ser
225                 230                 235

<210> SEQ ID NO 65
<211> LENGTH: 223
<212> TYPE: PRT
<213> ORGANISM: Human metapneumovirus

<400> SEQUENCE: 65

```
                65                  70                  75                  80
Arg Tyr His Met Gly Gly Ile Glu Gly Trp Cys Gln Lys Leu Trp Thr
                    85                  90                  95

Met Glu Ala Ile Ser Leu Leu Asp Val Val Ser Val Lys Thr Arg Cys
                    100                 105                 110

Gln Met Thr Ser Leu Leu Asn Gly Asp Asn Gln Ser Ile Asp Val Ser
                    115                 120                 125

Lys Pro Val Lys Leu Ser Glu Gly Leu Asp Glu Val Lys Ala Asp Tyr
                130                 135                 140

Ser Leu Ala Val Lys Met Leu Lys Glu Ile Arg Asp Ala Tyr Arg Asn
145                 150                 155                 160

Ile Gly His Lys Leu Lys Glu Gly Glu Thr Tyr Ile Ser Arg Asp Leu
                    165                 170                 175

Gln Phe Ile Ser Lys Val Ile Gln Ser Glu Gly Val Met His Pro Thr
                    180                 185                 190

Pro Ile Lys Lys Ile Leu Arg Val Gly Pro Trp Ile Asn Thr Ile Leu
                    195                 200                 205

Asp Asp Ile Lys Thr Ser Ala Glu Ser Ile Gly Ser Leu Cys Gln
                210                 215                 220

<210> SEQ ID NO 66
<211> LENGTH: 223
<212> TYPE: PRT
<213> ORGANISM: Avian pneumovirus A

<400> SEQUENCE: 66

Asn Tyr Ile Ala Arg Ala Ser Ile Val Thr Asp Leu Ser Lys Phe Asn
1               5                   10                  15

Gln Ala Phe Arg Tyr Glu Thr Thr Ser Val Cys Ala Asp Val Ala Asp
                20                  25                  30

Glu Leu His Gly Thr Gln Ser Leu Phe Cys Trp Leu His Leu Thr Val
                35                  40                  45

Ser Ser Thr Thr Met Ile Cys Thr Tyr Arg His Ala Pro Pro Asp Thr
        50                  55                  60

Gly Gly Ile Tyr Asp Ile Asp Gln Ile Pro Glu Gln Ser Gly Leu Tyr
65                  70                  75                  80

Arg Phe His Met Gly Gly Ile Glu Gly Trp Cys Gln Lys Met Trp Thr
                    85                  90                  95

Met Glu Ala Ile Ser Leu Leu Asp Val Val Ser Val Arg Asn Arg Val
                    100                 105                 110

Gln Leu Thr Ser Leu Leu Asn Gly Asp Asn Gln Ser Ile Asp Val Ser
                    115                 120                 125

Lys Pro Val Arg Leu Thr Gly Ala Gln Thr Glu Ile Gln Ala Asp Tyr
                130                 135                 140

Ser Leu Ala Ile Lys Met Leu Thr Ala Val Arg Asp Ala Tyr Tyr Asn
145                 150                 155                 160

Ile Gly His Lys Leu Lys Glu Gly Glu Thr Tyr Val Ser Arg Asp Leu
                    165                 170                 175

Gln Phe Met Ser Lys Thr Ile Gln Ser Glu Gly Val Met Tyr Pro Ala
                    180                 185                 190

Ala Ile Lys Lys Val Leu Arg Val Gly Pro Trp Ile Asn Thr Ile Leu
                    195                 200                 205

Asp Asp Ile Lys Thr Ser Met Glu Ala Ile Gly Ser Leu Cys Gln
                210                 215                 220
```

```
<210> SEQ ID NO 67
<211> LENGTH: 224
<212> TYPE: PRT
<213> ORGANISM: Human respiratory syncytial virus A

<400> SEQUENCE: 67

Asn Tyr Ile Ser Lys Cys Ser Ile Ile Thr Asp Leu Ser Lys Phe Asn
1               5                   10                  15

Gln Ala Phe Arg Tyr Glu Thr Ser Cys Ile Cys Ser Asp Val Leu Asp
            20                  25                  30

Glu Leu His Gly Val Gln Ser Leu Phe Phe Trp Leu His Leu Ala Ile
        35                  40                  45

Pro His Val Thr Ile Ile Cys Thr Tyr Arg His Ala Pro Pro Tyr Ile
    50                  55                  60

Arg Asp His Ile Val Asp Leu Asn Asn Val Asp Glu Gln Ser Gly Leu
65                  70                  75                  80

Tyr Arg Tyr His Met Gly Gly Ile Glu Gly Trp Cys Gln Lys Leu Trp
                85                  90                  95

Thr Ile Glu Ala Ile Ser Leu Leu Asp Leu Ile Ser Leu Lys Gly Lys
            100                 105                 110

Phe Ser Ile Thr Ala Leu Ile Asn Gly Asp Asn Gln Ser Ile Asp Ile
        115                 120                 125

Ser Lys Pro Val Arg Leu Met Glu Gly Gln Thr His Ala Gln Ala Asp
    130                 135                 140

Tyr Leu Leu Ala Leu Asn Ser Leu Lys Leu Leu Tyr Lys Glu Tyr Ala
145                 150                 155                 160

Gly Ile Gly His Lys Leu Lys Gly Thr Glu Thr Tyr Ile Ser Arg Asp
                165                 170                 175

Met Gln Phe Met Ser Lys Thr Ile Gln His Asn Gly Val Tyr Tyr Pro
            180                 185                 190

Ala Ser Ile Lys Lys Val Leu Arg Val Gly Pro Trp Ile Asn Thr Ile
        195                 200                 205

Leu Asp Asp Phe Lys Val Ser Leu Glu Ser Ile Gly Ser Leu Thr Gln
    210                 215                 220

<210> SEQ ID NO 68
<211> LENGTH: 224
<212> TYPE: PRT
<213> ORGANISM: Human respiratory syncytial virus B

<400> SEQUENCE: 68

Asn Tyr Ile Ser Lys Cys Ser Ile Ile Thr Asp Leu Ser Lys Phe Asn
1               5                   10                  15

Gln Ala Phe Arg Tyr Glu Thr Ser Cys Ile Cys Ser Asp Val Leu Asp
            20                  25                  30

Glu Leu His Gly Val Gln Ser Leu Phe Ser Trp Leu His Leu Thr Ile
        35                  40                  45

Pro Leu Val Thr Ile Ile Cys Thr Tyr Arg His Ala Pro Pro Phe Ile
    50                  55                  60

Lys Asp His Val Val Asn Leu Asn Glu Val Asp Glu Gln Ser Gly Leu
65                  70                  75                  80

Tyr Arg Tyr His Met Gly Gly Ile Glu Gly Trp Cys Gln Lys Leu Trp
                85                  90                  95

Thr Ile Glu Ala Ile Ser Leu Leu Asp Leu Ile Ser Leu Lys Gly Lys
            100                 105                 110
```

Phe Ser Ile Thr Ala Leu Ile Asn Gly Asp Asn Gln Ser Ile Asp Ile
            115                 120                 125

Ser Lys Pro Val Arg Leu Ile Glu Gly Gln Thr His Ala Gln Ala Asp
        130                 135                 140

Tyr Leu Leu Ala Leu Asn Ser Leu Lys Leu Leu Tyr Lys Glu Tyr Ala
145                 150                 155                 160

Gly Ile Gly His Lys Leu Lys Gly Thr Glu Thr Tyr Ile Ser Arg Asp
                165                 170                 175

Met Gln Phe Met Ser Lys Thr Ile Gln His Asn Gly Val Tyr Tyr Pro
            180                 185                 190

Ala Ser Ile Lys Lys Val Leu Arg Val Gly Pro Trp Ile Asn Thr Ile
        195                 200                 205

Leu Asp Asp Phe Lys Val Ser Leu Glu Ser Ile Gly Ser Leu Thr Gln
210                 215                 220

<210> SEQ ID NO 69
<211> LENGTH: 224
<212> TYPE: PRT
<213> ORGANISM: bovine respiratory syncytial virus

<400> SEQUENCE: 69

Asn Tyr Ile Ser Lys Cys Ser Ile Ile Thr Asp Leu Ser Lys Phe Asn
1               5                   10                  15

Gln Ala Phe Arg Tyr Glu Thr Ser Cys Ile Cys Ser Asp Val Leu Asp
            20                  25                  30

Glu Leu His Gly Val Gln Ser Leu Phe Ser Trp Leu His Leu Thr Ile
        35                  40                  45

Pro Phe Ala Thr Val Ile Cys Thr Tyr Arg His Ala Pro Pro Tyr Ile
    50                  55                  60

Arg Asn His Ile Thr Asp Leu Asn Lys Val Asp Glu Gln Ser Gly Leu
65                  70                  75                  80

Tyr Arg Tyr His Met Gly Gly Ile Glu Gly Trp Cys Gln Lys Leu Trp
                85                  90                  95

Thr Ile Glu Ala Ile Ser Leu Leu Asp Leu Ile Ser Ile Lys Gly Lys
            100                 105                 110

Phe Ser Ile Thr Ala Leu Ile Asn Gly Asp Asn Gln Ser Ile Asp Ile
            115                 120                 125

Ser Lys Pro Ile Lys Leu Asn Glu Gly Gln Thr His Ala Gln Ala Asp
        130                 135                 140

Tyr Leu Leu Ala Leu Lys Ser Leu Lys Leu Leu Tyr Lys Glu Tyr Ala
145                 150                 155                 160

Ser Ile Gly His Lys Leu Lys Gly Thr Glu Thr Tyr Ile Ser Arg Asp
                165                 170                 175

Met Gln Phe Met Ser Lys Thr Ile Gln His Asn Gly Val Tyr Tyr Pro
            180                 185                 190

Ala Ser Ile Lys Lys Val Leu Arg Val Gly Pro Trp Ile Asn Thr Ile
        195                 200                 205

Leu Asp Asp Phe Lys Val Ser Met Glu Ser Ile Gly Ser Leu Thr Gln
210                 215                 220

<210> SEQ ID NO 70
<211> LENGTH: 223
<212> TYPE: PRT
<213> ORGANISM: Human parainfluenza virus 2

<400> SEQUENCE: 70

```
Phe Glu Leu Ser Ala Cys Phe Ile Thr Thr Asp Leu Ala Lys Tyr Cys
 1               5                  10                  15
Leu Gln Trp Arg Tyr Gln Thr Ile Ile His Phe Ala Arg Thr Leu Asn
             20                  25                  30
Arg Met Tyr Gly Val Pro His Leu Phe Glu Trp Ile His Leu Arg Leu
             35                  40                  45
Ile Arg Ser Thr Leu Tyr Val Gly Asp Pro Phe Asn Pro Pro Ala Ala
 50                  55                  60
Thr Asp Ala Phe Asp Leu Asp Lys Val Leu Asn Gly Asp Ile Phe Ile
 65                  70                  75                  80
Val Ser Lys Gly Gly Ile Glu Gly Leu Cys Gln Lys Met Trp Thr Met
             85                  90                  95
Ile Ser Ile Ser Val Ile Leu Ser Ser Ala Glu Ser Lys Thr Arg
             100                 105                 110
Val Met Ser Met Val Gln Gly Asp Asn Gln Ala Ile Ala Val Thr Thr
             115                 120                 125
Arg Val Pro Arg Ser Leu Pro Ser Ile Gln Lys Lys Glu Leu Ala Tyr
 130                 135                 140
Ala Ala Ser Lys Leu Phe Phe Glu Arg Leu Arg Ala Asn Asn Tyr Gly
145                 150                 155                 160
Leu Gly His Gln Leu Lys Ala Gln Glu Thr Ile Ile Ser Ser Thr Phe
             165                 170                 175
Phe Ile Tyr Ser Lys Arg Val Phe Tyr Gln Gly Arg Ile Leu Thr Gln
             180                 185                 190
Ala Leu Lys Asn Ala Ser Lys Leu Cys Leu Thr Ala Asp Val Leu Gly
             195                 200                 205
Glu Cys Thr Gln Ala Ser Cys Ser Asn Ser Ala Thr Thr Ile Met
 210                 215                 220

<210> SEQ ID NO 71
<211> LENGTH: 224
<212> TYPE: PRT
<213> ORGANISM: Newcastle disease virus

<400> SEQUENCE: 71

Arg Arg Arg Val Ala Thr Phe Ile Thr Thr Asp Leu Gln Lys Tyr Cys
 1               5                  10                  15
Leu Asn Trp Arg Tyr Gln Thr Ile Lys Leu Phe Ala His Ala Ile Asn
             20                  25                  30
Gln Leu Met Gly Leu Pro His Phe Phe Glu Trp Ile His Leu Arg Leu
             35                  40                  45
Met Asp Thr Thr Met Phe Val Gly Asp Pro Phe Asn Pro Pro Ser Asp
 50                  55                  60
Pro Thr Asp Cys Asp Leu Ser Arg Val Pro Asn Asp Asp Ile Tyr Ile
 65                  70                  75                  80
Val Ser Ala Arg Gly Gly Ile Glu Gly Leu Cys Gln Lys Leu Trp Thr
             85                  90                  95
Met Ile Ser Ile Ala Ala Ile Gln Leu Ala Ala Ala Arg Ser His Cys
             100                 105                 110
Arg Val Ala Cys Met Val Gln Gly Asp Asn Gln Val Ile Ala Val Thr
             115                 120                 125
Arg Glu Val Arg Ser Asp Asp Ser Pro Glu Met Val Leu Thr Gln Leu
 130                 135                 140
His Gln Ala Ser Asp Asn Phe Phe Lys Glu Leu Ile His Val Asn His
145                 150                 155                 160
```

```
Leu Ile Gly His Asn Leu Lys Asp Arg Glu Thr Ile Arg Ser Asp Thr
                165                 170                 175

Phe Phe Ile Tyr Ser Lys Arg Ile Phe Lys Asp Gly Ala Ile Leu Ser
            180                 185                 190

Gln Val Leu Lys Asn Ser Ser Lys Leu Val Leu Val Ser Gly Asp Leu
        195                 200                 205

Ser Glu Asn Thr Val Met Ser Cys Ala Asn Ile Ala Ser Thr Val Ala
    210                 215                 220

<210> SEQ ID NO 72
<211> LENGTH: 224
<212> TYPE: PRT
<213> ORGANISM: Sendai virus

<400> SEQUENCE: 72

Tyr Glu Thr Leu Ser Cys Phe Leu Thr Thr Asp Leu Lys Lys Tyr Cys
1               5                   10                  15

Leu Asn Trp Arg Phe Glu Ser Thr Ala Leu Phe Gly Gln Arg Cys Asn
            20                  25                  30

Glu Ile Phe Gly Phe Lys Thr Phe Phe Asn Trp Met His Pro Val Leu
        35                  40                  45

Glu Lys Cys Thr Ile Tyr Val Gly Asp Pro Tyr Cys Pro Val Ala Asp
    50                  55                  60

Arg Met His Arg Gln Leu Gln Asp His Ala Asp Ser Gly Ile Phe Ile
65                  70                  75                  80

His Asn Pro Arg Gly Gly Ile Glu Gly Tyr Cys Gln Lys Leu Trp Thr
                85                  90                  95

Leu Ile Ser Ile Ser Ala Ile His Leu Ala Ala Val Arg Val Gly Val
            100                 105                 110

Arg Val Ser Ala Met Val Gln Gly Asp Asn Gln Ala Ile Ala Val Thr
        115                 120                 125

Ser Arg Val Pro Val Ala Gln Thr Tyr Lys Gln Lys Lys Asn His Val
    130                 135                 140

Tyr Glu Glu Ile Thr Arg Tyr Phe Gly Ala Leu Arg His Val Met Phe
145                 150                 155                 160

Asp Ile Gly His Glu Leu Lys Leu Asn Glu Thr Ile Ile Ser Ser Lys
                165                 170                 175

Met Phe Val Tyr Ser Lys Arg Ile Tyr Tyr Asp Gly Lys Ile Leu Pro
            180                 185                 190

Gln Cys Leu Lys Ala Leu Thr Arg Cys Val Phe Trp Ser Glu Thr Leu
        195                 200                 205

Val Asp Glu Asn Arg Ser Ala Cys Ser Asn Ile Ser Thr Ser Ile Ala
    210                 215                 220

<210> SEQ ID NO 73
<211> LENGTH: 224
<212> TYPE: PRT
<213> ORGANISM: Human parainfluenza virus 3

<400> SEQUENCE: 73

Tyr Glu Thr Val Ser Cys Phe Leu Thr Thr Asp Leu Lys Lys Tyr Cys
1               5                   10                  15

Leu Asn Trp Arg Tyr Glu Ser Thr Ala Leu Phe Gly Glu Thr Cys Asn
            20                  25                  30

Gln Ile Phe Gly Leu Asn Lys Leu Phe Asn Trp Leu His Pro Arg Leu
        35                  40                  45
```

Glu Gly Ser Thr Ile Tyr Val Gly Asp Pro Tyr Cys Pro Ser Asp
            50                  55                  60

Lys Glu His Ile Ser Leu Glu Asp His Pro Asp Ser Gly Phe Tyr Val
65                  70                  75                  80

His Asn Pro Arg Gly Gly Ile Glu Gly Phe Cys Gln Lys Leu Trp Thr
                85                  90                  95

Leu Ile Ser Ile Ser Ala Ile His Leu Ala Ala Val Arg Ile Gly Val
            100                 105                 110

Arg Val Thr Ala Met Val Gln Gly Asp Asn Gln Ala Ile Ala Val Thr
        115                 120                 125

Thr Arg Val Pro Asn Asn Tyr Asp Tyr Arg Ile Lys Lys Glu Ile Val
    130                 135                 140

Tyr Lys Asp Val Val Arg Phe Phe Asp Ser Leu Arg Glu Val Met Asp
145                 150                 155                 160

Asp Leu Gly His Glu Leu Lys Leu Asn Glu Thr Ile Ile Ser Ser Lys
                165                 170                 175

Met Phe Ile Tyr Ser Lys Arg Ile Tyr Tyr Asp Gly Arg Ile Leu Pro
            180                 185                 190

Gln Ala Leu Lys Ala Leu Ser Arg Cys Val Phe Trp Ser Glu Thr Val
        195                 200                 205

Ile Asp Glu Thr Arg Ser Ala Ser Ser Asn Leu Ala Thr Ser Phe Ala
    210                 215                 220

<210> SEQ ID NO 74
<211> LENGTH: 224
<212> TYPE: PRT
<213> ORGANISM: Measles virus

<400> SEQUENCE: 74

Tyr Glu Thr Val Ser Ala Phe Ile Thr Thr Asp Leu Lys Lys Tyr Cys
1               5                   10                  15

Leu Asn Trp Arg Tyr Glu Thr Ile Ser Leu Phe Ala Gln Arg Leu Asn
            20                  25                  30

Glu Ile Tyr Gly Leu Pro Ser Phe Phe Gln Trp Leu His Lys Arg Leu
        35                  40                  45

Glu Thr Ser Val Leu Tyr Val Ser Asp Pro His Cys Pro Pro Asp Leu
    50                  55                  60

Asp Ala His Ile Pro Leu Tyr Lys Val Pro Asn Asp Gln Ile Phe Ile
65                  70                  75                  80

Lys Tyr Pro Met Gly Gly Ile Glu Gly Tyr Cys Gln Lys Leu Trp Thr
                85                  90                  95

Ile Ser Thr Ile Pro Tyr Leu Tyr Leu Ala Ala Tyr Glu Ser Gly Val
            100                 105                 110

Arg Ile Ala Ser Leu Val Gln Gly Asp Asn Gln Thr Ile Ala Val Thr
        115                 120                 125

Lys Arg Val Pro Ser Thr Trp Pro Tyr Asn Leu Lys Lys Arg Glu Ala
    130                 135                 140

Ala Arg Val Thr Arg Asp Tyr Phe Val Ile Leu Arg Gln Arg Leu His
145                 150                 155                 160

Asp Ile Gly His His Leu Lys Ala Asn Glu Thr Ile Val Ser Ser His
                165                 170                 175

Phe Phe Val Tyr Ser Lys Gly Ile Tyr Tyr Asp Gly Leu Leu Val Ser
            180                 185                 190

Gln Ser Leu Lys Ser Ile Ala Arg Cys Val Phe Trp Ser Glu Thr Ile

```
            195                 200                 205
Val Asp Glu Thr Arg Ala Ala Cys Ser Asn Ile Ala Thr Thr Met Ala
    210                 215                 220

<210> SEQ ID NO 75
<211> LENGTH: 224
<212> TYPE: PRT
<213> ORGANISM: Nipah virus

<400> SEQUENCE: 75

Phe Asp Thr Val Ser Ala Phe Leu Thr Thr Asp Leu Lys Lys Phe Cys
1               5                   10                  15

Leu Asn Trp Arg Tyr Glu Ser Met Ala Ile Phe Ala Glu Arg Leu Asp
            20                  25                  30

Glu Ile Tyr Gly Leu Pro Gly Phe Phe Asn Trp Met His Lys Arg Leu
        35                  40                  45

Glu Arg Ser Val Ile Tyr Val Ala Asp Pro Asn Cys Pro Pro Asn Ile
    50                  55                  60

Asp Lys His Met Glu Leu Gly Lys Thr Pro Glu Asp Asp Ile Phe Ile
65                  70                  75                  80

His Tyr Pro Lys Gly Gly Ile Glu Gly Tyr Ser Gln Lys Thr Trp Thr
                85                  90                  95

Ile Ala Thr Ile Pro Phe Leu Phe Leu Ser Ala Tyr Glu Thr Asn Thr
            100                 105                 110

Arg Ile Ala Ala Ile Val Gln Gly Asp Asn Glu Ser Ile Ala Ile Thr
        115                 120                 125

Gln Lys Val His Pro Asn Leu Pro Tyr Lys Val Lys Lys Glu Ile Cys
    130                 135                 140

Ala Lys Gln Ala Gln Leu Tyr Phe Glu Arg Leu Arg Met Asn Leu Arg
145                 150                 155                 160

Ala Leu Gly His Asn Leu Lys Ala Thr Glu Thr Ile Ile Ser Thr His
                165                 170                 175

Leu Phe Ile Tyr Ser Lys Lys Ile His Tyr Asp Gly Ala Val Leu Ser
            180                 185                 190

Gln Ala Leu Lys Ser Met Ser Arg Cys Cys Phe Trp Ser Glu Thr Leu
        195                 200                 205

Val Asp Glu Thr Arg Ser Ala Cys Ser Asn Ile Ser Thr Thr Ile Ala
    210                 215                 220

<210> SEQ ID NO 76
<211> LENGTH: 57
<212> TYPE: RNA
<213> ORGANISM: Human metapneumovirus 00-1

<400> SEQUENCE: 76
acgagaaaaa aacgcguaua aauuagauuc caaaaaaaua ugggacaagu gaaaaug      57

<210> SEQ ID NO 77
<211> LENGTH: 29
<212> TYPE: RNA
<213> ORGANISM: Human metapneumovirus 00-1

<400> SEQUENCE: 77
uaauuaaaaa agugggacaa gucaaaaug                                     29

<210> SEQ ID NO 78
<211> LENGTH: 38
<212> TYPE: RNA
```

```
<213> ORGANISM: Human metapneumovirus 00-1

<400> SEQUENCE: 78
uaguuuaaua aaaauaaaca augggacaag uaaaaaug                                   38

<210> SEQ ID NO 79
<211> LENGTH: 128
<212> TYPE: RNA
<213> ORGANISM: Human metapneumovirus 00-1

<400> SEQUENCE: 79
uaacaaccaa gcaccuuggc caagagcuac uaacccuauc ucauagauca uaaagucacc           60
auucuaguua uauaaaaauc aaguuagaac aagaauuaaa ucaaucaaga acgggacaaa          120
uaaaaaug                                                                  128

<210> SEQ ID NO 80
<211> LENGTH: 71
<212> TYPE: RNA
<213> ORGANISM: Human metapneumovirus 00-1

<400> SEQUENCE: 80
uaguuaauua aaauaaagu aaauuaaaau aauuaaaau uaaaaauaaa aauuugggac             60
aaaucauaau g                                                               71

<210> SEQ ID NO 81
<211> LENGTH: 36
<212> TYPE: RNA
<213> ORGANISM: Human metapneumovirus

<400> SEQUENCE: 81
uaguaaaaac acaucagagu gggauaaaug acaaug                                    36

<210> SEQ ID NO 82
<211> LENGTH: 207
<212> TYPE: RNA
<213> ORGANISM: Human metapneumovirus 00-1

<400> SEQUENCE: 82
uaaauguuaa caccagauua ggauccaucc aagucuguua guucaaccaau uuaguuauuu          60 aaaaauauuu ugaaaacaag uaaguuucua ugauacuuca uaauaauaag uaauaauuaa         120
uugcuuaauc aucaucacaa cauuauucga aaccauaacu auucaauuua aaagucaaaa         180
aacaauaaca ugggacaagu aguuaug                                             207

<210> SEQ ID NO 83
<211> LENGTH: 215
<212> TYPE: RNA
<213> ORGANISM: Human metapneumovirus 00-1

<400> SEQUENCE: 83
uaacaaaaaa uacaaaauaa cucuaagaua aaccaugcag acaccaacaa uggagaagcc          60
aaaagacaau ucacaaucuc cccaaaaagg caacaacacc auauuagcuc ugcccaaauc         120
ucccuggaaa aaacacucgc ccauauacca aaaauaccac aaccaccca agaaaaaaac          180 ugggcaaaac aacacccaag agacaaauaa caaug                                    215

<210> SEQ ID NO 84
<211> LENGTH: 182
<212> TYPE: RNA
<213> ORGANISM: Human metapneumovirus 00-1
```

-continued

<400> SEQUENCE: 84
ugaaaaauga uaaaaaugau aaaauaggug acaacuucau acuauuccaa aguaaucauu    60
ugauuaugca auuauguaau aguuaauuaa aaacuaaaaa ucaaaaguua gaaacuaaca   120
acugucauua aguuuauuaa aaauaagaaa uuauaauugg auguauacgg uuuuuuucuc   180
gu                                                                  182

<210> SEQ ID NO 85
<211> LENGTH: 45
<212> TYPE: RNA
<213> ORGANISM: Human metapneumovirus 00-1

<400> SEQUENCE: 85
ucccauauuu uuuggaauc uaauuuauac gcguuuuuu cucgu                      45

<210> SEQ ID NO 86
<211> LENGTH: 44
<212> TYPE: RNA
<213> ORGANISM: Human metapneumovirus 00-1

<400> SEQUENCE: 86
acgagaaaaa aaccguauac auccaauuau aauuucuuau uuuu                     44

<210> SEQ ID NO 87
<211> LENGTH: 45
<212> TYPE: RNA
<213> ORGANISM: Human metapneumovirus 00-1

<400> SEQUENCE: 87
acgagaaaaa aaccguauac auccaauuau aauuucuuau uuuua                    45

<210> SEQ ID NO 88
<211> LENGTH: 45
<212> TYPE: RNA
<213> ORGANISM: Human metapneumovirus 00-1

<400> SEQUENCE: 88
acgagaaaaa aaccguauuc aucaaauuuu uagcuuuuag uuuuu                    45

<210> SEQ ID NO 89
<211> LENGTH: 44
<212> TYPE: RNA
<213> ORGANISM: Human metapneumovirus 00-1

<400> SEQUENCE: 89
cccauauuuu uuuggaaucu aauuuauacg cguuuuuuuc ucgu                     44

<210> SEQ ID NO 90
<211> LENGTH: 44
<212> TYPE: RNA
<213> ORGANISM: Human metapneumovirus 00-1

<400> SEQUENCE: 90
cccauuauuu uucuagaacc ugcuugaaug cguuuuuuuc ucgu                     44

<210> SEQ ID NO 91
<211> LENGTH: 394
<212> TYPE: PRT
<213> ORGANISM: Human metapneumovirus 99-1

<400> SEQUENCE: 91

```
Met Ser Leu Gln Gly Ile His Leu Ser Asp Leu Ser Tyr Lys His Ala
1               5                   10                  15

Ile Leu Lys Glu Ser Gln Tyr Thr Ile Lys Arg Asp Val Gly Thr Thr
            20                  25                  30

Thr Ala Val Thr Pro Ser Ser Leu Gln Gln Glu Ile Thr Leu Leu Cys
        35                  40                  45

Gly Glu Ile Leu Tyr Thr Lys His Thr Asp Tyr Lys Tyr Ala Ala Glu
    50                  55                  60

Ile Gly Ile Gln Tyr Ile Cys Thr Ala Leu Gly Ser Glu Arg Val Gln
65                  70                  75                  80

Gln Ile Leu Arg Asn Ser Gly Ser Glu Val Gln Val Val Leu Thr Lys
                85                  90                  95

Thr Tyr Ser Leu Gly Lys Gly Lys Asn Ser Lys Gly Glu Glu Leu Gln
            100                 105                 110

Met Leu Asp Ile His Gly Val Glu Lys Ser Trp Ile Glu Glu Ile Asp
        115                 120                 125

Lys Glu Ala Arg Lys Thr Met Val Thr Leu Leu Lys Glu Ser Ser Gly
    130                 135                 140

Asn Ile Pro Gln Asn Gln Arg Pro Ser Ala Pro Asp Thr Pro Ile Ile
145                 150                 155                 160

Leu Leu Cys Val Gly Ala Leu Ile Phe Thr Lys Leu Ala Ser Thr Ile
                165                 170                 175

Glu Val Gly Leu Glu Thr Thr Val Arg Arg Ala Asn Arg Val Leu Ser
            180                 185                 190

Asp Ala Leu Lys Arg Tyr Pro Arg Ile Asp Ile Pro Lys Ile Ala Arg
        195                 200                 205

Ser Phe Tyr Glu Leu Phe Glu Gln Lys Val Tyr Tyr Arg Ser Leu Phe
    210                 215                 220

Ile Glu Tyr Gly Lys Ala Leu Gly Ser Ser Thr Gly Ser Lys Ala
225                 230                 235                 240

Glu Ser Leu Phe Val Asn Ile Phe Met Gln Ala Tyr Gly Ala Gly Gln
                245                 250                 255

Thr Leu Leu Arg Trp Gly Val Ile Ala Arg Ser Ser Asn Asn Ile Met
            260                 265                 270

Leu Gly His Val Ser Val Gln Ser Glu Leu Lys Gln Val Thr Glu Val
        275                 280                 285

Tyr Asp Leu Val Arg Glu Met Gly Pro Glu Ser Gly Leu Leu His Leu
    290                 295                 300

Arg Gln Ser Pro Lys Ala Gly Leu Leu Ser Leu Ala Asn Cys Pro Asn
305                 310                 315                 320

Phe Ala Ser Val Val Leu Gly Asn Ala Ser Gly Leu Gly Ile Ile Gly
                325                 330                 335

Met Tyr Arg Gly Arg Val Pro Asn Thr Glu Leu Phe Ser Ala Ala Glu
            340                 345                 350

Ser Tyr Ala Arg Ser Leu Lys Glu Ser Asn Lys Ile Asn Phe Ser Ser
        355                 360                 365

Leu Gly Leu Thr Asp Glu Glu Lys Glu Ala Ala Glu His Phe Leu Asn
370                 375                 380

Met Ser Gly Asp Asn Gln Asp Asp Tyr Glu
385                 390

<210> SEQ ID NO 92
<211> LENGTH: 294
<212> TYPE: PRT
```

<213> ORGANISM: Human metapneumovirus 99-1

<400> SEQUENCE: 92

```
Met Ser Phe Pro Glu Gly Lys Asp Ile Leu Phe Met Gly Asn Glu Ala
1               5                   10                  15

Ala Lys Ile Ala Glu Ala Phe Gln Lys Ser Leu Lys Lys Ser Gly His
            20                  25                  30

Lys Arg Thr Gln Ser Ile Val Gly Glu Lys Val Asn Thr Ile Ser Glu
        35                  40                  45

Thr Leu Glu Leu Pro Thr Ile Ser Lys Pro Ala Arg Ser Ser Thr Leu
    50                  55                  60

Leu Glu Pro Lys Leu Ala Trp Ala Asp Asn Ser Gly Ile Thr Lys Ile
65                  70                  75                  80

Thr Glu Lys Pro Ala Thr Lys Thr Thr Asp Pro Val Glu Glu Glu Glu
                85                  90                  95

Phe Asn Glu Lys Lys Val Leu Pro Ser Ser Asp Gly Lys Thr Pro Ala
            100                 105                 110

Glu Lys Lys Ser Lys Phe Ser Thr Ser Val Lys Lys Lys Val Ser Phe
        115                 120                 125

Thr Ser Asn Glu Pro Gly Lys Tyr Thr Lys Leu Glu Lys Asp Ala Leu
    130                 135                 140

Asp Leu Leu Ser Asp Asn Glu Glu Asp Ala Glu Ser Ser Ile Leu
145                 150                 155                 160

Thr Phe Glu Glu Lys Asp Thr Ser Ser Leu Ser Ile Glu Ala Arg Leu
                165                 170                 175

Glu Ser Ile Glu Glu Lys Leu Ser Met Ile Leu Gly Leu Leu Arg Thr
            180                 185                 190

Leu Asn Ile Ala Thr Ala Gly Pro Thr Ala Ala Arg Asp Gly Ile Arg
        195                 200                 205

Asp Ala Met Ile Gly Ile Arg Glu Glu Leu Ile Ala Glu Ile Ile Lys
    210                 215                 220

Glu Ala Lys Gly Lys Ala Ala Glu Met Met Glu Glu Glu Met Asn Gln
225                 230                 235                 240

Arg Ser Lys Ile Gly Asn Gly Ser Val Lys Leu Thr Glu Lys Ala Lys
                245                 250                 255

Glu Leu Asn Lys Ile Val Glu Asp Glu Ser Thr Ser Gly Glu Ser Glu
            260                 265                 270

Glu Glu Glu Glu Pro Lys Glu Thr Gln Asp Asn Asn Gln Gly Glu Asp
        275                 280                 285

Ile Tyr Gln Leu Ile Met
    290
```

<210> SEQ ID NO 93
<211> LENGTH: 254
<212> TYPE: PRT
<213> ORGANISM: Human metapneumovirus 99-1

<400> SEQUENCE: 93

```
Met Glu Ser Tyr Leu Val Asp Thr Tyr Gln Gly Ile Pro Tyr Thr Ala
1               5                   10                  15

Ala Val Gln Val Asp Leu Val Glu Lys Asp Leu Leu Pro Ala Ser Leu
            20                  25                  30

Thr Ile Trp Phe Pro Leu Phe Gln Ala Asn Thr Pro Pro Ala Val Leu
        35                  40                  45

Leu Asp Gln Leu Lys Thr Leu Thr Ile Thr Thr Leu Tyr Ala Ala Ser
```

```
            50                  55                  60
Gln Asn Gly Pro Ile Leu Lys Val Asn Ala Ser Ala Gln Gly Ala Ala
 65                  70                  75                  80

Met Ser Val Leu Pro Lys Lys Phe Glu Val Asn Ala Thr Val Ala Leu
                 85                  90                  95

Asp Glu Tyr Ser Lys Leu Asp Phe Asp Lys Leu Thr Val Cys Asp Val
            100                 105                 110

Lys Thr Val Tyr Leu Thr Thr Met Lys Pro Tyr Gly Met Val Ser Lys
            115                 120                 125

Phe Val Ser Ser Ala Lys Ser Val Gly Lys Lys Thr His Asp Leu Ile
            130                 135                 140

Ala Leu Cys Asp Phe Met Asp Leu Glu Lys Asn Ile Pro Val Thr Ile
145                 150                 155                 160

Pro Ala Phe Ile Lys Ser Val Ser Ile Lys Glu Ser Glu Ser Ala Thr
                165                 170                 175

Val Glu Ala Ala Ile Ser Ser Glu Ala Asp Gln Ala Leu Thr Gln Ala
            180                 185                 190

Lys Ile Ala Pro Tyr Ala Gly Leu Ile Met Ile Met Thr Met Asn Asn
            195                 200                 205

Pro Lys Gly Ile Phe Lys Lys Leu Gly Ala Gly Thr Gln Val Ile Val
210                 215                 220

Glu Leu Gly Ala Tyr Val Gln Ala Glu Ser Ile Ser Arg Ile Cys Lys
225                 230                 235                 240

Ser Trp Ser His Gln Gly Thr Arg Tyr Val Leu Lys Ser Arg
                245                 250

<210> SEQ ID NO 94
<211> LENGTH: 539
<212> TYPE: PRT
<213> ORGANISM: Human metapneumovirus 99-1

<400> SEQUENCE: 94

Met Ser Trp Lys Val Met Ile Ile Ile Ser Leu Leu Ile Thr Pro Gln
  1               5                  10                  15

His Gly Leu Lys Glu Ser Tyr Leu Glu Glu Ser Cys Ser Thr Ile Thr
                 20                  25                  30

Glu Gly Tyr Leu Ser Val Leu Arg Thr Gly Trp Tyr Thr Asn Val Phe
             35                  40                  45

Thr Leu Glu Val Gly Asp Val Glu Asn Leu Thr Cys Thr Asp Gly Pro
 50                  55                  60

Ser Leu Ile Lys Thr Glu Leu Asp Leu Thr Lys Ser Ala Leu Arg Glu
 65                  70                  75                  80

Leu Lys Thr Val Ser Ala Asp Gln Leu Ala Arg Glu Glu Gln Ile Glu
                 85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Ile Ala Ile Ala Lys Thr Ile
            115                 120                 125

Arg Leu Glu Ser Glu Val Asn Ala Ile Lys Gly Ala Leu Lys Gln Thr
            130                 135                 140

Asn Glu Ala Val Ser Thr Leu Gly Asn Gly Val Arg Val Leu Ala Thr
145                 150                 155                 160

Ala Val Arg Glu Leu Lys Glu Phe Val Ser Lys Asn Leu Thr Ser Ala
                165                 170                 175
```

-continued

```
Ile Asn Arg Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Tyr Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Ile Lys Ala
        275                 280                 285

Ala Pro Ser Cys Ser Glu Lys Asn Gly Asn Tyr Ala Cys Leu Leu Arg
    290                 295                 300

Glu Asp Gln Gly Trp Tyr Cys Lys Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Arg Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Trp Val Gly Ile Ile
385                 390                 395                 400

Lys Gln Leu Pro Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Lys Ile
465                 470                 475                 480

Leu Asn Ser Ala Glu Lys Gly Asn Thr Gly Phe Ile Ile Val Val Ile
                485                 490                 495

Leu Val Ala Val Leu Gly Leu Thr Met Ile Ser Val Ser Ile Ile Ile
            500                 505                 510

Ile Ile Lys Lys Thr Arg Lys Pro Thr Gly Ala Pro Pro Glu Leu Asn
        515                 520                 525

Gly Val Thr Asn Gly Gly Phe Ile Pro His Ser
    530                 535

<210> SEQ ID NO 95
<211> LENGTH: 187
<212> TYPE: PRT
<213> ORGANISM: Human metapneumovirus 99-1

<400> SEQUENCE: 95

Met Ser Arg Lys Ala Pro Cys Lys Tyr Glu Val Arg Gly Lys Cys Asn
1               5                   10                  15
```

-continued

Arg Gly Ser Asp Cys Lys Phe Asn His Asn Tyr Trp Ser Trp Pro Asp
            20                  25                  30

Arg Tyr Leu Leu Leu Arg Ser Asn Tyr Leu Leu Asn Gln Leu Leu Arg
            35                  40                  45

Asn Thr Asp Lys Ala Asp Gly Leu Ser Ile Ile Ser Gly Ala Gly Arg
 50                  55                  60

Glu Asp Arg Thr Gln Asp Phe Val Leu Gly Ser Thr Asn Val Val Gln
65                  70                  75                  80

Gly Tyr Ile Asp Asp Asn Gln Gly Ile Thr Lys Ala Ala Ala Cys Tyr
                85                  90                  95

Ser Leu His Asn Ile Ile Lys Gln Leu Gln Glu Thr Glu Val Arg Gln
            100                 105                 110

Ala Arg Asp Asn Lys Leu Ser Asp Ser Lys His Val Ala Leu His Asn
            115                 120                 125

Leu Ile Leu Ser Tyr Met Glu Met Ser Lys Thr Pro Ala Ser Leu Ile
130                 135                 140

Asn Asn Leu Lys Lys Leu Pro Arg Glu Lys Leu Lys Lys Leu Ala Arg
145                 150                 155                 160

Leu Ile Ile Asp Leu Ser Ala Gly Thr Asp Asn Asp Ser Ser Tyr Ala
                165                 170                 175

Leu Gln Asp Ser Glu Ser Thr Asn Gln Val Gln
            180                 185

<210> SEQ ID NO 96
<211> LENGTH: 71
<212> TYPE: PRT
<213> ORGANISM: Human metapneumovirus 99-1

<400> SEQUENCE: 96

Met Thr Leu His Met Pro Cys Lys Thr Val Lys Ala Leu Ile Lys Cys
1               5                   10                  15

Ser Lys His Gly Pro Lys Phe Ile Thr Ile Glu Ala Asp Asp Met Ile
            20                  25                  30

Trp Thr His Lys Glu Leu Lys Glu Thr Leu Ser Asp Gly Ile Val Lys
            35                  40                  45

Ser His Thr Asn Ile Tyr Ser Cys Tyr Leu Glu Asn Ile Glu Ile Ile
 50                  55                  60

Tyr Val Lys Thr Tyr Leu Ser
65                  70

<210> SEQ ID NO 97
<211> LENGTH: 176
<212> TYPE: PRT
<213> ORGANISM: Human metapneumovirus 99-1

<400> SEQUENCE: 97

Met Lys Thr Leu Asp Val Ile Lys Ser Asp Gly Ser Ser Glu Thr Cys
1               5                   10                  15

Asn Gln Leu Lys Lys Ile Ile Lys Lys His Ser Gly Lys Val Leu Ile
            20                  25                  30

Ala Leu Lys Leu Ile Leu Ala Leu Leu Thr Phe Phe Thr Ala Thr Ile
            35                  40                  45

Thr Val Asn Tyr Ile Lys Val Glu Asn Asn Leu Gln Ala Cys Gln Pro
 50                  55                  60

Lys Asn Glu Ser Asp Lys Lys Val Thr Lys Pro Asn Thr Thr Ser Thr
65                  70                  75                  80

```
Thr Ile Arg Pro Thr Pro Asp Pro Thr Val Val His His Leu Lys Arg
                85                  90                  95

Leu Ile Gln Arg His Thr Asn Ser Val Thr Lys Asp Ser Asp Thr Cys
            100                 105                 110

Trp Arg Ile His Lys Asn Gln Thr Asn Ile Lys Ile Tyr Lys Phe Leu
            115                 120                 125

Cys Ser Gly Phe Thr Asn Ser Lys Gly Thr Asp Cys Glu Glu Pro Thr
130                 135                 140

Ala Leu Cys Asp Lys Lys Leu Lys Thr Ile Val Glu Lys His Arg Lys
145                 150                 155                 160

Ala Glu Cys His Cys Leu His Thr Thr Glu Trp Gly Cys Leu His Pro
            165                 170                 175

<210> SEQ ID NO 98
<211> LENGTH: 224
<212> TYPE: PRT
<213> ORGANISM: Human metapneumovirus 99-1

<400> SEQUENCE: 98

Met Glu Val Arg Val Glu Asn Ile Arg Ala Ile Asp Met Phe Lys Ala
1               5                   10                  15

Lys Ile Lys Asn Arg Ile Arg Ser Ser Arg Cys Tyr Arg Asn Ala Thr
            20                  25                  30

Leu Ile Leu Ile Gly Leu Thr Ala Leu Ser Met Ala Leu Asn Ile Phe
        35                  40                  45

Leu Ile Ile Asp His Ala Thr Leu Arg Asn Met Ile Lys Thr Glu Asn
    50                  55                  60

Cys Ala Asn Met Pro Ser Ala Glu Pro Ser Lys Lys Thr Pro Met Thr
65                  70                  75                  80

Ser Thr Ala Gly Pro Asn Thr Lys Pro Asn Pro Gln Gln Ala Thr Gln
                85                  90                  95

Trp Thr Thr Glu Asn Ser Thr Ser Pro Val Ala Thr Pro Glu Gly His
            100                 105                 110

Pro Tyr Thr Gly Thr Thr Gln Thr Ser Asp Thr Thr Ala Pro Gln Gln
            115                 120                 125

Thr Thr Asp Lys His Thr Ala Pro Leu Lys Ser Thr Asn Glu Gln Ile
130                 135                 140

Thr Gln Thr Thr Thr Glu Lys Lys Thr Ile Arg Ala Thr Thr Gln Lys
145                 150                 155                 160

Arg Glu Lys Gly Lys Glu Asn Thr Asn Gln Thr Thr Ser Thr Ala Ala
            165                 170                 175

Thr Gln Thr Thr Asn Thr Thr Asn Gln Ile Arg Asn Ala Ser Glu Thr
            180                 185                 190

Ile Thr Thr Ser Asp Arg Pro Arg Thr Asp Thr Thr Gln Ser Ser
        195                 200                 205

Glu Gln Thr Thr Arg Ala Thr Asp Pro Ser Ser Pro Pro His His Ala
            210                 215                 220

<210> SEQ ID NO 99
<211> LENGTH: 499
<212> TYPE: PRT
<213> ORGANISM: Human metapneumovirus 00-1

<400> SEQUENCE: 99

Met Asp Pro Leu Asn Glu Ser Thr Val Asn Val Tyr Leu Pro Asp Ser
1               5                   10                  15
```

```
Tyr Leu Lys Gly Val Ile Ser Phe Ser Glu Thr Asn Ala Ile Gly Ser
             20                  25                  30

Cys Leu Leu Lys Arg Pro Tyr Leu Lys Asn Asp Asn Thr Ala Lys Val
         35                  40                  45

Ala Ile Glu Asn Pro Val Ile Glu His Val Arg Leu Lys Asn Ala Val
     50                  55                  60

Asn Ser Lys Met Lys Ile Ser Asp Tyr Lys Ile Val Glu Pro Val Asn
 65                  70                  75                  80

Met Gln His Glu Ile Met Lys Asn Val His Ser Cys Glu Leu Thr Leu
                 85                  90                  95

Leu Lys Gln Phe Leu Thr Arg Ser Lys Asn Ile Ser Thr Leu Lys Leu
            100                 105                 110

Asn Met Ile Cys Asp Trp Leu Gln Leu Lys Ser Thr Ser Asp Asp Thr
        115                 120                 125

Ser Ile Leu Ser Phe Ile Asp Val Glu Phe Ile Pro Ser Trp Val Ser
130                 135                 140

Asn Trp Phe Ser Asn Trp Tyr Asn Leu Asn Lys Leu Ile Leu Glu Phe
145                 150                 155                 160

Arg Lys Glu Glu Val Ile Arg Thr Gly Ser Ile Leu Cys Arg Ser Leu
                165                 170                 175

Gly Lys Leu Val Phe Val Val Ser Ser Tyr Gly Cys Ile Val Lys Ser
            180                 185                 190

Asn Lys Ser Lys Arg Val Ser Phe Phe Thr Tyr Asn Gln Leu Leu Thr
        195                 200                 205

Trp Lys Asp Val Met Leu Ser Arg Phe Asn Ala Asn Phe Cys Ile Trp
210                 215                 220

Val Ser Asn Ser Leu Asn Glu Asn Gln Glu Gly Leu Gly Leu Arg Ser
225                 230                 235                 240

Asn Leu Gln Gly Ile Leu Thr Asn Lys Leu Tyr Glu Thr Val Asp Tyr
                245                 250                 255

Met Leu Ser Leu Cys Cys Asn Glu Gly Phe Ser Leu Val Lys Glu Phe
            260                 265                 270

Glu Gly Phe Ile Met Ser Glu Ile Leu Arg Ile Thr Glu His Ala Gln
        275                 280                 285

Phe Ser Thr Arg Phe Arg Asn Thr Leu Leu Asn Gly Leu Thr Asp Gln
290                 295                 300

Leu Thr Lys Leu Lys Asn Lys Asn Arg Leu Arg Val His Gly Thr Val
305                 310                 315                 320

Leu Glu Asn Asn Asp Tyr Pro Met Tyr Glu Val Val Leu Lys Leu Leu
                325                 330                 335

Gly Asp Thr Leu Arg Cys Ile Lys Leu Leu Ile Asn Lys Asn Leu Glu
            340                 345                 350

Asn Ala Ala Glu Leu Tyr Tyr Ile Phe Arg Ile Phe Gly His Pro Met
        355                 360                 365

Val Asp Glu Arg Asp Ala Met Asp Ala Val Lys Leu Asn Asn Glu Ile
370                 375                 380

Thr Lys Ile Leu Arg Trp Glu Ser Leu Thr Glu Leu Arg Gly Ala Phe
385                 390                 395                 400

Ile Leu Arg Ile Ile Lys Gly Phe Val Asp Asn Asn Lys Arg Trp Pro
                405                 410                 415

Lys Ile Lys Asn Leu Lys Val Leu Ser Lys Arg Trp Thr Met Tyr Phe
            420                 425                 430
```

Lys Ala Lys Ser Tyr Pro Ser Gln Leu Glu Leu Ser Glu Gln Asp Phe
            435                 440                 445

Leu Glu Leu Ala Ala Ile Gln Phe Gln Gln Phe Ser Val Pro Glu
    450                 455                 460

Lys Thr Asn Leu Glu Met Val Leu Asn Asp Lys Ala Ile Ser Pro Pro
465                 470                 475                 480

Lys Arg Leu Ile Trp Ser Val Tyr Pro Lys Asn Tyr Leu Pro Glu Lys
                485                 490                 495

Ile Lys Asn

<210> SEQ ID NO 100
<211> LENGTH: 499
<212> TYPE: PRT
<213> ORGANISM: Human metapneumovirus 99-1

<400> SEQUENCE: 100

Met Asp Pro Phe Cys Glu Ser Thr Val Asn Val Tyr Leu Pro Asp Ser
1               5                   10                  15

Tyr Leu Lys Gly Val Ile Ser Phe Ser Glu Thr Asn Ala Ile Gly Ser
            20                  25                  30

Cys Leu Leu Lys Arg Pro Tyr Leu Lys Asn Asp Asn Thr Ala Lys Val
        35                  40                  45

Ala Val Glu Asn Pro Val Val Glu His Val Arg Leu Arg Asn Ala Val
    50                  55                  60

Met Thr Lys Met Lys Ile Ser Asp Tyr Lys Val Val Glu Pro Val Asn
65                  70                  75                  80

Met Gln His Glu Ile Met Lys Asn Ile His Ser Cys Glu Leu Thr Leu
                85                  90                  95

Leu Lys Gln Phe Leu Thr Arg Ser Lys Asn Ile Ser Ser Leu Lys Leu
            100                 105                 110

Asn Met Ile Cys Asp Trp Leu Gln Leu Lys Ser Thr Ser Asp Asn Thr
        115                 120                 125

Ser Ile Leu Asn Phe Ile Asp Val Glu Phe Ile Pro Val Trp Val Ser
    130                 135                 140

Asn Trp Phe Ser Asn Trp Tyr Asn Leu Asn Lys Leu Ile Leu Glu Phe
145                 150                 155                 160

Arg Arg Glu Glu Val Ile Arg Thr Gly Ser Ile Leu Cys Arg Ser Leu
                165                 170                 175

Gly Lys Leu Val Phe Ile Val Ser Ser Tyr Gly Cys Val Val Lys Ser
            180                 185                 190

Asn Lys Ser Lys Arg Val Ser Phe Phe Thr Tyr Asn Gln Leu Leu Thr
        195                 200                 205

Trp Lys Asp Val Met Leu Ser Arg Phe Asn Ala Asn Phe Cys Ile Trp
    210                 215                 220

Val Ser Asn Asn Leu Asn Lys Asn Gln Glu Gly Leu Gly Leu Arg Ser
225                 230                 235                 240

Asn Leu Gln Gly Met Leu Thr Asn Lys Leu Tyr Glu Thr Val Asp Tyr
                245                 250                 255

Met Leu Ser Leu Cys Cys Asn Glu Gly Phe Ser Leu Val Lys Glu Phe
            260                 265                 270

Glu Gly Phe Ile Met Ser Glu Ile Leu Lys Ile Thr Glu His Ala Gln
        275                 280                 285

Phe Ser Thr Arg Phe Arg Asn Thr Leu Leu Asn Gly Leu Thr Glu Gln
    290                 295                 300

-continued

```
Leu Ser Val Leu Lys Ala Lys Asn Arg Ser Arg Val Leu Gly Thr Ile
305                 310                 315                 320

Leu Glu Asn Asn Asn Tyr Pro Met Tyr Glu Val Val Leu Lys Leu Leu
            325                 330                 335

Gly Asp Thr Leu Lys Ser Ile Lys Leu Leu Ile Asn Lys Asn Leu Glu
        340                 345                 350

Asn Ala Ala Glu Leu Tyr Tyr Ile Phe Arg Ile Phe Gly His Pro Met
            355                 360                 365

Val Asp Glu Arg Glu Ala Met Asp Ala Val Lys Leu Asn Asn Glu Ile
    370                 375                 380

Thr Lys Ile Leu Lys Leu Glu Ser Leu Thr Glu Leu Arg Gly Ala Phe
385                 390                 395                 400

Ile Leu Arg Ile Ile Lys Gly Phe Val Asp Asn Asn Lys Arg Trp Pro
                405                 410                 415

Lys Ile Lys Asn Leu Lys Val Leu Ser Lys Arg Trp Ala Met Tyr Phe
            420                 425                 430

Lys Ala Lys Ser Tyr Pro Ser Gln Leu Glu Leu Ser Val Gln Asp Phe
        435                 440                 445

Leu Glu Leu Ala Ala Val Gln Phe Glu Gln Glu Phe Ser Val Pro Glu
    450                 455                 460

Lys Thr Asn Leu Glu Met Val Leu Asn Asp Lys Ala Ile Ser Pro Pro
465                 470                 475                 480

Lys Lys Leu Ile Trp Ser Val Tyr Pro Lys Asn Tyr Leu Pro Glu Thr
                485                 490                 495

Ile Lys Asn

<210> SEQ ID NO 101
<211> LENGTH: 18
<212> TYPE: DNA
<213> ORGANISM: artificial
<220> FEATURE:
<223> OTHER INFORMATION: description of artificial sequence: primer

<400> SEQUENCE: 101
aagcgaacgc aaggaggc                                                   18

<210> SEQ ID NO 102
<211> LENGTH: 18
<212> TYPE: DNA
<213> ORGANISM: artificial
<220> FEATURE:
<223> OTHER INFORMATION: description of artificial sequence: primer

<400> SEQUENCE: 102
cgaacgcaag gaggcaag                                                   18

<210> SEQ ID NO 103
<211> LENGTH: 18
<212> TYPE: DNA
<213> ORGANISM: artificial
<220> FEATURE:
<223> OTHER INFORMATION: description of artificial sequence: primer

<400> SEQUENCE: 103
acgcaaggag gcaagcga                                                   18

<210> SEQ ID NO 104
<211> LENGTH: 18
<212> TYPE: DNA
<213> ORGANISM: artificial
```

```
<220> FEATURE:
<223> OTHER INFORMATION: description of artificial sequence: primer

<400> SEQUENCE: 104
caaggaggca agcgaacg                                                        18

<210> SEQ ID NO 105
<211> LENGTH: 49
<212> TYPE: PRT
<213> ORGANISM: Human metapneumovirus
<220> FEATURE:
<221> NAME/KEY: misc_feature
<222> LOCATION: (2)..(22)
<223> OTHER INFORMATION: Xaa can be any naturally occurring amino acid
<220> FEATURE:
<221> NAME/KEY: misc_feature
<222> LOCATION: (29)..(48)
<223> OTHER INFORMATION: Xaa can be any naturally occurring amino acid

<400> SEQUENCE: 105

Lys Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Gly Glu Gly Ala Gly Asn Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Lys

<210> SEQ ID NO 106
<211> LENGTH: 49
<212> TYPE: PRT
<213> ORGANISM: Human metapneumovirus
<220> FEATURE:
<221> NAME/KEY: misc_feature
<222> L

```
<223> OTHER INFORMATION: description of artificial sequence: primer

<400> SEQUENCE: 108
ctgtggtctc tagtcccact tc                                              22

<210> SEQ ID NO 109
<211> LENGTH: 18
<212> TYPE: DNA
<213> ORGANISM: artificial
<220> FEATURE:
<223> OTHER INFORMATION: description of artificial sequence: primer

<400> SEQUENCE: 109
catgcaagct tatggggc                                                   18

<210> SEQ ID NO 110
<211> LENGTH: 21
<212> TYPE: DNA
<213> ORGANISM: artificial
<220> FEATURE:
<223> OTHER INFORMATION: description of artificial sequence: primer

<400> SEQUENCE: 110
cagagtggtt attgtcaggg t                                               21

<210> SEQ ID NO 111
<211> LENGTH: 19
<212> TYPE: DNA
<213> ORGANISM: artificial
<220> FEATURE:
<223> OTHER INFORMATION: description of artificial sequence: primer

<400> SEQUENCE: 111
gtagaactag gagcatatg                                                  19

<210> SEQ ID NO 112
<211> LENGTH: 22
<212> TYPE: DNA
<213> ORGANISM: artificial
<220> FEATURE:
<223> OTHER INFORMATION: description of artificial sequence: primer

<400> SEQUENCE: 112
tccccaatgt agatactgct tc                                              22

<210> SEQ ID NO 113
<211> LENGTH: 20
<212> TYPE: DNA
<213> ORGANISM: artificial
<220> FEATURE:
<223> OTHER INFORMATION: description of artificial sequence: primer

<400> SEQUENCE: 113
gcactcaaga gataccctag                                                 20

<210> SEQ ID NO 114
<211> LENGTH: 22
<212> TYPE: DNA
<213> ORGANISM: artificial
<220> FEATURE:
<223> OTHER INFORMATION: description of artificial sequence: primer

<400> SEQUENCE: 114
agactttctg ctttgctgcc tg                                              22
```

```
<210> SEQ ID NO 115
<211> LENGTH: 20
<212> TYPE: DNA
<213> ORGANISM: artificial
<220> FEATURE:
<223> OTHER INFORMATION: description of artificial sequence: primer

<400> SEQUENCE: 115
ccctgacaat aaccactctg                                               20

<210> SEQ ID NO 116
<211> LENGTH: 22
<212> TYPE: DNA
<213> ORGANISM: artificial
<220> FEATURE:
<223> OTHER INFORMATION: description of artificial sequence: primer

<400> SEQUENCE: 116
gccaactgat ttggctgagc tc                                            22

<210> SEQ ID NO 117
<211> LENGTH: 25
<212> TYPE: DNA
<213> ORGANISM: artificial
<220> FEATURE:
<223> OTHER INFORMATION: description of artificial sequence: primer

<400> SEQUENCE: 117
tgcactatct cctcttgggg ctttg                                         25

<210> SEQ ID NO 118
<211> LENGTH: 22
<212> TYPE: DNA
<213> ORGANISM: artificial
<220> FEATURE:
<223> OTHER INFORMATION: description of artificial sequence: primer

<400> SEQUENCE: 118
tcaaagctgc ttgacactgg cc                                            22

<210> SEQ ID NO 119
<211> LENGTH: 22
<212> TYPE: DNA
<213> ORGANISM: artificial
<220> FEATURE:
<223> OTHER INFORMATION: description of artificial sequence: primer

<400> SEQUENCE: 119
catgcccact ataaaggtc ag                                             22

<210> SEQ ID NO 120
<211> LENGTH: 20
<212> TYPE: DNA
<213> ORGANISM: artificial
<220> FEATURE:
<223> OTHER INFORMATION: description of artificial sequence: primer

<400> SEQUENCE: 120
caccccagtc tttcttgaaa                                               20

<210> SEQ ID NO 121
<211> LENGTH: 18
<212> TYPE: DNA
<213> ORGANISM: artificial
<220> FEATURE:
<223> OTHER INFORMATION: description of artificial sequence: primer
```

<400> SEQUENCE: 121
tgcttgtact tcccaaag                    18

<210> SEQ ID NO 122
<211> LENGTH: 18
<212> TYPE: DNA
<213> ORGANISM: artificial
<220> FEATURE:
<223> OTHER INFORMATION: description of artificial sequence: primer

<400> SEQUENCE: 122
tatttgaaca aaaagtgt                    18

<210> SEQ ID NO 123
<211> LENGTH: 19
<212> TYPE: DNA
<213> ORGANISM: artificial
<220> FEATURE:
<223> OTHER INFORMATION: description of artificial sequence: primer

<400> SEQUENCE: 123
tggtgtggga tattaacag                   19

<210> SEQ ID NO 124
<211> LENGTH: 20
<212> TYPE: DNA
<213> ORGANISM: artificial
<220> FEATURE:
<223> OTHER INFORMATION: description of artificial sequence: primer

<400> SEQUENCE: 124
gcactcaaga gataccctag                  20

<210> SEQ ID NO 125
<211> LENGTH: 22
<212> TYPE: DNA
<213> ORGANISM: artificial
<220> FEATURE:
<223> OTHER INFORMATION: description of artificial sequence: primer

<400> SEQUENCE: 125
agactttctg ctttgctgcc tg               22

<210> SEQ ID NO 126
<211> LENGTH: 20
<212> TYPE: DNA
<213> ORGANISM: artificial
<220> FEATURE:
<223> OTHER INFORMATION: description of artificial sequence: primer

<400> SEQUENCE: 126
ccctgacaat aaccactctg                  20

<210> SEQ ID NO 127
<211> LENGTH: 22
<212> TYPE: DNA
<213> ORGANISM: artificial
<220> FEATURE:
<223> OTHER INFORMATION: description of artificial sequence: primer

<400> SEQUENCE: 127
gccaactgat ttggctgagc tc               22

<210> SEQ ID NO 128
<211> LENGTH: 22

```
<212> TYPE: DNA
<213> ORGANISM: artificial
<220> FEATURE:
<223> OTHER INFORMATION: description of artificial sequence: primer

<400> SEQUENCE: 128
catgcccact ataaaggtc ag                                              22

<210> SEQ ID NO 129
<211> LENGTH: 20
<212> TYPE: DNA
<213> ORGANISM: artificial
<220> FEATURE:
<223> OTHER INFORMATION: description of artificial sequence: primer

<400> SEQUENCE: 129
caccccagtc tttcttgaaa                                                20

<210> SEQ ID NO 130
<211> LENGTH: 24
<212> TYPE: DNA
<213> ORGANISM: artificial
<220> FEATURE:
<223> OTHER INFORMATION: description of artificial sequence: primer

<400> SEQUENCE: 130
aaagaattca cgagaaaaaa acgc                                           24

<210> SEQ ID NO 131
<211> LENGTH: 22
<212> TYPE: DNA
<213> ORGANISM: artificial
<220> FEATURE:
<223> OTHER INFORMATION: description of artificial sequence: primer

<400> SEQUENCE: 131
ctctggtctc tagtcccact tc                                             22

<210> SEQ ID NO 132
<211> LENGTH: 20
<212> TYPE: DNA
<213> ORGANISM: artificial
<220> FEATURE:
<223> OTHER INFORMATION: description of artificial sequence: primer

<400> SEQUENCE: 132
tgttgtcgag actattccaa                                                20

<210> SEQ ID NO 133
<211> LENGTH: 20
<212> TYPE: DNA
<213> ORGANISM: artificial
<220> FEATURE:
<223> OTHER INFORMATION: description of artificial sequence: primer
<220> FEATURE:
<221> NAME/KEY: misc_feature
<222> LOCATION: (6)..(6)
<223> OTHER INFORMATION: n is a, c, g, or t

<400> SEQUENCE: 133
tgttgnacca gttgcagtct                                                20

<210> SEQ ID NO 134
<211> LENGTH: 23
<212> TYPE: DNA
<213> ORGANISM: artificial
<220> FEATURE:
```

```
<223> OTHER INFORMATION: description of artificial sequence: primer

<400> SEQUENCE: 134
tgctgcttct attgagaaac gcc                                          23

<210> SEQ ID NO 135
<211> LENGTH: 19
<212> TYPE: DNA
<213> ORGANISM: artificial
<220> FEATURE:
<223> OTHER INFORMATION: description of artificial sequence: primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 135
ggtgantcna atagggcca                                               19

<210> SEQ ID NO 136
<211> LENGTH: 21
<212> TYPE: DNA
<213> ORGANISM: artificial
<220> FEATURE:
<223> OTHER INFORMATION: description of artificial sequence: primer

<400> SEQUENCE: 136
ctcgaggttg tcaggatata g                                            21

<210> SEQ ID NO 137
<211> LENGTH: 21
<212> TYPE: DNA
<213> ORGANISM: artificial
<220> FEATURE:
<223> OTHER INFORMATION: description of artificial sequence: primer

<400> SEQUENCE: 137
ctttgggagt tgaacacagt t                                            21

<210> SEQ ID NO 138
<211> LENGTH: 20
<212> TYPE: DNA
<213> ORGANISM: artificial
<220> FEATURE:
<223> OTHER INFORMATION: description of artificial sequence: primer
<220> FEATURE:
<221> NAME/KEY: misc_feature
<222> LOCATION: (4)..(4)
<223> OTHER INFORMATION: n is a, c, g, or t

<400> SEQUENCE: 138
ttcngtttta gctgcttacg                                              20

<210> SEQ ID NO 139
<211> LENGTH: 21
<212> TYPE: DNA
<213> ORGANISM: artificial
<220> FEATURE:
<223> OTHER INFORMATION: description of artificial sequence: primer

<400> SEQUENCE: 139
aggcaaatct ctggataatg c                                            21
```

```
<210> SEQ ID NO 140
<211> LENGTH: 18
<212> TYPE: DNA
<213> ORGANISM: artificial
<220> FEATURE:
<223> OTHER INFORMATION: description of artificial sequence: primer

<400> SEQUENCE: 140
tcgtaacgtc tcgtgacc                                                   18

<210> SEQ ID NO 141
<211> LENGTH: 20
<212> TYPE: DNA
<213> ORGANISM: artificial
<220> FEATURE:
<223> OTHER INFORMATION: description of artificial sequence: primer

<400> SEQUENCE: 141
ggagatcttt ctagagtgag                                                 20

<210> SEQ ID NO 142
<211> LENGTH: 21
<212> TYPE: DNA
<213> ORGANISM: artificial
<220> FEATURE:
<223> OTHER INFORMATION: description of artificial sequence: primer
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 142
ccttggtgan tctatccgna g                                               21

<210> SEQ ID NO 143
<211> LENGTH: 25
<212> TYPE: DNA
<213> ORGANISM: artificial
<220> FEATURE:
<223> OTHER INFORMATION: description of artificial sequence: primer
<220> FEATURE:
<221> NAME/KEY: misc_feature
<222> LOCATION: (17)..(17)
<223> OTHER INFORMATION: n is a, c, g, or t

<400> SEQUENCE: 143
ctgccactgc tagttgngat aatcc                                           25

<210> SEQ ID NO 144
<211> LENGTH: 25
<212> TYPE: DNA
<213> ORGANISM: artificial
<220> FEATURE:
<223> OTHER INFORMATION: description of artificial sequence: primer

<400> SEQUENCE: 144
gggcttctaa gcgacccaga tcttg                                           25

<210> SEQ ID NO 145
<211> LENGTH: 27
<212> TYPE: DNA
<213> ORGANISM: artificial
<220> FEATURE:
<223> OTHER INFORMATION: description of artificial sequence: primer
```

```
<400> SEQUENCE: 145
gaatttcctt atggacaagc tctgtgc                                    27

<210> SEQ ID NO 146
<211> LENGTH: 25
<212> TYPE: DNA
<213> ORGANISM: artificial
<220> FEATURE:
<223> OTHER INFORMATION: description of artificial sequence: primer

<400> SEQUENCE: 146
gctcaacctc atcacatact aaccc                                      25

<210> SEQ ID NO 147
<211> LENGTH: 25
<212> TYPE: DNA
<213> ORGANISM: artificial
<220> FEATURE:
<223> OTHER INFORMATION: description of artificial sequence: primer

<400> SEQUENCE: 147
gctcaacctc atcacatact aaccc                                      25

<210> SEQ ID NO 148
<211> LENGTH: 27
<212> TYPE: DNA
<213> ORGANISM: artificial
<220> FEATURE:
<223> OTHER INFORMATION: description of artificial sequence: primer

<400> SEQUENCE: 148
gagatgggcg ggcaagtgcg gcaacag                                    27

<210> SEQ ID NO 149
<211> LENGTH: 28
<212> TYPE: DNA
<213> ORGANISM: artificial
<220> FEATURE:
<223> OTHER INFORMATION: description of artificial sequence: primer

<400> SEQUENCE: 149
gcctttgcaa tcaggatcca aatttggg                                   28

<210> SEQ ID NO 150
<211> LENGTH: 24
<212> TYPE: DNA
<213> ORGANISM: artificial
<220> FEATURE:
<223> OTHER INFORMATION: description of artificial sequence: primer

<400> SEQUENCE: 150
ctgctgcagt tcaggaaaca tcag                                       24

<210> SEQ ID NO 151
<211> LENGTH: 22
<212> TYPE: DNA
<213> ORGANISM: artificial
<220> FEATURE:
<223> OTHER INFORMATION: description of artificial sequence: primer

<400> SEQUENCE: 151
accggatgtg ctcacagaac tg                                         22

<210> SEQ ID NO 152
<211> LENGTH: 18
```

```
<212> TYPE: DNA
<213> ORGANISM: artificial
<220> FEATURE:
<223> OTHER INFORMATION: description of artificial sequence: primer

<400> SEQUENCE: 152
ttaaccagca aagtgtta                                                   18

<210> SEQ ID NO 153
<211> LENGTH: 18
<212> TYPE: DNA
<213> ORGANISM: artificial
<220> FEATURE:
<223> OTHER INFORMATION: description of artificial sequence: primer

<400> SEQUENCE: 153
ttaaccagca aagtgtta                                                   18

<210> SEQ ID NO 154
<211> LENGTH: 21
<212> TYPE: DNA
<213> ORGANISM: artificial
<220> FEATURE:
<223> OTHER INFORMATION: description of artificial sequence: primer

<400> SEQUENCE: 154
ttagggcaag agatggtaag g                                               21

<210> SEQ ID NO 155
<211> LENGTH: 19
<212> TYPE: DNA
<213> ORGANISM: artificial
<220> FEATURE:
<223> OTHER INFORMATION: description of artificial sequence: primer

<400> SEQUENCE: 155
ttataacaat gatggaggg                                                  19

<210> SEQ ID NO 156
<211> LENGTH: 21
<212> TYPE: DNA
<213> ORGANISM: artificial
<220> FEATURE:
<223> OTHER INFORMATION: description of artificial sequence: primer

<400> SEQUENCE: 156
cattaaaaag ggcacagacg c                                               21

<210> SEQ ID NO 157
<211> LENGTH: 17
<212> TYPE: DNA
<213> ORGANISM: artificial
<220> FEATURE:
<223> OTHER INFORMATION: description of artificial sequence: primer

<400> SEQUENCE: 157
tggacattct ccgcagt                                                    17

<210> SEQ ID NO 158
<211> LENGTH: 18
<212> TYPE: DNA
<213> ORGANISM: artificial
<220> FEATURE:
<223> OTHER INFORMATION: description of artificial sequence: primer

<400> SEQUENCE: 158
```

-continued cccaccacca gagagaaa                                        18

<210> SEQ ID NO 159
<211> LENGTH: 18
<212> TYPE: DNA
<213> ORGANISM: artificial
<220> FEATURE:
<223> OTHER INFORMATION: description of artificial sequence: primer

<400> SEQUENCE: 159
accaccagag agaaaccc                                        18

<210> SEQ ID NO 160
<211> LENGTH: 18
<212> TYPE: DNA
<213> ORGANISM: artificial
<220> FEATURE:
<223> OTHER INFORMATION: description of artificial sequence: primer

<400> SEQUENCE: 160
accagagaga aacccacc                                        18

<210> SEQ ID NO 161
<211> LENGTH: 18
<212> TYPE: DNA
<213> ORGANISM: artificial
<220> FEATURE:
<223> OTHER INFORMATION: description of artificial sequence: primer

<400> SEQUENCE: 161
agagagaaac ccaccacc                                        18

<210> SEQ ID NO 162
<211> LENGTH: 18
<212> TYPE: DNA
<213> ORGANISM: artificial
<220> FEATURE:
<223> OTHER INFORMATION: description of artificial sequence: primer

<400> SEQUENCE: 162
gagaaaccca ccaccaga                                        18

<210> SEQ ID NO 163
<211> LENGTH: 18
<212> TYPE: DNA
<213> ORGANISM: artificial
<220> FEATURE:
<223> OTHER INFORMATION: description of artificial sequence: primer

<400> SEQUENCE: 163
aaacccacca ccagagag                                        18

<210> SEQ ID NO 164
<211> LENGTH: 18
<212> TYPE: DNA
<213> ORGANISM: artificial
<220> FEATURE:
<223> OTHER INFORMATION: description of artificial sequence: primer

<400> SEQUENCE: 164
ggaggcaagc gaacgcaa                                        18

<210> SEQ ID NO 165
<211> LENGTH: 18
<212> TYPE: DNA
<213> ORGANISM: artificial

```
<220> FEATURE:
<223> OTHER INFORMATION: description of artificial sequence: primer

<400> SEQUENCE: 165
ggcaagcgaa cgcaagga                                                        18

<210> SEQ ID NO 166
<211> LENGTH: 9
<212> TYPE: RNA
<213> ORGANISM: metapneumovirus

<400> SEQUENCE: 166 gggacaagu                                                                   9

<210> SEQ ID NO 167
<211> LENGTH: 9
<212> TYPE: RNA
<213> ORGANISM: metapneumovirus

<400> SEQUENCE: 167 gggauaaau                                                                   9

<210> SEQ ID NO 168
<211> LENGTH: 9
<212> TYPE: RNA
<213> ORGANISM: metapneumovirus

<400> SEQUENCE: 168 gagacaaau                                                                   9

<210> SEQ ID NO 169
<211> LENGTH: 9
<212> TYPE: DNA
<213> ORGANISM: APV

<400> SEQUENCE: 169 aggaccaat                                                                   9

<210> SEQ ID NO 170
<211> LENGTH: 9
<212> TYPE: DNA
<213> ORGANISM: APV

<400> SEQUENCE: 170 gggaccagt                                                                   9

<210> SEQ ID NO 171
<211> LENGTH: 9
<212> TYPE: RNA
<213> ORGANISM: APV

<400> SEQUENCE: 171 uaguuaauu                                                                   9

<210> SEQ ID NO 172
<211> LENGTH: 7
<212> TYPE: RNA
<213> ORGANISM: artificial
<220> FEATURE:
<223> OTHER INFORMATION: decription of artificial sequence: consensus
      sequence

<400> SEQUENCE: 172 uaaaaah                                                                     7
```

```
<210> SEQ ID NO 173
<211> LENGTH: 49
<212> TYPE: PRT
<213> ORGANISM: Human metapneumovirus
<220> FEATURE:
<221> NAME/KEY: misc_feature
<222> LOCATION: (2)..(22)
<223> OTHER INFORMATION: Xaa can be any naturally occurring amino acid

<400> SEQUENCE: 173

Lys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Gly Glu Gly Ala Gly Asn Met Met Met Met
                20                  25                  30

Met Met Met Met Met Met Met Met Met Met Met Met Met Met Met
            35                  40                  45

Lys
```

VIRUS CAUSING RESPIRATORY TRACT ILLNESS IN SUSCEPTIBLE MAMMALS

CROSS-REFERENCE TO RELATED APPLICATIONS

This application is a continuation of U.S. patent application Ser. No. 16/235,030, filed Dec. 28, 2018, pending, which is a continuation of U.S. patent application Ser. No. 15/796,500, filed Oct. 27, 2017, issued Jan. 1, 2019, now U.S. Pat. No. 10,167,524, which is a continuation of U.S. patent application Ser. No. 15/453,764, filed Mar. 8, 2017, issued Oct. 31, 2017, now U.S. Pat. No. 9,803,252, which is a continuation of U.S. patent application Ser. No. 15/147,653, filed May 5, 2016, now U.S. Pat. No. 9,593,386, issued Mar. 14, 2017, which is a continuation of U.S. patent application Ser. No. 14/553,957, filed Nov. 25, 2014, now U.S. Pat. No. 9,334,543, issued May 10, 2016, which is a continuation of U.S. patent application Ser. No. 10/466,811, which was filed on Mar. 4, 2004, now U.S. Pat. No. 8,927,206, issued Jan. 6, 2015, which is a national stage application of International Application PCT/NL02/00040, international filing date Jan. 18, 2002, which claimed priority to European Patent Application Serial No. 01200213.5, filed Jan. 19, 2001, and to European Patent Application Serial No. 01203985.5, filed Oct. 18, 2001, the disclosure of each of which is hereby incorporated herein in its entirety by this reference.

STATEMENT ACCORDING TO 37 C.F.R. § 1.821(c) or (e) SEQUENCE LISTING SUBMITTED AS A TXT FILE

Pursuant to 37 C.F.R. § 1.821(c) or (e), a file containing a TXT version of the Sequence Listing has been submitted concomitant with this application, the contents of which are hereby incorporated by reference.

TECHNICAL FIELD

The invention relates to the field of virology.

BACKGROUND

In the past decades several etiological agents of mammalian disease, in particular of respiratory tract illnesses (RTI), in particular of humans, have been identified. Classical etiological agents of RTI with mammals are respiratory syncytial viruses belonging to the genus *Pneumovirus* found with humans (hRSV) and ruminants such as cattle or sheep (bRSV and/or oRSV). In human RSV differences in reciprocal cross-neutralization assays, reactivity of the G proteins in immunological assays and nucleotide sequences of the G gene are used to define 2 hRSV antigenic subgroups. Within the subgroups the aa sequences show 94% (subgroup A) or 98% (subgroup B) identity, while only 53% aa sequence identity is found between the subgroups. Additional variability is observed within subgroups based on monoclonal antibodies, RT-PCR assays and RNAse protection assays. Viruses from both subgroups have a worldwide distribution and may occur during a single season. Infection may occur in presence of pre-existing immunity and the antigenic variation is not strictly required to allow re-infection. See, for example, W. M. Sullender, Respiratory Syncytial Virus Genetic and Antigenic Diversity, *Clinical Microbiology Reviews*, 2000, 13(1):1-15; P. L. Collins, K. McIntosh, and R. M. Chanock, Respiratory syncytial virus, *Fields virology*, ed. B. N. Knipe, P. M. Howley, 1996, Philadelphia: Lippencott-Raven, pp. 1313-1351; P. R. Johnson, et al., The G glycoprotein of human respiratory syncytial viruses of subgroups A and B: extensive sequence divergence between antigenically related proteins, *Proc. Natl. Acad. Sci. U.S.A.*, 1987, 84(16):5625-9; P. L. Collins, The molecular Biology of Human Respiratory Syncytial Virus (RSV) of the Genus *Pneumovirus*, in *The Paramyxoviruses*, D. W. Kingsbury, Editor, 1991, Plenum Press: New York. p. 103-153.

Another classical *Pneumovirus* is the pneumonia virus of mice (PVM), in general only found with laboratory mice. However, a proportion of the illnesses observed among mammals can still not be attributed to known pathogens.

BRIEF SUMMARY

The invention provides an isolated essentially mammalian negative-sense single-stranded RNA virus (MPV) belonging to the sub-family Pneumovirinae of the family Paramyxoviridae and identifiable as phylogenetically corresponding to the genus *Metapneumovirus*. The virus is identifiable as phylogenetically corresponding to the genus *Metapneumovirus* by determining a nucleic acid sequence of the virus and testing it in phylogenetic analyses, for example wherein maximum likelihood trees are generated using 100 bootstraps and 3 jumbles and finding it to be more closely phylogenetically corresponding to a virus isolate deposited as I-2614 with CNOM, Paris than it is corresponding to an essentially avian virus isolate of avian *Pneumovirus* (APV) also known as turkey rhinotracheitis virus (TRTV), the etiological agent of avian rhinotracheitis. For phylogenetic analyses, it is most useful to obtain the nucleic acid sequence of a non-MPV as outgroup to be compared with, a very useful outgroup isolate can be obtained from avian *Pneumovirus* serotype C (APV-C), as is for example demonstrated in FIG. 5 herein.

Although phylogenetic analyses provides a convenient method of identifying a virus as an MPV several other possibly more straightforward albeit somewhat more course methods for identifying the virus or viral proteins or nucleic acids from the virus are herein also provided. As a rule of thumb an MPV can be identified by the percentages of a homology of the virus, proteins or nucleic acids to be identified in comparison with isolates, viral proteins, or nucleic acids identified herein by sequence or deposit. It is generally known that virus species, especially RNA virus species, often constitute a quasi species wherein a cluster of the viruses displays heterogeneity among its members. Thus it is expected that each isolate may have a somewhat different percentage relationship with one of the various isolates as provided herein.

When one wishes to compare with the deposited virus I-2614, the invention provides an isolated essentially mammalian negative-sense single-stranded RNA virus (MPV) belonging to the sub-family Pneumovirinae of the family Paramyxoviridae and identifiable as phylogenetically corresponding to the genus *Metapneumovirus* by determining an amino acid sequence of the virus and determining that the amino acid sequence has a percentage amino acid homology to a virus isolate deposited as I-2614 with CNCMK Paris which is essentially higher than the percentages provided herein for the L protein, the M protein, the N protein, the P protein, or the F protein, in comparison with APV-C or, likewise, an isolated essentially mammalian negative-sense single-stranded RNA virus (NPV) belonging to the sub-family Pneumovirinae of the family Paramyxoviridae is provided as identifiable as phylogenetically corresponding to the genus *Metapneumovirus* by determining a nucleic acid sequence of the virus and determining that the nucleic acid sequence has a percentage nucleic acid identity to a virus isolate deposited as I-2614 with CNCM, Paris which is essentially higher than the percentages identified herein for the nucleic acids encoding the L protein, the M protein, the N protein, the P protein, or the F protein as identified herein below in comparison with APV-C.

Again as a rule of thumb one may consider an MPV as belonging to one of the two serological groups of MPV as identified herein when the isolates or the viral proteins or nuclear acids of the isolates that need to be identified have percentages homology that fall within the bounds and metes of the percentages of homology identified herein for both separate groups, taking isolates 00-1 or 99-1 as the respective isolates of comparison. However, when the percentages of homology are smaller or there is more need to distinguish the viral isolates from for example APV-C it is better advised to resort to the phylogenetic analyses as identified herein.

Again one should keep in mind that the percentages can vary somewhat when other isolates are selected in the determination of the percentage of homology.

With the provision of this MPV, the invention provides diagnostic means and methods and therapeutic means and methods to be employed in the diagnosis and/or treatment of disease, in particular of respiratory disease, in particular of mammals, more in particular in humans. However, due to the, albeit distant, genetic relationship of the essentially mammalian MPV with the essentially avian APV, in particular with APV-C, the invention also provides means and methods to be employed in the diagnosis and treatment of avian disease. In virology, it is most advisory that diagnosis and/or treatment of a specific viral infection is performed with reagents that are most specific for the specific virus causing the infection. In this case this means that it is preferred that the diagnosis and/or treatment of an MPV infection is performed with reagents that are most specific for MPV. This by no means however excludes the possibility that less specific, but sufficiently cross-reactive reagents are used instead, for example because they are more easily available and sufficiently address the task at hand. Herein it is for example provided to perform virological and/or serological diagnosis of MPV infections in mammals with reagents derived from APV, in particular with reagents derived from APV-C, in the detailed description herein it is for example shown that sufficiently trustworthy serological diagnosis of MPV infections in mammals can be achieved by using an ELISA specifically designed to detect APV antibodies in birds. A particular useful test for this purpose is an ELISA test designed for the detection of APV antibodies (e.g., in serum or egg yolk), one commercially available version of which is known as APV-Ab SVANO-VIR® which is manufactured by SVANOVA Biotech AB, Uppsal Science Park Glunten SE-751 83 Uppsala Sweden. The reverse situation is also the case, herein it is for example provided to perform virological and/or serological diagnosis of APV infections in mammals with reagents derived from MPV, in the detailed description herein it is for example shown that sufficiently trustworthy serological diagnosis of APV infections in birds can be achieved by using an ELISA designed to detect MPV antibodies. Considering that antigens and antibodies have a lock-and-key relationship, detection of the various antigens can be achieved by selecting the appropriate antibody having sufficient cross-reactivity. Of course, for relying on such cross-reactivity, it is best to select the reagents (such as antigens or antibodies) under guidance of the amino acid homologies that exist between the various (glyco)proteins of the various viruses, whereby reagents relating to the most homologous proteins will be most useful to be used in tests relying on the cross-reactivity.

For nucleic acid detection, it is even more straightforward, instead of designing primers or probes based on heterologous nucleic acid sequences of the various viruses and thus that detect differences between the essentially mammalian or avian Metapneumoviruses, it suffices to design or select primers or probes based on those stretches of virus-specific nucleic acid sequences that show high homology. In general, for nucleic acid sequences, homology percentages of 90% or higher guarantee sufficient cross-reactivity to be relied upon in diagnostic tests utilizing stringent conditions of hybridization.

The invention for example provides a method for virologically diagnosing a MPV infection of an animal in particular of a mammal, more in particular of a human being, comprising determining in a sample of the animal the presence of a viral isolate or component thereof by reacting the sample with a MPV-specific nucleic acid a or antibody according to the invention, and a method for serologically diagnosing an MPV infection of a mammal comprising determining in a sample of the mammal the presence of an antibody specifically directed against an MPV or component thereof by reacting the sample with a MPV-specific proteinaceous molecule or fragment thereof or an antigen according to the invention. The invention also provides a diagnostic kit for diagnosing an MPV infection comprising an MPV, an MPV-specific nucleic acid, proteinaceous molecule or fragment thereof, antigen and/or an antibody according to the invention, and preferably a means for detecting the MPV, MPV-specific nucleic acid, proteinaceous molecule or fragment thereof, antigen and/or an antibody, the means for example comprising an excitable group such as a fluorophore or enzymatic detection system used in the art (examples of suitable diagnostic kit format comprise IF, ELISA, neutralization assay, RT-PCR assay). To determine whether an as yet unidentified virus component or synthetic analogue thereof such as nucleic acid, proteinaceous molecule or fragment thereof can be identified as MPV-specific, it suffices to analyze the nucleic acid or amino acid sequence of the component, for example for a stretch of the nucleic acid or amino acid, preferably of at least 10, more preferably at least 25, more preferably at least 40 nucleotides or amino acids (respectively), by sequence homology comparison with known MPV sequences and with known non-MPV sequences APV-C is preferably used) using for example phylogenetic analyses as. provided herein. Depending on the degree of relationship with the MPV or non-MPV sequences, the component or synthetic analogue can be identified.

The invention also provides method for virologically diagnosing an MPV infection of a mammal comprising determining in a sample of the mammal the presence of a viral isolate or component thereof by reacting the sample with a cross-reactive nucleic acid derived from APV (preferably serotype C) or a cross-reactive antibody reactive with the APV, and a method for serologically diagnosing an MPV infection of a mammal comprising determining in a sample of the mammal the presence of a cross-reactive antibody that is also directed against an APV or component thereof by reacting the sample with a proteinaceous molecule or fragment thereof or an antigen derived from APV. Furthermore, the invention provides the use of a diagnostic kit initially designed for AVP or AVP-antibody detection for diagnosing an MPV infection, in particular for detecting the MPV infection in humans.

The invention also provides method for virologically diagnosing an APV infection in a bird comprising determining in a sample of the bird the presence of a viral isolate or component thereof by reacting the sample with a cross-reactive nucleic acid derived from MPV or a cross-reactive antibody reactive with the MPV, and a method for serologically diagnosing an APV infection of a bird comprising determining in a sample of the bird the presence of a cross-reactive antibody that is also directed against an MPV or component thereof by reacting the sample with a proteinaceous molecule or fragment thereof or an antigen derived from MPV.

Furthermore, the invention provides the use of a diagnostic kit initially designed for MPV or MPV-antibody detection for diagnosing an APV infection, in particular for detecting the APV infection in poultry such as a chicken, duck or turkey.

As the, with treatment, similar use can be made of the cross-reactivity found, in particular when circumstances at hand make the use of the more homologous approach less straightforward. Vaccinations that cannot wait, such as emergency vaccinations against MPV infections can for example be performed with vaccine-preparations derived from APV (preferably type C) isolates when a more homologous MPV vaccine is not available, and, vice versa, vaccinations against APV infections can be contemplated with vaccine preparations derived from MPV. Also, reverse genetic techniques make it possible to generate chimeric APV-MPV virus constructs that are useful as a vaccine, being sufficiently dissimilar to field isolates of each of the respective strains to be attenuated to a desirable level. Similar reverse genetic techniques will make it also possible to generate chimeric paramyxovirus *Metapneumovirus* constructs, such as RSV-MPV or PI3-MPV constructs for us in a vaccine preparation. Such constructs are particularly useful as a combination vaccine to combat respiratory tract illnesses.

The invention thus provides a novel etiological agent, an isolated essentially mammalian negative-sense single-stranded RNA virus (herein also called MPV) belonging to the subfamily Pneumovirinae of the family Paramyxoviridae but not identifiable as a classical *Pneumovirus*, and belonging to the genus *Metapneumovirus*, and MPV-specific components or synthetic analogues thereof. Mammalian viruses resembling Metapneumoviruses, i.e., Metapneumoviruses isolatable from mammals that essentially function as natural host for the virus or cause disease in the mammals, have until now not been found. Metapneumoviruses, in general thought to be essentially restricted to poultry as natural host or etiological agent of disease, are also known as avian Pneumoviruses. Recently, an APV isolate of duck was described (OR 2 801 607), further demonstrating that APV infections are essentially restricted to birds as natural hosts.

The invention provides an isolated mammalian *Pneumovirus* (herein also called MPV) comprising a gene order and amino acid sequence distinct from that of the genus *Pneumovirus* and which is closely related and considering its phylogenetic relatedness likely belonging to the genus *Metapneumovirus* within the subfamily Pneumovirinae of the family Paramyxoviridae. Although until now, Metapneumoviruses have only been isolated from birds, it is now shown that related, albeit materially distinct, viruses can be identified in other animal species such as mammals. Herein we show repeated isolation of MPV from humans, whereas no such reports exists for APV. Furthermore, unlike APV, MPV essentially does not or only little replicates in chickens and turkeys where it easily does in cynomolgus macaques.

No reports have been found on replication of APV in mammals. In addition, whereas specific anti-sera raised against MPV neutralize MPV, anti-sera raised against APV A, B or C do not neutralize MPV to the same extent, and this lack of full cross-reactivity provides another proof for MPV being a different *Metapneumovirus*. Furthermore, where APV and MPV share a similar gene order, the G and SH proteins of MPV are largely different from the ones known of APV in that they show no significant sequence homologies on both the amino acid or nucleic acid level. Diagnostic assays to discriminate between APV and MPV isolates or antibodies directed against these different viruses can advantageously be developed based on one or both of these proteins (examples are IF, ELISA, neutralization assay, RT-PCR assay). However, also sequence and/or antigenic information obtained from the more related N, P, M, F and L proteins of MPV and analyses of sequence homologies with the respective proteins of APV, can also be used to discriminate between APV and MPV. For example, phylogenetic analyses of sequence information obtained from MNV revealed that MV and APV are two different viruses. In particular, the phylogenetic trees show that APV and MPV are two different lineages of virus. We have also shown that MPV is circulating in the human population for at least 50 years, therefore interspecies transmission has probably taken place at least 50 years ago and is not an everyday event. Since MPV CPE was virtually indistinguishable from that caused by hRSV or hPIV-1 in tMK or other cell cultures, the MPV may have well gone unnoticed until now. tMK (tertiary monkey kidney cells, i.e., ME cells in a third passage in cell culture) are preferably used due to their lower costs in comparison to primary or secondary cultures. The CPE is, as well as with some of the classical Paramyxoviridae, characterized by syncytium formation after which the cells showed rapid internal disruption, followed by detachment of the cells from the monolayer. The cells usually (but not always) displayed CPE after three passages of virus from original material, at day 10 to 14 post inoculation, somewhat later than CPE caused by other viruses such as hRSV or hPIV-1.

Classically, as devastating agents of disease, paramyxoviruses account for many animal and human deaths worldwide each year. The Paramyxoviridae form a family within the order of Mononegavirales (negative-sense single-stranded RNA viruses), consisting of the sub-families Paramyxovirinae and Pneumovirinae. The latter sub-family is at present taxonomically divided in the genera *Pneumovirus* and *Metapneumovirus*.[1] Human respiratory syncytial virus (hRSV), the type species of the *Pneumovirus* genus, is the single-most important cause of lower respiratory tract infections during infancy and early childhood worldwide.[2] Other members of the *Pneumovirus* genus include the bovine and ovine respiratory syncytial viruses and pneumonia virus of mice (PVM).

Avian *Pneumovirus* (APV) also known as turkey rhinotracheitis virus (TRTV), the etiological agent of avian rhinotracheitis, an upper respiratory tract infection of turkeys,[3] is the sole member of the recently assigned *Metapneumovirus* genus, which, as said was until now not associated with infections, or what is more, with disease of mammals. Serological subgroups of APV can be differentiated on the basis of nucleotide or amino acid sequences of the G glycoprotein and neutralization tests using monoclonal antibodies that also recognize the G glycoprotein, Within subgroups A, B and D the G protein shows 98.5 to 99.7% aa sequence identity within subgroups while between the subgroups only 31.2-38% aa identity is observed. See, for example, M. S. Collins, R. E. Gough, and D. J. Alexander, Antigenic differentiation of avian *Pneumovirus* isolates using polyclonal antisera and mouse monoclonal antibodies, *Avian Pathology*, 1993, 22:469-479; J. K. A. Cook, B. V. Jones, M. M. Ellis, Antigenic differentiation of strains of turkey rhinotracheitis virus using monoclonal antibodies, *Avian Pathology*, 1993, 22:257-273; M. H. Bayon-Auboyer, et al., Nucleotide sequences of the F, L and G protein genes of two non-A/non-B avian Pneumoviruses (APV) reveal a novel APV subgroup, *J. Gen. Virol.* 2000, 81 (Pt 11):2723-33; B. S. Seal, Matrix protein gene nucleotide and predicted amino acid sequence demonstrate that the first US avian *Pneumovirus* isolate is distinct from European strains, *Virus Res.*, 1998, 58(1-2):45-52; M. H. Bayon-Auboyer, et al., Comparison of F-, G- and N-based RT-PCR protocols with conventional virological procedures for the detection and typing of turkey rhinotracheitis virus, *Arch. Virol.* 1999. 144(6):1091-109; K. Juhasz and A. J. Easton, Extensive sequence variation in the attachment (G) protein gene of avian *Pneumovirus*: evidence for two distinct subgroups, *J. Gen. Virol.* 1994. 75 (Pt 11):2873-80.

A further serotype of APV is provided in WO00/20600, which describes the Colorado isolate of APV and compared it to known APV or TRT strains with in vitro serum neutralization tests. First, the Colorado isolate was tested against monospecific polyclonal antisera to recognized TRT isolates. The Colorado isolate was not neutralized by monospecific antisera to any of the TRT strains. It was, however, neutralized by a hyperimmune antiserum raised against a subgroup A strain. This antiserum neutralized the homologous virus to a titer of 1:400 and the Colorado isolate to a titer of 1:80. Using the above method, the Colorado isolate was then tested against TRT monoclonal antibodies. In each case, the reciprocal neutralization titer was <10. Monospecific antiserum raised to the Colorado isolate was also tested against TRT strains of both subgroups. None of the TRT strains tested were neutralized by the antiserum to the Colorado isolate.

The Colorado strain of APV does not protect SPF chicks against challenge with either a subgroup A or a subgroup B strain of TRT virus. These results suggest that the Colorado isolate may be the first example of a further serotype of avian *Pneumovirus*, as also suggested by Bayon-Auboyer et al. (*J. Gen. Vir.* 81:2723-2733 (2000)).

In a preferred embodiment, the invention provides an isolated MPV taxonomically corresponding to a (hereto unknown mammalian) *Metapneumovirus* comprising a gene order distinct from that of the Pneumoviruses within the sub-family Pneumovirinae of the family Paramyxoviridae. The classification of the two genera is based primarily on their gene constellation; Metapneumoviruses generally lack non-structural proteins such NS1 or NS2 (see also Randhawa et al., *J. Vir.* 71:9849-9854 (1997), and the gene order is different from that of Pneumoviruses (RSV: '3-NS1-NS2-N-P-M-SH-G-F-M2-5', APV: '3-N-P-M-F-M2-SH-G-L-5').[4, 5, 6] MPV as provided by the invention or a virus isolate taxonomically corresponding therewith is upon EM analysis revealed by paramyxovirus-like particles. Consistent with the classification, MPV or virus isolates phylogenetically corresponding or taxonomically corresponding therewith are sensitive to treatment with chloroform; are cultured optimally on tMK cells or cells functionally equivalent thereto and are essentially trypsine dependent in most cell cultures. Furthermore, the typical CPE and lack of hemagglutinating activity with most classically used red blood cells suggested that a virus as provided herein is, albeit only distantly, related to classical Pneumoviruses such as RSV. Although most paramyxoviruses have hemagglutinating activity, most of the Pneumoviruses do not.[13] An MPV according to the invention also contains a second overlapping ORF (M2-2) in the nucleic acid fragment encoding the M2 protein, as in general most other Pneumoviruses such as for example also demonstrated in Ahmadian et al., *J. Gen. Vir.* 80:2011-2016 (1999).

To find further viral isolates as provided by the invention it suffices to test a sample, optionally obtained from a diseased animal or human, for the presence of a virus of the sub-family Pneumovirinae, and test a thus obtained virus for the presence of genes encoding (functional) NS1 or NS2 or essentially demonstrate a gene order that is different from that of Pneumoviruses such as RSV as already discussed above. Furthermore, a virus isolate phylogenetically corresponding and thus taxonomically corresponding with MPV may be found by cross-hybridization experiments using nucleic acid from a here provided MPV isolate, or in classical cross-serology experiments using monoclonal antibodies specifically directed against and/or antigens and/or immunogens specifically derived from an MPV isolate.

Newly isolated viruses are phylogenetically corresponding to and thus taxonomically corresponding to MPV when comprising a gene order and/or amino acid sequence sufficiently similar to our prototypic MPV isolate(s), or are structurally corresponding therewith, and show close relatedness to the genus *Metapneumovirus* within the subfamily Pneumovirinae. The highest amino sequence homology, and defining the structural correspondence on the individual protein level between MPV and any of the known other viruses of the same family to date (APV subtype C) is for matrix 87%, for nucleoprotein 88%, for phosphoprotein 68%, for fusion protein 81% and for parts of the polymerase protein 56-64%, as can be deduced when comparing the sequences given in FIGS. 6A-6E with sequences of other viruses, in particular of AVP-C. Individual proteins or whole virus isolates with, respectively, higher homology to these mentioned maximum values are considered phylogenetically corresponding and thus taxonomically corresponding to MPV, and comprise a nucleic acid sequence structurally corresponding with a sequence as shown in FIGS. 6A-6E. Herewith the invention provides a virus phylogenetically corresponding to the deposited virus. It should be noted that, similar to other viruses, a certain degree of variation is found between different isolated essentially mammalian negative-sense single-stranded RNA virus isolates as provided herein. In phylogenetic trees, we have identified at least two genetic clusters of virus isolates based on comparative sequence analyses of parts of the L, M, N and F genes. Based on nucleotide and amino-acid differences in the viral nucleic acid or amino acid sequences (the viral sequences), and in analogy to other Pneumoviruses such as RSV, these MPV genotypes represent subtypes of MPV. Within each of the genetic clusters of MPV isolates, the percentage identity at the nucleotide level was found to be 94-100 for L, 91-100 for M, 90-100 for N and 93-100 for F and at the amino acid level the percentage identity was found to be 91-100 for L, 98-100 for M, 96-100 for N and 98-100 for F. A further comparison can be found in FIGS. 18 to 28. The minimum percentage identity at the nucleotide level for the entire group of isolated essentially mammalian negative-sense single-stranded RNA virus as provided herein (MPV isolates) identified so far was 81 for L and M, 83 for N and 82 for F. At the amino acid level, this percentage was 91 for L and N, 94 for M, and 95 for F. The viral sequence of a MPV isolate or an isolated MPV F gene as provided herein for example shows less than 81% nucleotide sequence identity or less than 82% (amino acid sequence identity with the respective nucleotide or amino acid sequence of an APV-C fusion (F) gene as, for example, provided by Seal et al., *Vir. Res.* 66:139147 (2000).

Also, the viral sequence of a MPV isolate or an isolated MPV L gene as provided herein for example shows less than 61% nucleotide sequence identity or less than 63% amino acid sequence identity with the respective nucleotide or amino acid sequence of an APV-A polymerase gene as for example provided by Randhawa et al., *J. Gen. Vir.* 77:3047-3051 (1996).

Sequence divergence of MPV strains around the world may be somewhat higher, in analogy with other viruses. Consequently, two potential genetic clusters are identified by analyses of partial nucleotide sequences in the N, M, F and L ORFs of 9 virus isolates. 90-100% nucleotide identity was observed within a cluster, and 81-88% identity was observed between the clusters. Sequence information obtained on more virus isolates confirmed the existence of two genotypes. Virus isolate ned/00/01 as prototype of cluster A, and virus isolate ned/99/01 as prototype of cluster B have been used in cross-neutralization assays to test whether the genotypes are related to different serotypes or subgroups. From these data we conclude that essentially mammalian virus isolates displaying percentage amino acid homology higher than 64 for L, 87 for M, 88 for N, 68 for P, 81 for F 84 for M2-1 or 58 for M2-2 to isolate I-2614 may be classified as an isolated essentially mammalian negative-sense single-stranded RNA virus as provided herein. In particular, those virus isolates in general that have a minimum percentage identity at the nucleotide sequence level with a prototype MPV isolate as provided herein of 81 for L and M, 83 for N and/or 82 for F are members of the group of MPV isolates as provided herein. At the amino acid level, these percentages are 91 for L and N, 94 for M, and/or 95 for F. When the percentage amino acid sequence homology for a given virus isolate is higher than 90 for L and N, 93 for M, or 94 for F, the virus isolate is similar to the group of MPV isolates displayed in FIG. 5. When the percentage amino acid sequence homology for a given virus isolate is higher than 94 for L, 95 for N or 97 for M and F the virus isolate can be identified to belong to one of the genotype clusters represented in FIG. 5. It should be noted that these percentages of homology, by which genetic clusters are defined, are similar to the degree of homology found among genetic clusters in the corresponding genes of RSV.

In short, the invention provides an isolated essentially mammalian negative-sense single-stranded RNA virus (MPV) belonging to the sub-family Pneumovirinae of the family Paramyxoviridae and identifiable as phylogenetically corresponding to the genus *Metapneumovirus* by determining a nucleic acid sequence of a suitable fragment of the genome of the virus and testing it in phylogenetic tree analyses wherein maximum likelihood trees are generated using 100 bootstraps and 3 jumbles and finding it to be more closely phylogenetically corresponding to a virus isolate deposited as I-2614 with CNCM, Paris than it is corresponding to a virus isolate of avian *Pneumovirus* (APV) also known as turkey rhinotracheitis virus (TV), the etiological agent of avian rhinotracheitis.

Suitable nucleic acid genome fragments each useful for such phylogenetic tree analyses are for example any of the RAP-PCR fragments 1 to 10 as disclosed herein in the detailed description, leading to the various phylogenetic tree analyses as disclosed herein in FIG. 4 or 5. Phylogenetic tree analyses of the nucleoprotein (N), phosphoprotein (P), matrix protein (M) and fusion protein (F) genes of MPV revealed the highest degree of sequence homology with APV serotype C, the avian *Pneumovirus* found primarily in birds in the United States.

In a preferred embodiment, the invention provides an isolated essentially mammalian negative-sense single-stranded RNA virus (MPV) belonging to the sub-family Pneumovirinae of the family Paramyxoviridae and identifiable as phylogenetically corresponding to the genus *Metapneumovirus* by determining a nucleic acid sequence of a suitable fragment of the genome of the virus and testing it in phylogenetic tree analyses wherein maximum likelihood trees are generated using 100 bootstraps and 3 jumbles and finding it to be more closely phylogenetically corresponding to a virus isolate deposited as I-2614 with CNCM, Paris than it is corresponding to a virus isolate of avian *Pneumovirus* (APV) also known as turkey rhinotracheitis virus (TRTV), the etiological agent of avian rhinotracheitis, wherein the suitable fragment comprises an open reading frame encoding a viral protein of the virus.

A suitable open reading frame (ORF) comprises the ORF encoding the N protein. When an overall amino acid identity of at least 91%, preferably of at least 95% of the analyzed N-protein with the N-protein of isolate I-2614 is found, the analyzed virus isolate comprises a preferred MPV isolate according to the invention. As shown, the first gene in the genomic map of MPV codes for a 394 amino acid (aa) protein and shows extensive homology with the N protein of other Pneumoviruses. The length of the N ORF is identical to the length of the N ORF of APV-C (Table 5) and is smaller than those of other paramyxoviruses (Barr et al., 1991). Analysis of the amino acid sequence revealed the highest homology with APV-C (88%), and only 7-11% with other paramyxoviruses (Table 6).

Barr et al. (1991) identified 3 regions of similarity between viruses belonging to the order Mononegavirales: A, B and C (FIG. 8). Although similarities are highest within a virus family, these regions are highly conserved between virus families. In all three regions MPV revealed 97% aa sequence identity with APV-C, 89% with APV-B, 92 with APV-A, and 66-73% with RSV and PVM. The region between aa residues 160 and 340 appears to be highly conserved among Metapneumoviruses and to a somewhat lesser extent the Pneumovirinae (Miyahara et al., 1992; Li et al., 1996; Barr et al., 1991). This is in agreement with MPV being a *Metapneumovirus*, this particular region showing 99% similarity with APV C.

Another suitable open reading frame (ORF) useful in phylogenetic analyses comprises the ORF encoding the P protein. When an overall amino acid-identity of at least 70%, preferably of at least 85% of the analyzed P-protein with the P-protein of isolate I-2614 is found, the analyzed virus isolate comprises a preferred MPV isolate according to the invention. The second ORF in the genome map codes for a 294 aa protein which shares 68% aa sequence homology with the P protein of APV-C, and only 22-26% with the P protein of RSV (Table 6). The P gene of MPV contains one substantial ORF and in that respect is similar to P from many other paramyxoviruses (Reviewed in Lamb and Kolakofsky, 1996; Sedlmeier et al., 1998). In contrast to APV A and B and PVM and similar to RSV and APV-C the MPV P ORF lacks cysteine residues. Ling (1995) suggested that a region of high similarity between all Pneumoviruses (aa 185-241) plays a role in either the RNA synthesis process or in maintaining the structural integrity of the nucleocapsid complex. This region of high similarity is also found in MPV (FIG. 9), specifically when conservative substitutions are taken in account, showing 100% similarity with APV-C, 93% with APV-A and B, and approximately 81% with RSV. The C-terminus of the MPV P protein is rich in glutamate residues as has been described for APVs (Ling et al., 1995).

Another suitable open reading frame (ORF) useful in phylogenetic analyses comprises the ORF encoding the M protein. When an overall amino acid identity of at least 94%, preferably of at least 97% of the analyzed M-protein with the M-protein of isolate I-2614 is found, the analyzed virus isolate comprises a preferred MPV isolate according to the invention. The third ORF of the MPV genome encodes a 254 aa protein, which resembles the M ORFs of other Pneumoviruses. The M ORF of MPV has exactly the same size as the M ORFs of other Metapneumoviruses (Table 5) and shows high aa sequence homology with the matrix proteins of APV (76-87%) lower homology with those of RSV and PVM (37-38%) and 10% or less homology with those of other paramyxoviruses (Table 6). Easton (1997) compared the sequences of matrix proteins of all Pneumoviruses and found a conserved hexapeptide at residue 14 to 19 that is also conserved in MPV (FIG. 10). For RSV, PVM and APV small secondary ORFs within or overlapping with the major ORF of M have been identified (52 aa and 51 aa in bRSV, 75 aa in RSV, 46 aa in PVM and 51 aa in APV) (Yu et al., 1992; Easton et al., 1997; Samal et al., 1991; Satake et al., 1984). We noticed two small ORFs in the M ORF of MPV. One small ORF of 54 aa residues was found within the major M ORF, starting at nucleotide 2281 and one small ORF of 33 aa residues was found overlapping with the major ORF of M starting at nucleotide 2893 (data not shown). Similar to the secondary ORFs of RSV and APV there is no significant homology between these secondary ORFs and secondary ORFs of the other Pneumoviruses, and apparent start or stop signals are lacking. In addition, evidence for the synthesis of proteins corresponding to these secondary ORFs of APV and RSV has not been reported.

Another suitable open reading frame (ORF) useful in phylogenetic analyses comprises the ORF encoding the F protein. When an overall amino acid identity of at least 95%, preferably of at least 97% of the analyzed F-protein with the F-protein of isolate I-2614 is found, the analyzed virus isolate comprises a preferred MPV isolate according to the invention. The F ORF of MPV is located adjacent to the M ORF, which is characteristic for members of the *Metapneumovirus* genus. The F gene of MPV encodes a 539 aa protein, which is two aa residues longer than F of APV-C (Table 5). Analysis of the aa sequence revealed 81% homology with APV-C, 67% with APV-A and B, 33-39% with *Pneumovirus* F proteins and only 10-18% with other paramyxoviruses (Table 6). One of the conserved features among F proteins of paramyxoviruses, and also seen in MPV is the distribution of cysteine residues (Morrison, 1988; Yu et al., 1991). The Metapneumoviruses share 12 cysteine residues in F1 (7 are conserved among all paramyxoviruses), and two in F2 (1 is conserved among all paramyxoviruses). Of the three potential N-linked glycosylation sites present in the F ORF of MPV, none are shared with RSV and two (position 66 and 389) are shared with APV. The third, unique, potential N-linked glycosylation site for MPV is located at position 206 (FIG. 11). Despite the low sequence homology with other paramyxoviruses, the F protein of MPV revealed typical fusion protein characteristics consistent with those described for the F proteins of other Paramyxoviridae family members (Morrison, 1988). F proteins of Paramyxoviridae members are synthesized as inactive precursors (F0) that are cleaved by host cell proteases which generate amino terminal F2 subunits and large carboxy terminal F1 subunits. The proposed cleavage site (Collins et al., 1996) is conserved among all members of the Paramyxoviridae family. The cleavage site of MPV contains the residues RQSR. Both arginine (R) residues are shared with APV and RSV, but the glutamine (Q) and serine (S) residues are shared with other paramyxoviruses such as human parainfluenza virus type 1, Sendai virus and morbilliviruses (data not shown). The hydrophobic region at the amino terminus of F1 is thought to function as the membrane fusion domain an shows high sequence similarity among paramyxoviruses and morbilliviruses and to a lesser extent the Pneumoviruses (Morrison, 1988). These 26 residues (position 137-163, FIG. 11) are conserved between MPV and APV.C, which is in agreement with this region being highly conserved among the Metapneumoviruses (Naylor et al., 1998; Seal et al., 2000).

As is seen for the F2 subunits of APV and other paramyxoviruses, MPV revealed a deletion of 22 aa residues compared with RSV (position 107-128, FIG. 11). Furthermore, for RSV and APV, the signal peptide and anchor domain were found to be conserved within subtypes and displayed high variability between subtypes (Plows et al., 1995; Naylor et al., 1998). The signal peptide of MPV (aa 10-35, FIG. 11) at the amino terminus of F2 exhibits some sequence similarity with APV-C (18 out of 26 aa residues are similar) and less conservation with other APVs or RSV. Much more variability is seen in the membrane anchor domain at the carboxy terminus of F1, although some homology is still seen with APV-C.

Another suitable open reading frame (ORF) useful in phylogenetic analyses comprises the ORF encoding the M2 protein. When an overall amino acid identity of at least 85%, preferably of at least 90% of the analyzed M2-protein with the M2-protein of isolate I-2614 is found, the analyzed virus isolate comprises a preferred MPV isolate according to the invention. M2 gene is unique to the Pneumovirinae and two overlapping ORFs have been observed in all Pneumoviruses. The first major ORF represents the M2-1 protein which enhances the processivity of the viral polymerase (Collins et al., 1995; Collins, 1996) and its read through of intergenic regions (Hardy et al., 1998; Fearns et al., 1999). The M2-1 gene for MPV, located adjacent to the F gene, encodes a 187 aa protein (Table 5), and reveals the highest (84%) homology with M2-1 of APV-C (Table 6). Comparison of all *Pneumovirus* M2-1 proteins revealed the highest conservation in the amino-terminal half of the protein (Collins et al., 1990; Zamora et al., 1992; Ahmadian et al., 1999), which is in agreement with the observation that MPV displays 100% similarity with APV-C in the first 80 aa residues of the protein (FIG. 12A). The MPV M2-1 protein contains 3 cysteine residues located within the first 30 aa residues that are conserved among all Pneumoviruses. Such a concentration of cysteines is frequently found in zincbinding proteins (Ahmadian et al., 1991; Cuesta et al., 2000).

The secondary ORFs (M2-2) that overlap with the M2-1 ORFs of Pneumoviruses are conserved in location but not in sequence and are thought to be involved in the control of the switch between virus RNA replication and transcription (Collins et al., 1985; Elango et al., 1985; Baybutt et al., 1987; Collins et al., 1990; Ling et al., 1992; Zamora et al., 1992; Alansari et al., 1994; Ahmadian et al., 1999; Bermingham et al., 1999). For MPV, the M2-2 ORF starts at nucleotide 512 in the M2-1 ORF (FIG. 7), which is exactly the same start position as for APV-C. The length of the M2-2 ORFs are the same for APV-C and MPV, 71 aa residues (Table 5). Sequence comparison of the M2-2 ORF (FIG. 12B) revealed 56% aa sequence homology between MPV and APV-C and only 26-27% aa sequence homology between MPV and APV-A and B (Table 6).

Another suitable open reading frame (ORF) useful in phylogenetic analyses comprises the ORF encoding the L protein. When an overall amino acid identity of at least 91%, preferably of at least 95% of the analyzed L-protein with the L-protein of isolate I-2614 is found, the analyzed virus isolate comprises a preferred MPV isolate according to the invention. In analogy to other negative strand viruses, the last ORF of the MPV genome is the RNA-dependent RNA polymerase component of the replication and transcription complexes. The L gene of MPV encodes a 2005 aa protein, which is 1 residue longer than the APV-A protein (Table 5). The L protein of MPV shares 64% homology with APV-A, 42-44% with RSV, and approximately 13% with other paramyxoviruses (Table 6). Poch et al. (1989; 1990) identified six conserved domains within the L proteins of non-segmented negative strand RNA viruses, from which domain III contained the four core polymerase motifs that are thought to be essential for polymerase function. These motifs (A, B, C and D) are well conserved in the MPV L protein: in motifs A, B and C: MPV shares 100% similarity with all Pneumoviruses and in motif D MPV shares 100% similarity with APV and 92% with RSVs. For the entire domain III (aa 625-847 in the L ORF), MPV shares 83% identity with APV, 67-68% with RSV and 26-30% with other paramyxoviruses (FIG. 15). In addition to the polymerase motifs the *Pneumovirus* L proteins contain a sequence which conforms to a consensus ATP binding motif $K(X)_{21}GEGAGN(X)_{20}K$ (SEQ ID NO:105) (Stec, 1991). The MPV L ORF contains a similar motif as APV, in which the spacing of the intermediate residues is off by one: $K(x)_{22}GEGAGN(X)_{19}K$ (SEQ ID NO:106).

A much preferred suitable open reading frame (ORF) useful in phylogenetic analyses comprises the ORF encoding the SH protein. When an overall amino acid identity of at least 30%, preferably of at least 50%, more preferably of at least 75% of the analyzed SH-protein with the SH-protein of isolate I-2614 is found, the analyzed virus isolate comprises a preferred MPV isolate according to the invention. The gene located adjacent to M2 of MPV encodes a 183 aa protein (FIG. 7). Analysis of the nucleotide sequence and its deduced amino acid sequence revealed no discernible homology with other RNA virus genes or gene products. The SH ORF of MPV is the longest SH ORF known to date (Table 5). The composition of the aa residues of the SH ORF is relatively similar to that of APV, RSV and PVM, with a high percentage of threonine and serine (22%, 18%, 19%, 20.0%, 21% and 28% serine/threonine content for MPV, APV, RSV A, RSV B, bRSV and PVM respectively). The SH ORF of MPV contains ten cysteine residues, whereas APV SH contains 16 cysteine residues. All Pneumoviruses have similar numbers of potential N-glycosylation sites (MPV 2, APV 1, RSV 2, bRSV 3, PVM 4).

The hydrophobicity profiles for the MPV SH protein and SH of APV and RSV revealed similar structural characteristics (FIG. 13B). The SH ORFs of APV and MPV have a hydrophilic N-terminus (aa 1-30), a central hydrophobic domain (aa 30-53) which can serve as a potential membrane spanning domain, a second hydrophobic domain around residue 160 and a hydrophilic C-terminus. In contrast, RSV SH appears to lack the C-terminal half of the APV and MPV ORFs. In all *Pneumovirus* SH proteins the hydrophobic domain is flanked by basic amino acids, which are also found in the SH ORF for MPV (aa 29 and 64).

Another much preferred suitable open reading frame (ORF) useful-in phylogenetic analyses comprises the ORF encoding the G protein. When an overall amino acid identity of at least 30%, preferably of at least 50%, more preferably of at least 75% of the analyzed G-protein with the G-protein of isolate I-2614 is found, the analyzed virus isolate comprises a preferred MPV isolate according to the invention. The G ORF of MPV is located adjacent to the SH gene and encodes a 236 amino acid protein. A secondary small ORF is found immediately following this ORF, potentially coding for 68 aa residues (pos. 6973-7179), but lacking a start codon. A third major ORF, in a different reading frame, of 194 aa residues (fragment 4, FIG. 7) is overlapping with both of these ORFs, but also lacks a start codon (nucleotide 6416-7000). This major ORF is followed by a fourth ORF in the same reading frame (nt 7001-7198), possibly coding for 65 aa residues but again lacking a start codon. Finally, a potential ORF of 97 aa residues (but lacking a start codon) is found in the third reading frame (nt 6444-6737, FIG. 1). Unlike the first ORF, the other ORFs do not have apparent gene start or gene end sequences (see below). Although the 236 aa residue G ORF probably represents at least a part of the MPV attachment protein it cannot be excluded that the additional coding sequences are expressed as separate proteins or as part of the attachment protein through some RNA editing event. It should be noted that for APV and RSV no secondary ORFs after the primary G ORF have been identified but that both APV and RSV have secondary ORFs within the major ORF of G. However, evidence for expression of these ORFEs is lacking and there is no homology between the predicted aa sequences for different viruses (Ling et al., 1992). The secondary ORFs in MPV G do not reveal characteristics of other G proteins and whether the additional ORFs are expressed requires further investigation. BLAST® analyses with all four ORFs revealed no discernible homology at the nucleotide or aa sequence level with other known virus genes or gene products. This is in agreement with the low sequence homologies found for other G proteins such as hRSV A and B (53%) (Johnson et al., 1987) and APV A and B (38%) (Juhasz et al., 1994). Whereas most of the MPV ORFs resemble those of APV both in length and sequence, the G ORF of MPV is considerably smaller than the G ORF of APV (Table 5). The aa sequence revealed a serine and threonine content of 34%, which is even higher than the 32% for RSV and 24% for APV. The G ORF also contains 8.5% proline residues, which is higher than the 8% for RSV and 7% for APV. The unusual abundance of proline residues in the G proteins of APV, RSV and MPV has also been observed in glycoproteins of mucinous origin where it is a major determinant of the proteins three dimensional structure (Collins et al., 1983; Wertz et al., 1985; Jentoft, 1990). The number of potential N-linked glycosylation sites in G of MPV is similar to other Pneumoviruses: MPV has 5, whereas hRSV has 7, bRSV has 5, and APV has 3 to 5.

The predicted hydrophobicity profile of MPV G revealed characteristics similar to the other Pneumoviruses. The amino-terminus contains a hydrophilic region followed by a short hydrophobic area (aa 33-53) and a mainly hydrophilic carboxy terminus (FIG. 14B). This overall organization is consistent with that of an anchored type II transmembrane protein and corresponds well with these regions in the G protein of APV and RSV. The G ORF of MPV contains only 1 cysteine residue in contrast to RSV and APV (5 and 20, respectively).

According to classical serological analyses as for example known from R. I. B. Francki, C. M. Fauquet, D. L. Knudson, and F. Brown, Classification and nomenclature of viruses, Fifth report of the international Committee on Taxonomy of Viruses, *Arch Virol.* 1991, Supplement 2:140-144, an MPV isolate is also identifiable as belonging to a serotype as provided herein, being defined on the basis of its immunological distinctiveness, as determined by quantitative neutralization with animal antisera (obtained from for example ferrets or guinea pigs as provided in the detailed description). Such a serotype has either no cross-reaction with others or shows a homologous-to heterologous titer ratio >16 in both directions. If neutralization shows a certain degree of cross-reaction between two viruses in either or both directions (homologous-to-heterologous tier ration of eight or 16), distinctiveness of serotype is assumed if substantial biophysical/biochemical differences of DNAs exist. If neutralization shows a distinct degree of cross-reaction between two viruses in either or both directions (homologous-to-heterologous tier ration of smaller than eight), identity of serotype of the isolates under study is assumed. As said, useful prototype isolates, such as isolate I-2614, herein also known as MPV isolate 00-1, are provided herein.

A further classification of a virus as an isolated essentially mammalian negative-sense single-stranded RNA virus as provided herein can be made on the basis of homology to the G and/or SH proteins. Where in general the overall amino acid sequence identity between APV (isolated from birds) and MPV (isolated from humans) N, P, M, F, M2 and L ORFs was 64 to 88 percent, and nucleotide sequence homology was also found between the non-coding regions of the APV and MPV genomes, essentially no discernible amino acid sequence homology was found between two of the ORFs of the human isolate (MPV) and any of the ORFs of other paramyxoviruses. The amino acid content, hydrophobicity profiles and location of these ORFs in the viral genome show that they represent G and SH protein analogues. The sequence homology between APV and MPV, their similar genomic organization (3'-N-P-M-F-M2-SH-G-L5') as well as phylogenetic analyses provide further evidence for the proposed classification of MPV as the first mammalian *Metapneumovirus*. New MPV isolates are for thus example identified as such by virus isolation and characterization on tMK or other cells, by RT-PCR and/or sequence analysis followed by phylogenetic tree analyses, and by serologic techniques such as virus neutralization assays, indirect immunofluorescence assays, direct immunofluorescence assays, FACs analyses or other immunological techniques.

Preferably these techniques are directed at the SH and/or G protein analogues.

For example the invention provides herein a method to identify further isolates of MPV as provided herein, the method comprising inoculating an essentially MPV-uninfected or specific pathogen-free guinea pig or ferret (in the detailed description the animal is inoculated intranasally but other ways of inoculation such as intramuscular or intradermal inoculation, and using another experimental animal, is also feasible) with the prototype isolate I-2614 or related isolates. Sera are collected from the animal at day zero, two weeks and three weeks post inoculation. The animal specifically seroconverted as measured in virus neutralization (VN) assay and indirect IFA against the respective isolate I-2614 and the sera from the seroconverted animal are used in the immunological detection of the further isolates.

As an example, the invention provides the characterization of a new member in the family of Paramyxoviridae, a human *Metapneumovirus* or *Metapneumovirus*-like virus (since its final taxonomy awaits discussion by a viral taxonomy committee the MPV is herein for example described as taxonomically corresponding to APV) (MPV) which may cause severe RTI in humans. The clinical signs of the disease caused by MPV are essentially similar to those caused by hRSV, such as cough, myalgia, vomiting, fever, bronchiolitis or pneumonia, possible conjunctivitis, or combinations thereof. As is seen with hRSV-infected children, especially very young children may require hospitalization. As an example an MPV which was deposited Jan. 19, 2001 as I-2614 with CNCM, Institute Pasteur, Paris or a virus isolate phylogenetically corresponding therewith is herewith provided. Therewith, the invention provides a virus comprising a nucleic acid or functional fragment phylogenetically corresponding to a nucleic acid sequence shown in FIGS. 6A-6E, or structurally corresponding therewith. In particular the invention provides a virus characterized in that after testing it in phylogenetic tree analyses wherein maximum likelihood trees are generated using 100 bootstraps and 3 jumbles it is found to be more closely phylogenetically corresponding to a virus isolate deposited as I-2614 with CNCM, Paris than it is related to a virus isolate of avian *Pneumovirus* (APV) also known as turkey rhinotracheitis virus (TRTV), the etiological agent of avian rhinotracheitis. It is particularly useful to use an AVP-C virus isolate as outgroup in the phylogenetic tree analyses, it being the closest relative, albeit being an essentially non-mammalian virus.

We propose the new human virus to be named human *Metapneumovirus* or *Metapneumovirus*-like virus (MPV) based on several observations. EM analysis revealed paramyxovirus-like particles. Consistent with the classification, MPV appeared to be sensitive to treatment with chloroform. WPV is cultured optimal on tMK cells and is trypsine dependent. The clinical symptoms caused by MPV as well as the typical CPE and lack of hemagglutinating activity suggested that this virus is closely related to hRSV. Although most paramyxoviruses have hemagglutinating activity, most of the Pneumoviruses do not.[13]

As an example, the invention provides a not previously identified paramyxovirus from nasopharyngeal aspirate samples taken from 28 children suffering from severe RTI. The clinical symptoms of these children were largely similar to those caused by hRSV. Twenty-seven of the patients were children below the age of five years and half of these were between 1 and 12 months old. The other patient was 18 years old. All individuals suffered from upper RTI, with symptoms ranging from cough, myalgia, vomiting and fever to bronchiolitis and severe pneumonia. The majority of these patients were hospitalized for one to two weeks.

The virus isolates from these patients had the paramyxovirus morphology in negative contrast electron microscopy but did not react with specific antisera against known human and animal paramyxoviruses. They were all closely related to one another as determined by indirect immunofluorescence assays (IFA) with sera raised against two of the isolates. Sequence analyses of nine of these isolates revealed that the virus is somewhat related to APV. Based on virological data, sequence homology as well as the genomic organization we propose that the virus is a member of *Metapneumovirus* genus. Serological surveys showed that this virus is a relatively common pathogen since the seroprevalence in The Netherlands approaches 100% of humans by the age of five years. Moreover, the seroprevalence was found to be equally high in sera collected from humans in 1958, indicating this virus has been circulating in the human population for more than 40 years. The identification of this proposed new member of the *Metapneumovirus* genus now also provides for the development of means and methods for diagnostic assays or test kits and vaccines or serum or antibody compositions for viral respiratory tract infections, and for methods to test or screen for antiviral agents useful in the treatment of MPV infections.

To this extent, the invention provides among others an isolated or recombinant nucleic acid or virus-specific functional fragment thereof obtainable from a virus according to the invention. In particular, the invention provides primers and/or probes suitable for identifying an MPV nucleic acid.

Furthermore, the invention provides a vector comprising a nucleic acid according to the invention. To begin with, vectors such as plasmid vectors containing (parts of) the genome of MPV, virus vectors containing (parts of) the genome of MPV. (For example, but not limited to other paramyxoviruses, vaccinia virus, retroviruses, baculovirus), or MPV containing (parts of) the genome of other viruses or other pathogens are provided. Furthermore, a number of reverse genetics techniques have been described for the generation of recombinant negative strand viruses, based on two critical parameters. First, the production of such virus relies on the replication of a partial or full-length copy of the negative sense viral RNA (vRNA) genome or a complementary copy thereof (cRNA). This vRNA or cRNA can be isolated from infectious virus, produced upon in vitro transcription, or produced in cells upon transfection of nucleic acids. Second, the production of recombinant negative strand virus relies on a functional polymerase complex. Typically, the polymerase complex of Pneumoviruses consists of N, P, L and possibly M2 proteins, but is not necessarily limited thereto. Polymerase complexes or components thereof can be isolated from virus particles, isolated from cells expressing one or more of the components, or produced upon transfection of specific expression vectors.

Infectious copies of MPV can be obtained when the above mentioned vRNA, cRNA, or vectors expressing these RNAs are replicated by the above mentioned polymerase complex.[16, 17, 18, 19, 20, 21, 22] For the generation of minireplicons or, a reverse genetics system for generating a full-length copy comprising most or all of the genome of MPV it suffices to use 3' end and/or 5' end nucleic acid sequences obtainable from for example APV (Randhawa et al., 1997) or MPV itself.

Also, the invention provides a host cell comprising a nucleic acid or a vector according to the invention. Plasmid or viral vectors containing the polymerase components of MPV (presumably N, P, L and M2, but not necessarily limited thereto) are generated in prokaryotic cells for the expression of the components in relevant cell types (bacteria, insect cells, eukaryotic cells). Plasmid or viral vectors containing full-length or partial copies of the MPV genome will be generated in prokaryotic cells for the expression of viral nucleic acids in vitro or in vivo. The latter vectors may contain other viral sequences for the generation of chimeric viruses or chimeric virus proteins, may lack parts of the viral genome for the generation of replication defective virus, and may contain mutations, deletions or insertions for the generation of attenuated viruses.

Infectious copies of MPV (being wild type, attenuated, replication-defective or chimeric) can be produced upon co-expression of the polymerase components according to the state-of-the-art technologies described above.

In addition, eukaryotic cells, transiently or stably expressing one or more full-length or partial MPV proteins can be used. Such cells can be made by transfection (proteins or nucleic acid vectors), infection (viral vectors) or transduction (viral vectors) and may be useful for complementation of mentioned wild type, attenuated, replication-defective or chimeric viruses.

A chimeric virus may be of particular use for the generation of recombinant vaccines protecting against two or more viruses.[23, 24, 26] For example, it can be envisaged that a MPV virus vector expressing one or more proteins of RSV or a RSV vector expressing one or more proteins of MPV will protect individuals vaccinated with such vector against both virus infections. A similar approach can be envisaged for PI3 or other paramyxoviruses. Attenuated and replication-defective viruses may be of use for vaccination purposes with live vaccines as has been suggested for other viruses.[25, 26]

In a preferred embodiment, the invention provides a proteinaceous molecule or *Metapneumovirus*-specific viral protein or functional fragment thereof encoded by a nucleic acid according to the invention. Useful proteinaceous molecules are for example derived-from any of the genes or genomic fragments derivable from a virus according to the invention. Such molecules, or antigenic fragments thereof, as provided herein, are for example useful in diagnostic methods or kits and in pharmaceutical compositions such as sub-unit vaccines. Particularly useful are the F, SH and/or G protein or antigenic fragments thereof for inclusion as antigen or subunit immunogen, but inactivated whole virus can also be used. Particularly useful are also those proteinaceous substances that are encoded by recombinant nucleic acid fragments that are identified for phylogenetic analyses, of course preferred are those that are within the preferred bounds and metes of ORFs useful in phylogenetic analyses, in particular for eliciting MPV-specific antibodies, whether in vivo (e.g., for protective purposes or for providing diagnostic antibodies) or in vitro (e.g., by phage display technology or another technique useful for generating synthetic antibodies).

Also provided herein are antibodies, be it natural polyclonal or monoclonal or synthetic (e.g., (phage) library-derived binding molecules) antibodies that specifically react with an antigen comprising a proteinaceous molecule or MPV-specific functional fragment thereof according to the invention. Such antibodies are useful in a method for identifying a viral isolate as an MPV comprising reacting the viral isolate or a component thereof with an antibody as provided herein. This can for example be achieved by using purified or non-purified MPV or parts thereof (proteins, peptides) using ELISA, RIA, FACS or similar formats of antigen detection assays (*Current Protocols in Immunology*). Alternatively, infected cells or cell cultures may be used to identify viral antigens using classical immunofluorescence or immunohistochemical techniques.

Other methods for identifying a viral isolate as a MPV comprise reacting the viral isolate or a component thereof with a virus-specific nucleic acid according to the invention, in particular where the mammalian virus comprises a human virus.

In this way the invention provides a viral isolate identifiable with a method according to the invention as a mammalian virus taxonomically corresponding to a negative-sense single-stranded RNA virus identifiable as likely belonging to the genus *Metapneumovirus* within the subfamily Pneumovirinae of the family Paramyxoviridae.

The method is useful in a method for virologically diagnosing an MPV infection of a mammal, the method for example comprising determining in a sample of the mammal the presence of a viral isolate or component thereof by reacting the sample with a nucleic acid or an antibody according to the invention. Examples are further given in the detailed description, such as the use of PCR (or other amplification or hybridization techniques well known in the art) or the use of immunofluorescence detection (or other immunological techniques known in the art).

The invention also provides a method for serologically diagnosing a MPV infection of a mammal comprising determining in a sample of the mammal the presence of an antibody specifically directed against a MPV or component thereof by reacting the sample with a proteinaceous molecule or fragment thereof or an antigen according to the invention.

Methods and means provided herein are particularly useful in a diagnostic kit for diagnosing a MPV infection, be it by virological or serological diagnosis. Such kits or assays may for example comprise a virus, a nucleic acid, a proteinaceous molecule or fragment thereof, an antigen and/or an antibody according to the invention. Use of a virus, a nucleic acid, a proteinaceous molecule or fragment thereof an antigen and/or an antibody according to the invention is also provided for the production of a pharmaceutical composition, for example, for the treatment or prevention of MPV infections and/or for the treatment or prevention of respiratory tract illnesses, in particular in humans. Attenuation of the virus can be achieved by established methods developed for this purpose, including but not limited to the use of related viruses of other species, serial passages through laboratory animals or/and tissue/cell cultures, site directed mutagenesis of molecular clones and exchange of genes or gene fragments between related viruses.

A pharmaceutical composition comprising a virus, a nucleic acid, a proteinaceous molecule or fragment thereof, an antigen and/or an antibody according to the invention can for example be used in a method for the treatment or prevention of a MPV infection and/or a respiratory illness comprising providing an individual with a pharmaceutical composition according to the invention. This is most useful when the individual comprises a human, especially when the human is below 5 years of age, since such infants and young children are most likely to be infected by a human MPV as provided herein. Generally, in the acute phase patients will suffer from upper respiratory symptoms predisposing for other respiratory and other diseases. Also lower respiratory illnesses may occur, predisposing for more and other serious conditions.

The invention also provides method to obtain an antiviral agent useful in the treatment of respiratory tract illness comprising establishing a cell culture or experimental animal comprising a virus according to the invention, treating the culture or animal with an candidate antiviral agent, and determining the effect of the agent on the virus or its infection of the culture or animal. An example of such an antiviral agent comprises a MPV-neutralizing antibody, or functional component thereof, as provided herein, but antiviral agents of other nature are obtained as well. The invention also provides use of an antiviral agent according to the invention for the preparation of a pharmaceutical composition, in particular for the preparation of a pharmaceutical composition for the treatment of respiratory tract illness, especially when caused by an MPV infection, and provides a pharmaceutical composition comprising an antiviral agent according to the invention, useful in a method for the treatment or prevention of an MPV infection or respiratory illness, the method comprising providing an individual with such a pharmaceutical composition.

The invention is further explained in the detailed description without limiting it thereto.

Deposit of Biological Material

Mammalian *Metapneumovirus* isolate NL/1/00 "MPV-isolate 00-1" has been deposited with the international depository authority Collection Nationale de Cultures de Microorganismes (CNCM) as deposit accession number I-2614. The address of the CNCM is Institut Pasteur, 26, Rue du Docteur Roux, F-75724 Paris Cedex 15, France. The deposits were received on Jan. 19, 2001.

BRIEF SUMMARY OF THE DRAWINGS

FIG. 1A comprises table 1: Percentage homology found between the amino acid sequence of isolate 00-1 and other members of the Pneumovirinae. Percentages (×100) are given for the amino acid sequences of N, P, M, F and two RAP-PCR fragments in L (8 and 9/10). Accession numbers used for the analyses are described in the materials and methods section.

For all phylogenetic trees (FIGS. 3A-5), DNA sequences were aligned using the ClustalW software package and maximum likelihood trees were generated using the DNA-ML software package of the Phylip 3.5 program using 100 bootstraps and 3 jumbles.[15] Previously published sequences that were used for the generation of phylogenetic trees are available from Genbank under accessions numbers: For all ORFs: hRSV: NC001781; bRSV: NC001989; For the F ORF: PVM, D11128; APV-A, D00850; APV-B, Y14292; APV-C, AF187152; For the N ORF: PVM, D10331; APV-A, U39295; APV-B, U39296; APV-C, AF176590; For the M ORF: PMV, U66893; APV-A, X58639; APV-B, U37586; APV-C, AF262571; For the P ORF: PVM, 09649; APV-A, U22110, APV-C, AF176591. Phylogenetic analyses for the nine different virus isolates of MPV were performed with APV strain C as outgroup. Abbreviations used in figures: hRSV: human RSV; bRSV: bovine RSV, PVM: pneumonia virus of mic⁻; APV-A, B, and C: avian *Pneumovirus* type A, B and C.

FIGS. 3A-3E: Comparison of the N (SEQ ID NOS:1-7), P (SEQ ID NOS:8-13), M (SEQ ID NOS:14-20) and F (SEQ ID NOS:21-27) ORFs of members of the subfamily Pneumovirinae and virus isolate 00-1. The alignment shows the amino acid sequence of the complete N (SEQ ID NO:1), P (SEQ ID NO:8), M (SEQ ID NO:14) and F (SEQ ID NO:21) proteins and partial L proteins (SEQ ID NO:28 and SEQ ID NO:32) of virus isolate 00-1. Amino acids that differ between isolate 00-1 and the other viruses are shown, identical amino acids are represented by periods, gaps are represented as dashes. Numbers correspond to amino acid positions in the proteins. Accession numbers used for the analyses are described in the materials and methods section. APV-A, B or C: Avian *Pneumovirus* type A (SEQ ID NO:2, SEQ ID NO:9, SEQ ID NO:16, SEQ ID NO:22, SEQ ID NO:29, SEQ ID NO:33), B (SEQ ID NO:3, SEQ ID NO:15, SEQ ID NO:23) or C (SEQ ID NO:4, SEQ ID NO:10, SEQ ID NO:17, SEQ ID NO:24), b- or hRSV: bovine (SEQ ID NO:5, SEQ ID NO:11, SEQ ID NO:18, SEQ ID NO:25, SEQ ID NO:30, SEQ ID NO:34) or human (SEQ ID NO:6, SEQ ID NO:12, SEQ ID NO:19, SEQ ID NO:26, SEQ ID NO:31, SEQ ID NO:35) respiratory syncytial virus, PVM: pneumonia virus of mice (SEQ ID NO:7, SEQ ID NO:13, SEQ ID NO:20, SEQ ID NO:27). L8: fragment 8 obtained with RAP-PCR located in L, L9/10: consensus of fragment 9 and 10 obtained with RAP-PCR, located in L. For the P alignment, no APV-B sequence was available from the Genebank. For the L alignment only bRSV, hRSV and APV-A sequences were available.

Figure 4:
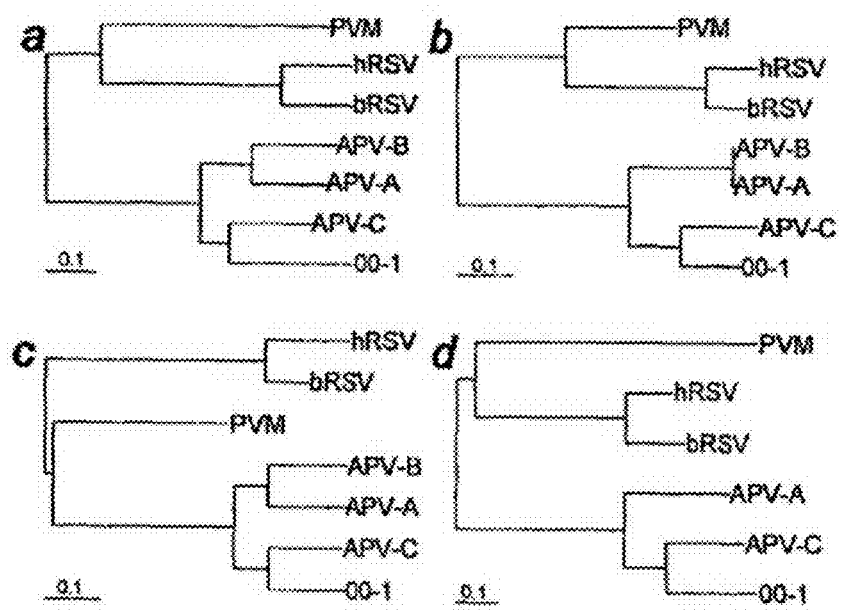

FIG. 4: Phylogenetic analyses of the N, P, M, and F ORFs of members of the genus Pneumovirinae and virus isolate 00-1. Phylogenetic analysis was performed on viral sequences from the following genes: F (panel A), N (panel B), M (panel C), and P (panel D). The phylogenetic trees are based on maximum likelihood analyses using 100 bootstraps and 3 jumbles. The scale representing the number of nucleotide changes is shown for each tree.

Figure 5:
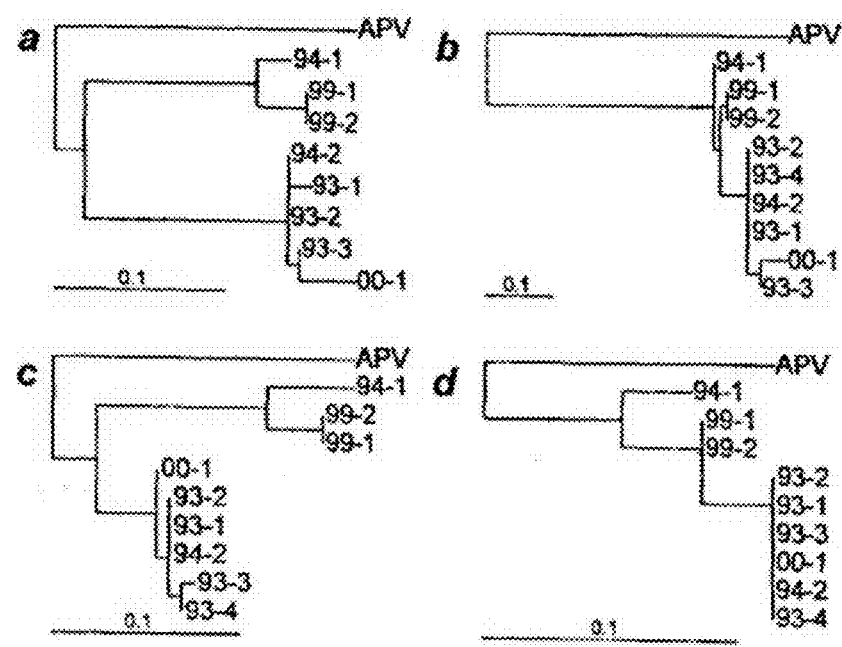

FIG. 5: Phylogenetic relationship for parts of the F (panel A), N (panel B), M (panel C) and L (panel D) ORFs of nine of the primary MPV isolates with APV-C, its closest relative genetically. The phylogenetic trees are based on maximum likelihood analyses. The scale representing the number of nucleotide changes is shown for each tree. Accession numbers for APV-C: panel A-D00850; panel B: U39295; panel C: X58639; and panel D: U65312.

FIGS. 6A-6C: Nucleotide (SEQ ID NO:36) and amino acid (SEQ ID NO:37, SEQ ID NO:8, SEQ ID NO:14, SEQ ID NO:21) sequence information from the 3' end of the genome of MPV isolate 00-1. ORFs are given. N: ORF for nucleoprotein; P: ORF for phosphoprotein; M: ORF for matrix protein; F: ORF for fusion protein; GE: gene end; GS: gene start.

FIGS. 6D and 6E: Nucleotide and amino acid sequence information from obtained fragments in the polymerase gene (L) of MPV isolates 00-1. Positioning of the fragments in L is based on protein homologies with APV-C (accession number U65312). The translated fragment 8 (FIG. 6D) (SEQ ID NO:38 and SEQ ID NO:39) is located at amino acid number 8 to 243, and the consensus of fragments 9 and 10 (FIG. 6E) (SEQ ID NO:40 and SEQ ID NO:41) is located at amino acid number 1358 to 1464 of the APV-C L ORF.

Figure 7:
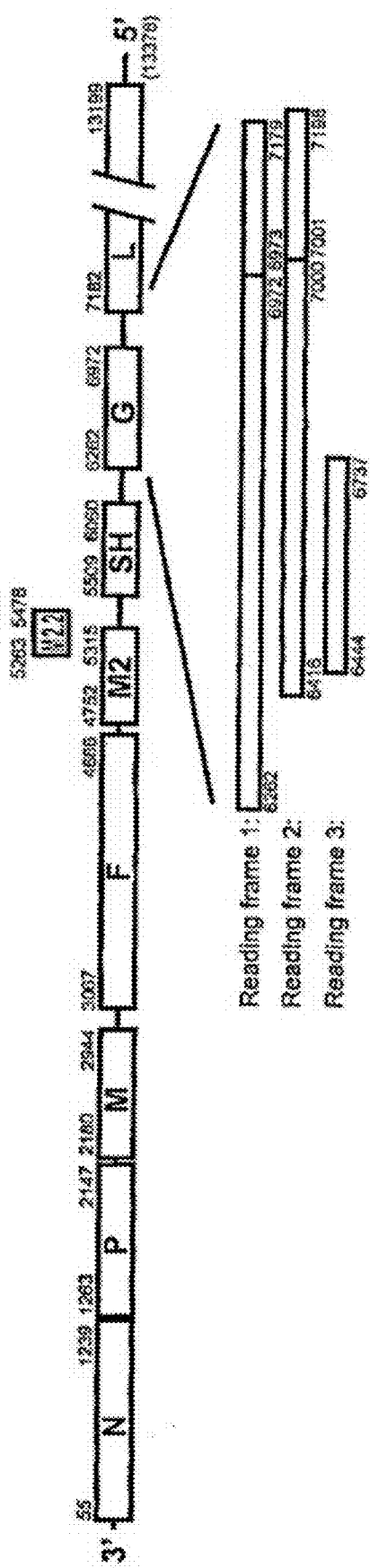

FIG. 7: Genomic map of NPV isolate 00-1. The nucleotide positions of the start and stop codons are indicated under each ORF. The double lines which cross the L ORF indicate the shortened representation of the L gene. The three reading frames below the map indicate the primary G ORF (nt 6262-6972) and overlapping potential secondary ORFS.

FIG. 8: Alignment of the predicted amino acid sequence of the nucleoprotein of MPV (SEQ ID NO:1) with those of other Pneumoviruses (SEQ ID NO:4, SEQ ID NO:3, SEQ ID NO:2, SEQ ID NO:42, SEQ ID NO:6, SEQ ID NO:5, SEQ ID NO:7). The conserved regions identified by Barr (1991) are represented by boxes and labeled A, B, and C. The conserved region among Pneumoviruses (Li, 1996) is shown gray shaded. Gaps are represented by dashes, periods indicate the positions of identical amino acid residues compared to MPV.

FIG. 9: Amino acid sequence comparison of the phosphoprotein of MPV (SEQ ID NO:8) with those of other Pneumoviruses (SEQ ID NO:10, SEQ ID NO:43, SEQ ID NO:9, SEQ ID NO:44, SEQ ID NO:12, SEQ ID NO:11, SEQ ID NO:13). The region of high similarity (Ling, 1995) is boxed, and the glutamate rich region is grey shaded. Gaps are represented by dashes and periods indicate the position of identical amino acid residues compared to MPV.

FIG. 10: Comparison of the deduced amino acid sequence of the matrix protein of MPV (SEQ ID NO:14) with those of other Pneumoviruses (SEQ ID NO:17, SEQ ID NO:15, SEQ ID NO:16, SEQ ID NO:45, SEQ ID NO:19, SEQ ID NO:18, SEQ ID NO:20). The conserved hexapeptide sequence (Easton, 1997) is grey shaded. Gaps are represented by dashes and periods indicate the position of identical amino acid residues relative to MPV.

FIG. 11: Alignment of the predicted amino acid sequence of the fusion protein of MPV (SEQ ID NO:21) with those of other Pneumoviruses (SEQ ID NO:24, SEQ ID NO:23, SEQ ID NO:22, SEQ ID NO:46, SEQ ID NO:26, SEQ ID NO:25, SEQ ID NO:27). The conserved cysteine residues are boxed, N-linked glycosylation sites are underlined, the cleavage site of F0 is double underlined, the fusion peptide, signal peptide and membrane anchor domain are shown grey shaded. Gaps are represented by dashes and periods indicate the position of identical amino acids relative to MPV.

FIG. 12: Comparison of amino acid sequence of the M2 ORFs of MPV with those of other Pneumoviruses. The alignment of M2-1 ORFs is shown in panel A (SEQ ID NO:47, SEQ ID NO:48, SEQ ID NO:49, SEQ ID NO:50, SEQ ID NO:51, SEQ ID NO:52, SEQ ID NO:53, SEQ ID NO:54), with the conserved amino terminus (Collins, 1990; Zamora, 1999) shown grey shaded. The three conserved cysteine residues are printed bold face and indicated by #. The alignment of M2-2 ORFs is shown in panel B (SEQ ID NO:55, SEQ ID NO:56, SEQ ID NO:57, SEQ ID NO:58, SEQ ID NO:59, SEQ ID NO:60, SEQ ID NO:61, SEQ ID NO:62). Gaps are represented by dashes and periods indicate the position of identical amino acids relative to MPV.

Figure 13:
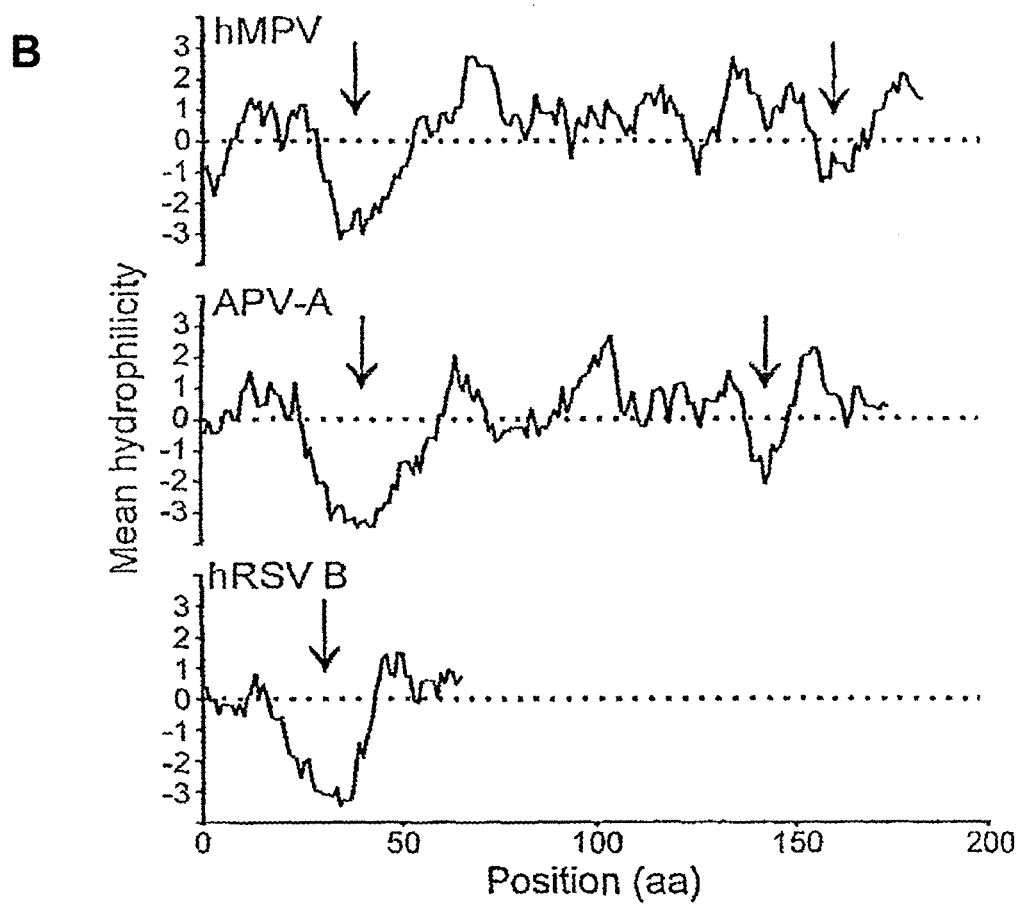

FIG. 13: Amino acid sequence analyses of the SH ORF of MPV. (A) Amino acid sequence of the SH ORF of MPV (SEQ ID NO:63), with the serine and threonine residues grey shaded, cysteine residues in bold face and the hydrophobic region double underlined. Potential N-linked glycosylation sites are single underlined. Numbers indicate the positions of the basic amino acids flanking the hydrophobic domain. (B) Alignment of the hydrophobicity plots of the SH proteins of MPV, APV-A and hRSV-B. The procedure of Kyte and Doolittle (1982) was used with a window of 17 amino acids. Arrows indicate a strong hydrophobic domain. Positions within the ORF are given on the X-axis.

Figure 14:
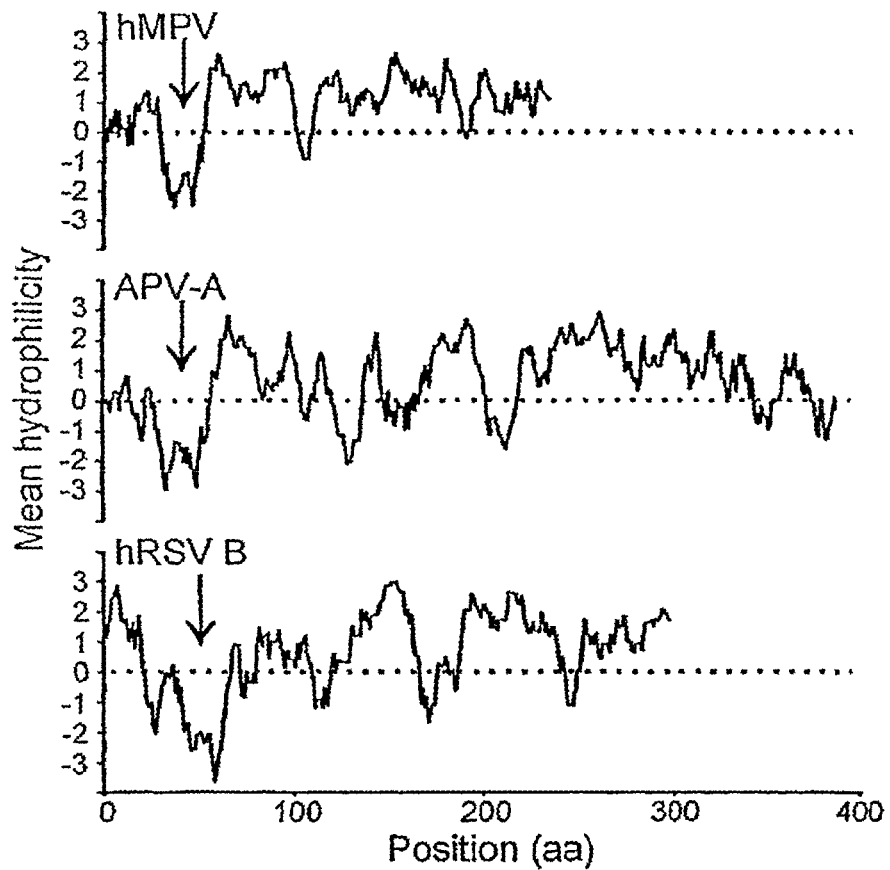

FIG. 14: Amino acid sequence analyses of the G ORF of MPV. (A) Amino acid sequence of the G ORF of MPV (SEQ ID NO:64), with serine, threonine and proline residues grey shaded, the cysteine residue is in bold face and the hydrophobic region double underlined. The potential N-linked glycosylation sites are single underlined. (B) Alignment of the hydrophobicity plots of the G proteins of MPV, APV-A and hRSV-B. The procedure of Kyte and Doolittle (1982) was used with a window of 17 amino acids. Arrows indicate the hydrophobic region, and positions within the ORF are given at the X-axis.

FIG. 15: Comparison of the amino acid sequences of a conserved domain of the polymerase gene of MPV (SEQ ID NO:65) and other paramyxoviruses (SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75). Domain III is shown with the four conserved polymerase motifs (A, B, C, D) in domain III (Poch 1998, 1999) boxed. Gaps are represented by dashes and periods indicate the position of identical amino acid residues relative to MPV. hPIV3: human parainfluenza virus type 3; SV: Sendai virus; hPIV-2: human parainfluenza virus type 2; NDV: New castle disease virus; MV: measles virus; nipah: Nipah virus.

Figure 16:
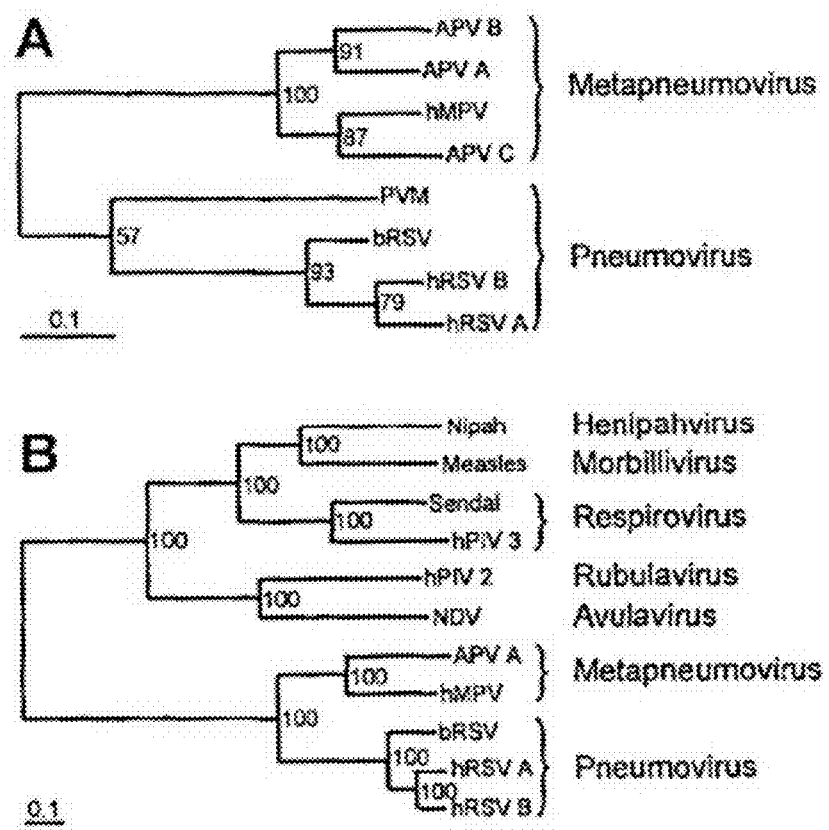

FIG. 16: Phylogenetic analyses of the M2-1 and L ORFs of MPV and selected paramyxoviruses. The M2-1 ORF was aligned with the M2-1 ORFs of other members of the genus Pneumovirinae (A) and the L ORF was aligned with L ORFs members of the genus Pneumovirinae and selected other paramyxoviruses as described in the legends of FIG. 15(B). Phylogenetic trees were generated by maximum likelihood analyses using 100 bootstraps and 3 jumbles. The scale representing the number of nucleotide changes is shown for each tree. Numbers in the trees represent bootstrap values based on the consensus trees.

Figure 17:
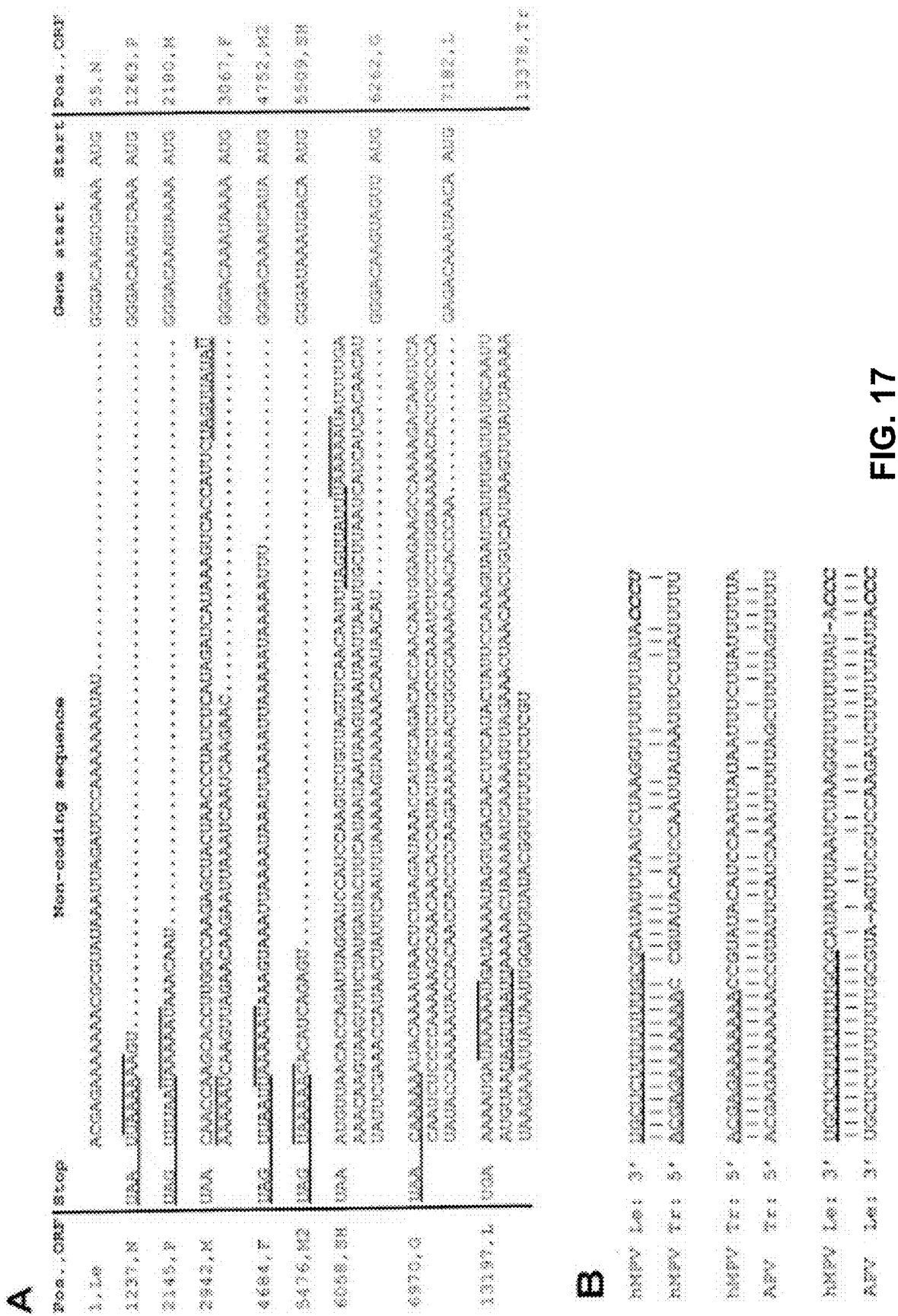

FIG. 17: Noncoding sequences of hMPV isolate 00-1. (A) The noncoding sequences between the ORFs and at the genomic termini are shown in the positive sense. From left to right, stop codons of indicated ORFs are shown, followed by the noncoding sequences, the gene start signals and start codons of the indicated subsequent ORFs. Numbers indicate the first position of start and stop codons in the hMPV map. Sequences that display similarity to published gene end signals are underlined and sequences that display similarity to UAAAAAU/A/C (SEQ ID NO:172) are represented with a line above the sequence (SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84). (B) Nucleotide sequences of the genomic termini of Hmpv (SEQ ID NO:85, SEQ ID NO:86, SEQ ID NO:87, SEQ ID NO:88, SEQ ID NO:89, SEQ ID NO:90). The genomic termini of hMPV are aligned with each other and with those of APV. Underlined regions represent the primer sequences used in RT-PCR assays which are based on the 3' and 5' end sequences of APV and RSV (Randhawa et al., 1997; Mink et al., 1991). Bold italicized nucleotides are part of the gene start signal of the N gene. Le: leader, Tr: trailer.

FIG. 18: Comparison of two prototypic hMPV isolates with APV-A and APV-C; DNA similarity matrices for nucleic acids encoding the various viral proteins.

FIG. 19: Comparison of two prototypic hMPV isolates with APV-A and APV-C; protein similarity matrices for the various viral proteins.

FIG. 20: Amino acid alignment of the nucleoprotein of two prototype hMPV isolates (SEQ ID NO:1, SEQ ID NO:91).

FIG. 21: Amino acid alignment of the phosphoprotein of two prototype hMPV isolates (SEQ ID NO:8, SEQ ID NO:92).

FIG. 22: Amino acid alignment of the matrix protein of two prototype hMPV isolates (SEQ ID NO:14, SEQ ID NO:93).

FIG. 23: Amino acid alignment of the fusion protein of two prototype hMPV isolates (SEQ ID NO:21, SEQ ID NO:94).

FIG. 24: Amino acid alignment of the M2-1 protein of two prototype hMPV isolates (SEQ ID NO:47, SEQ ID NO:95).

FIG. 25: Amino acid alignment of the M2-2 protein of two prototype hMPV isolates (SEQ ID NO:55, SEQ ID NO:96).

FIG. 26: Amino acid alignment of the short hydrophobic protein of two prototype hMPV isolates (SEQ ID NO:63, SEQ ID NO:97).

FIG. 27. Amino acid alignment of the attachment glycoprotein of two prototype hMPV isolates (SEQ ID NO:64, SEQ ID NO:98).

FIG. 28: Amino acid alignment of the N-terminus of the polymerase protein of two prototype hMPV isolates (SEQ ID NO:99, SEQ ID NO:100).

FIG. 29: Results of RT-PCR assays on throat and nose swabs of 12 guinea pigs inoculated with ned/00/01 and/or ned/99/01.

Figure 30A:
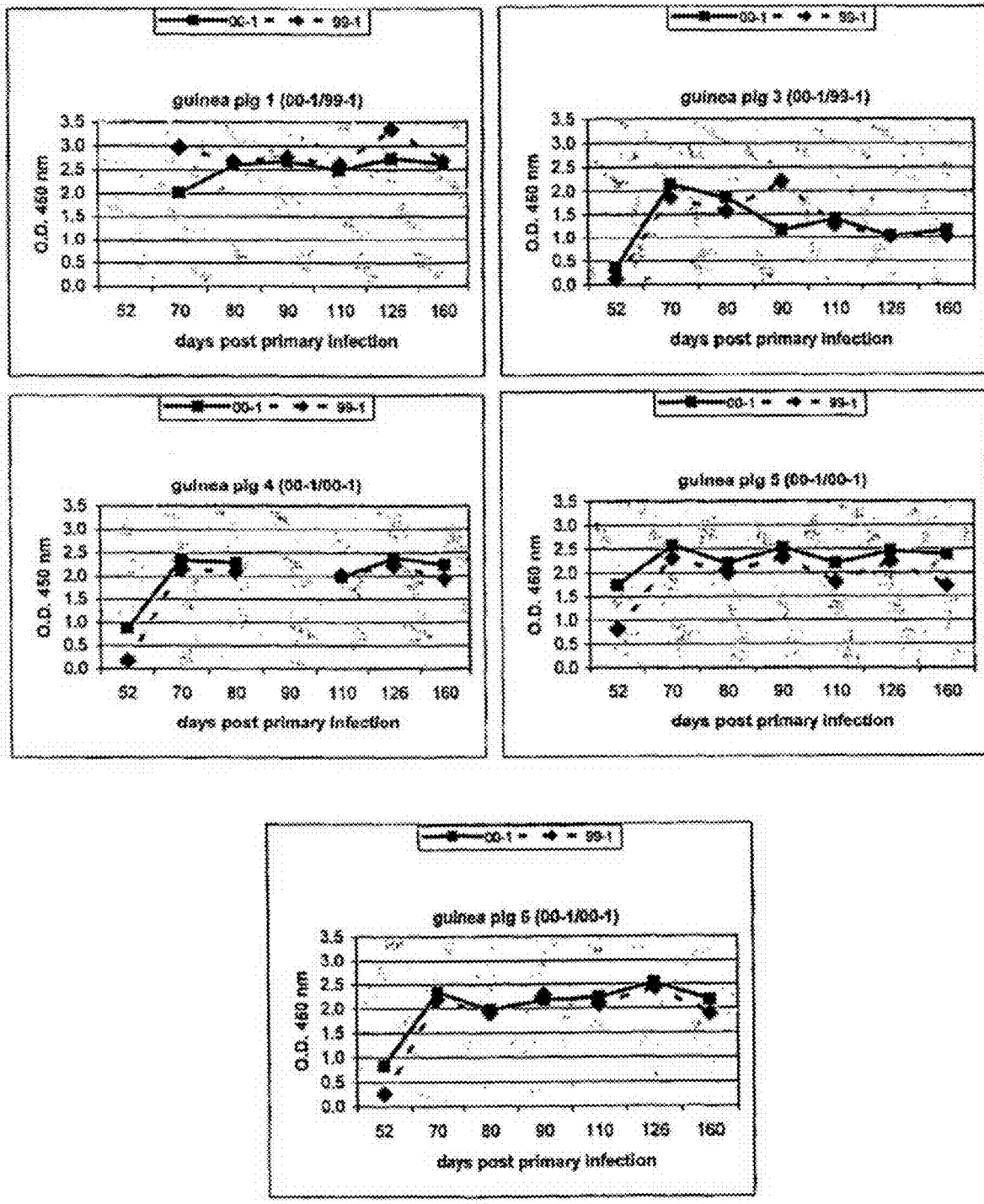

FIG. 30A: IgG response against ned/00/01 and ned/99/01 for guinea pigs infected with ned/00/01 and re-infected with ned/00/01 (GP 4, 5 and 6) or ned/99/01 (GP 1 and 3).

Figure 30B:
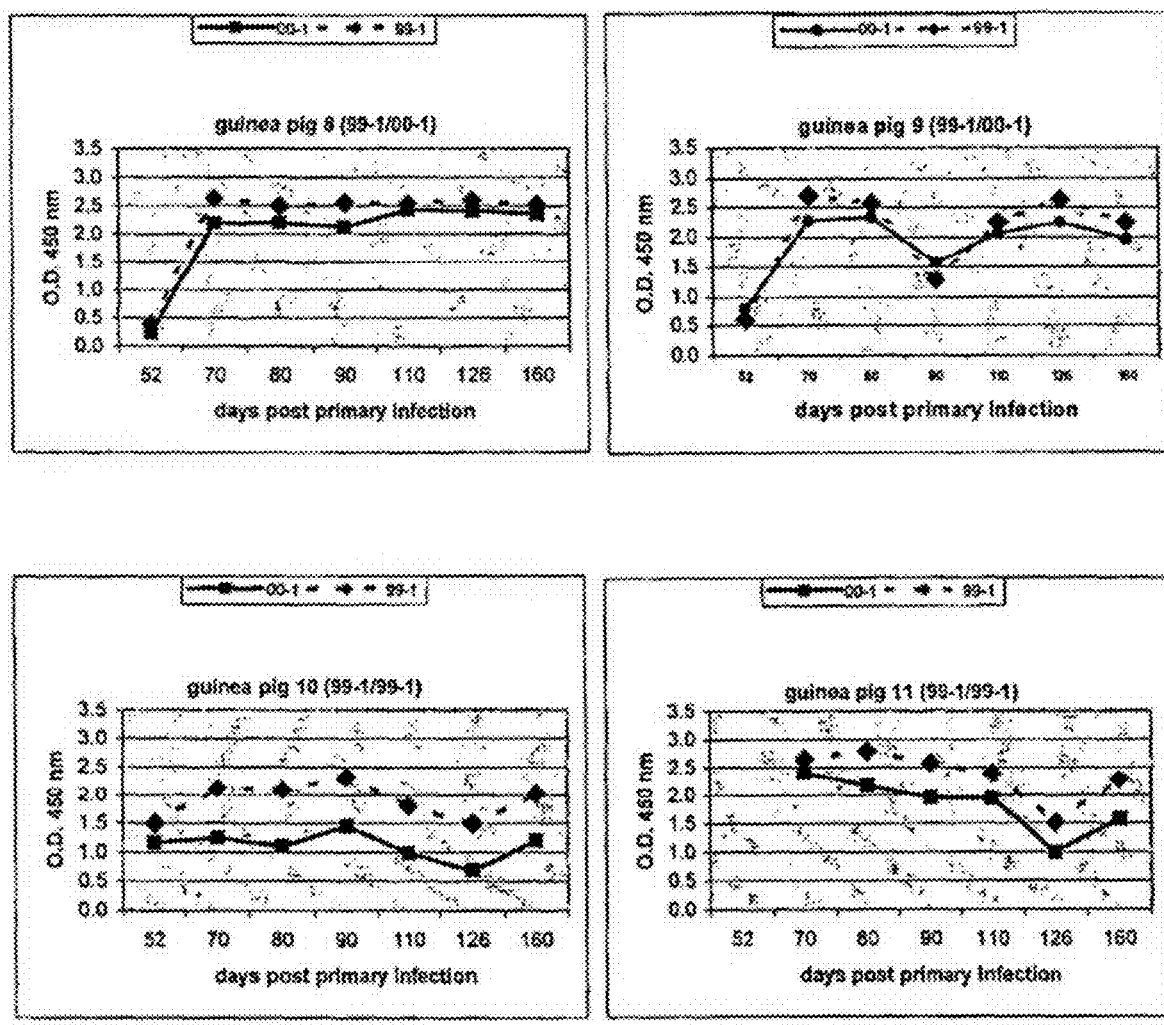

FIG. 30B: IgG response against ned/00/01 and ned/99/01 for guinea pigs infected with ned/99/01 and re-infected with either ned/00/01 (GPs 8 and 9) or with ned/99/01 (GPs 10, 11, 12).

Figure 31:
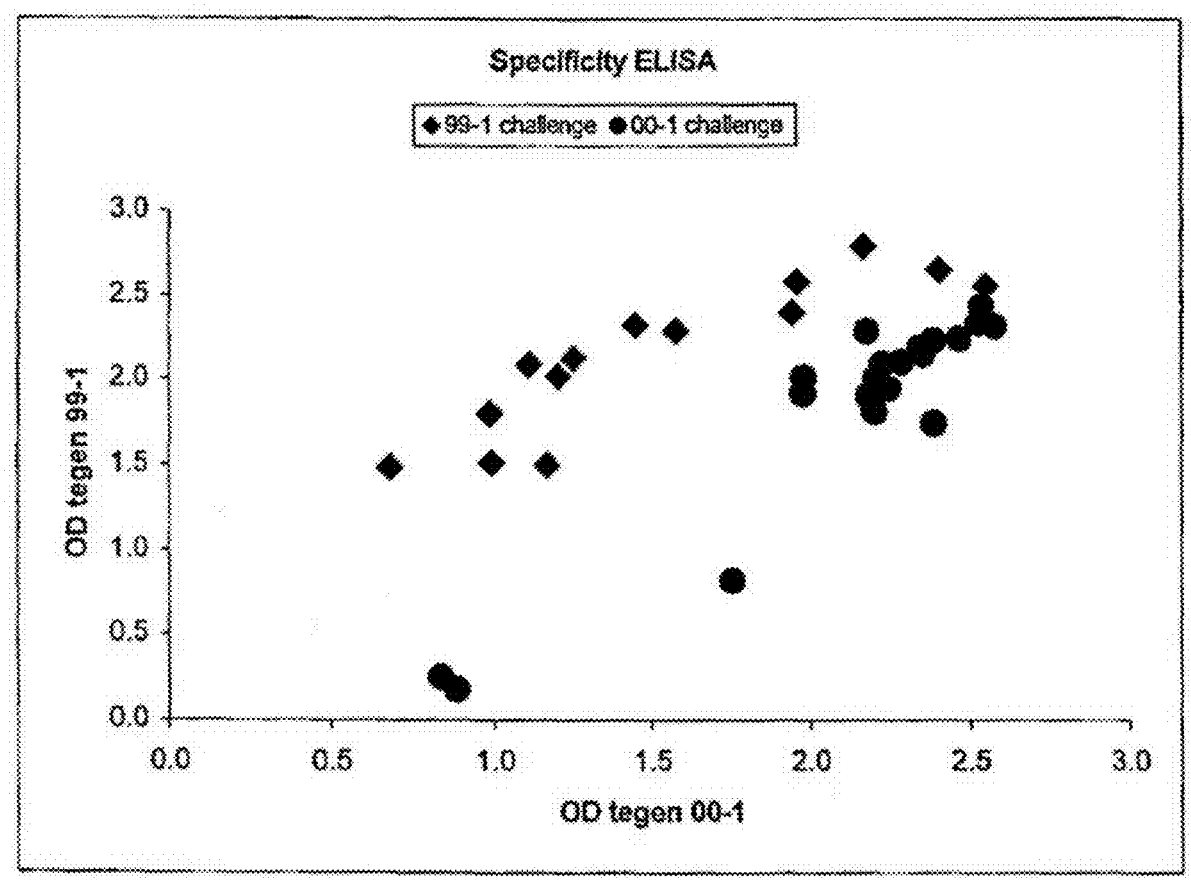

FIG. 31: Specificity of the ned/00/01 and ned/99/01 ELISA on sera taken from guinea pigs infected with either ned/00/01 or ned/99/01.

Figure 32:
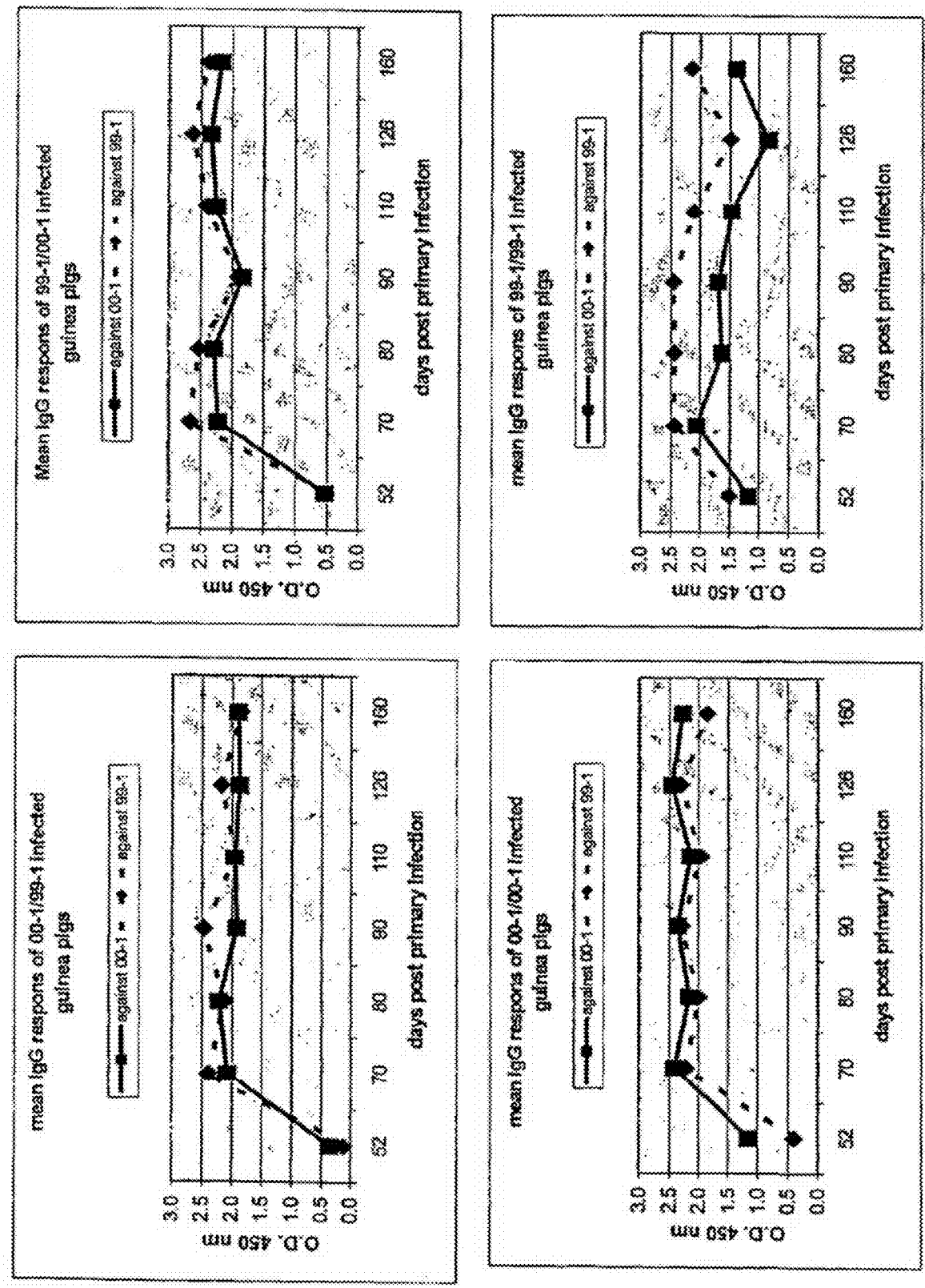

FIG. 32: Mean IgG response against ned/00/01 and ned/99/01 ELISA of 3 homologous (00-1/00-1), 2 homologous (99-1/99-1), 2 heterologous (99-1/00-1) and 2 heterologous (00-1/99-1) infected guinea pigs.

Figures 33, 34, 35:
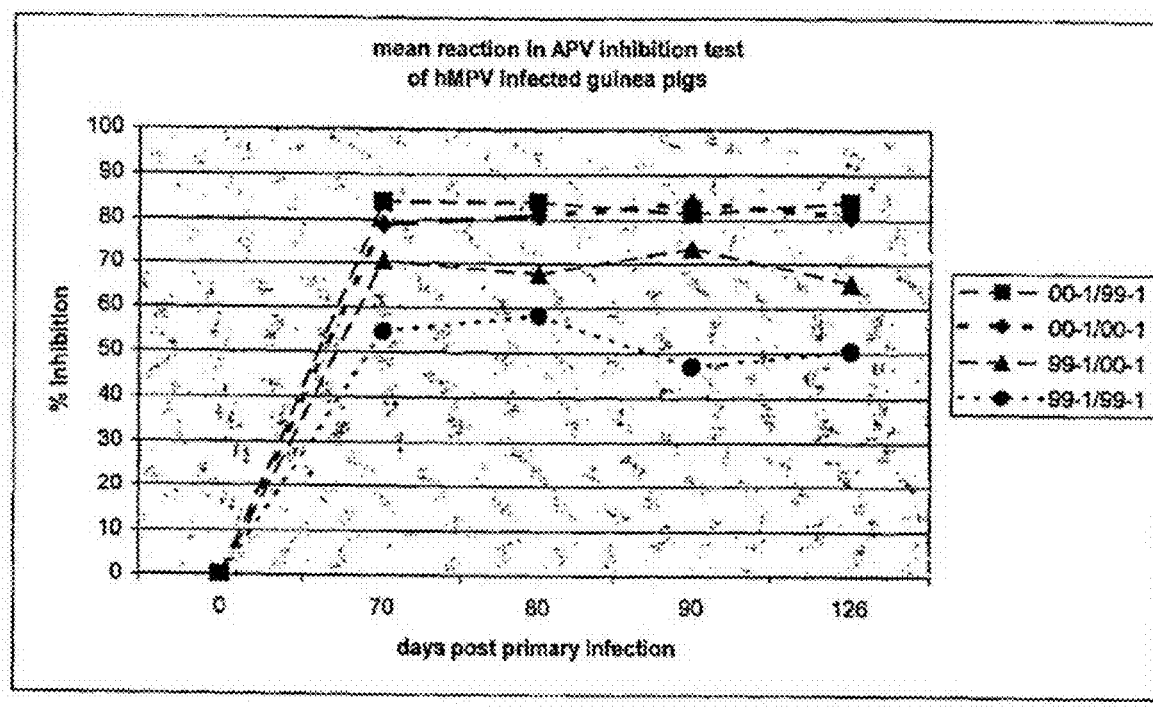

FIG. 33: Mean percentage of APV inhibition of hMPV-infected guinea pigs.

FIG. 34: Virus neutralization titers of ned/00/01 and ned/99/01 infected guinea pigs against ned/00/01, ned/99/01 and APV-C.

FIG. 35: Results of RT-PCR assays on throat swabs of cynomolgus macaques inoculated (twice) with ned/00/01.

FIG. 36 A (top two panels): IgA, IgM and IgG response against ned/00/01 of 2 cynomolgus macaques (re)infected with ned/00/01.

FIG. 36B (bottom panels): IgG response against APV of 2 cynomolgus macaques infected with ned/00/01.

Figure 37:
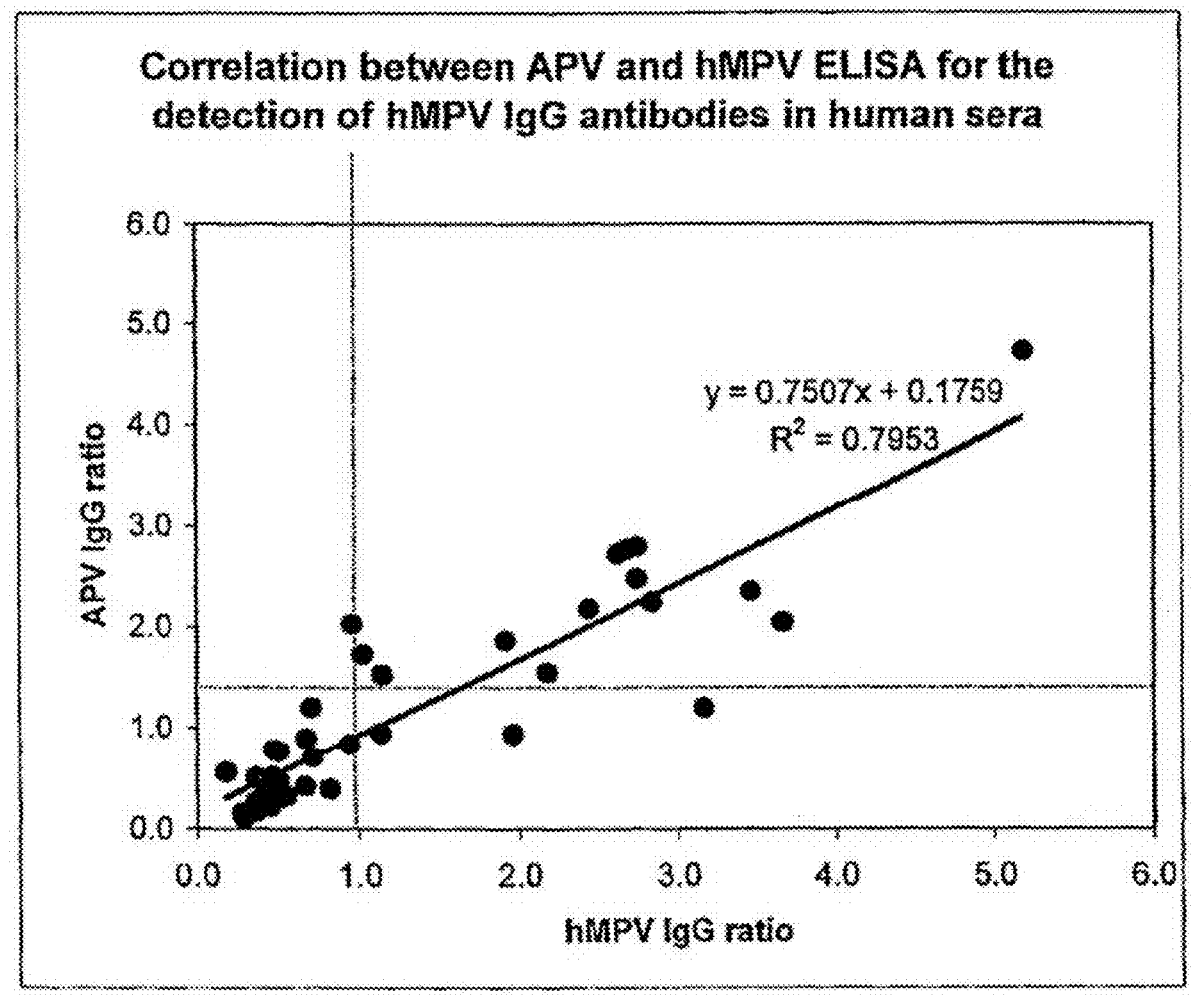

FIG. 37: Comparison of the use of the hMPV ELISA and the APV inhibition ELISA for the detection of IgG antibodies in human sera.

DETAILED DESCRIPTION

Virus Isolation and Characterization

From 1980 till 2000 we found 28 unidentified virus isolates from patients with severe Respiratory disease. These 28 unidentified virus isolates grew slowly in tMK cells, poorly in VERO cells and A549 cells and could not or only little be propagated in MDCK or chicken embryonated fibroblast cells. Most of these virus isolates induced CPE after three passages on tMK cells, between day ten and fourteen. The CPE was virtually indistinguishable from that caused by hRSV or hPIV in tMK or other cell cultures, characterized by syncytium formation after which the cells showed rapid internal disruption, followed by detachment of the cells from the monolayer. The cells usually (sometimes later) displayed CPE after three passages of virus from original material, at day 10 to 14 post inoculation, somewhat later than CPE caused by other viruses such as hRSV or hPIV.

We used the supernatants of infected tMK cells for EM analysis which revealed the presence of paramyxovirus-like virus particles ranging from 150 to 600 nanometers, with short envelope projections ranging from 13 to 17 nanometers. Consistent with the biochemical properties of enveloped viruses such as the Paramyxoviridae, standard chloroform or ether treatment resulted in >$10^4$ TCID50 reduction of infectivity for tMK cells. Virus-infected tMK cell culture supernatants did not display hemagglutinating activity with turkey, chicken and guinea pig erythrocytes. During culture, the virus replication appeared to be trypsine dependent on the cells tested. These combined virological data allowed that the newly identified virus was taxonomically classified as a member of the Paramyxoviridae family.

We isolated RNA from tMK cells infected with 15 of the unidentified virus isolates for reverse transcription and polymerase chain reaction (RT-PCR) analyses using primer-sets specific for Paramyxovirinae,[9] hPIV 1-4, Sendai virus, simian virus type 5, New-Castle disease virus, hRSV, morbilli, mumps, Nipah, Hendra, Tupaia and Mapuera viruses. RT-PCR assays were carried out at low stringency in order to detect potentially related viruses and RNA isolated from homologous virus stocks were used as controls. Whereas the available controls reacted positive with the respective virus-specific primers, the newly identified virus isolates did not react with any primer set, indicating the virus was not closely related to the viruses tested.

We used two of the virus-infected tMK cell culture supernatants to inoculate guinea pigs and ferrets intranasally. Sera were collected from these animals at day zero, two weeks and three weeks post inoculation. The animals displayed no clinical symptoms but all seroconverted as measured in virus neutralization (VN) assays and indirect IFA against the homologous viruses. The sera did not react in indirect IFA with any of the known paramyxoviruses described above and with PVM. Next, we screened the so far unidentified virus isolates using the guinea pig and ferret pre- and post-infection sera, of which 28 were clearly positive by indirect IFA with the post-infection sera suggesting they were serological closely related or identical.

RAP PCR

To obtain sequence information on the unknown virus isolates, we used a random PCR amplification strategy known as RAP-PCR.[10] To this end, tMK cells were infected with one of the virus isolates (isolate 00-1) as well as with hPIV-1 which served as a control. After both cultures displayed similar levels of CPE, virus in the culture supernatants was purified on continuous 20-60% sucrose gradients. The gradient fractions were inspected for virus-like particles by EM, and RNA was isolated from the fraction containing approximately 50% sucrose, in which nucleocapsids were observed. Equivalent amounts of RNA isolated from both virus fractions were used for RAP-PCR, after which samples were run side by side on a 3% NuSieve agarose gel. Twenty differentially displayed bands specific for the unidentified virus were subsequently purified from the gel, cloned in plasmid pCR2.1 (Invitrogen) and sequenced with vector-specific primers. When we used these sequences to search for homologies against sequences in the Genbank database using the BLAST® software (on the World Wide Web at ncbi.nlm.nih.gov/BLAST/) 10 out of 20 fragments displayed resemblance to APV/TRTV sequences.

Figures 1B, 2:
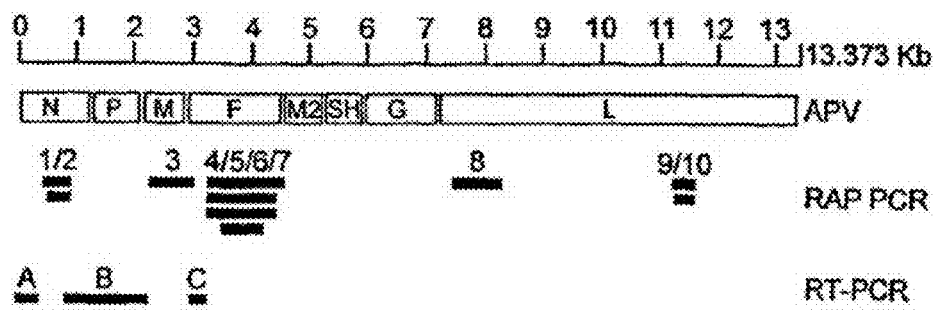
FIG. 1B comprises table 2: Seroprevalence of MPV in humans categorized by age group using immunofluorescence and virus neutralization assays.
FIG. 2: Schematic representation of the genome of APV with the location and size of the fragments obtained with RAP-PCR and RT-PCR on virus isolate 00-1. Fragments 1 to 10 were obtained using RAP-PCR. Fragment A was obtained with a primer in RAP-PCR fragment 1 and 2 and a primer designed based on alignment of leader and trailer sequences of APV and RSVS. Fragment B was obtained using primers designed in RAP-PCR fragments 1 and 2 and RAP-PCR fragment 3. Fragment C was obtained with primers designed in RAP-PCR fragment 3 and RAP-PCR fragments 4, 5, 6 and 7.

These ten fragments were located in the genes coding for the nucleoprotein (N; fragments 1 and 2), the matrix protein (M; fragment 3), the fusion protein A; fragments 4, 5, 6, 7) and the polymerase protein a; fragments 8, 9, 10) (FIG. 2). We next designed PCR primers to complete the sequence information for the 3' end of the viral genome based on our RAP PCR fragments as well as published leader and trailer sequences for the Pneumovirinae.[6] Three fragments were amplified, of which fragment A spanned the extreme 3' end of the N open reading frame (ORF), fragment B spanned the phosphoprotein (P) ORF and fragment C closed the gap between the M and F ORFs (FIG. 2). Sequence analyses of these three fragments revealed the absence of NS1 and NS2 ORFs at the extreme 3' end of the viral genome and positioning of the F ORF immediately adjacent to the M ORF. This genomic organization resembles that of the *Metapneumovirus* APV, which is also consistent with the sequence homology. Overall the translated sequences for the N, P, M and F ORFs showed an average of 30-33% homology with members of the genus *Pneumovirus* and 66-68% with members of the genus *Metapneumovirus*. For the SH and G ORFs, no discernible homology was found with members of either of the genera. The amino acid homologies found for N showed about 40% homology with hRSV and 88% with APV-C, its closest relative genetically, as for example can be deduced by comparing the amino acid sequence of FIGS. 3A-3E with the amino acid sequence of the respective N proteins of other viruses. The amino acid sequence for P showed about 25% homology with hRSV and about 66-68% with APV-C, M showed about 36-39% with hRSV and about 87-89% with APV-C, F showed about 40% homology with hRSV and about 81% with APV-C, M2-1 showed about 34-36% homology with Pneumoviruses and 84-86% with APV-C, M2-2 showed 15-17% homology with Pneumoviruses and 56% with APV-C and the fragments obtained in L showed an average of 44% with Pneumoviruses and 64% with APV-C.

Phylogeny

Although BLAST® searches using nucleotide sequences obtained from the unidentified virus isolate revealed homologies primarily with members of the Pneumovirinae, homologies based on protein sequences revealed some resemblance with other paramyxoviruses as well (data not shown). As an indication for the relation between the newly identified virus isolate and members of the Pneumovirinae, phylogenetic trees were constructed based on the N, P, M and F ORFs of these viruses. In all four phylogenetic trees, the newly identified virus isolate was most closely related to APV (FIG. 4). From the four serotypes of APV that have been described.[11] APV serotype C, the *Metapneumovirus* found primarily in birds in the USA, showed the closest resemblance to the newly identified virus. It should be noted however, that only partial sequence information for APV serotype D is available.

To determine the relationship of our various newly identified virus isolates, we constructed phylogenetic trees based on sequence information obtained from eight to nine isolates (8 for F, 9 for N, M and L). To this end, we used RT-PCR with primers designed to amplify short fragments in the N, M, F and L ORFs, that were subsequently sequenced directly. The nine virus isolates that were previously found to be related in serological terms (see above) were also found to be closely related genetically. In fact, all nine isolates were more closely related to one another than to APV. Although the sequence information used for these phylogenetic trees was limited, it appears that the nine isolates can be divided in two groups, with isolate 94-1, 99-1 and 99-2 clustering in one group and the other six isolates (94-2; 93-1; 93-2; 93-3; 93-4; 00-1) in the other (FIG. 5).

Seroprevalence

To study the seroprevalence of this virus in the human population, we tested sera from humans in different age categories by indirect IFA using tMK cells infected with one of the unidentified virus isolates. This analysis revealed that 25% of the children between six and twelve months had antibodies to the virus, and by the age of five nearly 100% of the children were seropositive. In total 56 serum samples tested by indirect IFA were tested by VN assay. For 51 (91%) of the samples the results of the VN assay (titer >8) coincided with the results obtained with indirect IFA (titer >32). Four samples that were found positive in IFA, were negative by VN test (titer <8) whereas one serum reacted negative in IFA (titer <32) and positive in the VN test (titer 16) (table 2).

IFA conducted with 72 sera taken from humans in 1958 (ages ranging from 8-99 years)[13,27] revealed a 100% seroprevalence, indicating the virus has been circulating in the human population for more than 40 years. In addition a number of these sera were used in VN assays to confirm the IFA data (table 2).

Genetic analyses of the N, M, P and F genes revealed that MPV has higher sequence homology to the recently proposed genus Metapneumovirinae (average of 63%) as compared to the genus Pneumovirinae (average of 30%) and thus demonstrates a genomic organization similar to and resembling that of APV/TRTV. In contrast to the genomic organization of the RSVs ('3-NS1-NS2-N-P-M-SH-G-F-M2-L-5'), Metapneumoviruses lack NS1 and NS2 genes and have a different positioning of the genes between M and L ('3-N-P-M-F-M2-SH-G-L-5'). The lack of ORFs between the M and F genes in our virus isolates and the lack of NS1 and NS2 adjacent to N, and the high amino acid sequence homology found with APV are reasons to propose the classification of NPV isolated from humans as a first member of the *Metapneumovirus* genus of mammalian, in particular of human origin.

Phylogenetic analyses revealed that the nine MPV isolates from which sequence information was obtained are closely related. Although sequence information was limited, they were in fact more closely related to one another than to any of the avian Metapneumoviruses. Of the four serotypes of APV that have been described, serotype C was most closely related to MPV based on the N, P, M and F genes. It should be noted however that for serotype D only partial sequences for the F gene were available from Genbank and for serotype B only M, N and F sequences were available. Our MPV isolates formed two clusters in phylogenetic trees. For both hRSV and APV different genetic and serological subtypes have been described. Whether the two genetic clusters of MPV isolates represent serological subgroups that are also functionally different remains unknown at present. Our serological surveys showed that MPV is a common human pathogen. The repeated isolation of this virus from clinical samples from children with severe RTI indicates that the clinical and economic impact of MPV may be high. New diagnostic assays based on virus detection and serology will allow a more detailed analysis of the incidence and clinical and economic impact of this viral pathogen.

The slight differences between the IFA and VN results (5 samples) maybe due to the fact that in the IFA only IgG serum antibodies were detected whereas the VN assay detects both classes and sub-classes of antibodies or differences may be due to the differences in sensitivity between both assays. For IFA a cut off value of 16 is used, whereas for VN a cut off value of 8 is used.

On the other hand, differences between IFA versus VN assay may also indicate possible differences between different serotypes of this newly identified virus. Since MPV seems most closely related to APV, we speculate that the human virus may have originated from birds. Analysis of serum samples taken from humans in 1958 revealed that MPV has been widespread in the human population for more than 40 years indicating that a tentative zoonosis event must have taken place long before 1958.

Materials and Methods

Specimen Collection

Over the past decades our laboratory has collected nasopharyngeal aspirates from children suffering from RTI, which are routinely tested for the presence of viruses. All nasopharyngeal aspirates were tested by direct immunofluorescence assays (DIF) using fluorescence labeled antibodies against influenza virus types A, and B, hRSV and human parainfluenza virus (hP) types 1 to 3. The nasopharyngeal aspirates were also processed for virus isolation using rapid shell vial techniques' on various cell lines including VERO cells, tertiary cynomolgus monkey kidney (tMK) cells, human endothelial lung (HEL) cells and marbin dock kidney (MDCK) cells. Samples showing cytopathic effects (CPE) after two to three passages, and which were negative in DIF, were tested by indirect immunofluorescence assays (IFA) using virus-specific antibodies against influenza virus types A, B and C, hRSV types A and B, measles virus, mumps virus, human parainfluenza virus (hPIV) types 1 to 4, Sendai virus, simian virus type 5, and New-Castle disease virus. Although for many cases the etiological agent could be identified, some specimens were negative for all these viruses tested.

Direct Immunofluorescence Assay (DIF)

Nasopharyngeal aspirate samples from patients suffering from RTI were used for DIF and virus isolation as described.[14, 15] Samples were stored at −70° C. In brief, nasopharyngeal aspirates were diluted with 5 ml Dulbecco MEM (BioWhittaker, Walkersville, Md.) and thoroughly mixed on a vortex mixer for one minute. The suspension was thus centrifuged for ten minutes at 840×g. The sediment was spread on a multispot slide (Nutacon, Leimuiden, The Netherlands), the supernatant was used for virus isolation. After drying, the cells were fixed in aceton for 1 minute at room temperature. After washing the slides were incubated for 15 minutes at 37° C. with commercially available FITC-labeled virus-specific anti-sera such as influenza A and B, hRSV and hPIV 1 to 3 (Dako, Glostrup, Denmark). After three washings in PBS and one in tap water, the slides were included in a glycerol/PBS solution (Citifluor, UKC, Canterbury, UK) and covered. The slides were analyzed using an Axioscop fluorescence microscope (Carl Zeiss B. V, Weesp, The Netherlands.

Virus Isolation

For virus isolation tMK cells (RIVM, Bilthoven, The Netherlands) were cultured in 24-well plates containing glass slides (Costar, Cambridge, UK), with the medium described below supplemented with 10% fetal bovine serum (BioWhittaker, Vervier, Belgium). Before inoculation the plates were washed with PBS and supplied with Eagle's MEM with Hanks' salt (ICN, Costa mesa, Calif.) of which half a liter was supplemented with 0.26 gram $HaHCO_3$, 0.025 M Hepes (Biowhittaker), 2 mM L-glutamine (Biowhittaker), 100 units penicillin, 100 μg streptomycin (Biowhittaker), 0.5 gram lactal bumnine (Sigma-Aldrich, Zwijndrecht, The Netherlands), 1.0 gram D-glucose (Merck, Amsterdam, The Netherlands), 5.0 gram peptone (Oxoid, Haarlem, The Netherlands) and 0.02% trypsine (Life Technologies, Bethesda, Md.). The plates were inoculated with supernatant of the nasopharyngeal aspirate samples, 0.2 ml per well in triplicate, followed by centrifuging at 840×g for one hour. After inoculation the plates were incubated at 37° C. for a maximum of 14 days changing the medium once a week and cultures were checked daily for CPE. After 14 days cells were scraped from the second passage and incubated 14 days. This step was repeated for the third passage. The glass slides were used to demonstrate the presence of the virus by indirect IFA as described below.

Animal Immunization

Ferret and guinea pig-specific antisera for the newly discovered virus were generated by experimental intranasal infection of two specific pathogen free ferrets and two guinea pigs, housed in separate pressurized glove boxes. Two to three weeks later all the animals were bled by cardiac puncture, and their sera were used as reference sera. The sera were tested for all previous described viruses with indirect IFA as described below.

Antigen Detection by Indirect IFA

We performed indirect IFA on slides containing infected tMK cells. After washing with PBS the slides were incubated for 30 minutes at 37° C. with virus-specific anti-sera. We used monoclonal antibodies in DIF against influenza A, B and C, hPIV type 1 to 3 and hRSV as described above. For hPIV type 4, mumps virus, measles virus, Sendai virus, simian virus type 5, New-Castle Disease virus polyclonal antibodies (RIVM) and ferret and guinea pig reference sera were used. After three washings with PBS and one wash with tap water, the slides were stained with a secondary antibodies directed against the sera used in the first incubation. Secondary antibodies for the polyclonal anti sera were goat-anti-ferret (KPL, Guilford, UK, 40-fold diluted), mouse-anti-rabbit (Dako, Glostrup, Denmark, 20-fold diluted), rabbit-anti-chicken (KPL, 20-fold dilution) and mouse-anti-guinea pig (Dako, 20-fold diluted). Slides were processed as described for DIF.

Detection of Antibodies in Humans by Indirect IFA

For the detection of virus-specific antibodies, infected tMK cells were fixed with cold acetone on coverslips, washed with PBS and stained with serum samples at a 1 to 16 dilution. Subsequently, samples were stained with FITC-labeled rabbit anti human antibodies 80 times diluted in PBS (Dako). Slides were processed as described above.

Virus Culture of MPV

Sub-confluent mono-layers of tMK cells in media as described above were inoculated with supernatants of samples that displayed CPE after two or three passages in the 24-well plates. Cultures were checked for CPE daily and the media was changed once a week. Since CPE differed for each isolate, all cultures were tested at day 12 to 14 with indirect IFA using ferret antibodies against the new virus isolate. Positive cultures were freeze-thawed three times, after which the supernatants were clarified by low-speed centrifugation, aliquoted and stored frozen at −70° C. The 50% tissue culture infectious doses (TCID50) of virus in the culture supernatants were determined as described.[16]

Virus Neutralization Assay

VN assays were performed with serial two-fold dilutions of human and animal sera starting at an eight-fold dilution. Diluted sera were incubated for one hour with 100 TCID50 of virus before inoculation of tMK cells grown in 96-well plates, after which the plates were centrifuged at 840×g. The media was changed after three and six days and IFA was conducted with ferret antibodies against MPV 8 days after inoculation. The VN titer was defined as the lowest dilution of the serum sample resulting in negative IFA and inhibition of CPE in cell cultures.

Virus Characterization

Hemagglutination assays and chloroform sensitivity tests were performed as described.[8, 14] For EM analyses, virus was concentrated from infected cell culture supernatants in a micro-centrifuge at 4° C. at 17000×g, after which the pellet was resuspended in PBS and inspected by negative contrast EM. For RAP-PGR, virus was concentrated from infected tMK cell supernatants by ultra-centrifugation on a 60% sucrose cushion (2 hours at 150000×g, 4° C.). The 60% sucrose interphase was subsequently diluted with PBS and layered on top of a 20-60% continuous sucrose gradient which was centrifuged for 16 hours at 275000×g at 4° C. Sucrose gradient fractions were inspected for the presence of virus-like particles by EM and poly-acrylamide gel electrophoresis followed by silver staining. The approximately 50% sucrose fractions that appeared to contain nucleocapsids were used for RNA isolation and RAP-PCR.

RNA Isolation

RNA was isolated from the supernatant of infected cell cultures or sucrose gradient fractions using a High Pure RNA Isolation kit according to instructions from the manufacturer (Roche Diagnostics, Almere, The Netherlands).

RT-PCR

Virus-specific oligonucleotide sequences for RT-PCR assays on known paramyxoviruses are described in addenda 1. A one-step RT-PCR was performed in 50 µl reactions containing 50 mM Tris.HCl pH 8.5, 50 mM NaCl, 4 mM $MgCl_2$, 2 mM dithiotreitol, 200 µM each dNTP, 10 units recombinant RNAsin (Promega, Leiden, The Netherlands), 10 units AMV RT (Promega, Leiden, The Netherlands), 5 units AMPLITAQ® Gold DNA polymerase (PE Biosystems, Nieuwerkerk aan de Ijssel The Netherlands) and 5 µl RNA. Cycling conditions were 45 min. at 42° C. and 7 min. at 95° C. once, 1 min at 95° C., 2 min. at 42° C. and 3 min. at 72° C. repeated 40 times and 10 min. at 72° C. once.

RAP-PCR

RAP-PCR was performed essentially as described.[10] The oligonucleotide sequences are described in addenda 2. For the RT reaction, 2 µl RNA was used in a 10 µl reaction containing 10 ng/µl oligonucleotide, 10 mM dithiotreitol, 500 µm each dNTP, 25 mM Tris-HCl pH 8.3, 75 mM KCl and 3 mM $MgCl_2$. The reaction mixture was incubated for 5 min. at 70° C. and 5 min. at 37° C., after which 200 units SUPERSCRIPT® RT enzyme (LifeTechnologies) were added. The incubation at 37° C. was continued for 55 min. and the reaction terminated by a 5 min. incubation at 72° C. The RT mixture was diluted to give a 50 µl PCR reaction containing 8 ng/µl oligonucleotide, 300 µm each dNTP, 15 mM Tris-HCL pH 8.3, 65 mM KCl, 3.0 mM $MgCl_4$ and 5 units Taq DNA polymerase (PE Biosystems). Cycling conditions were 6 min. at 94° C., 5 min. at 40° C. and 1 min. at 72° C. once, followed by 1 min. at 94° C., 2 min. at 56° C. and 1 min. at 72° C. repeated 40 times and 6 min. at 72° C. once. After RAP-PCR, 15 µl the RT-PCR products were run side by side on a 3% NuSieve agarose gel (FMC BioProducts, Heerhugowaard, The Netherlands). Differentially displayed fragments specific for MPV were purified from the gel with QIAQUICK® Gel Extraction kit (Qiagen, Leusden, The Netherlands) and cloned in pCR2.1 vector (Invitrogen, Groningen, The Netherlands) according to instructions from the manufacturer.

Sequence Analysis

RAP-PCR products cloned in vector pCR2.1 (Invitrogen) were sequenced with M13-specific oligonucleotides. DNA fragments obtained by RT-PCR were purified from agarose gels using QIAQUICK ® Gel Extraction kit (Qiagen, Leusden, The Netherlands), and sequenced directly with the same oligonucleotides used for PCR. Sequence analyses were performed using a DYENAMIC™ ET terminator sequencing kit (Amersham Pharmacia Biotech, Roosendaal, The Netherlands) and an ABI 373 automatic DNA sequencer (PE Biosystem). All techniques were performed according to the instructions of the manufacturer.

Generating Genomic Fragments of MPV by RT-PCR

To generate PCR fragments spanning gaps A, B and C between the RAP-PCR fragments (FIG. 2) we used RT-PCR assays as described before on RNA isolated from virus isolate 00-1. The following primers were used:

For fragment A: TR1 designed in the leader: (5'-AAAGAATTCACGAGAAAAAAACGC-3') (SEQ ID NO:107) and N1 designed at the 3' end of the RAP- PCR fragments obtained in N (5'-CTGTGGTCT-CTAGTCCCACTTC-3') (SEQ ID NO:108).

For fragment B: N2 designed at the 5' end of the RAP-PCR fragments obtained in N: (5'-CATGCAAGCT-TATGGGGC-3') (SEQ ID NO:19) and M1 designed at the 3' end of the RAP-PCR fragments obtained in M: (5'-CAGAGTGGTTATTGTCAGGGT-3) (SEQ ID NO:110).

For fragment C: M2 designed at the 5' end of the RAP-PCR fragment obtained in M: (5'-GTAGAACTAG-GAGCATATG-3') (SEQ ID NO:111) and F1 designed at the 3' end of the RAP-PCR fragments obtained in F: (5'-TCCCCAATGTAGATACTGCTTC-3') (SEQ ID NO:112).

Fragments were purified from the gel, cloned and sequenced as described before.

RT-PCR for Diagnosing MPV

For the amplification and sequencing of parts of the N, M, F and L ORFs of nine of the MPV isolates, we used primers N3 (5'-GCACTCAAGAGATACCCTAG-3') (SEQ ID NO:113) and N4 (5'-AGACTTTCTGCTTTGCTGCCTG-3') (SEQ ID NO:114), amplifying a 151 nucleotide fragments, M3 (5'-CCCTGACAATAACCACTCTG-3') (SEQ ID NO:115) and M4 (5'-GCCAACTGATTTGGCT-GAGCTC-3') (SEQ ID NO:116) amplifying a 252 nucleotide fragment, F7 (5'-TGCACTATCTCCTCTT-GGGGCTTTG-3') (SEQ ID NO:117) and F8 (5'-TCAAAGCTGCTTGACACTGGCC-3') (SEQ ID NO:118) amplifying a 221 nucleotide fragment and L6 (5'-CATGCC-CACTATAAAAGGTCAG-3') (SEQ ID NO:119) and L7 (5'-CACCCCAGTCTTTCTTGAAA-3') (SEQ ID NO:120) amplifying a 173 nucleotide fragment respectively. RT-PCR, gel purification and direct sequencing were performed as described above. Furthermore, probes used were:

```
                                    (SEQ ID NO: 121)
Probe used in M: 5'-TGC TTG TAC TTC CCA AAG-3'

(SEQ ID NO: 122)
Probe used in N: 5'-TAT TTG AAC AAA AAG TGT-3'

(SEQ ID NO: 123)
Probe used in L: 5'-TGGTGTGGGATATTAACAG-3'
```

Phylogenetic Analyses

For all phylogenetic trees, DNA sequences were aligned using the ClustalW software package and maximum likelihood trees were generated using the DNA-ML software package of the Phylip 3.5 program using 100 bootstraps and 3 jumbles.[15] Previously published sequences that were used for the generation of phylogenetic trees are available from Genbank under accessions numbers: For all ORFs: hRSV: NC001781; bRSV: NC001989; For the F ORF: PVM, D11128; APV-A, D00850; APV-B, Y14292; APV-C, AF187152; For the N ORF: PVM, D10331; APV-A, U39295; APV-B, U39296; APV-C, AF176590; For the M ORF: PMV, U66893; APV-A, X58639; APV-B, U37586; APV-C, AF262571; For the P ORF: PVM, 09649; APV-A, U22110, APV-C, AF176591. Phylogenetic analyses for the nine different virus isolates of MPV were performed with APV strain C as outgroup.

Abbreviations used in figures: hRSV: human RSV; bRSV: bovine RSV; PVM: pneumonia virus of mice; APV-A, B, and C: avian *Pneumovirus* type A, B and C.

Examples of Methods to Identify MPV

Specimen Collection

In order to find virus isolates nasopharyngeal aspirates, throat and nasal swabs, bronchoalveolar lavages preferably from mammals such as humans, carnivores (dogs, cats, mustelids, seals etc.), horses, ruminants (cattle, sheep, goats etc.), pigs, rabbits, birds (poultry, ostriches, etc.) should be examined. From birds cloaca swabs and droppings can be examined as well Sera should be collected for immunological assays, such as ELISA and virus neutralization assays.

Collected virus specimens were diluted with 5 ml Dulbecco MEM medium (BioWhittaker, Walkersville, Md.) and thoroughly mixed on a vortex mixer for one minute. The suspension was thus centrifuged for ten minutes at 840×g. The sediment was spread on a multispot slide (Nutacon, Leimuiden, The Netherlands) for immunofluorescence techniques, and the supernatant was used for virus isolation.

Virus Isolation

For virus isolation tMK cells (RIVM, Bilthoven, The Netherlands) were cultured in 24-well plates containing glass slides (Costar, Cambridge, UK, with the medium described below supplemented with 10% fetal bovine serum (BioWhittaker, Vervier, Belgium). Before inoculation the plates were washed with PBS and supplied with Eagle's MEM with Hanks' salt (ICN, Costa Mesa, Calif.) supplemented with 0.52/liter gram $NaHCO_3$, 0.025 M Hepes (Biowhittaker), 2 mM Iglutamine (Biowhittaker), 200 units/liter penicillin, 200 µg/liter streptomycin (Biowhittaker), 1 gram/liter lactalbumin (Sigma-Aldiich, Zwindrecht, The Netherlands), 2.0 gram/liter D-glucose (Merck, Amsterdam, The Netherlands), 10 gram/liter peptone (Oxoid, Haarlem, The Netherlands) and 0.02% trypsine (Life Technologies, Bethesda, Md.).

The plates were inoculated with supernatant of the nasopharyngeal aspirate samples, 0.2 ml per well in triplicate, followed by centrifuging at 840×g for one hour. After inoculation the plates were incubated at 37° C. for a maximum of 14 days changing the medium once a week and cultures were checked daily for CPE. After 14 days, cells were scraped from the second passage and incubated for another 14 days. This step was repeated for the third passage. The glass slides were used to demonstrate the presence of the virus by indirect IFA as described below.

CPE was generally observed after the third passage, at day 8 to 14 depending on the isolate. The CPE was virtually indistinguishable from that caused by hRSV or hPIV in tMK or other cell cultures. However, hRSV induces CPE starting around day 4. CPE was characterized by syncytia formation, after which the cells showed rapid internal disruption, followed by detachment of cells from the monolayer. For some isolates CPE was difficult to observe, and IFA was used to confirm the presence of the virus in these cultures.

Virus Culture of MPV

Sub-confluent monolayers of tMK cells in media as described above were inoculated with supernatants of samples that displayed CPE after two or three passages in the 24-well plates. Cultures were checked for CPE daily and the media was changed once a week. Since CPE differed for each isolate, all cultures were tested at day 12 to 14 with indirect IFA using ferret antibodies against the new virus isolate. Positive cultures were freeze-thawed three times, after which the supernatants were clarified by low-speed centrifugation, aliquoted and stored frozen at −70° C. The 50% tissue culture infectious doses (TCID50) of virus in the culture supernatants were determined following established techniques used in the field.[16]

Virus Characterization

Hemagglutination assays and chloroform sensitivity tests were performed following well established and described techniques used in the field.[14] For EM analyses, virus was concentrated from infected cell culture supernatants in a micro-centrifuge at 4° C. at 17000×g, after which the pellet was resuspended in PBS and inspected by negative contrast EM.

Antigen Detection by Indirect IFA

Collected specimens were processed as described and sediment of the samples was spread on a multispot slide. After drying, the cells were fixed in aceton for 1 minute at room temperature.

Alternatively, virus was cultured on tMK cells in 24 well slides containing glass slides. These glass slides were washed with PBS and fixed in aceton for 1 minute at room temperature.

After washing with PBS the slides were incubated for 30 minutes at 37° C. with polyclonal antibodies at a dilution of 1:50 to 1:100 in PBS. We used immunized ferrets and guinea pigs to obtain polyclonal antibodies, but these antibodies can be raised in various animals, and the working dilution of the polyclonal antibody can vary for each immunization. After three washes with PBS and one wash with tap water, the slides were incubated at 37° C. for 30 minutes with FITC labeled goat-anti-ferret antibodies (KPL, Guilford, UK, 40-fold diluted). After three washes in PBS and one in tap water, the slides were included in a glycerol/PBS solution (Citifluor, UKC, Canterbury, UK) and covered. The slides were analyzed using an Axioscop fluorescence microscope (Carl Zeiss B. V., Weesp, The Netherlands). Detection of antibodies in humans, mammals, ruminants or other animals by indirect.

IFA

For the detection of virus-specific antibodies, infected tMK cells with MPV were fixed with acetone on coverslips (as described above), washed with PBS and incubated 30 minutes at 37° C. with serum samples at a 1 to 16 dilution. After two washes with PBS and one with tap water, the slides were incubated 30 minutes at 37° C. with FITC-labeled secondary antibodies to the species used (Dako). Slides were processed as described above.

Antibodies can be labeled directly with a fluorescent dye, which will result in a direct immuno fluorescence assay. FITC can be replaced with any fluorescent dye.

Animal Immunization

Ferret and guinea pig-specific antisera for the newly discovered virus were generated by experimental intranasal infection of two specific pathogen free ferrets and two guinea pigs, housed in separate pressurized glove boxes. Two to three weeks later the animals were bled by cardiac puncture, and their sera were used as reference sera.

The sera were tested for all previous described viruses with indirect IFA as described below. Other animal species are also suitable for the generation of specific antibody preparations and other antigen preparations may be used.

Virus Neutralization Assay (VN Assay)

VN assays were performed with serial two-fold dilutions of human and animal sera starting at an eight-fold dilution. Diluted sera were incubated for one hour with 100 TCID50 of virus before inoculation of tMK cells grown in 96-well plates, after which the plates were centrifuged at 840×g. The same culture media as described above was used. The media was changed after three and six days, and after 8 days IFA was performed (see above). The VN titer was defined as the lowest dilution of the serum sample resulting in negative IFA and inhibition of CPE in cell cultures.

RNA Isolation

RNA was isolated from the supernatant of infected cell cultures or sucrose gradient fractions using a High Pure RNA Isolation kit according to instructions from the manufacturer (Roche Diagnostics, Almere, The Netherlands). RNA can also be isolated following other procedures known in the field (*Current Protocols in Molecular Biology*).

RT-PCR

A one-step RT-PCR was performed in 50 µl reactions containing 50 mM Tris.HCl pH 8.5, 50 mM NaCl, 4 mM $MgCl_2$, 2 mM dithiotreitol, 200 µM each dNTP, 10 units recombinant RNAsin (Promega, Leiden, The Netherlands), 10 units AMV RT (Promega, Leiden, The Netherlands), 5 units AMPLITAQ® Gold DNA polymerase (PE Biosystems, Nieuwerkerk aan de Ijssel, The Netherlands) and 5 µl RNA. Cycling conditions were 45 min. at 42° C. and 7 min. at 95° C. once, 1 min at 95° C., 2 min. at 42° C. and 3 min. at 72° C. repeated 40 times and 10 min. at 72° C. once.

Primers used for diagnostic PCR:
- In the nucleoprotein: N3 (5'-GCACTCAAGAGA-TACCCTAG-3') (SEQ ID NO:124) and N4 (5'-AGACTTTCTGCTTTGCTGCCTG-3') (SEQ ID NO:125), amplifying a 151 nucleotide fragment.
- In the matrix protein: M3 (5'-CCCTGACAATAAC-CACTCTG-3') (SEQ ID NO:126) and M4 (5'-GC-CAACTGATTTGGCTGAGCTC-3') (SEQ ID NO:127) amplifying a 252 nucleotide fragment.
- In the polymerase protein: L6 (5'-CATGCCCAC-TATAAAAGGTCAG-3') (SEQ ID NO:128) and L7 (5'-CACCCCAGTCTTTCTTGAAA-3') (SEQ ID NO:129) amplifying a 173 nucleotide fragment.

Other primers can be designed based on MPV sequences, and different buffers and assay conditions may be used for specific purposes.

Sequence Analysis

Sequence analyses were performed using a DYENAMIC™ ET terminator sequencing kit (Amersham Pharmacia Biotech, Roosendaal, The Netherlands) and an ABI 373 automatic DNA sequencer (PE Biosystem). All techniques were performed according to the instructions of the manufacturer. PCR fragments were sequenced directly with the same oligonucleotides used for PCR, or the fragments were purified from the gel with QIAQUICK® Gel Extraction kit (Qiagen, Leusden, The Netherlands) and cloned in pCR2.1 vector (Invitrogen, Groningen, The Netherlands) according to instructions from the manufacturer and subsequently sequenced with M13-specific oligonucleotides.

Oligonucleotides Used for Analyzing the 3' End of the Genome (Absence of NS1/NS2).

Primer TR1 (5'-AAAGAATTCACGAGAAAAAAA-CGC-3') (SEQ ID NO:130) was designed based on published sequences of the trailer and leader for hRSV and APV, published by Randhawa (1997) and primer N1 (5'-CTGTGGTCTCTAGTCCCACTTC-3') (SEQ ID NO:131) was designed based on obtained sequences in the N protein. The RT-PCR assay and sequencing was performed as described above.

The RT-PCR gave a product of approximately 500 base pairs which is too small to contain information for two ORFS, and translation of these sequences did not reveal an ORF.

Detection of Antibodies in Humans, Mammals, Ruminants or Other Animals by ELISA

In Paramyxoviridae, the N protein is the most abundant protein, and the immune response to this protein occurs early in infection. For these reasons, a recombinant source of the N proteins is preferably used for developing an ELISA assay for detection of antibodies to MPV. Antigens suitable for antibody detection include any MPV protein that combines with any MPV-specific antibody of a patient exposed to or infected with MPV virus. Preferred antigens of the invention include those that predominantly engender the immune response in patients exposed to MPV, which therefore, typically are recognized most readily by antibodies of a patient. Particularly preferred antigens include the N, F and G proteins of MPV. Antigens used for immunological techniques can be native antigens or can be modified versions thereof. Well known techniques of molecular biology can be used to alter the amino acid sequence of a MPV antigen to produce modified versions of the antigen that may be used in immunologic techniques.

Methods for cloning genes, for manipulating the genes to and from expression vectors, and for expressing the protein encoded by the gene in a heterologous host are well-known, and these techniques can be used to provide the expression vectors, host cells, and the for expressing cloned genes encoding antigens in a host to produce recombinant antigens for use in diagnostic assays. See for instance: *Molecular cloning, A laboratory manual and Current Protocols in Molecular Biology*.

A variety of expression systems may be used to produce MPV antigens. For instance, a variety of expression vectors suitable to produce proteins in *E. coli, B. subtilis*, yeast, insect cells and mammalian cells have been described, any of which might be used to produce a MPV antigen suitable to detect anti-MPV antibodies in exposed patients.

The baculovirus expression system has the advantage of providing necessary processing of proteins, and is therefore preferred. The system utilizes the polyhedrin promoter to direct expression of MPV antigens. (Matsuura et al. 1987, *J. Gen. Virol.* 68:1233-1250).

Antigens produced by recombinant baculo-viruses can be used in a variety of immunological assays to detect anti-MPV antibodies in a patient. It is well established, that recombinant antigens can be used in place of natural virus in practically any immunological assay for detection of virus-specific antibodies. The assays include direct and indirect assays, sandwich assays, solid phase assays such as those using plates or beads among others, and liquid phase assays. Assays suitable include those that use primary and secondary antibodies, and those that use antibody binding reagents such as protein A. Moreover, a variety of detection methods can be used in the invention, including calorimetric, fluorescent, phosphorescent, chemiluminescent, luminescent and radioactive methods.

Example 1

Of Indirect Anti-MPV IgG EIA Using Recombinant N Protein

An indirect IgG EIA using a recombinant N protein (produced with recombinant baculo-virus in insect (Sf9) cells) as antigen can be performed. For antigen preparation, Sf9 cells are infected with the recombinant baculovirus and harvested 3-7 days post infection. The cell suspension is washed twice in PBS, pH 7.2, adjusted to a cell density of $5.0\times10^6$ cells/ml, and freeze-thawed three times. Large cellular debris is pelleted by low speed centrifugation (500×g for 15 min.) and the supernatant is collected and stored at −70° C. until use. Uninfected cells are processed similarly for negative control antigen.

100 µl of a freeze-thaw lysate is used to coat microtiter plates, at dilutions ranging from 1:50 to 1:1000. An uninfected cell lysate is run in duplicate wells and serves as a negative control. After incubation overnight, plates are washed twice with PBS/0.05% TWEEN®. Test sera are diluted 1:50 to 1:200 in ELISA buffer (PBS, supplemented to 2% with normal goat sera, and with 0.5% bovine serum albumin and 0.1% milk), followed by incubation wells for 1 hour at 37° C.

Plates are washed two times with PBS/0.05% TWEEN®. Horseradish peroxidase labeled goat anti-human (or against other species) IgG, diluted 1:3000 to 1:5000 in ELISA buffer, added to wells, and incubated for 1 hour at 37° C. The plates are then washed two times with PBS/0.05% TWEEN® and once with tap water, incubated for 15 minutes at room temperature with the enzyme substrate TMB, 3, 3', 5, 5' tetramethylbenzidine, such as that obtained from Sigma, and the reaction is stopped with 100 µl of 2 M phosphoric acid. Colorimetric readings are measured at 450 nm using an automated microtiter plate reader.

Example 2

Capture Anti-MPV IgM EIA Using a Recombinant Nucleoprotein

A capture IgM EIA using the recombinant nucleoprotein or any other recombinant protein as antigen can be performed by modification of assays as previously described by Erdman et al. (1990), *J. Clin. Microb.* 29:1466-1471.

Affinity purified anti-human IgM capture antibody (or against other species), such as that obtained from Dako, is added to wells of a microtiter plate in a concentration of 250 ng per well in 0.1 M carbonate buffer pH 9.6. After overnight incubation at room temperature, the plates are washed two times with PBS/0.05% TWEEN®. 100 µl of test serum diluted 1:200 to 1:1000 in ELISA buffer is added to triplicate wells and incubated for 1 hour at 37° C. The plates are then washed two times with in PBS/0.05% TWEEN®.

The freeze-thawed (infected with recombinant virus) Sf21 cell lysate is diluted 1:100 to 1:500 in ELISA buffer is added to the wells and incubated for 2 hours at 37° C. Uninfected cell lysate serves as a negative control and is run in duplicate wells.

The plates are then washed three times in PBS/0.05% TWEEN® and incubated for 1 hour at 37° C. with 100 µl of a polyclonal antibody against MPV in an optimal dilution in ELISA buffer. After two washes with PBS/0.05% TWEEN®, the plates are incubated with horseradish peroxide labeled secondary antibody (such as rabbit anti ferret), and the plates are incubated 20 minutes at 37° C.

The plates are then washed five times in PBS/0/05% TWEEN®, incubated for 15 minutes at room temperature with the enzyme substrate TMB 3, 3', 5, 5' tetramethylbenzidine, as, for instance obtained from Sigma, and the reaction is stopped with 100 µl of 2 M phosphoric acid. Colorimetric readings are measured at 450 nm using automated microtiter plate reader.

The sensitivities of the capture IgM EIAs using the recombinant nucleoprotein (or other recombinant protein) and whole MPV virus are compared using acute- and convalescent-phase serum pairs form persons with clinical MPV virus infection. The specificity of the recombinant nucleoprotein capture EIA is determined by testing serum specimens from healthy persons and persons with other paramyxovirus infections.

Potential for ELAs for Using Recombinant MPV Fusion and Glycoprotein Proteins Produced by the Baculovirus Expression.

The glycoproteins G and F are the two transmembraneous envelope glycoproteins of the MPV virion and represent the major neutralization and protective antigens. The expression of these glycoproteins in a vector virus system such as a baculovirus system provides a source of recombinant antigens for use in assays for detection of MPV-specific antibodies. Moreover, their use in combination with the nucleoprotein, for instance, further enhances the sensitivity of enzyme immunoassays in the detection of antibodies against MPV.

A variety of other immunological assays (*Current Protocols in Immunology*) may be used as alternative methods to those described here.

In order to find virus isolates nasopharyngeal aspirates, throat and nasal swabs, bronchoalveolar lavages and throat swabs preferable from but not limited to humans, carnivores (dogs, cats, seals, etc.), horses, ruminants (cattle, sheep, goats, etc.), pigs, rabbits, birds (poultry, ostriches, etc.) can be examined. From birds, cloaca and intestinal swabs and droppings can be examined as well. For all samples, serology (antibody and antigen detection, etc.), virus isolation and nucleic acid detection techniques can be performed for the detection of virus. Monoclonal antibodies can be generated by immunizing mice (or other animals) with purified MPV or parts thereof (proteins, peptides) and subsequently using established hybridoma technology (*Current Protocols in Immunology*). Alternatively, phage display technology can be used for this purpose (*Current Protocols in Immunology*). Similarly, polyclonal antibodies can be obtained from infected humans or animals, or from immunized humans or animals (*Current Protocols in Immunology*).

The detection of the presence or absence of NS1 and NS2 proteins can be performed using Western blotting, IFA, immuno precipitation techniques using a variety of antibody preparations. The detection of the presence or absence of NS1 and NS2 genes or homologues thereof in virus isolates can be performed using PCR with primer sets designed on the basis of known NS1 and/or NS2 genes as well as with a variety of nucleic acid hybridization techniques.

To determine whether NS1 and NS2 genes are present at the 3' end of the viral genome, a PCR can be performed with primers specific for this 3' end of the genome. In our case, we used a primer specific for the 3' untranslated region of the viral genome and a primer in the N ORF. Other primers may be designed for the same purpose. The absence of the NS1/NS2 genes is revealed by the length and/or nucleotide sequence of the PCR product. Primers specific for NS1 and/or NS2 genes may be used in combination with primers specific for other parts of the 3' end of the viral genome (such as the untranslated region or N, M or F ORFs) to allow a positive identification of the presence of NS1 or NS2 genes. In addition to PCR, a variety of techniques such as molecular cloning, nucleic acid hybridization may be used for the same purpose.

Example 3

Different Serotypes/Subgroups of MPV

Two potential genetic clusters are identified by analyses of partial nucleotide sequences in the N, M, F and L ORFs of 9 virus isolates. 90-100% nucleotide identity was observed within a cluster, and 81-88% identity was observed between the clusters. Sequence information obtained on more virus isolates confirmed the existence of two genotypes. Virus isolate ned/00/01 as prototype of cluster A, and virus isolate ned/99/01 as prototype of cluster B have been used in cross-neutralization assays to test whether the genotypes are related to different serotypes or subgroups.

Results

Using RT-PCR assays with primers located in the polymerase gene, we identified 30 additional virus isolates from nasopharyngeal aspirate samples. Sequence information of parts of the matrix and polymerase genes of these new isolates together with those of the previous 9 isolates were used to construct phylogenetic trees (FIG. 16). Analyses of these trees confirmed the presence of two genetic clusters, with virus isolate ned/00/00-1 as the prototype virus in group A and virus isolate ned/99/01 as the prototype virus in group B. The nucleotide sequence identity within a group was more than 92%, while between the clusters the identity was 81-85%.

Virus isolates ned/00/01 and ned/99/01 have been used to inoculate ferrets to raise virus-specific antisera. These antisera were used in virus neutralization assays with both viruses.

TABLE 3

| | Virus neutralization titers | |
|---|---|---|
| | isolate 00-1 | isolate 99-1 |
| preserum ferret A (00-1) | .2 | .2 |
| ferret A 22 dpi (00-1) | 64 | .2 |
| preserum ferret B (99-1) | .2 | .2 |
| ferret B 22 dpi (99-1) | 4 | 64 |

For isolate 00-1 the titer differs 32-fold (64/2)
For isolate 99-1 the titer differs 16-fold (64/4)

In addition, 6 guinea pigs have been inoculated with either one of the viruses (ned/00/01 and ned/99/01). RT-PCR assays on nasopharyngeal aspirate samples showed virus replication from day 2 till day 10 post infection. At day 70 post infection the guinea pigs have been challenged with either the homologous or the heterologous virus, and for in all four cases virus replication has been noticed.

TABLE 4

| | primary infection | virus replication | secondary infection | virus replication |
|---|---|---|---|---|
| guinea pig 1-3 | 00-1 | 2 out of 3 | 99-1 | 1 out of 2 |
| guinea pig 4-6 | 00-1 | 3 out of 3 | 00-1 | 1 out of 3 |
| guinea pig 7-9 | 99-1 | 3 out of 3 | 00-1 | 2 out of 2 |
| guinea pig 10-12 | 99-1 | 3 out of 3 | 99-1 | 1 out of 3 | note:
for the secondary infection guinea pig 2 and 9 were not there anymore.

Virus neutralization assays with antisera after the first challenge showed essentially the same results as in the VN assays performed with the ferrets (>16-fold difference in VN titer).

The results presented in this example confirm the existence of two genotypes, which correspond to two serotypes of MPV, and show the possibility of repeated infection with heterologous and homologous virus.

Example 4

Further Sequence Determination

This example describes the further analysis of the sequences of MPV open reading frames (ORFs) and intergenic sequences as well as partial sequences of the genomic termini.

Sequence analyses of the nucleoprotein (N), phosphoprotein (P), matrix protein (M) and fusion protein (F) genes of MPV revealed the highest degree of sequence homology with APV serotype C, the avian *Pneumovirus* found primarily in birds in the United States. These analyses also revealed the absence of non-structural proteins NS1 and NS2 at the 3' end of the viral genome and positioning of the fusion protein immediately adjacent to the matrix protein. Here we present the sequences of the 22K (M2) protein, the small hydrophobic (SH) protein, the attachment (G) protein and the polymerase (L) protein genes, the intergenic regions and the trailer sequence. In combination with the sequences described previously the sequences presented here complete the genomic sequence of MPV with the exception of the extreme 12-15 nucleotides of the genomic termini and establish the genomic organization of MPV. Side by side comparisons of the sequences of the MPV genome with those of APV subtype A, B and C, RSV subtype A and B, PVM and other paramyxoviruses provides strong evidence for the classification of MPV in the *Metapneumovirus* genus.

Results

Sequence Strategy

MTV isolate 00-1 (van den Hoogen et al., 2001) was propagated in tertiary monkey kidney (tMK) cells and RNA isolated from the supernatant 3 weeks after inoculation was used as template for RT-PCR analyses. Primers were designed on the basis of the partial sequence information available for MPV 00-1 (van den Hoogen et al., 2001) as well as the leader and trailer sequences of APV and RSV (Randhawa et al., 1997; Mink et al., 1991). Initially, fragments between the previously obtained products, ranging in size from 500 bp to 4 Kb in length, were generated by RT-PCR amplification and sequenced directly. The genomic sequence was subsequently confirmed by generating a series of overlapping RT-PCR fragments ranging in size from 500 to 800 bp that represented the entire MPV genome. For all PCR fragments, both strands were sequenced directly to minimize amplification and sequencing errors. The nucleotide and amino acid sequences were used to search for homologies with sequences in the Genbank database using the BLAST® software (on the Internet at ncbi.nlm.nih.gov/BLAST). Protein names were assigned to open reading frames (ORFs) based on homology with known viral genes as well as their location in the genome. Based on this information, a genomic map for MPV was constructed (FIG. 7). The MPV genome is 13378 nucleotides in length and its organization is similar to the genomic organization of APV. Below, we present a comparison between the ORFs and non-coding sequences of MPV and those of other paramyxoviruses and discuss the important similarities and differences.

The Nucleoprotein (N) Gene

As shown, the first gene in the genomic map of MPV codes for a 394 amino acid (aa) protein and shows extensive homology with the N protein of other Pneumoviruses. The length of the N ORF is identical to the length of the N ORF of APV-C (Table 5) and is smaller than those of other paramyxoviruses (Barr et al., 1991). Analysis of the amino acid sequence revealed the highest homology with APV-C (88%), and only 7-11% with other paramyxoviruses (Table 6).

Barr et al. (1991) identified three regions of similarity between viruses belonging to the order Mononegavirales: A, B and C (FIG. 8). Although similarities are highest within a virus family, these regions are highly conserved between virus families. In all three regions MPV revealed 97% aa sequence identity with APV-C, 89% with APV-B, 92% with APV-A, and 66-73% with RSV and PVM. The region between aa residues 160 and 340 appears to be highly conserved among Metapneumoviruses and to a somewhat lesser extent the Pneumovirinae (Miyahara et al., 1992; Li et al., 1996; Barr et al., 1991). This is in agreement with MPV being a *Metapneumovirus*, showing 100% similarity with APV C.

Th Phosphoprotein (P) Gene

The second ORF in the genome map codes for a 294 aa protein which shares 68% aa sequence homology with the P protein of APV-C, and only 22-26% with the P protein of RSV (Table 6). The P gene of MPV contains one substantial ORF and in that respect is similar to P from many other paramyxoviruses (reviewed in Lamb and Kolakofsky, 1996; Sedlieier et al., 1998).

In contrast to APV A and B and PVM and similar to RSV and APV-C the MPV P ORF lacks cysteine residues. Ling (1995) suggested that a region of high similarity between all Pneumoviruses (aa 185-241) plays a role in either the RNA synthesis process or in maintaining the structural integrity of the nucleocapsid complex. This region of high similarity is also found in MPV (FIG. 9) especially when conservative substitutions are taken in account, showing 100% similarity with APV-C, 93% with APV-A and B, and approximately 81% with RSV. The C-terminus of the MPV P protein is rich in glutamate residues as has been described for APVs (Ling et al., 1995).

The Matrix (M) Protein Gene

The third ORF of the MPV genome encodes a 254 aa protein, which resembles the M ORFs of other Pneumoviruses. The M ORF of MPV has exactly the same size as the M ORFs of other Metapneumoviruses (Table 5) and shows high aa sequence homology with the matrix proteins of APV (78-87%), lower homology with those of RSV and PVM (37-38%) and 10% or less homology with those of other paramyxoviruses (Table 6).

Easton (1997) compared the sequences of matrix proteins of all Pneumoviruses and found a conserved heptapeptide at residue 14 to 19 that is also conserved in MPV (FIG. 10). For RSV, PVM and APV small secondary ORFs within or overlapping with the major ORF of M have been identified (52 aa and 51 aa in bRSV, 76 aa in RSV, 46 aa in PVM and 51 aa in APV) (Yu et al., 1992; Easton et al., 1997; Samal et al., 1991; Satake et al., 1984). We noticed two small ORFs in the M ORF of MPV. One small ORF of 54 aa residues was found within the major M ORF (fragment 1, FIG. 7), starting at nucleotide 2281 and one small ORF of 33 aa residues was found overlapping with the major ORF of M starting at nucleotide 2893 (fragment 2, FIG. 7) Similar to the secondary ORFs of RSV and APV there is no significant homology between these secondary ORFs and secondary ORFs of the other Pneumoviruses, and apparent start or stop signals are lacking. In addition, evidence for the synthesis of proteins corresponding to these secondary ORFs of APV and RSV has not been reported.

The Fusion Protein (F) Gene

The F ORF of MPV is located adjacent to the M ORF, which is characteristic for members of the *Metapneumovirus* genus. The F gene of MPV encodes a 639 aa protein, which is two aa residues longer than F of APV-C (Table 5). Analysis of the aa sequence revealed 81% homology with APV-C, 67% with APV-A and B, 33-39% with *Pneumovirus* F proteins and only 10-18% with other paramyxoviruses (Table 6). One of the conserved features among F proteins of paramyxoviruses, and also seen in MPV is the distribution of cysteine residues (Morrison, 1988; Yu et al., 1991). The Metapneumoviruses share 12 cysteine residues in F1 (7 are conserved among all paramyxoviruses), and two in F2 (1 is conserved among all paramyxoviruses). Of the 3 potential N-linked glycosylation sites present in the F ORF of MPV, none are shared with RSV and two (position 74 and 389) are shared with APV. The third, unique, potential N-linked glycosylation site for MPV is located at position 206 (FIG. 11).

Despite the low sequence homology with other paramyxoviruses, the F protein of MPV revealed typical fusion protein characteristics consistent with those described for the F proteins of other Paramyxoviridae family members (Morrison, 1988). F proteins of Paramyxoviridae members are synthesized as inactive precursors (F0) that are cleaved by host cell proteases which generate amino terminal F2 subunits and large carboxy terminal F1 subunits. The proposed cleavage site (Collins et al., 1996) is conserved among all members of the Paramyxoviridae family. The cleavage site of MPV contains the residues RQSR. Both arginine (E) residues are shared with APV and RSV, but the glutamine (Q) and serine (S) residues are shared with other paramyxoviruses such as human parainfluenza virus type 1, Sendai virus and morbilliviruses (data not shown).

The hydrophobic region at the amino terminus of F1 is thought to function as the membrane fusion domain and shows high sequence similarity among paramyxoviruses and morbilliviruses and to a lesser extent the Pneumoviruses (Morrison, 1988). These 26 residues (position 137-163, FIG. 11) are conserved between MPV and APV-C, which is in agreement with this region being highly conserved among the Metapneumoviruses (Naylor et al., 1998; Seal et al., 2000). As is seen for the F2 subunits of APV and other paramyxoviruses, MPV revealed a deletion of 22 aa residues compared with RSV (position 107-128, FIG. 11). Furthermore, for RSV and APV, the signal peptide and anchor domain were found to be conserved within subtypes and displayed high variability between subtypes (Plows et al., 1995; Naylor et al., 1998). The signal peptide of MPV (aa 10-35, FIG. 11) at the amino terminus of F2 exhibits some sequence similarity with APV-C (18 out of 26 aa residues are similar) and less conservation with other APVs or RSV. Much more variability is seen in the membrane anchor domain at the carboxy terminus of F1, although some homology is still seen with APV-C.

The 22K (M2) Protein

The M2 gene is unique to the Pneumovirinae and two overlapping ORFs have been observed in all Pneumoviruses. The first major ORF represents the M2-1 protein which enhances the processivity of the viral polymerase (Collins et al., 1995; Collins, 1996) and its readthrough of intergenic regions (Hardy et al., 1998; Fearns et al., 1999). The M2-1 gene for MPV, located adjacent to the F gene, encodes a 187 aa protein (Table 5), and reveals the highest (84%) homology with M2-1 of APV-C (Table 6). Comparison of all *Pneumovirus* M2-1 proteins revealed the highest conservation in the amino-terminal half of the protein (Collins et al., 1990; Zamora et al., 1992; Ahmadian et al., 1999), which is in agreement with the observation that MPV displays 100% similarity with APV-C in the first 80 aa residues of the protein (FIG. 12A). The MPV M2-1 protein contains 3 cysteine residues located within the first 30 aa residues that are conserved among all Pneumoviruses. Such a concentration of cysteines is frequently found in zinc-binding proteins (Ahmadian et al., 1991; Cuesta et al., 2000).

The secondary ORFs (M2-2) that overlap with the M2-1 ORFs of Pneumoviruses are conserved in location but not in sequence and are thought to be involved in the control of the switch between virus RNA replication and transcription (Collins et al., 1985; Elango et al., 1985; Baybutt et al., 1987; Collins et al., 1990; Ling et al., 1992; Zamora et al., 1992; Alansari et al., 1994; Ahmadian et al., 1999; Bermingham et al., 1999). For MPV, the M2-2 ORF starts at nucleotide 512 in the M2-1 ORF (FIG. 7), which is exactly the same start position as for APV-C. The length of the M2-2 ORFs are the same for APV-C and MPV, 71 aa residues (Table 5). Sequence comparison of the M2-2 ORF (FIG. 12B) revealed 64% aa sequence homology between MPV and APV-C and only 44-48% aa sequence homology between MPV and APV-A and B (Table 6).

The Small Hydrophobic Protein (SH) ORF

The gene located adjacent to M2 of hMPV probably encodes a 183 aa SH protein (FIGS. 1 and 7). There is no discernible sequence identity between this ORF and other RNA virus genes or gene products. This is not surprising since sequence similarity between *Pneumovirus* SH proteins is generally low. The putative SH ORF of hMPV is the longest SH ORF known to date (Table 1). The aa composition of the SH ORF is relatively similar to that of APV, RSV and PVM, with a high percentage of threonine and serine residues (22%, 18%, 19%, 20.0%, 21% and 28% for hMPV, APV, RSVA, RSV B, bRSV and PVM respectively). The SH ORF of hMPV contains 10 cysteine residues, whereas APV SH contains 16 cysteine residues. The 511 ORF of hMPV contains two potential N-linked glycosylation sites (aa 76 and 121), whereas APV has one, RSV has two or three and PVM has four.

The hydrophilicity profiles for the putative hMPV SH protein and SH of APV and RSV revealed similar characteristics (FIG. 7B). The SH ORFs of APV and hMPV have a hydrophilic N-terminus, a central hydrophobic domain which can serve as a potential membrane spanning domain (aa 30-53 for hMPV), a second hydrophobic domain (aa 155-170) and a hydrophilic C-terminus. In contrast, RSV SH appears to lack the C-terminal part of the APV and hMPV ORFs. In all *Pneumovirus* SH proteins the hydrophobic domain is flanked by basic aa residues, which are also found in the SH ORF for hMPV (aa 29 and 54).

The Attachment Glycoprotein (G) ORF

The putative G ORF of hMPV is located adjacent to the putative SH gene and encodes a 236 aa protein (nt 6262-6972, FIG. 1). A secondary small ORF is found immediately following this ORF, potentially coding for 68 aa residues (nt 6973-7179) but lacking a start codon. A third potential ORF in the second reading frame of 194 aa residues is overlapping with both of these ORFs but also lacks a start codon (nt 6416-7000). This ORF is followed by a potential fourth ORF of 65 aa residues in the same reading frame (nt 7001-7198), again lacking a start codon. Finally, a potential ORF of 97 aa residues (but lacking a start codon) is found in the third reading frame (nt 6444-6737, FIG. 1). Unlike the first ORF, the other ORFs do not have apparent gene start or gene end sequences (see below). Although the 236 aa G ORF probably represents at least a part of the hMPV attachment protein it cannot be excluded that the additional coding sequences ale expressed as separate proteins or as part of the attachment protein through some RNA editing event. It should be noted that for APV and RSV no secondary ORFs after the primary G ORF have been identified but that both APV and RSV have secondary ORFs within the major ORF of G. However, evidence for expression of these ORFs is lacking and there is no sequence identity between the predicted aa sequences for different viruses (Ling et al., 1992). The secondary ORFs in hMPV G do not reveal characteristics of other G proteins and whether the additional ORFs are expressed requires further investigation.

BLAST® analyses with all ORFs revealed no discernible sequence identity at the nucleotide or aa sequence level with other known virus genes or gene products. This is in agreement with the low percentage sequence identity found for other G proteins such as those of hRSV A and B (53%) (Johnson et al., 1987) and APV A and B (38%) (Juhasz and Easton, 1994).

Whereas most of the hMPV ORFs resemble those of APV both in length and sequence, the putative G ORF of 236 aa residues of iMPV is considerably smaller than the G ORF of APV (Table 1). The aa sequence revealed a serine and threonine content of 34%, which is even higher than the 32% for BSV and 24% for APV. The putative G ORF also contains 8.5% proline residues, which is higher than the 8% for RSV and 7% for APV. The unusual abundance of proline residues in the G proteins of APV, RSV and iMPV has also been observed in glycoproteins of mucinous origin where it is a major determinant of the proteins three dimensional structure (Collins and Wertz, 1983; Wertz et al., 1985; Jentoft, 1990). The G ORF of hMPV contains five potential N-linked glycosylation sites, whereas hRSV has seven, bRSV has five and APV has three to five.

The predicted hydrophilicity profile of hMPV G revealed characteristics similar to the other Pneumoviruses. The N-terminus contains a hydrophilic region followed by a short hydrophobic area (aa 33-53 for hMPV) and a mainly hydrophilic C-terminus (FIG. 8B). This overall organization is consistent with that of an anchored type II transmembrane protein and corresponds well with these regions in the G protein of APV and RSV. The putative G ORF of hMPV contains only 1 cysteine residue in contrast to RSV and APV (5 and 20 respectively). Of note, only two of the four secondary ORFs in the G gene contained one additional cysteine residue and these four potential ORFs revealed 12-20% serine and threonine residues and 6-11% proline residues.

The Polymerase Gene (L)

In analogy to other negative strand viruses, the last ORF of the MPV genome is the RNA-dependent RNA polymerase component of the replication and transcription complexes. The L gene of MPV encodes a 2005 aa protein, which is 1 residue longer than the APV-A protein (Table 5). The L protein of MPV shares 64% homology with APV-A, 42-44% with RSV, and approximately 13% with other paramyxoviruses (Table 6). Poch et al. (1989; 1990) identified six conserved domains within the L proteins of non-segmented negative strand RNA viruses, from which domain III contained the four core polymerase motifs that are thought to be essential for polymerase function. These motifs (A, B, C and D) are well conserved in the MPV L protein: in motifs A, B and C: MPV shares 100% similarity with all Pneumoviruses and in motif D MPV shares 100% similarity with APV and 92% with RSVs. For the entire domain I (aa 627-903 in the L ORF), MPV shares 77% identity with APV, 61-62% with RSV and 23-27% with other paramyxoviruses (FIG. 15). In addition to the polymerase motifs the *Pneumovirus* L proteins contain a sequence which conforms to a consensus ATP binding motif $K(X)_{21}GEGAGNM20K$ (SEQ ID NO:173) (Stec, 1991). The MWV L ORF contains a similar motif as APV, in which the spacing of the intermediate residues is off by one: $K(x)_{22}GEGAGN(X)_{19}K$ (SEQ ID NO:106).

Phylogenetic Analyses

As an indicator for the relationship between MPV and members of the Pneumovirinae, phylogenetic trees based on the N, P, M and F ORFs have been constructed previously (van den Hoogen et al., 2001) and revealed a close relationship between MPV and APV-C. Because of the low homology of the MPV SH and G genes with those of other paramyxoviruses, reliable phylogenetic trees for these genes cannot be constructed. In addition, the distinct genomic organization between members of the *Pneumovirus* and *Metapneumovirus* genera make it impossible to generate phylogenetic trees based on the entire genomic sequence. We therefore only constructed phylogenetic trees for the M2 and L genes in addition to those previously published. Both these trees confirmed the close relation between APV and MPV within the Pneumovirinae subfamily (FIG. 16).

MPV Non-Coding Sequences

The gene junctions of the genomes of paramyxoviruses contain short and highly conserved nucleotide sequences at the beginning and end of each gene (gene start and gene end signals), possibly playing a role in initiation and termination of transcription (Curran et al., 1999). Comparing the intergenic sequences between all genes of MPV revealed a consensus sequence for the gene start signal of the N, P, M, F, M2 and G: GGGACAAGU (SEQ ID NO:166) (FIG. 17A), which is identical to the consensus gene start signal of the Metapneumoviruses (Ling et al., 1992; Yu et al., 1992; Li et al., 1996; Bäyon-Auboyer et al., 2000). The gene start signals for the SH and L genes of MPV were found to be slightly different from this consensus (SH: GGGAUAAAU, (SEQ ID NO:167) L: GAGACAAAU). (SEQ ID NO:168) For APV the gene start signal of L was also found to be different from the consensus: AGGACCAAT (SEQ ID NO:169) (APV-A) (Randhawa et al., 1996) and GGGACCAGT (SEQ ID NO:170) (APV-D) (Bäyon-Auboyer et al., 2000).

In contrast to the similar gene start sequences of MPV and APV, the consensus gene end sequence of APV, UAGUUAAUU (SEQ ID NO:171) (Randhawa et al., 1996), could not be found in the MPV intergenic sequences. The repeated sequence found in most genes, except the G-L intergenic region, was U AAAAA U/A/C (SEQ ID NO:172), which could possibly act as gene end signal. However, since we sequenced viral RNA rather than mRNA, definitive gene end signals could not be assigned and thus requires further investigation. The intergenic regions of Pneumoviruses vary in size and sequence (Curran et al., 1999; Blumberg et al., 1991; Collins et al., 1983). The intergenic regions of MPV did not reveal homology with those of APV and RSV and range in size from 10 to 228 nucleotides (FIG. 17B). The intergenic region between the M and F ORFs of MPV contains part of a secondary ORF, which starts in the primary M ORF (see above).

The intergenic region between SH and G contains 192 nucleotides, and does not appear to have coding potential based on the presence of numerous stop-codons in all three reading frames. The intergenic region between G and L contains 241 nucleotides, which may include additional ORFs (see above). Interestingly, the start of the L ORF is located in these secondary ORFs. Whereas the L gene of APV does not start in the preceding G ORF, the L ORF of RSV also starts in the preceding M2 gene. At the 3' and 5' extremities of the genome of paramyxoviruses short extragenic region are referred to as the leader and trailer sequences, and approximately the first 12 nucleotides of the leader and last 12 nucleotides of the trailer are complementary, probably because they each contain basic elements of the viral promoter (Curran et al., 1999; Blumberg et al., 1991; Mink et al., 1986). The 3' leader of MPV and APV are both 41 nucleotides in length, and some homology is seen in the region between nucleotide 16 and 41 of both viruses (18 out of 26 nucleotides) (FIG. 17B). As mentioned before the first 15 nucleotides of the MPV genomic map are based on a primer sequence based on the APV genome. The length of the 5' trailer of MPV (188 nucleotides) resembles the size of the RSV 5' trailer (155 nucleotides), which is considerably longer than that of APV (40 nucleotides). Alignments of the extreme 40 nucleotides of the trailer of MPV and the trailer of APV revealed 21 out of 32 nucleotides homology, apart from the extreme 12 nucleotides which represent primer sequences based on the genomic sequence of APV. Our sequence analyses revealed the absence of NS1 and NS2 genes at the 3' end of the genome and a genomic organization resembling the organization of Metapneumoviruses (3'-N-P-M-F-M2-SH-G-L-5'). The high sequence homology found between MPV and APV genes further emphasizes the close relationship between these two viruses. For the N, P, M, F, M2-1 and M2-2 genes of MPV an overall amino acid homology of 79% is found with APV-C. In fact, for these genes APV-C and MPV revealed sequence homologies which are in the same range as sequence homologies found between subgroups of other genera, such as RSV-A and B or APV-A and B. This close relationship between APV-C and MPV is also seen in the phylogenetic analyses which revealed MPV and APV-C always in the same branch, separate from the branch containing APV-A and B. The identical genomic organization, the sequence homologies and phylogenetic analyses are all in favor of the classification of MPV as the first member in the *Metapneumovirus* genus that is isolatable from mammals. It should be noted that the found sequence variation between different virus isolates of MPV in the N, M, F and L genes revealed the possible existence of different genotypes (van den Hoogen et al., 2001). The close relationship between MPV and APV-C is not reflected in the host range, since APV infects birds in contrast to MPV (van den Hoogen et al., 2001). This difference in host range may be determined by the differences between the SH and G proteins of both viruses that are highly divergent. The SH and G proteins of MPV did not reveal significant aa sequence homology with SH and G proteins of any other virus. Although the amino acid content and hydrophobicity plots are in favor of defining these ORFs as SH and G, experimental data are required to assess their function. Such analyses will also shed light on the role of the additional overlapping ORFs in these SH and G genes. In addition, sequence analyses on the SH and G genes of APV-C might provide more insight in the function of the SH and G proteins of MPV and their relationship with those of APV-C. The noncoding regions of MPV were found to be fairly similar to those of APV. The 3' leader and 5' trailer sequences of APV and MPV displayed a high degree of homology. Although the lengths of the intergenic regions were not always the same for APV and MPV, the consensus gene start signals of most of the ORFs were found to be identical. In contrast, the gene end signals of APV were not found in the MPV genome. Although we did find a repetitive sequence (U AAAAA U/A/C) (SEQ ID NO:172) in most intergenic regions, sequence analysis of viral mRNAs is required to formally delineate those gene end sequences. It should be noted that sequence information for 15 nucleotides at the extreme 3' end and 12 nucleotides at the extreme 5' end is obtained by using modified rapid amplification of cDNA ends (RACE) procedures. This technique has been proven to be successful by others for related viruses (J. S. Randhawa, et al., Rescue of synthetic minireplicons establishes the absence of the NS1 and NS2 genes from avian *Pneumovirus, J. Virol.* 71, 9849-9854 (1997); M. A. Mink, et al., Nucleotide sequences of the 3' leader and 5' trailer regions of human respiratory syncytial virus genomic RNA, *Virology* 185, 615-24 (1991).) To determine the sequence of the 3' vRNA leader sequence, a homopolymer A tail is added to purified vRNA using poly-A-polymerase and the leader sequence subsequently amplified by PCR using a poly-T primer and a primer in the N gene. To determine the sequence of the 5' vRNA trailer sequence, a cDNA copy of the trailer sequence is made using reverse transcriptase and a primer in the L gene, followed by homopolymer dG tailing of the cDNA with terminal transferase. Subsequently, the trailer region is amplified using a poly-C primer and a primer in the L gene. As an alternative strategy, vRNA is ligated to itself or synthetic linkers, after which the leader and trailer regions are amplified using primers in the L and N genes and linker-specific primers. For the 5' trailer sequence direct dideoxynucleotide sequencing of purified vRNA is also feasible (Randhawa, 1997). Using these approaches, we can analyze the exact sequence of the ends of the hMPV genome. The sequence information provided here is of importance for the generation of diagnostic tests, vaccines and antivirals for MPV and MPV infections.

Materials and Methods

Sequence Analysis

Virus isolate 00-1 was propagated to high titers (approximately 10,000 TCID50/ml) on tertiary monkey kidney cells as described previously (van den Hoogen et al., 2001). Viral RNA was isolated from supernatants from infected cells using a High Pure RNA Isolating Kit according to instructions from the manufacturer (Roch Diagnostics, Almere, The Netherlands). Primers were designed based on sequences published previously (van den Hoogen et al., 2001) in addition to sequences published for the leader and trailer of APV/RSV (Randhawa et al., 1997; Mink et al., 1991) and are available upon request. RT-PCR assays were conducted with viral RNA, using a one-tube assay in a total volume of 50 µl with 50 mM Tris pH 8.5, 50 mM NaCl, 4.5 mM MgCl$_2$, 2 mM DTT, 1 µM forward primer, 1 µM reverse primer, 0.6 mM dNTPs, 20 units RNAsin (Promega, Leiden, The Netherlands), 10 U AMV reverse transcriptase (Promega, Leiden, The Netherlands), and 5 units Taq Polymerase (PE Applied Biosystems, Nieuwerkerk aan de IJssel, The Netherlands). Reverse transcription was conducted at 42° C. for 30 minutes, followed by 8 minutes inactivation at 95° C. The cDNA was amplified during 40 cycles of 95° C., 1 min.; 42° C., 2 min. 72° C., 3 min. with a final extension at 72° C. for 10 minutes. After examination on a 1% agarose gel, the RT-PCR products were purified from the gel using a QIAQUICK ® Gel Extraction kit (Qiagen, Leusden, The Netherlands) and sequenced directly using a DYENAMIC™ ET terminator sequencing kit (Amersham Pharmacia Biotech, Roosendaal, The Netherlands) and an ABI 373 automatic DNA sequencer (PE Applied Biosystem, Nieuwerkerk aan den IJssel, The Netherlands), according to the instructions of the manufacturer.

Sequence alignments were made using the clustal software package available in the software package of BioEdit version 5.0.6. (on the Internet at jwbrown.mbio.ncsu.edu/Bioedit//bioedit.html; Hall, 1999).

Phylogenetic Analysis

To construct phylogenetic trees, DNA sequences were aligned using the ClustalW software package and maximum likelihood trees were generated using the DNA-ML software package of the Phylip 3.5 program using 100 bootstraps and 3 jumbles. Bootstrap values were computed for consensus trees created with the consense package (Felsenstein, 1989).

The MPV genomic sequence is available from Genbank under accession number AF371337. All other sequences used here are available from Genbank under accession numbers AB046218 (measles virus, all ORFs), NC-001796 (human parainfluenza virus type 3, all ORFs), NC-001552 (Sendai virus, all ORFs), X57559 (human parainfluenza virus type 2, all ORFs), NC-002617 (New Castle Disease virus, all ORFs), NC-002728 (Nipah virus, all ORFs), NC-001989 (bRSV, all ORFs), M11486 RSV A, all ORFs except L), NC-001803 (HRSV, L ORM, NC-001781 (hRSV B, all ORFs), D10331 (PVM, N ORF), U09649 (PVM, P ORF), U66893 (PVM, M ORF), U66893 (PVM, SH ORF), D11130 (PVM, G ORF), D11128 (F ORF). The PVM M2 ORF was taken from Ahmadian (1999), AF176590 (APV-C, N ORF), U39295 (APV-A, N ORF), U39296 (APV-B, N ORF), AF262571 (APV-C, M ORM), U37586 (APV-B, M ORF), X58639 (APV-A, M ORF), AF176591 (APV-C, P ORF), AF325443 (APV-B, P ORF), U22110 (APV-A, P ORF), AF187152 (APV-C, F ORF), Y14292 (APV-B, F ORF), D00850 (APV-A, F ORF), AF176592 (APV-C, M2 ORF), AF35650 (APV-B, M2 ORF), X63408 (APV-A, M2 ORF), U65312 (APV-A, L ORF), S40185 (APV-A, SH ORF).

TABLE 5

Lengths of the ORFs of MPV and other paramyxoviruses

|         | N[1]    | P    | M    | F    | M2-1 | M2-2 | SH   | G    | L    |
|---------|---------|------|------|------|------|------|------|------|------|
| MPV     | 394     | 294  | 254  | 539  | 187  | 71   |      | 183  | 236  | 2005 |
| APV A   | 391     | 278  | 254  | 538  | 186  | 73   |      | 174  | 391  | 2004 |
| APV B   | 391     | 279  | 254  | 538  | 186  | 73   | —[2] | 414  | —[2] |
| APV C   | 394     | 294  | 254  | 537  | 184  | 71   | —[2] | —[2] | —[2] |
| APV D   | —[2]    | —[2] | —[2] | —[2] | —[2] | —[2] | —[2] | 389  | —[2] |
| hRSV A  | 391     | 241  | 256  | 574  | 194  | 90   | 64   | 298  | 2165 |
| hRSV B  | 391     | 241  | 249  | 574  | 195  | 93   | 65   | 299  | 2166 |
| bRSV    | 391     | 241  | 256  | 569  | 186  | 93   | 81   | 257  | 2162 |
| PVM     | 393     | 295  | 257  | 537  | 176  | 77   | 92   | 396  | —[2] |
| others[3] | 418-542 | 225-709 | 335-393 | 539-565 | —[4] | —[4] | —[4] | —[4] | 2183-2262 |

Footnotes:
[1]length in amino acid residues.
[2]sequences not available
[3]others: human parainfluenza virus type 2 and 3, Sendai virus, measles virus, nipah virus, phocine distemper virus, and New Castle Disease virus.
[4]ORF not present in viral genome

TABLE 6

Amino acid sequence identity between the ORFs of MPV and those of other paramyxoviruses[1]

|       | N  | P  | M  | F  | M2-1 | M2-2 | L   |
|-------|----|----|----|----|------|------|-----|
| APV A | 69 | 55 | 78 | 67 | 72   | 26   | 64  |
| APV B | 69 | 51 | 76 | 67 | 71   | 27   | —[2] |

TABLE 6-continued

Amino acid sequence identity between the ORFs of MPV and those of other paramyxoviruses[1]

|         | N    | P   | M    | F     | M2-1 | M2-2 | L     |
|---------|------|-----|------|-------|------|------|-------|
| APV C   | 88   | 68  | 87   | 81    | 84   | 56   | —[2]  |
| hRSV A  | 42   | 24  | 38   | 34    | 36   | 18   | 42    |
| hRSV B  | 41   | 23  | 37   | 33    | 35   | 19   | 44    |
| bRSV    | 42   | 22  | 38   | 34    | 35   | 13   | 44    |
| PVM     | 45   | 26  | 37   | 39    | 33   | 12   |       |
| others[3] | 7-11 | 4-9 | 7-10 | 10-18 | —[4] | —[4] | 13-14 |

Footnotes:
[1]No sequence homologies were found with known G and SH proteins and were thus excluded
[2]Sequences not available.
[3]See list in table 5, footnote 3.
[4]ORF absent in viral genome.

REFERENCES

Current Protocols in Molecular Biology, volume 1-3 (1994-1998). Ed. by F. M. Ausubel, R. Brent, R. E. Kinston, D. D. Moore, J. G. Seidman, J. A. Smith, and K. Struh. Published by John Wiley and Sons, Inc., USA.

Current Protocols in Immunology, volume 1-3. Ed. by J. E. Coligan, A. M. Kruisbeek, D. H. Margulies, E. M. Shevach, and W. Strobe. Published by John Wiley and Sons, Inc., USA Sambrook et al. Molecular cloning, a laboratory manual, second ed., vol. 1-3. (Cold Spring Harbor Laboratory, 1989).

Fields, Virology, 1996. Vol. 1-2 3rd. Edition, Ed. by B. N. Fields, D. M. Knipe, and P. M. Howley, Lippincott-Raven, Philadelphia, USA.

1. Pringle C. R. Virus taxonomy at the Xith international congress of virology, Sydney, Australia 1999, Arch. Virol. 144/2:2065-2070 (1999).
2. Domachowske J. B. and H. R. Rosenberg. Respiratory syncytial virus infection: immune response, immunopathogenesis, and treatment. Clin. Microbio. Rev. 12(2): 298-309 (1999). Review.
3. Giraud P., G. Bennejean, M. Guittet, and D. Toquin. Turkey rhinotracheitis in France: preliminary investigations on a ciliostatic virus. Vet. Rec. 119:606-607 (1986).
4. Ling R., A. J. Easton, and C. R. Pringle. Sequence analysis of the 22E, SH and G genes of turkey rhinotracheitis virus and their intergenic regions reveals a gene order different from that of other Pneumoviruses. J. Gen. Virol. 73:1709-1715 (1992).
5. Yu Q., P. J. Davis, J. Li, and D. Cavanagh. Cloning and sequencing of the matrix protein (M) gene of turkey rhinotracheitis virus reveal a gene order different from that of respiratory syncytial virus. Virology 186:426-434 (1992).
6. Randhawa J. S., A. C. Marriott, C. R. Pringle, and A. J. Easton. Rescue of synthetic minireplicons establishes the absence of the NS1 and NS2 genes from avian Pneumovirus. J. Virol. 71:9849-9854 (1997).
7. Evans A. S. In: Viral Infections of Humans. Epidemiology and control. 3rd edn. (ed. A. S. Evans) 22-28 (Plenum Publishing Corporation, New York, 1989).
8. Osterhaus A. D. M. E., H. Yang, H. E. M. Spijkers, J. Groen, J. S. Teppema, and G. van Steenis. The isolation and partial characterization of a highly pathogenic herpes virus from the Harbor Seal (Phoca vitulina). Arch. of Virol. 86:239-251 (1985).

9. Chua K. B. et al. Nipah virus: a recently emergent deadly paramyxovirus. *Science* 288:1432-1435 (2000).
10. Welsh J., K. Chada, S. S. Dalai, R. Cheng, D. Ralph, and M. McClelland. Arbitrarily primed PCR fingerprinting of RNA. *NAR.* 20:4965-4970 (1992).
11. Bayon-Auboyer M., C. Arnauld, D. Toquin, and N. Eterradossi. Nucleotide sequences of the F, L and G protein genes of two non-A/non-B avian Pneumoviruses (APV) reveal a novel APV subgroup. *J. of Gen. Virol.* 81:2723-2733 (2000).
12. Mulder J. and N. Masurel. Pre-epidemic antibody against 1957 strain of asiatic influenza in serum of older people living in The Netherlands. *The Lancet*, April 19, 810-814 (1958).
13. Pringle C. R. In: *The Paramyxoviruses.* 11th edn. (ed. D. W. Kingsbury) 1-39 (Plenum Press, New York, 1991).
14. Rothbarth P. H., J. Groen, A. M. Bohnen, R. de Groot, and A. D. M. E. Osterhaus. Influenza virus serology-a comparative study. *J. of Virol. Methods* 78:163-169 (1999).
15. Brandenburg A. H., J. Groen, H. A. van Steensel-Moll, E. J. C. Claas, P. H. Rothbarth, H. J. Neiens, and A. D. M. E. Osterhaus. Respiratory syncytial virus-specific serum antibodies in infants under six months of age: limited serological response upon infection. *J. Med. Virol.* 52:97-104 (1997).
16. Lennette D. A. et al. In: *Diagnostic procedures for viral, rickettsial, and chlamydial infections.* 7th edn. (eds. E. H. Lennette, D. A. Lennette, and E. T. Lennette) 3-25; 37-138; 431-463; 481-494; 539-563 (American public health association, Washington, 1995).
15. Felsenstein J. Department of Genetics, University of Washington. On the Internet at evolution.genetics.washington.edu/phylip.html.
16. Schnell et al. *EMBO J.* 13:4195-4203, 1994.
17. Collins P. L., M. G. Hill, E. Camargo, H. Grosfeld, R. M. Chanock, and B. R. Murphy. Production of infectious human respiratory syncytial virus from cloned cDNA confirms an essential role for the transcription elongation factor from the 5' proximal open reading frame of the M2 mRNA in gene expression and provides a capability for vaccine development. *PNAS* 92:11563-11567 (1995).
18. Hoffmann E., G. Neumann, Y Kawakao, G. Hobom, and R. G. Webster. A DNA transfection system for generation of influenza virus from eight plasmids. *PNAS* 97:6108-6113 (2000).
19. Bridgen A. and R. M. Elliot. Rescue of a segmented negative-strand virus entirely from cloned complementary DNAs. *PNAS* 93:15400-15404 (1996).
20. Palese P., H. Zheng, O. G. Engelhardt, S. Pleschka, and A. Garcia-Sastre. Negative-strand RNA viruses: genetic engineering and applications. *PNAS* 93:11354-11358 (1996).
21. Peeters B. P., O. S. de Leeuw, G. Koch, and A. L. Gielkens. Rescue of Newcastle disease virus from cloned cDNA: evidence that cleavability of the fusion protein is a major determinant for virulence. *J. Virol.* 73:5001-5009 (1999).
22. Durbin A. P., S. L. Hall, J. W. Siew, S. S. Whitehead, P. L. Collins, and B. R. Murphy. Recovery of infectious human parainfluenza virus type 3 from cDNA. *Virology* 235:323-332 (1997).
23. Tao T., A. P. Durbin, S. S. Whitehead, F. Davoodi, P. L. Collins, B. R. Murphy. Recovery of a fully viable chimeric human parainfluenza virus (PIV) type 3 in which the hemagglutinin-neuraminidase and fusion glycoproteins have been replaced by those of PIV type 1. *J. Virol.* 72:2955-2961 (1998).
24. Durbin A. P., M. H. Skiadopoulos, J. M. McAuliffe, J. M. Riggs, S. R. Surman, P. L. Collins and B. R. Murphy. Human parainfluenza virus type 3 (PIV3) expressing the hemagglutinin protein of measles virus provides a potential method for immunization against measles virus and PIV3 in early infancy. *J. Virol.* 74:6821-6831 (2000).
25. Skiadopoulos M. H., A. P. Durbin, J. M. Tatem, S. L. Wu, M. Paschalis, T. Tao, P. L. Collins, and B. R. Murphy. Three amino acid substitutions in the L protein of the human parainfluenza virus type 3 cp45 live attenuated vaccine candidate contribute to its temperature-sensitive and attenuation phenotypes. *J. Virol.* 72:1762-1768 (1998).
26. Teng N., S. S. Whitehead, A. Bermingham, M. St. Claire, W. R. Elkins, B. R. Murphy, and P. L. Collins. *J. Virol.* 74:9317-9321 (2000).
27. Masurel N. Relation between Hong Kong virus and former human A2 isolates and the A/EQU12 virus in human sera collected before 1957. *The Lancet* May 3, 907-910 (1969).

FURTHER REFERENCES USED WITH EXAMPLE 4

Ahmadian G., P. Chambers, and A. J. Easton (1999). Detection and characterization of proteins encoded by the second ORF of the M2 gene of Pneumoviruses. *J. Gen. Virol.* 80:2011-6.

Lansari A. H. and L. N. Potgieter (1994). Molecular cloning and sequence analysis of the phosphoprotein, nucleocapsid protein, matrix protein and 22K (M2) protein of the ovine respiratory syncytial virus. *J. Gen. Virol.* 75:3597-601.

Barr J., P. Chambers, C. R. Pringle, and A. J. Easton (1991). Sequence of the major nucleocapsid protein gene of pneumonia virus of mice: sequence comparisons suggest structural homology between nucleocapsid proteins of Pneumoviruses, paramyxoviruses, rhabdoviruses and filoviruses. *J. Gen. Virol.* 72: 677-85.

Baybutt H. N. and C. R. Pringle (1987). Molecular cloning and sequencing of the F and 22K membrane protein genes of the RSS-2 strain of respiratory syncytial virus. *J. Gen. Virol.* 68:2789-96.

Byon-Auboyer M. H., C. Arnauld, D. Toquin, and N. Eterradossi (2000). Nucleotide sequences of the F, L and G protein genes of two non-A/non-B avian Pneumoviruses (APV) reveal a novel APV subgroup. *J. Gen. Virol.* 81:2723-33.

Bermingham A. and P. L. Collins (1999). The M2-2 protein of human respiratory syncytial virus is a regulatory factor involved in the balance between RNA replication and transcription. *Proc. Natl. Acad. Sci. U.S.A.* 96:11259-64.

Blumberg B. M., J. Chan, and S. A. Udem (1991). Function of Paramyxovirus 3' and 5' end sequences: In theory and practice. In "the Paramyxoviruses" (D. Kingsbury, Ed.), pp. 235-247. Plenum, N.Y.

Collins P. L. and G. W. Wertz (1983). cDNA cloning and transcriptional mapping of nine polyadenylated RNAs encoded by the genome of human respiratory syncytial virus. *Proc. Natl. Acad. Sci. U.S.A.* 80:3208-12.

Collins P. L. and G. W. Wertz (1985). The envelope-associated 22K protein of human respiratory syncytial virus: nucleotide SEQUENCE of the mRNA and a related polytranscript. *J. Virol.* 54:65-71.

Collins P. L., L. E. Dickens, A. Buceler-White, R. A. Olmsted, M. K. Spriggs, E. Camargo, and K. V. W. Coeelingh (1986). Nucleotide sequences for the gene junctions of human respiratory syncytial virus reveal distinctive features of intergenic structure and gene order. *Proc. Natl. Acad. Sci. U.S.A* 83:4594-98.

Collins P. L., M. G. Hill, and P. R. Johnson (1990). The two open reading frames of the 22K mRNA of human respiratory syncytial virus: sequence comparison of antigenic subgroups A and B and expression in vitro. *J. Gen. Virol.* 71:3015-20.

Collins P. L., M. G. Hill, E. Camargo, H. Grosfeld, R. M. Chanock, and B. R. Murphy (1995). Production of infectious human respiratory syncytial virus from cloned cDNA confirms an essential role for the transcription elongation factor from the 5' proximal open reading frame of the M2 mRNA in gene expression and provides a capability for vaccine development. *Proc. Natl. Acad. Sci. U.S.A.* 92:11563-7.

Collins P. L., K. McIntosh, and R. M. Chanock (1996). "Respiratory syncytial virus." In: *Fields virology* (B. N. Knipe, P. M. Howley, Ed.) Lippencott-Raven, Philadelphia.

Cook J. K. (2000). Avian rhinotracheitis. *Rev. Sci. Tech.* 19:602-13.

Cuesta I., X. Geng, A. Asenjo, and N. Vianue (2000). Structural phosphoprotein M2-1 of the human respiratory syncytial virus is an RNA binding protein. *J. Gen. Virol.* 74:9858-67.

Curran J. and D. Kolakofsky (1999). Replication of paramyxoviruses. *Adu. Virus Res.* 50:403-422.

Easton A. J. and P. Chambers (1997). Nucleotide sequence of the genes encoding the matrix and small hydrophobic proteins of pneumonia virus of mice. *Virus Res.* 48:27-33.

Elango N., M. Satake, and S. Venkatesan (1985). mRNA sequence of three respiratory syncytial virus genes encoding two nonstructural proteins and a 22K structural protein. *J. Virol.* 55:101-10.

Fearns R. and P. L. Collins (1999). Role of the M2-1 transcription antitermination protein of respiratory syncytial virus in sequential transcription. *J. Virol.* 73:5852-64.

Felsenstein J. (1989). "PHYLIP-Phylogeny Inference Package (Version 3.2. Cladistics 5)."

Giraud P., G. Bennejean, M. Guittet, and D. Toquin (1986). Turkey rhinotracheitis in France: preliminary investigations on a ciliostatic virus. *Vet. Rec.* 119:606-7.

Hall T. A. (1999). BioEdit: a user-friendly biological sequence alignment editor and analysis program for Windows 95/98/NT. *Nucl. Acids. Symp. Ser.* 41:95-98.

Hardy R. W. and G. W. Wertz (1998). The product of the respiratory syncytial virus M2 gene ORF1 enhances readthrough of intergenic junctions during viral transcription. *J. Virol.* 72:520-6.

Horvath C. M. and R. A. Lamb (1992). Studies on the fusion peptide of a paramyxovirus fusion glycoprotein: roles of conserved residues in cell fusion. *J. Virol.* 66:2443-55.

Jentoft, N. (1990). Why are proteins O-glycosylated? *Trends Biochem. Sci.* 15:291-4.

Johnson P. R. Jr., R. A. Olmsted, G. A. Prince, B. I. Murphy, D. W. Alling, E. E. Walsh, and P. L. Collins (1987). Antigenic relatedness between glycoproteins of human respiratory syncytial virus subgroups A and B: evaluation of the contributions of F and G glycoproteins to immunity. *J. Virol.* 61:3163-6.

Juhasz K. and A. J. Easton (1994). Extensive sequence variation in the attachment (G) protein gene of avian *Pneumovirus*: evidence for two distinct subgroups. *J. Gen. Virol.* 75:2873-80.

Kyte J. and R. F. Doolittle (1982). A Simple Method for Displaying the Hydrophobic Character of a Protein. *J. Mol. Biol.* 157:105-142.

Lamb R. A. and D. Kolakofsky (1996). "Paramyxoviridae: the viruses and their replication". In: *Fields virology* (B. N. Knipe, P. M. Howley, Ed.) Lippencott-Raven, Philadelphia.

Li J., R. Ling, J. S. Randhawa, K. Shaw, P. J. Davis, K. Juhasz, C. R. Pringle, A. J. Easton, and D. Cavanagh (1996). Sequence of the nucleocapsid protein gene of subgroup A and B avian Pneumoviruses. *Virus Res.* 41:185-91.

Ling R., A. J. Easton, and C. R. Pringle (1992). Sequence analysis of the 22K SH and G genes of turkey rhinotracheitis virus and their intergenic regions reveals a gene order different from that of other Pneumoviruses. *J. Gen. Virol.* 73:1709-15.

Ling R., P. J. Davis, Q. Yu, C. M. Wood, C. R. Pringle, D. Cavanagh, and A. J. Easton (1995). Sequence and in vitro expression of the phosphoprotein gene of avian *Pneumovirus*. *Virus Res.* 36:247-57.

Marriot A. C., J. M. Smith, and A. Easton (2001). Fidelity of leader and trailer sequence usage by the respiratory syncytial virus and avian *Pneumovirus* replication complexes. *J. Virol.* 75:6265-72.

Mink M. A., D. S. Stec, and P. L. Collins (1991). Nucleotide sequences of the 3' leader and 5' trailer regions of human respiratory syncytial virus genomic RNA. *Virology* 185: 615-24.

Miyahara K., S. Kitada, M. Yoshimoto, H. Matsuimura, M. Kawano, H. Komada, M. Tsurudome, S. Kusagawa, M. Nishio, and Y. Ito (1992). Molecular evolution of human paramyxoviruses. Nucleotide sequence analyses of the human parainfluenza type 1 virus NP and M protein genes and construction of phylogenetic trees for all the human paramyxoviruses. *Arch. Virol.* 124:255-68.

Morrison T. G. (1988). Structure, function, and intracellular processing of paramyxovirus membrane proteins. *Virus Res.* 10:113-35.

Naylor C. J., P. Britton, and D. Cavanagh (1998). The ectodomains but not the transmembrane domains of the fusion proteins of subtypes A and B avian *Pneumovirus* are conserved to a similar extent as those of human respiratory syncytial virus. *J. Gen. Virol.* 79:1393-8.

Plows D. J. and C. R. Pringle (1995). Variation in the fusion glycoprotein gene of human respiratory syncytial virus subgroup A. *Virus Genes* 11:37-45.

Poch O., B. M. Blumberg, L. Bougueleret, and N. Tordo (1990). Sequence comparison of five polymerases (L proteins) of unsegmented negative-strand RNA viruses: theoretical assignment of functional domains *J. Gen. Virol.* 71:1153-62.

Poch O., I. Sauvaget, M. Delarue, and N. Tordo (1989). Identification of four conserved motifs among the RNA-dependent polymerase encoding elements. *Embo. J.* 8:3867-74.

Randhawa J. S., A. C. Marriott, C. R. Pringle, and A. J. Easton (1997). Rescue of synthetic minireplicons establishes the absence of the NS1 and NS2 genes from avian *Pneumovirus*. *J. Virol.* 71:9849-54.

Randhawa J. S., S. D. Wilson, K. P. Tolley, D. Cavanagh, C. R. Pringle, and A. J. Easton (1996). Nucleotide sequence of the gene encoding the viral polymerase of avian *Pneumovirus*. *J. Gen. Virol.* 77:3047-51.

Samal S. K. and M. Zamora (1991). Nucleotide sequence analysis of a matrix and small hydrophobic protein dicistronic mRNA of bovine respiratory syncytial virus demonstrates extensive sequence divergence of the small hydrophobic protein from that of human respiratory syncytial virus. *J. Gen. Virol.* 72:1715-20.

Sataxe M. and S. Venkatesan (1984). Nucleotide sequence of the gene encoding respiratory syncytial virus matrix protein. *J. Virol.* 50:92-9.

Seal B. S., H. S. Sellers, and R. J. Meinersmann (2000). Fusion protein predicted amino acid sequence of the first US avian *Pneumovirus* isolate and lack of heterogeneity among other US isolates. *Virus Res.* 66:139-47.

Sedlmeier R. and W. J. Neubert (1998). The replicative complex of paramyxoviruses: structure and function. *Adv. Virus Res.* 50:101-39.

Stec D. S., M. G. Hill. 3rd, and P. L. Collins (1991). Sequence analysis of the polymerase L gene of human respiratory syncytial virus and predicted phylogeny of nonsegmented negative-strand viruses. *Virology* 183:273-87

Van Den Hoogen B. G., J. C. De Jong, J. Groen, T. Kuiken, R. De Groot, R. A. Fouchier, and A. D. Osterhaus (2001). A newly discovered human *Pneumovirus* isolated from young children with respiratory tract disease. *Nat. Med.* 7(6):719-24.

*Virus Taxonomy* (2000). Seventh report of the international Committee on Taxonomy of Viruses.

Wertz G. W., P. L. Collins, Y. Huang, C. Gruber, S. Levine, and L. A. Ball (1985). Nucleotide sequence of the G protein gene of human respiratory syncytial virus reveals an unusual type of viral membrane protein. *Proc. Natl. Acad. Sci. U.S.A.* 82:4075-9.

Yu Q., P. J. Davis, T. Barrett, M. M. Binns, M. E. Boursnell, and D. Cavanagh (1991). Deduced amino acid sequence of the fusion glycoprotein of turkey rhinotracheitis virus has greater identity with that of human respiratory syncytial virus, a *Pneumovirus*, than that of paramyxoviruses and morbilliviruses. *J. Gen. Virol.* 72:75-81.

Yu Q., P. J. Davis, J. Li, and D. Cavanagh (1992). Cloning and sequencing of the matrix protein (M) gene of turkey rhinotracheitis virus reveal a gene order different from that of respiratory syncytial virus. *Virology* 186:426-34.

Zamora M. and S. K. Samal (1992). Sequence analysis of M2 mRNA of bovine respiratory syncytial virus obtained from an F-M2 dicistronic mRNA suggests structural homology with that of human respiratory syncytial virus. *J. Gen. Virol.* 73:737-41.

Primers used for RT-PCR detection of known paramyxoviruses. Primers for hPIV-1 to 4, mumps, measles, Tupaia, Mapuera and Hendra are developed in house and based on alignments of available sequences. Primers for New Castle Disease Virus are taken from Seal, J., J. et al; *Clin. Microb.*, 2624-2630, 1995. Primers for Nipah and general paramyxovirus-PCR are taken from: Chua, K. B., et al; *Science*, 288 26 May 2000.

| Virus | | primers | located in protein |
|---|---|---|---|
| HPIV-1 | fwd | 5'-TGTTGTCGAGACTATTCCAA-3' (SEQ ID NO: 132) | HN |
| | Rev | 5'-TGTTG(T/A)ACCAGTTGCAGTCT-3' (SEQ ID NO: 133) | |
| HPIV-2 | Fwd | 5'-TGCTGCTTCTATTGAGAAACGCC-3' (SEQ ID NO: 134) | N |
| | Rev | 5'-GGTGAC/T TC(T/C)AATAGGGCCA-3' (SEQ ID NO: 135) | |
| HPIV-3 | Fwd | 5'-CTCGAGGTTGTCAGGATATAG-3' (SEQ ID NO: 136) | HN |
| | Rev | 5'-CTTTGGGAGTTGAACACAGTT-3' (SEQ ID NO: 137) | |
| HPIV-4 | Fwd | 5'-TTC(A/G)GTTTTAGCTGCTTACG-3' (SEQ ID NO: 138) | N |
| | Rev | 5'-AGGCAAATCTCTGGATAATGC-3' (SEQ ID NO: 139) | |
| Mumps | Fwd | 5'-TCGTAACGTCTCGTGACC-3' (SEQ ID NO: 140) | SH |
| | Rev | 5'-GGAGATCTTTCTAGAGTGAG-3' (SEQ ID NO: 141) | |
| NDV | Fwd | 5'-CCTTGGTGAiTCTATCCGIAG-3' (SEQ ID NO: 142) | F |
| | Rev | 5'-CTGCCACTGCTAGTTGiGATAATCC-3' (SEQ ID NO: 143) | |
| Tupaia | Fwd | 5'-GGGCTTCTAAGCGACCCAGATCTTG-3' (SEQ ID NO: 144) | N |
| | Rev | 5'-GAATTTCCTTATGGACAAGCTCTGTGC-3' (SEQ ID NO: 145) | |
| Mapuera | Fwd | 5'-GGAGCAGGAACTCCAAGACCTGGAG-3' (SEQ ID NO: 146) | N |
| | Rev | 5'-GCTCAACCTCATCACATACTAACCC-3' (SEQ ID NO: 147) | |
| Hendra | Fwd | 5'-GAGATGGGCGGGCAAGTGCGGCAACAG-3' (SEQ ID NO: 148) | N |
| | Rev | 5'-GCCTTTGCAATCAGGATCCAAATTTGGG-3' (SEQ ID NO: 149) | |
| Nipah | Fwd | 5'-CTGCTGCAGTTCAGGAAACATCAG-3' (SEQ ID NO: 150) | N |
| | Rev | 5'-ACCGGATGTGCTCACAGAACTG-3' (SEQ ID NO: 151) | |
| HRSV | Fwd | 5'-TTTGTTATAGGCATATCATTG-3' (SEQ ID NO: 152) | F |
| | Rev | 5'-TTAACCAGCAAAGTGTTA-3' (SEQ ID NO: 153) | |
| Measles | Fwd | 5'-TTAGGGCAAGAGATGGTAAGG-3' N (SEQ ID NO: 154) | N |
| | Rev | 5'-TTATAACAATGATGGAGGG-3' (SEQ ID NO: 155) | |

| Virus | primers | located in protein |
|---|---|---|
| General Paramyxoviridae: | | |
| | Fwd 5'-CATTAAAAAGGGCACAGACGC-3' (SEQ ID NO: 156)<br>Rev 5'-TGGACATTCTCCGCAGT-3' (SEQ ID NO: 157) | P |
| Primers for RAP-PCR: | | |
| ZF1: | 5'-CCCACCACCAGAGAGAAA-3' (SEQ ID NO: 158) | |
| ZF4: | 5'-ACCACCAGAGAGAAACCC-3' (SEQ ID NO: 159) | |
| ZF7: | 5'-ACCAGAGAGAAACCCACC-3' (SEQ ID NO: 160) | |
| ZF10: | 5'-AGAGAGAAACCCACCACC-3' (SEQ ID NO: 161) | |
| ZF13: | 5'-GAGAAACCCACCACCAGA-3' (SEQ ID NO: 162) | |
| ZF16: | 5'-AAACCCACCACCAGAGAG-3' (SEQ ID NO: 163) | |
| CS1: | 5'-GGAGGCAAGCGAACGCAA-3' (SEQ ID NO: 164) | |
| CS4: | 5'-GGCAAGCGAACGCAAGGA-3' (SEQ ID NO: 165) | |
| CS7: | 5'-AAGCGAACGCAAGGAGGC-3' (SEQ ID NO: 101) | |
| CS10 | 5'-CGAACGCAAGGAGGCAAG-3' (SEQ ID NO: 102) | |
| CS13: | 5'-ACGCAAGGAGGCAAGCGA-3' (SEQ ID NO: 103) | |
| CS16: | 5'-CAAGGAGGCAAGCGAACG-3' (SEQ ID NO: 104) | |

20 fragments successfully purified and sequenced:
10 fragments found with sequence homology in APV

| Fragment 1 | ZF 7, 335 bp | N gene |
|---|---|---|
| Fragment 2 | ZF 10, 235 bp | N gene |
| Fragment 3 | ZF 10, 800 bp | M gene |
| Fragment 4 | CS 1, 1250 bp | F gene |
| Fragment 5 | CS 10, 400 bp | F gene |
| Fragment 6 | CS 13, 1450 bp | F gene |
| Fragment 7 | CS 13, 750 bp | F gene |
| Fragment 8 | ZF 4, 780 bp | L gene (protein level) |
| Fragment 9 | ZF 10, 330 bp | L gene (protein level) |
| Fragment 10 | ZF10, 250 bp | L gene (protein level) |

Primers Used for RAP-PCR Amplification of Nucleic Acids from the Prototype Isolate.

Example 5

Further Exploration of the Two Subtypes of hMPV

Based on phylogenetic analysis of the different isolates of hMPV obtained so far, two genotypes have been identified with virus isolate 00-1 being the prototype of genotype A and isolate 99-1 the prototype of genotype B.

We hypothesize that the genotypes are related to subtypes and that re-infection with viruses from both subgroups occur in the presence of pre-existing immunity and the antigenic variation may not be strictly required to allow re-infection.

Furthermore, hMPV appears to be closely related to avian *Pneumovirus*, a virus primarily found in poultry. The nucleotide sequences of both viruses show high percentages of homology, with the exception of the SH and G proteins. Here we show that the viruses are cross-reacting in tests, which are based primarily on the nucleoprotein and matrix protein, but they respond differently in tests, which are based on the attachment proteins. The differences in virus neutralization titers provide further proof that the two genotypes of hMPV are two different serotypes of one virus, where APV is a different virus.

The Cross-Reaction Between the Two Serotypes and the Cross-Reaction Between APV and hMPV Methods Protocol for IgG, IgA and IgM Antibody Detection for hMPV:

The indirect IgG EIA for hMPV was performed in microtiter plates essentially as described previously (Rothbarth, P. H. et al., 1999; Influenza virus serology-a comparative study. *J. of Vir. Methods* 78 (1999) 163-169.

Briefly, concentrated hMPV was solubilized by treatment with 1% TRITON® X-100 an coated for 16 hours at room temperature into microtiter plates in PBS after determination of the optimal working dilution by checkerboard titration. Subsequently, 100 μl volumes of 1:100 diluted human serum samples in EIA buffer were added to the wells and incubated for 1 hour at 37° C. Binding of human IgG was detected by adding a goat anti-human IgG peroxidase conjugate (Biosource, USA). Adding TMB as substrate developed plates and OD was measured at 450 nm. the results were expressed as the S(ignal)/N(egative) ratio of the OD. A serum was considered positive for IgG, if the SIN ratio was beyond the negative control plus three times the standard.

hMPV antibodies of the IgM and IgA classes were detected in sera by capture EIA essentially as described previously (P. H. Rothbarth et al. 1999, Influenza virus serology-a comparative study. *J. Vir. Methods* 78 (1999) 163-169). For the detection of IgA and IgM commercially available microtiter plates coated with anti-human IgM or IgA-specific monoclonal antibodies were used. Sera were diluted 1:100 and after incubation of 1 hour at 37° C., an optimal working dilution of hMPV is added at each well (100 µl). Incubated 1 hour 37° C. After washing polyclonal anti hMPV labeled with peroxidase was added, the plate was incubated 1 hour 37° C. Adding TMB as substrate developed plates and OD was measured at 450 nm. the results were expressed as the S(ignal)/N(egative) ratio of the OD. A serum was considered positive for IgG, if the S/N ratio was beyond the negative control plus three times the standard.

AVP antibodies were detected in an AVP inhibition assay. Protocol for APV inhibition test is included the APV-Ab SVANOVIR® enzyme immunoassay which is manufactured by SVANOVA Biotech AB, Uppsal Science Park Glunten SE-751 83 Uppsala Sweden. The results were expressed as the S(ignal)/N(egative) ratio of the OD. A serum was considered positive for IgG, if the S/N ratio was beyond the negative control plus three times the standard.

1. Guinea Pigs

A. (Re)Infection of Guinea Digs with Both Subtypes of hMPV

Virus isolates ned/00/01 (subtype A) and ned/99/01 (subtype B) have been used to inoculate 6 guinea pigs per subtype (intratracheal, nose and eyes).

6 GPs infected with hMPV 00-1 (10e6,6 TCID50)

6 GPs infected with hMPV 99-1 (10e4,1 TCED50)

54 Days after the primary infection, the guinea pigs have been inoculated with the homologous and heterologous subtypes (10e4 TCED50/ml):

2 guinea pigs: 1" infection 00-1; 2' 99-1 (heterologous)

3 guinea pigs: 1" infection 00-1; 2' 00-1 (homologous)

2 guinea pigs: 1" infection 99-1; 2' 00-1 (heterologous)

3 guinea pigs: 1" infection 99-1; 2' 99-1 (homologous)

Throat and nose swabs have been collected for 12 days (1" infection) or 8 days (2' infection) post infection, and have been tested for presence of the virus by RT-PCR assays.

Results of RT-PCR Assay: FIG. 29

Summary of results: guinea pigs inoculated with virus isolate ned/00/01 show infection of the upper respiratory tract day 1 to 10 post infection. Guinea pigs inoculated with ned/99/01 show infection of the upper respiratory tract day 1 to 5 post infection. Infection with ned/99/01 appears to be less severe than infection with ned/00/01. A second inoculation of the guinea pigs with the heterologous virus results in re-infection in 3 out of 4 guinea pigs and with the homologous virus in 2 out of 6 guinea pigs. No or only little clinical symptoms were noted in those animals that became re-infected, and no clinical symptoms were seen in those animals that were protected against the re-infections, demonstrating that even with wild-type virus, a protective effect of the first infection is evident, showing the possible use of heterologous (and of course homologues) isolates as a vaccine, even in an unattenuated form.

Both subtypes of hMPV are able to infect guinea pigs, although infection with subtype B (ned/99/01) seems less severe (shorter period of presence of the virus in nose and throat) than infection with subtype A (ned/00/01). This may be due to the higher dose given for subtype A, or to the lower virulence of subtype B.

Although the presence of pre-existing immunity does not completely protect against re-infection with both the homologous and heterologous virus, the infection appears to be less prominent in that a shorter period of presence of virus was noted and not all animals became virus positive.

B. Serology of Guinea Pigs Infected with Both Subtypes of hMPV

At day 0, 52, 70, 80, 90, 110, 126 and 160 sera were collected from the guinea pigs and tested at a 1:100 dilution in a whole virus ELISA against ned/00/01 and ned/99/01 antigen.

FIGS. 30A and 30B: IgG response against ned/00/01 and ned/99/01 for each individual guinea pig FIG. 31: Specificity of the ned/00/01 and ned/99/01 ELISA. Only data from homologous reinfected guinea pigs have been used.

FIG. 32: Mean IgG response against ned/00/01 and ned/99/01 ELISA of 3 homologous (00-1/00-1), 2 homologous (99-1/99-1), 2 heterologous (99-1/00-1) and 2 heterologous (00-1/99-1) infected guinea pigs.

Summary of Results:

Only a minor difference in response to the two different ELISAs is observed. Whole virus ELISA against 00-1 or 99-1 cannot be used to discriminate between the two subtypes.

C. Reactivity of Sera Raised Against hM:PV in Guinea Pigs with APV Antigen

Sera collected from the infected guinea pigs have been tested with an APV inhibition ELISA.

FIG. 33: Mean percentage of APV inhibition of hMPV-infected guinea pigs.

Summary of Results:

Sera raised against hMPV in guinea pigs, react in the APV inhibition test in a same manner as they react in the hbNV IgG ELISAs.

Sera raised against ned/99/01 reveal a lower percentage of inhibition in the APV inhibition ELISA than sera raised against ned/00/01. Guinea pigs infected with ned/99/01 might have a lower titer (as is seen in the hMPV EUISAs) or the cross-reaction of ned/99/01 with APV is less than that of ned/00/01. Nevertheless, the APV-Ab inhibition ELISA can be used to detect hMPV antibodies in guinea pigs.

D. Virus Neutralization Assays with Sera Raised Against hMPV in Guinea Pigs.

Sera collected at day 0, day 52, 70 and 80 post infection were used in a virus (cross) neutralization assay with ned/00/01, ned/99/01 and APV-C. Starting dilution was 1 to 10 and 100 TCID50 virus per well was used. After neutralization, the virus was brought on tMK cells, 15 minutes centrifuged at 3500 RPM, after which the media was refreshed.

The APV tests were grown for 4 days and the hMPV tests were grown for 7 days. Cells were fixed with 80% aceton, and IFAs were conducted with monkey-anti hMPV fitc labeled. Wells that were negative in the staining were considered as the neutralizing titer. For each virus a 10-log titration of the virus stock and 2-fold titration of the working solution was included.

FIG. 34: Virus neutralization titers of ned/00/01 and ned/99/01 infected guinea pigs against ned/00/01, ned/99/01 and APV-C 2. Cynomolgus Macaques A. (Re)Infection of Cynomolgus Macaques with Both Subtypes of hMPV Virus isolates ned/00/01 (subtype A) and ned/99/01 (subtype B) (1*5 TCID50) have been used to inoculate 2 cynomolgus macaques per subtype (intratracheal, nose and eyes). Six months after the primary infection, the macaque have been inoculated for the second time with ned/00/01. Throat swabs have been collected for 14 days ($1^{st}$ infection) or 8 days ($2^{nd}$ infection) post infection, and have been tested for presence of the virus by RT-PCR assays.

FIG. 35: Results of RT-PCR assays on throat swabs of cynomolgus macaques inoculated (twice) with ned/00/01.

Summary of Results:

Summary of results: cynomolgus macaques inoculated with virus isolate ned/00/01 show infection of the upper respiratory tract day 1 to 10 post infection. Clinical symptoms included a suppurative rhinitis. A second inoculation of the macaques with the homologous virus results in re-infection, as demonstrated by PCR, however, no clinical symptoms were seen.

B. Serology on Sera Collected of hMPV-Infected Cynomolgus Macaques.

From the macaques which received ned/00/01 sera were collected during 6 months after the primary infection (re-infection occurred at day 240 for monkey 3 and day 239 for monkey 6).

Sera were used to test for the presence of IgG antibodies against either ned/00/01 or APV, and for the presence against IgA and IgM antibodies against ned/00/01.

Results: FIG. 36A: IgA, IgM and IgG response against ned/00/01 of 2 cynomolgus macaques (re)infected with ned/00/01.

FIG. 36B: IgG response against APV of 2 cynomolgus macaques infected with ned/00/01.

Summary of Results:

Two macaques have been successfully infected with ned/00/01 and in the presence of antibodies against ned/00/01 been reinfected with the homologous virus. The response to IgA and IgM antibodies shows the raise in IgM antibodies after the first infection, and the absence of it after the reinfection. IgA antibodies are only detected after the re-infection, showing the immediacy of the immune response after a first infection. Sera raised against hMPV in macaques which were tested in an APV inhibition ELISA show a similar response as to the hMPV IgG EUSA Discussion/Conclusion hMPV antibodies in cynomolgus macaques are detected with the APV inhibition ELISA with a similar sensitivity as with an hMPV ELISA, and therefore the APV inhibition EIA is suitable for testing human samples for the presence of hMPV antibodies.

C. Virus (Cross) Neutralization Assays with Sera Collected from hMPV-Infected Cynomolgus Macaques Summary of results: The sera taken from day 0 to day 229 post primary infection show only low virus neutralization titers against ned/00/01 (0-80), the sera taken after the secondary infection show high neutralization titers against ned/00/01: >1280. Only sera taken after the secondary infection show neutralization titers against ned/99/01 (80-640), and none of the sera neutralize the APV C virus.

There is no cross-reaction between APV-C and hMPV in virus (cross) neutralization assays, where there is a cross-reaction between ned/00/01 and ned/99/01 after a boost of the antibody response.

3. Humans

Sera of patients ranging in age of <6 months to >20 years of age have previously been tested in IFA and virus neutralization assays against ned/00/01. (See Table 1 of patent.)

Here we have tested a number of these sera for the presence of IgG, IgM and IgA antibodies in an ELISA against ned/00/01, and we tested the samples in the APV inhibition ELISA.

Results: FIG. 37 Comparison of the use of the hMPV ELISA and the APV inhibition ELISA for the detection of IgG antibodies in human sera, there is a strong correlation between the IgG hMPV test and the APV-Ab test, therefore the APV-Ab test is essentially able to detect IgG antibodies to hmPV in humans.

4. Poultry 96 chickens have been tested in both the APV inhibition ELISA and the ned/00/01 ELISA for the presence of IgG antibodies against APV.

Summary of results: Both the hMPV ELISA and the APV inhibition ELISA detect antibodies against APV (data not shown).

Summary of Results.

We found two genotypes of hMPV with ned/00/01 being the prototype of subgroup A and ned/99/01 the prototype of subgroup B.

"According to classical serological analyses (as, for example, known R. I. B. Francki, C. M. Fauquet, D. L. Knudson, and F. Brown, Classification and nomenclature of viruses, Fifth report of the international Committee on Taxonomy of Viruses, *Arch. Virol.,* 1991. Supplement 2: p. 140-144), two subtypes can be defined on the basis of its immunological distinctiveness, as determined by quantitative neutralization assays with animal antisera. Two distinct serotypes have either no cross-reaction with each other or show a homologous-to heterologous titer ratio >16 in both directions. If neutralization shows a certain degree of cross-reaction between two viruses in either or both directions (homologous-to-heterologous titer ration of eight or 16), distinctiveness of serotype is assumed if substantial biophysical/biochemical differences of DNAs exist. If neutralization shows a distinct degree of cross-reaction between two viruses in either or both directions (homologous-to-heterologous titer ration of smaller than eight), identity of serotype of the isolates under study is assumed."

For RSV, it is known that re-infection occurs in the presence of pre-existing immunity (both homologous and heterologous). Infection of guinea pigs and cynomolgus macaques with both the homologous and heterologous serotypes of hMPV revealed that this is also true for hMPV. In addition, IgA and IgM ELISAs against hMPV revealed the reaction of IgA antibodies only occurs after re-infection. Sera raised against hMPV or APV respond in an equal way in APV and hMPV ELISAs. From the nucleotide sequence comparisons, it is known that the viruses show about 80% amino acid homology for the N, P, M, and F genes. In ELISAs, the N and M proteins are the main antigens to react. Virus neutralization assays (known to react against the surface glycoproteins G, SH and F) show a difference between the two different sera. Although APV en hMPV cross-react in ELISAs, phylogenetic analyses of the nucleotide sequences of hMPV and APV, the differences in virus neutralization titers of sera raised against the two different viruses, and the differences in host usage again reveal that APV-C and hMPV are two different viruses. Based on the results we speculate that hMPV infection in mammals is possible a result of a zoonotic event from birds to mammals. But the virus has adapted in such a way (i.e., the G and SH proteins) that a return (from mammals to birds) zoonotic event seems unlikely, considering the presence of AVP in birds.

Addendum

Background Information on Pneumovirinae

The family of Paramyxoviridae contains two subfamilies: the Paramyxovirinae and the Pneumovirinae. The subfamily Pneumovirinae consists of two genera: *Pneumovirus* and *Metapneumovirus*. The genus *Pneumovirus* contains the human, bovine, ovine and caprine respiratory syncytial viruses and the pneumonia virus of mice (PVM). The genus *Metapneumovirus* contains the avian Pneumoviruses (APV, also referred to as TRTV).

The classification of the genera in the subfamily Pneumovirinae is based on classical virus characteristics, gene order and gene constellation. Viruses of the genus *Pneumovirus* are unique in the family of Paramyxoviridae in having two nonstructural proteins at the 3' end of the genome (3'-NS1-NS2-N-P-M-SH-G-F-M2-L-5'). In contrast, viruses in the genus *Metapneumovirus* lack the NS1 and NS2 genes and the organization of genes between the M and L coding regions is different: 3'-N-P-M-F-M2-SH-G-L-5'.

All members of the subfamily Paramyxovirinae have hemagglutinating activity, but this function is not a defining feature for the subfamily Pneumovirinae, being absent in RSV and APV but present in PMV. Neuraminidase activity is present in members of the genera *Paramyxovirus* and *Rubulavirus* (subfamily Paramyxovirinae) but is absent in the genus *Morbillivirus* (subfamily Paramyxovirinae) and the genera *Pneumovirus* and *Metapneumovirus* (subfamily Pneumovirinae).

A second distinguishing feature of the subfamily Pneumovirinae is the apparent limited utilization of alternative ORFs within mRNA by RSV. In contrast, several members of the subfamily Paramyxovirinae, such as Sendai and Measles viruses, access alternative ORFs within the mRNA encoding the phosphoprotein (P) to direct the synthesis of a novel protein.

The G protein of the Pneumovirinae does not have sequence relatedness or structural similarity to the HN or H proteins of Paramyxovirinae and is only approximately half the size of their chain length. In addition, the N and P proteins are smaller than their counterparts in the Paramyxovirinae and lack unambiguous sequence homology. Most nonsegmented negative-stranded RNA viruses have a single matrix (M) protein.

Members of the subfamily Pneumovirinae are an exception in having two such proteins, M and M2. The M protein is smaller than its Paramyxovirinae counterparts and lacks sequence relatedness with Paramyxovirinae.

When grown in cell cultures, members of the subfamily Pneumovirinae show typical cytopathic effects; they induce characteristic syncytia formation of cells. (Collins, 1996). The Subfamily Pneumovirinae, Genus *Pneumovirus* hRSV is the type-species of the genus *Pneumovirus* and is a major and widespread cause of lower respiratory tract illness during infancy and early childhood (Selwyn, 1990). In addition, hRSV is increasingly recognized as an important pathogen in other patient groups, including immune compromised individuals and the elderly. RSV is also an important cause of community-acquired pneumonia among hospitalized adults of all ages (Englund, 1991; Falsey, 2000; Dowell, 1996). Two major antigenic types for RSV (A and B) have been identified based on differences in their reactivity with monoclonal and polyclonal antibodies and by nucleic acid sequence analyses (Anderson, 1985; Johnson, 1987; Sullender, 2000). In particular the G protein is used in distinguishing the two subtypes. RSV-A and B share only 53% amino acid sequence homology in G, whereas the other proteins show higher homologies between the subtypes (Table 1) (Collins, 1996).

Detection of RSV infections has been described using monoclonal and polyclonal antibodies in immunofluorescence techniques (DIF, IFA), virus neutralization assays and ELISA or RT-PCR assays (Rothbarth, 1988; Van Milaan, 1994; Coggins, 1998). Closely related to hRSV are the bovine (bRSV), ovine (oRSV) and caprine RSV (oRSV), from which bRSV has been studied most extensively. Based on sequence homology with HRSV, the ruminant RSVs are classified within the *Pneumovirus* genus, subfamily Pneumovirinae (Collins, 1996). Diagnosis of ruminant RSV infection and subtyping is based on the combined use of serology, antigen detection, virus isolation and RT-PCR assays (Uttenthal, 1996; Valarcher, 1999; Oberst, 1993; Vilcek, 1994).

Several analyses on the molecular organization of bRSV have been performed using human and bovine antisera, monoclonal antibodies and cDNA probes. These analyses revealed that the protein composition of hRSV and bRSV are very similar and the genomic organization of bRSV resembles that of hRSV. For both bRSV and HRSV, the G and F proteins represent the major neutralization and protective antigens. The G protein is highly variable between the hRSV subtypes and between hRSV and bRSV (53 and 28% respectively) (Prozzi, 1997; Lerch, 1990). The F proteins of hRSV and bRSV strains present comparable structural characteristics and antigenic relatedness. The F protein of bRSV shows 80-81% homology with hRSV, while the two hRSV subtypes share 90% homology in F (K. Walravens, 1990).

Studies based on the use of hRSV and bRSV-specific monoclonal antibodies have suggested the existence of different antigenic subtypes of bRSV. Subtypes A, B, and AB are distinguished based on reaction patterns of monoclonal antibodies specific for the G protein (Furze, 1994; Prozzi, 1997; Elvander, 1998). The epidemiology of bRSV is very similar to that of hRSV. Spontaneous infection in young cattle is frequently associated with severe respiratory signs, whereas experimental infection generally results in milder disease with slight pathologic changes (Elvander, 1996).

RSV has also been isolated from naturally infected sheep (oRSV) (LeaMaster, 1983) and goats (cRSV) (Lehmkuhl, 1980). Both strains share 96% nucleotide sequence with the bovine RSV and are antigenically cross-reacting. Therefore, these viruses are also classified within the *Pneumovirus* genus.

A distinct member of the subfamily Pneumovirinae, genus *Pneumovirus* is the Pneumonia virus of mice (PVM).

PVM is a common pathogen in laboratory animal colonies, particularly those containing atymic mice. The naturally acquired infection is thought to be asymptomatic, though passage of virus in mouse lungs resulted in overt signs of disease ranging from an upper respiratory tract infection to a fatal pneumonia (Richter, 1988; Weir, 1988).

Restricted serological cross-reactivity between the nucleocapsid protein (N) and the phosphoprotein (P) of PVM and hRSV has been described but none of the external proteins show cross-reactivity, and the viruses can be distinguished from each other in virus neutralization assays (Chambers, 1990a; Gimenez, 1984; Ling, 1989a). The glycoproteins of PVM appear to differ from those of other paramyxoviruses and resemble those of RSV in terms of their pattern of glycosylation. They differ, however, in terms of processing. Unlike RSV, but similar to the other paramyxoviruses, PVM has hemagglutinating activity with murine erythrocytes, for which the G protein appears to be responsible since a monoclonal antibody to this protein inhibits hemagglutination (Ling, 1989b).

The genome of PVM resembles that of H-RSV, including two nonstructural proteins at its 3' end and a similar genomic organization (Chambers, 1990a; Chambers, 1990b). The nucleotide sequences of the PVM NS1/NS2 genes are not detectably homologous with those of hRSV (Chambers, 1991). Some proteins of PVM show strong homology with hRSV (N: 60%, and F: 38 to 40%) while G is distinctly different (the amino acid sequence is 31% longer) (Barr, 1991; Barr, 1994; Chambers, 1992). The PVM P gene, but not that of RSV or APV, has been reported to encode a second ORF, representing a unique PVM protein (Collins, 1996). New PVM isolates are identified by virus isolation, hemagglutination assays, virus neutralization assay and various immuno-fluorescence techniques.

Table with addendum:
Amino acid homology between the different viruses within the genus Pneumovirus of the subfamily Pneumovirinae

| Gene | hSRVs | bRSVs | oRSV vs. hRSV | bRSV vs. Hrsv | bRSV vs. oRSV | PVM vs. hRSV |
|---|---|---|---|---|---|---|
| NS1 | 87 | | | 68-69 | 89 | * |
| NS2 | 92 | | | 83-84 | 87 | * |
| N | 96 | | 93 | | | 60 |
| P | — | | 81 | | | |
| M | — | | 89 | | | |
| F | 89 | | | 80-81 | | 38-40 |
| G | 53 | 88-100 | 21-29 | 38-41 | 60-62 | * |
| M2 | 92 | | 94 | | | 41 |
| SH | 76 | | 45-50 | | 56 | |
| L | — | | | | | |

*No detectable sequence homology

The Genus Metapneumovirus

Avian Pneumoviruses (APV) has been identified as the etiological agent of turkey rhinotracheitis (McDougall, 1986; Collins, 1988) and is therefore often referred to as turkey rhinotracheitis virus (TRTV). The disease is an upper respiratory tract infection of turkeys, resulting in high morbidity and variable, but often high, mortality. In turkey hens, the virus can also induce substantial reductions in egg production. The same virus can also infect chickens, but in this species, the role of the virus as a primary pathogen is less clearly defined, although it is commonly associated with swollen head syndrome (SHS) in breeder chicken (Cook, 2000). The virions are pleiomorphic, though mainly spherical, with sizes ranging from 70 to 600 nm and the nucleocapsid, containing the linear, non-segmented, negative-sense RNA genome, shows helical symmetry (Collins, 1986; Giraud, 1986). This morphology resembles that of members of the family Paramyxoviridae. Analyses of the APV-encoded proteins and RNAs suggested that of the two subfamilies of this family (Paramyxoviridae and Pneumovirinae), APV most closely resembled the Pneumovirinae (Collins, 1988; Ling, 1988; Cavanagh, 1988).

APV has no non-structural proteins (NS1 and NS2) and the gene order (3'-N-P-M-F-M2-SH-G-L-5') is different from that of mammalian Pneumoviruses such as RSV. APV has therefore recently been classified as the type species for the new genus Metapneumovirus (Pringle, 1999).

Differences in neutralization patterns, ELISA and reactivity with monoclonal antibodies have revealed the existence of different antigenic types of APV. Nucleotide sequencing of the G gene led to the definition of two virus subtypes (A and B), which share only 38% amino acid homology (Collins, 1993; Juhasz, 1994). An APV isolated from Colorado, USA (Cook, 1999), was shown to cross-neutralize poorly with subtype A and B viruses and based on sequence information was designated to a novel subtype, C (Seal, 1998; Seal 2000). Two non-A/non-B APVs were isolated in France, and were shown to be antigenically distinct from subtypes A, B and C. Based on amino acid sequences of the F, L and G genes, these viruses were classified again as a novel subtype, D (Bayon-Auboyer, 2000).

Diagnosis of APV infection can be achieved by virus isolation in chicken or turkey tracheal organ cultures (TOCs) or in Vero cell cultures. A cytopathic effect (CPE) is generally observed after one or two additional passages. This CPE is characterized by scattered focal areas of cell rounding leading to syncytial formation (Buys, 1989). A number of serology assays, including IF and virus neutralization assays have been developed. Detection of antibodies to APV by ELISA is the most commonly used method (O'Loan, 1989; Gulati, 2000). Recently, the polymerase chain reaction (PCR) has been used to diagnose APV infections. Swabs taken from the esophagus can be used as the starting material (Bayon-Auboyer, 1999; Shin, 2000).

REFERENCES

Alansari H. and L. N. D. Potgieter 1994. Nucleotide and predicted amino acid sequence analysis of the ovine respiratory syncytial virus non-structural 1C and 1B genes and the small hydrophobic protein gene. J. Gen. Virol. 75:401-404.

Alansari H., R. B. Duncan, J. C. Baker, and L. N. Potgieter 1999. Analysis of ruminant respiratory syncytial virus isolates by RNAse protection of the G glycoprotein transcripts. J. Vet. Diagn. Invest. 11:215-20.

Anderson L. J, J. C. Hierholzer, C. Tsou, R. M. Hendry, B. F. Fernic, Y. Stone, and K. McIntosh 1985. Antigenic characterization of respiratory syncytial virus strains with monoclonal antibodies. J. Inf. Dis. 151:626-633.

Barr J., P. Chambers, C. R. Pringle, and A. J. Easton 1991. Sequence of the major nucleocapsid protein gene of pneumonia virus of mice: sequence comparisons suggest structural homology between nucleocapsid proteins of Pneumoviruses, paramyxoviruses, rhabdoviruses and filoviruses. J. Gen. Virol. 72:677-685.

Barr J., P. Chambers, P. Harriott, C. R. Pringle, and A. J. Easton 1994. Sequence of the phosphoprotein gene of pneumonia virus of mice: expression of multiple proteins from two overlapping reading frames. J. Virol. 68:5330-5334.

Bayon-Auboyer M. H., V. Jestin, D. Toquin, M. Cherbonnel and N. Eterradosi 1999. Comparison of F-, G- and N-based RT-PCR protocols with conventional virological procedures for the detection and typing of turkey rhinotracheitis virus. Arch. Vir. 144:1091-1109.

Bayon-Auboyer M. H., C. Arnauld, D. Toquin, and N. Eterradossi 2000. Nucleotide sequences of the F, L and G protein genes of two non-A/non-B avian Pneumoviruses (APV) reveal a novel APV subgroup. J. Gen. Virol. 81:2723-2733.

Buys S. B., J. H. Du Preez, and H. J. Els 1989. The isolation and attenuation of a virus causing rhinotracheitis in turkeys in South Africa. Onderstepoort J. Vet. Res. 56:87-98.

Cavanagh D. and T. Barrett 1988. Pneumovirus-like characteristics of the mRNA and proteins of turkey rhinotracheitis virus. Virus Res. 11:241-256.

Chambers P., C. R. Pringle, and A. J. Easton 1990a. Molecular cloning of pneumonia virus of mice. J. Virol. 64:1869-1872.

Chambers P., D. A. Matthews, C. R. Pringle, and A. J. Easton 1990b. The nucleotide sequences of intergenic regions between nine genes of pneumonia virus of mice establish the physical order of these genes in the viral genome. Virus Res. 18:263-270.

Chambers P., C. R. Pringle, and A. J. Easton 1991. Genes 1 and 2 of pneumonia virus of mice encode proteins which have little homology with the 1C and 1B proteins of human respiratory syncytial virus. *J. Gen. Vir.* 72:2545-2549.

Chambers P., C. R. Pringle, A. J. Easton 1992. Sequence analysis of the gene encoding the fusion glycoprotein of pneumonia virus of mice suggests possible conserved secondary structure elements in paramyxovirus fusion glycoproteins. *J. Gen. Virol.* 73:1717-1724.

Coggins W. B., E. J. Lefkowitz, and W. M. Sullender 1998. Genetic variability among group A and group B respiratory syncytial viruses in a children's hospital. *J. Clin. Microbiol.* 36:3552-3557.

Collins M. S., R. E. Gough, S. A. Lister, N. Chettle, and R. Eddy 1986. Further characterization of a virus associated with turkey rhinotracheitis. *Vet. Rec.* 119:606.

Collins M. S. and R. E. Gough 1988. Characterization of a virus associated with turkey rhinotracheitis. *J. Gen. Virol.* 69:909-916.

Collins M. S., R. E. Gough, and D. J. Alexander 1993. Antigenic differentiation of avian *Pneumovirus* isolates using polyclonal antisera and mouse monoclonal antibodies. *Avian Pathology* 22:469-479.

Collins P. L., K. McIntosh, and R. M. Chanock 1996. Respiratory syncytial virus. P. 1313-1351. In: B. N. Fields, D. M. Knipe, and P. M. Howley (ed.). *Fields virology*, 3rd ed., vol. 1 Lippincott-Raven, Philadelphia, Pa., USA.

Cook J. K. A., M. B. Huggins, S. J. Orbell, and D. A. Senne 1999. Preliminary antigenic characterization of an avian *Pneumovirus* isolated from commercial turkeys in Colorado, USA. *Avian Pathol.* 28:607-617.

Cook J. K. A. 2000. Avian rhinotracheitis. *Rev. Sci. tech. off int. Epiz.* 19: 602-613.

Dowell S. F., L. J. Anderson, H. E. Gary, D. D. Erdman, J. F. Plouffe, T. M. File, B. J. Marston, and R. F. Breiman 1996. Respiratory syncytial virus is an important cause of community-acquired lower respiratory infection among hospitalized adults. *J. Infect. Dis.* 174:456-462.

Elvander M. 1996. Severe respiratory disease in dairy cows caused by infection with bovine respiratory syncytial virus. *Vet. Rec.* 138:101-105.

Elvander M., S. Vilcek, C. Baule, A. Uttenthal, A. Ballagi-Pordany, and S. Belak 1998. Genetic and antigenic analysis of the G attachment protein of bovine respiratory syncytial virus strains. *J. Gen. Virol.* 79:2939-2946.

Englund J. A., L. J. Anderson, F. S. and Rhame 1991. Nosocomial transmission of respiratory syncytial virus in immunocompromised adults. *J. Clin. Microbiol.* 29:115-119.

Falsey A. R. and E. E. Walsh 2000. Respiratory syncytial virus infection in adults. *Clin. Microb. Rev.* 13:371-84.

Furze J., G. Wertz, R. Lerch, and G. Taylor 1994. Antigenic heterogeneity of the attachment protein of bovine respiratory syncytial virus. *J. Gen. Virol.* 75:363-370.

Gimenez H. B., P. Cash, and W. T. Melvin 1984. Monoclonal antibodies to human respiratory syncytial virus and their use in comparison of different virus isolates. *J. Gen. Virol.* 65:963-971.

Gulati B. R., K. T. Cameron, B. S. Seal, S. M. Goyal, D. A. Halvorson, and M. K. Njenga 2000. Development of a highly sensitive and specific enzyme-linked immunosorbent assay based on recombinant matrix protein for detection of avian *Pneumovirus* antibodies. *J. Clin. Microbiol.* 38:4010-4.

Johnson P. R., M. K. Spriggs, R. A. Olmsted, and P. L. Collins 1987. The G glycoprotein of human respiratory syncytial virus subgroups A and B: extensive sequence divergence between antigenically related proteins. *Proc. Natl. Acad. Sci. USA* 84:5625-5629.

Juhasz K. and A. J. Easton 1994. Extensive sequence variation in the attachment (G) protein gene of avian *Pneumovirus*: evidence for two distinct subgroups. *J. Gen. Virol.* 76:2873-2880.

LeaMaster B. R., J. F. Evermann, M. Y. Mueller, M. K. Prieur, and J. V. Schlie, 1983.

Serologic studies on naturally occurring respiratory syncytial virus and *Haemophilus sommus* infections in sheep. *American Association of Veterinary Laboratory Diagnosticians* 26:265-276.

Lehmkuhl H. D., M. H. Smith, R. C. Cutlip 1980. Morphogenesis and structure of caprine respiratory syncytial virus. *Arch. Vir.* 65:269-76.

Lerch R. A., K. Anderson, and G. W. Wertz 1990. Nucleotide sequence analysis and expression from recombinant vectors demonstrate that the attachment protein G of bovine respiratory syncytial virus is distinct from that of human respiratory syncytial virus. *J. Virol.* 64:5559-5569.

Ling R. and C. R. Pringle 1988. Turkey rhinotracheitis virus: in vivo and in vitro polypeptide synthesis. *J. Gen. Virol.* 69:917-923.

Ling R. and C. R. Pringle 1989a. Polypeptides of pneumonia virus of mice. I. Immunological cross-reactions and post-translational modifications. *J. Gen. Virol.* 70:1427-1440.

Ling R. and C. R. Pringle 1989b. Polypeptides of pneumonia virus of mice. II. Characterization of the glycoproteins. *J. Gen. Virol.* 70:1441-1452.

McDougall J. S. and J. K. A. Cook 1986. Turkey rhinotracheitis: preliminary investigations. *Vet. Rec.* 118:206-207.

Oberst R. D., M. P. Hays, K. J. Hennessy, L. C. Stine, J. F. Evermann, and C. L. Kelling 1993. Characteristic differences in reverse transcription polymerase chain reaction products of ovine, bovine and human respiratory syncytial viruses. *J. Vet. Diagn. Investig.* 5:322-328.

O'Loan C. J., G. Allan, C. Baxter-Jones, and M. S. McNulty 1989. An improved ELISA and serum neutralization test for the detection of turkey rhinotracheitis virus antibodies. *J. Virol. Meth.* 25:271-282.

Paccaud M. F. and C. Jacquier 1970. A respiratory syncytial virus of bovine origin. *Arch. Virol.* 30:327-342.

Pringle C. R. 1999. Virus taxonomy at the Xith international congress of virology, Sydney, Australia 1999. *Arch. Virol.* 144/2:2065-2070.

Prozzi D., K. Walravens, J. P. M. Langedijk, F. Daus, J. A. Kramps, and J. J. Letesson 1997. Antigenic and molecular analysis of the variability of bovine respiratory syncytial virus G glycoprotein. *J. Gen. Virol.* 78:359-366.

Randhawa J. S., A. C. Marriott, C. R. Pringle, and A. J. Easton 1997. Rescue of synthetic minireplicons establish the absence of the NS1 and NS2 genes from avian Pneumoviruses. *J. Virol.* 71:9849-9854.

Richter C. B., J. E. Thigpen, C. S. Richter, and J. M. Mackenzie 1988. Fatal pneumonia with terminal emaciation in nude mice caused by pneumonia virus of mice. *Lab. Anim. Sci.* 38:255-261.

Rothbarth P. H., J. J. Habova, and N. Masurel 1988. Rapid diagnosis of infections caused by respiratory syncytial virus. *Infection* 16:252.

Seal B. S. 1998. Matrix protein gene nucleotide and predicted amino acid sequence demonstrate that the first US avian *Pneumovirus* isolate is distinct form European strains. *Virus Res.* 58:45-52.

Seal B. S., H. S. Sellers, and R. J. Meinersmann 2000. Fusion protein predicted amino acid sequence of the first US avian *Pneumovirus* isolate and lack of heterogeneity among other US isolates. *Virus Res.* 66:139-147.

Selwyn B. J. 1990. The epidemiology of acute respiratory tract infection in young children: comparison findings from several developing countries. *Rev. Infect. Dis.* 12:S870-S888.

Shin H. J., G. Rajashekara, F. F. Jirjis, D. P. Shaw, S. M. Goyal, D. A. Halvorson, and K. V. Nagaraja 2000. Specific detection of avian *Pneumovirus* (APV) US isolates by RT-PCR. *Arch. Virol.* 145:1239-1246.

Sullender W. M. 2000. Respiratory syncytial virus genetic and antigenic diversity. *Clin. Microb. Rev.* 13:1-15.

Trudel M., F. Nadon, C. Sinnard, F. Belanger, R. Main, C. Seguin, and G. Lussier 1989. Comparison of caprine, human and bovine strains of respiratory syncytial virus. *Arch. Vir.* 107:141-149.

Uttenthal A., N. P. B. Jensen, and J. Y. Blom 1996. Viral etiology of enzootic pneumonia in Danish dairy herds, diagnostic tools and epidemiology. *Vet. Rec.* 139:114-117.

Valarcher J., H. Bourhy, J. Gelfi, and F. Schelcher 1999. Evaluation of a nested reverse transcription-PCR assay based on the nucleoprotein gene for diagnosis of spontaneous and experimental bovine respiratory syncytial virus infections. *J. Clin. Microb.* 37:1858-1862.

Van Milaan A. J., J. J. Sprenger, P. H. Rothbarth, A. H. Brandenburg, N. Masurel, and E. C. Claas 1994. Detection of respiratory syncytial virus by RNA-polymerase chain reaction and differentiation of subgroups with oligonucleotide probes. *J. Med. Virol.* 44:80-87.

Vilcek S., M. Elvander, A. Ballagi-Pordany, and S. Belak 1994. Development of nested PCR assays for detection of bovine respiratory syncytial virus in clinical samples. *J. Clin. Microb.* 32:2225-2231.

Walravens K, R. Kettmann, A. Collard, P. Coppe, and A. Burny 1990. Sequence comparison between the fusion protein of human and bovine respiratory syncytial viruses. *J. Gen. Virol.* 71:3009-3014.

Weir E. C., D. G. Brownstein, A. L. Smith, and E. A. Johnson 1988. Respiratory disease and wasting in athymic mice infected with pneumonia virus of mice. *Lab. Anim. Sci.* 34:35-37.

What is claimed is:

1. A kit for determining the presence of metapneumovirus (MPV) in a mammalian subject, the kit comprising:

a DNA probe of at least 10 nucleotides that hybridizes to a target polynucleotide under stringent conditions, wherein the target polynucleotide comprises a sequence encoding a polypeptide that is at least 90% identical to SEQ ID NO:28, SEQ ID NO:32, or SEQ ID NO:39, or the complement of the sequence of the sequence encoding the polypeptide, and wherein the DNA probe does not y hybridize to a polynucleotide from avian pneumovirus (APV) under stringent conditions.

2. The kit of claim 1, wherein the DNA probe comprises at least 25 nucleotides.

3. The kit of claim 1, wherein the DNA probe comprises at least 40 nucleotides.

4. The kit of claim 1, wherein the DNA probe further comprises detectable marker.

5. The kit of claim 1, wherein the target polynucleotide comprises a nucleic acid encoding SEQ ID NO:28, SEQ ID NO:32, or SEQ ID NO:39.

6. A method for detecting a human metapneumovirus infection in a mammal, the method comprising:

detecting, in a sample from the mammal, the presence of a component of human metapneumovirus by reacting the sample with a DNA probe of at least 10 nucleotides in length that hybridizes to a target polynucleotide under stringent conditions, wherein the target polynucleotide comprises a sequence encoding a polypeptide that is at least 90% identical to SEQ ID NO:28, SEQ ID NO:32, or SEQ ID NO:39 or the complement of the sequence encoding the polypeptide, and wherein the DNA probe does not hybridize to a polynucleotide from avian pneumovirus (APV) under stringent conditions.

7. The method according to claim 6, wherein the DNA probe is at least 18 nucleotides in length.

8. The method according to claim 6, wherein the DNA probe is at least 25 nucleotides in length.

9. The method according to claim 6, further comprising:

allowing the formation of a complex comprising the DNA probe and the target polynucleotide, and detecting the complex.

10. The method according to claim 6, further comprising performing a nucleic acid amplification reaction on a sample derived from the mammalian subject utilizing a set of primers for the amplification of at least a portion of the L gene of human metapneumovirus to create an amplified product.

11. The method according to claim 10, wherein the nucleic acid amplification reaction is selected from the group consisting of PCR, RAP, and RT-PCR.

12. The method according to claim 6, wherein the DNA probe comprises a label.

13. The method according to claim 9, wherein detecting the complex comprises detecting the label.

14. A method for classifying a virus as a human metapneumovirus, the method comprising:

detecting, in a sample comprising the virus, the presence of a component of human metapneumovirus by reacting the sample with a DNA probe of at least 10 nucleotides in length that hybridizes to a target polynucleotide under stringent conditions, and classifying the sample as containing human metapneumovirus;

wherein the target polynucleotide comprises a sequence encoding a polypeptide that is at least 77% identical to a sequence selected from the group consisting of SEQ ID NO:28, SEQ ID NO:32, or SEQ ID NO:39 or the complement of the sequence encoding the polypeptide.

15. The method according to claim 14, wherein the DNA probe does not hybridize to a polynucleotide from avian pneumovirus (APV) under stringent conditions.

16. The method according to claim 6, the method further comprising:

diagnosing the mammal as infected with human metapneumovirus based on the hybridization of the probe to the target polynucleotide.

* * * * *